US008202969B2

(12) United States Patent
Heinrich et al.

(10) Patent No.: US 8,202,969 B2

(45) Date of Patent: Jun. 19, 2012

(54) PLATELET DERIVED GROWTH FACTOR RECEPTOR ALPHA (PDGFRA) POLYPEPTIDES COMPRISING ACTIVATING MUTATION(S)

(75) Inventors: Michael C. Heinrich, Lake Oswego, OR (US); Christopher C. Corless, Portland, OR (US); Jonathan A. Fletcher, Brookline, MA (US); George D. Demetri, Brookline, MA (US)

(73) Assignees: Oregon Health & Science University, Portland, OR (US); U.S. Department of Veteran Affairs, Washington, DC (US); Dana-Farber Cancer Institute, Boston, MA (US); Brigham and Women's Hospital, Boston, MA (US)

( * ) Notice: Subject to any disclaimer, the term of this patent is extended or adjusted under 35 U.S.C. 154(b) by 0 days.

(21) Appl. No.: 12/959,588

(22) Filed: Dec. 3, 2010

(65) Prior Publication Data

US 2011/0081730 A1 Apr. 7, 2011

Related U.S. Application Data

(62) Division of application No. 12/466,218, filed on May 14, 2009, now Pat. No. 7,875,710, which is a division of application No. 10/517,905, filed as application No. PCT/US03/18901 on Jun. 13, 2003, now Pat. No. 7,595,154.

(60) Provisional application No. 60/389,107, filed on Jun. 13, 2002, provisional application No. 60/438,899, filed on Jan. 8, 2003.

(51) Int. Cl.

| | |
|---|---|
| ***C07K 14/71*** | (2006.01) |
| ***C07K 16/30*** | (2006.01) |
| ***C07K 7/00*** | (2006.01) |
| ***A61K 39/395*** | (2006.01) |
| *G01N 33/574* | (2006.01) |

(52) U.S. Cl. .................... 530/350; 435/7.23; 424/138.1; 424/139.1; 424/143.1; 530/300; 530/387.7; 530/387.9; 530/388.22; 514/7.5

(58) Field of Classification Search ........................ None
See application file for complete search history.

(56) References Cited

U.S. PATENT DOCUMENTS

| | | | | |
|---|---|---|---|---|
| 5,376,531 | A * | 12/1994 | Anderson et al. | 435/7.23 |
| 5,686,572 | A | 11/1997 | Wolf et al. | |
| 5,795,975 | A | 8/1998 | Wallach et al. | |
| 5,795,976 | A | 8/1998 | Oefner et al. | |
| 5,833,986 | A | 11/1998 | LaRochelle et al. | |
| 6,187,536 | B1 | 2/2001 | Weinberg et al. | |
| 6,194,158 | B1 | 2/2001 | Kroes et al. | |
| 6,291,661 | B1 | 9/2001 | Graddis et al. | |
| 7,595,154 | B2 * | 9/2009 | Heinrich et al. | 435/6 |
| 7,875,710 | B2 * | 1/2011 | Heinrich et al. | 536/23.5 |

OTHER PUBLICATIONS

Benjamini et al, 1991. Immunology: A Short Course, 2nd edition, p. 40 only.*
Houghten et al, 1991. Nature. 354: 84-86.*
"Gleevec™ Shows Promise for Type of Gastrointestinal Tumor," *National Cancer Institute—Clinical Trial Results* http://www.cancer.gove/clinicaltrials/results/gleevec-shows-promise0202, posted Jul. 20, 2001; printed Feb. 26, 2005.
Abu-Duhier et al., "FLT3 internal tandem duplication mutations in adult acute myeloid leukaemia define a high-risk group," *J. Haematol*, 111(1):190, 2000.
Abu-Duhier et al., "Identification of novel FLT-3 Asp835 mutations in adult acute myeloid leukaemia," *J. Haematol*, 113(4):983-988, 2001.
Al-Ali et al., "High incidence of BCR-ABL kinase domain mutations and absence of mutations of the PDGFR and KIT activation loops in CML patients with secondary resistance to imatinib," *Haematol J.* 5(1):55-60, 2004.
Bai et al., "The SH2-containing Adapter Protein GRB10 interacts with BCR-ABL" *Oncogene*, 17:941-948, 1998.
Baxter et al., "The t(4:22)(q12;q11) in Atypical Chronic Myeloid Leukaemia fuses BCR to PDGFRA" *Human Molecular Genetics*, 11(12):1391-1397, 2002.
Blanke et al., "Evaluation of the Safety and Efficacy of an Oral Molecularly-Targeted Therapy, STI571, in Patients (Pts) with Unresectable or Metastatic Gastrointestinal Stromal Tumors (GISTS) Expressing C-KIT (CD117),"*ASCO*, May 12-15, 2001 (*Meeting Abstract*).
Borg et al., "Novel mode of action of c-kit tyrosine kinase inhibitors leading to NK cell-dependent antitumor effects," *J. Clinical. Investigation*, 114(3):379-388, 2004.
Bork, "Powers and Pitfalls in Sequence Analyis: The 70% Hurdle," *Genome Research*, 10:398-400, 2000.
Brenner, "Errors in genome annotation," *Trends in Genetics*, 15(4):132-133, 1999.
Chen et al., "Imatinib inhibits various types of activating mutant kit found in gastrointestinal stromal tumors," *J. Cancer*, 105(1):130-135, 2003.
Corless et al., "Biology of gastrointestinal stromal tumors," *J. Clin. Oncol.*, 22(18):3813-3825, 2004.
Debiec-Rychter et al., "Use of c-KIT/PDGFRA mutational analysis to predict the clinical response to imatinib in patients with advanced gastrointestinal stromal tumours entered in phase I and II studies of the EORTC Soft Tissue and Bone Sarcoma Group," *Eur J Cancer*, 40(5):689-95, 2004.
Demetri et al., "Phase III dose-randomized study of imatinib mesylate (Gleevec, STI571) for GIST: intergroup S0033 early results," *ASCO*, May 18-21, 2002 (*Meeting Abstract*).
Demetri, "Targeting *c-kit* Mutations in Solid Tumors: Scientific Rationale and Novel Therapeutic Options," *Semin Oncol.*, 5 Suppl 17:19-26, 2001.
Doerks et al., "Protein annotation: detective work for function prediction," *Trends in Genetics*, 14(6):248-250, 1998.

(Continued)

*Primary Examiner* — Bridget E Bunner
*Assistant Examiner* — Zachary Howard
(74) *Attorney, Agent, or Firm* — Klarquist Sparkman, LLP

(57) ABSTRACT

This disclosure provides tyrosine kinase protein and nucleic acid variants, particularly PDGFRA variants, which are activating forms of these molecules and are linked to neoplasms and/or the development or progression of cancer. The disclosure further provides methods of diagnosis and prognosis, and development of new therapeutic agents using these molecules and fragments thereof, and kits for employing these methods and compositions.

15 Claims, 7 Drawing Sheets

OTHER PUBLICATIONS

Duensing et al., "Protein Kinase C theta (PKCtheta) expression and constitutive activation in gastrointestinal stromal tumors (GISTs)," *Cancer Res.*, 64(15):5127-5131, 2004.
Fenski et al., "Constitutive activation of FLT3 in acute myeloid leukaemia and its consequences for growth of 32D cells," *J. Haematol*, 108(2):322-330, 2000.
Gari et al., "c-kit proto-oncogene exon 8 in-frame deletion plus insertion mutations in acute myeloid leukaemia," *J. Haematol*, 105(4):894-900, 1999.
Griswold et al., "Effects of MLN518, a dual FLT3 and KIT inhibitor, on normal and malignant hematopoiesis," *Blood*, 104(9):2912-2918, 2004.
Heinrich et al., "Biology and genetic aspects of gastrointestinal stromal tumors: KIT activation and cytogenetic alternations," *Hum. Pathol.*, 33(5):484-95, 2002.
Heinrich et al., "Inhibition of c-kit receptor tyrosine kinase activity by STI 571, a selective tyrosine kinase inhibitor," *Blood*, 96(3):925-932, 2000.
Heinrich et al., "Inhibition of KIT Tyrosine Kinase Activity: A Novel Molecular Approach to the Treatment of KIT-Positive Malignancies," *J. Clinical Oncology*, 20(6):1692-1703, 2002.
Heinrich et al., "Kinase mutations and imatinib response in patients with metastatic gastrointestinal stromal tumor," *J. Clin Oncol.*, 21(23):4342-4349, 2003.
Heinrich et al., "KIT mutational status predicts clinical response to STI571 in patients with metastatic gastrointestinal stromal tumors (GISTs),"*ASCO*, May 18-21, 2002 (*Meeting Abstract*).
Heinrich et al., "*PDGFRA* Activating Mutations in Gastrointestinal Stromal Tumors," *Science*. 299:708-710, 2003.
Heinrich et al., "Targeting mutant kinases in gastrointestinal stromal tumors: a paradigm for molecular therapy of other sarcomas," *Cancer Treatment Res,*. 120:129-150, 2004.
Hirota et al., "Gain-of-function mutation at the extracellular domain of KIT in gastrointestinal stromal tumours," *J Pathol.* 193(4):505-510, 2001.
Hirota et al., "Gain-of-Function Mutations of Platelet-Derived Growth Factor Receptor α Gene in Gastrointestinal Stromal Tumors," *Gastroenterology*, 125:660-667, 2003.
Hochhaus et al., "Interim analysis of imatinib treatment in 300 patients with chronic myelogenous leukemia (CML): evaluation of response and resistance," *ASCO*, May 18-21, 2002 (*Meeting Abstract*).
*Homo sapiens* platelet-derived growth factor receptor, alpha polypeptide (PDGFRA), mRNA, Locus ID: XM_011186, PRI Feb. 7, 2002, *NCBI*, printed Apr. 18, 2002.
Human DNA for alpha-platelet-derived growth factor receptor, exon 1, Locus ID: D50001S01, PRI Apr. 14, 2000, *NCBI*, printed Jun. 5, 2002.
Joensuu et al., "Effect of the tyrosine kinase inhibitor STI571 in a patient with a metastatic gastrointestinal stromal tumor," *N Engl J Med*, 344(14):1052-1056, 2001.
Joensuu et al., "Gastrointestinal stromal tumor (GIST) patients who respond to imatinib (STI571, Gleevec) show marked decline of circulating levels of VEGF, KIT, and bFGF in serum, but not stem cell factor (SCF) levels," *ASCO*, May 18-21, 2002 (*Meeting Abstract*).
Johnson et al., "Phase II study of STI571 (Gleevec™) for patients with small cell lung cancer," *ASCO*, May 18-21, 2002 (*Meeting Abstract*).
Kaufman et al., "Transgenic Analysis of a 100-kb Human β-Globin Cluster—Containing DNA Fragment Propagated as a Bacterial Artificial Chromosome," *Blood*, 94:3178-3184, 1999.
Kubota et al., "Chemosensitivity of gastric cancer detected by cDNA microarray," *ASCO*, May 18-21, 2002 (*Meeting Abstract*).
Madani et al., "Expression of KIT and epidermal growth factor receptor (EGFR) in chemotherapy refractory non-seminomatous germ cell tumors (GCT)," *ASCO*, May 28-21, 2002 (*Meeting Abstract*).
Medeiros et al., "KIT-negative gastrointestinal stromal tumors: proof of concept and therapeutic implications," *Am J. Surg Pathol,*. 28(7):889-894, 2004.
Nakamura et al., "Abnormalities of the p53, N-ras, DCC and FLT-3 genes in myelodysplastic syndromes," *J. Nippon Med Sch*, 68(2):143-148 (Apr. 2001) (*English Abstract Only*).
Ngo et al., "The Protein Folding Problem and Tertiary Structure Prediction, Chapter 14: Computational Complexity Protein Structure Prediction, and the Levinthal Paradox," pp. 433-440 and 492-495 only, 1994.
O'Farrell et al., "Analysis of mechanism of action and biomarkers for kinase inhibitor SU5416 in AML patients," *ASCO*, May 18-21, 2002 (*Meeting Abstract*).
O'Farrell et al., "SU11248 is a novel FLT3 tyrosine kinase inhibitor with potent activity in vitro and in vivo," *Blood*, 101(9):3597-3605, 2003.
Omura et al., "Immunoglobulin-like Domain 4-mediated Receptor-Receptor Interactions contribute to Platelet-derived Growth Factor-induced Receptor Dimerization" *JBC*, 272(19):12676-12682, 1997.
PDGFRA: platelet-derived growth factor receptor, alpha polypeptide, Locus ID: 5156, *NCBI*, printed Jun. 5, 2002.
Phillips, A., "The challenge of gene therapy and DNA delivery," *J Pharm Pharmacology*, 53:1169-1174, 2001.
Rubin et al., "KIT Activation is a Ubiquitous Feature of Gastrointestinal Stromal Tumors," *Cancer Research*, 61:8118-8121, 2001.
Singer et al., "Prognostic Value of *KIT* Mutation Type, Mitotic Activity, and Histologic Subtype in Gastrointestinal Stromal Tumors," *J. Clinical Oncology*, 20(18):3898-3905, 2002.
Skolnick et al., "From genes to protein structure and function: novel application of computational approaches in the genomic era," *Trends in Biotech*, 18(1):34, 2000.
Subramanian et al., "Gastrointestinal stromal tumors (GISTs) with KIT and PDGFRA mutations have distinct gene expression profiles," *Oncogene*, 23(47):7780-7790, 2004.
van Oosterom et al., "Safety and efficacy of imatinib (STI571) in metastatic gastrointestinal stromal tumours: a phase I study," *Lancet*, 358(9291):1421-1423, 2001.
van Oosterom et al., "STI571, an Active Drug in Metastatic Gastro Intestinal Stromal Tumors (GIST), an EORTC Phase I Study," *ASCO*, May 12-15, 2001 (*Meeting Abstract*).
von Mehren et al., "High incidence of durable responses induced by imatinib mesylate (Gleevec) in patients with unresectable and metastatic gastrointestinal stromal tumors (GISTs)," *ASCO*, May 18-21, 2002 (*Meeting Abstract*).
Wang et al., "Rapid analysis of gene expression (RAGE) facilitates universal expression profiling," *Nuc. Acids Res.*, 27:4609-4618, 1999.
Wells, "Additivity of Mutational Effects in Proteins," *Biochemistry*, 29(37):8509-8517, 1990.
Corless et al., "*PDGRFA* Mutation in Gastrointestinal Stromal Tumors: Frequency, Spectrum and In Vitro Sensitivity to Imatinib," *J Clin Oncol.*, 23(23):5357-5364, 2005.
Guida et al., "Sorafenib Inhibits Imatinib-Resistant KIT and Platelet-Derived Growth Factor Receptor β Gatekeeper Mutants," *Clin Cancer Res.*, 13:3363-3369, 2007.
Heinrich et al., "Phase II, Open-Label Study Evaluating the Activity of Imatinib in Treating Life-Threatening Malignancies Known to Be Associated with Imatinib-Sensitive Tyrosine Kinases," *Clin Cnacer Res.*,14:2717-2725, 2008.
Lierman et al., "FIP1L1-PDGFRα D842V, a novel panresistant mutant, emerging after treatment of FIP1L1-PDGFRα T674I eosinophilic leukemia with a single agent sorafenib," *Leukemia*, 23(5):845-851, 2009.

* cited by examiner

FIGURE 7A

```
181551  GCTTTCTCTC TGTTGGGAGT GGGTGGAGTG AGAACCTGGG AGAAGGCCAG
        CGAAAGAGAG ACAACCCTCA CCCACCTCAC TCTTGGACCC TCTTCCGGTC

                                            PDGFrA 181634F
181601 CCCTTTATAT CCAGGCAGAC AGCTCCAAGT GCCACCATGG ATCAGCCAGT
       GGGAAATATA GGTCCGTCTG TCGAGGTTCA CGGTGGTACC TAGTCGGTCA

       PDGFrA 181640F          PDGFrA 181671F
181651 CTTGCAGGGG TGATGCTATT CAGCTACAGA TGGCTTGATC CTGAGTCATT
       GAACGTCCCC ACTACGATAA GTCGATGTCT ACCGAACTAG GACTCAGTAA

181701 TCTTCCTTTT CCATGCAGTG TGTCCACCGT GATCTGGCTG CTCGCAACGT   Exon 18
       AGAAGGAAAA GGTACGTCAC ACAGGTGGCA CTAGACCGAC GAGCGTTGCA
                                   C   V   H   R   D   L   A   A   R   N   V   Frame 3

        PDGFrA 181752F (SNP Exclusion)
181751 CCTCCTGGCA CAAGGAAAAA TTGTGAAGAT CTGTGACTTT GGCCTGGCCA
       GGAGGACCGT GTTCCTTTTT AACACTTCTA GACACTGAAA CCGGACCGGT
       L   L   A   Q   G   K   I   V   K   I   C   D   F   G   L   A   R   Frame 3

181801 GAGACATCAT GCATGATTCG AACTATGTGT CGAAAGGCAG TGTACGTCCT
       CTCTGTAGTA CGTACTAAGC TTGATACACA GCTTTCCGTC ACATGCAGGA
         D   I   M   H   D   S   N   Y   V   S   K   G   S

       PDGFrA 181862R          PDGFrA 181874R
181851 CACTTCCCTC ACTGGTCAGG CTCATCCTCC TTCACTTTAA TCTCTAAAGT
       GTGAAGGGAG TGACCAGTCC GAGTAGGAGG AAGTGAAATT AGAGATTTCA

181901 CAGGTGTTGC TTCTAGAGAT TCGGTGCCTG TTTTTTAAAA CATCAATAGA
       GTCCACAACG AAGATCTCTA AGCCACGGAC AAAAAATTTT GTAGTTATCT
```

FIGURE 7B

```
170551 AAGCATAGCA ACCTAGTTCA GTGCTTGGCA CAGAGAAGGA GCTCAGCAAT
       TTCGTATCGT TGGATCAAGT CACGAACCGT GTCTCTTCCT CGAGTCGTTA

                                                 PDGFrA 170636F
170601 TACATGTGGA GTGAACGTTG TTGGACTCTA CTGTGTCCAG TCACTGTGCT
       ATGTACACCT CACTTGCAAC AACCTGAGAT GACACAGGTC AGTGACACGA

              PDGFrA 170658F
170651 GCTTCAGTGA AGCTCTGGTG CACTGGGACT TTGGTAATTC ACCAGTTACC
       CGAAGTCACT TCGAGACCAC GTGACCCTGA AACCATTAAG TGGTCAATGG

170701 TGTCCTGGTC ATTTATAGAA ACCGAGGTAT GAAATTCGCT GGAGGGTCAT   Exon 12
       ACAGGACCAG TAAATATCTT TGGCTCCATA CTTTAAGCGA CCTCCCAGTA
                            K   P  R  Y   E  I  R  W   R  V  I   Frame 1

170751 TGAATCAATC AGCCCAGATG GACATGAATA TATTTATGTG GACCCGATGC
       ACTTAGTTAG TCGGGTCTAC CTGTACTTAT ATAAATACAC CTGGGCTACG
        E  S  I   S  P  D  G   H  E  Y   I  Y  V   D  P  M  Q   Frame 1

170801 AGCTGCCTTA TGACTCAAGA TGGGAGTTTC CAAGAGATGG ACTAGTGCTT
       TCGACGGAAT ACTGAGTTCT ACCCTCAAAG GTTCTCTACC TGATCACGAA
         L  P  Y   D  S  R   W  E  F  P   R  D  G   L  V  L     Frame 1

           PDGFrA 170866R                     PDGFrA 170894R
170851 GGTAAGTTCC ATGGGGTAAC CTCCCAAGAC TCCCTTTTCC CTTGCACACA
       CCATTCAAGG TACCCCATTG GAGGGTTCTG AGGGAAAAGG GAACGTGTGT

170901 ACTTTACAAT TTATAGGCCT TGGCAGAATA GAGATCTGAG CTTGTGCTTA
       TGAAATGTTA AATATCCGGA ACCGTCTTAT CTCTAGACTC GAACACGAAT
```

PLATELET DERIVED GROWTH FACTOR RECEPTOR ALPHA (PDGFRA) POLYPEPTIDES COMPRISING ACTIVATING MUTATION(S)

CROSS REFERENCE TO RELATED APPLICATION

This is a division of co-pending application Ser. No. 12/466,218, filed May 14, 2009, issued as U.S. Pat. No. 7,875,710 on Jan. 25, 2011, which is a division of U.S. application Ser. No. 10/517,905, filed Dec. 10, 2004, issued as U.S. Pat. No. 7,595,154 on Sep. 29, 2009, which is the U.S. National Stage of International Application No. PCT/US03/18901, filed Jun. 13, 2003, which was published in English under PCT Article 21(2), and which in turn claims the benefit of U.S. Provisional Applications No. 60/389,107, filed Jun. 13, 2002 and No. 60/438,899, filed Jan. 8, 2003. Each of these applications is incorporated herein in its entirety.

STATEMENT OF GOVERNMENT SUPPORT

This invention was made with United States government support pursuant to employment of one of the inventors as a Federal employee, as well as grant funding from a Veterans Affairs Merit Review Grant; the United States government has certain rights in the invention.

FIELD

This disclosure relates to tyrosine kinases, particularly receptor tyrosine kinases with one or more activation mutations. Further, it relates to methods of using these molecules in screens and analyses, including diagnoses, prognoses, and systems for identification and/or selection of pharmaceutical compounds.

BACKGROUND OF THE DISCLOSURE

Tyrosine kinases are expressed by many human cancers. These enzymes are attractive targets for the development of anticancer drugs, as it has been possible to optimize compounds with excellent inhibitory potency and selectivity to individual target tyrosine kinases. The utility of this approach has been highlighted by the success of imatinib mesylate (Gleevec™) in the treatment of chronic myelogenous leukemia (CML) and gastrointestinal stromal tumors (GISTs).

Expression of tyrosine kinases is ubiquitous in both cancers and normal tissues. Therefore, the efficacy of a kinase inhibitor is dependent on two factors: 1) the degree to which the target kinase is activated in a particular cancer, and 2) the degree to which the growth and survival of the cancer cells is dependent on the activated target kinase.

Gastrointestinal stromal tumors provide an excellent example of this principle. KIT tyrosine kinase is detectable by immunohistochemistry in a wide variety of cancers and normal tissues, but mutations of the KIT gene that yield constitutively active KIT kinase are found in only a small subset of tumors (Heinrich et al., *J. Clin. Oncol.,* 20: 1692-1703, 2002). More than 85% of GISTs harbor such activating mutations (Blanke et al., *Proceedings of ASCO* 20, 1a-1a. 2001; Heinrich et al., *J. Clin. Oncol.,* 20: 1692-1703, 2002; Hirota et al., *J. Pathol.,* 193: 505-510, 2001; Rubin et al., *Cancer Res,* 61: 8118-8121, 2001) and, correspondingly, phosphorylation of KIT kinase (a marker of activation) was recently demonstrated in most fresh-frozen GIST specimens (Rubin et al., *Cancer Res,* 61: 8118-8121, 2001). Such phosphorylation of KIT is rarely observed in other cancer specimens. Recent success in the treatment of advanced malignant GISTs with imatinib mesylate is thought to reflect an important role of KIT activation in the growth and/or survival of GIST tumor cells (Blanke et al., *Proceedings of ASCO* 20, 1a-1a. 2001; Joensuu et al., *N Engl J Med,* 344: 1052-1056, 2001; Van Oosterom et al., *Lancet,* 358:1421-1423, 2001). The observation that treatment results with imatinib mesylate are significantly better for tumors with evidence of mutational activation of KIT than for tumors with no KIT mutation further supports this view (Heinrich et al., *J. Clin. Oncol.,* 20: 1692-1703, 2002). Thus, in the case of GISTs, testing of clinical specimens for genomic mutations resulting in tyrosine kinase activation will be useful in determining which patients are most likely to respond to a tyrosine kinase inhibitor.

The PDGFRA (or PDGFR-α) protein is a type III receptor tyrosine kinase with homology to KIT, FLT3, CSF1-R and PDGFR-β (PDGFRB). Although PDGFRA activation has been hypothesized to be involved in certain cancers, most notably gliomas, evidence of genomic activation in human cancer has only recently been reported in two cases of myeloproliferative disease associated with translocation of the BCR and PDGFRA genes.

SUMMARY OF THE DISCLOSURE

Disclosed herein are novel mutations of PDGFRA that result in constitutive activation of this tyrosine kinase. These mutations were initially discovered in GISTs. Also disclosed are consensus PDGFRA nucleic acid and amino acid sequences, which summarize certain groups of activating mutations and regions of relatively active mutation.

Thus, this disclosure provides several novel PDGFRA variant proteins, and nucleic acids encoding these variants. Also disclosed are methods of using these molecules in detecting biological conditions associated with an activating PDGFRA mutation in a subject, methods of treating such conditions, methods of selecting treatments (e.g., specific tyrosine kinase inhibitors), and methods of screening for inhibitors of PDGFRA activity, particularly activated PDGFRA variant activity. Oligonucleotides for use in examples of such methods are also provided.

Also disclosed herein are protein specific binding agents, such as antibodies, that bind specifically to at least one epitope of a PDGFRA variant protein preferentially compared to wildtype PDGFRA, and methods of using such antibodies in diagnosis, treatment, and screening.

Kits are also provided for carrying out the methods described herein.

The foregoing and other features and advantages will become more apparent from the following detailed description of several embodiments, which proceeds with reference to the accompanying figures.

BRIEF DESCRIPTION OF THE FIGURES

FIG. 7 (including FIGS. 7A and 7B): Differential sensitivity of various KIT activation loop mutants to imatinib mesylate. FIG. 7 shows the genomic sequences of PDGFRA around exon 18 (FIG. 7A) (SEQ ID NO: 28 and its reverse complement) and exon 12 (FIG. 7B) (SEQ ID NO: 30 and its reverse complement). PDGFRA primers are indicated; PDGFRA exon sequences and amino acid translations (SEQ ID NOs: 29 and 31, respectively) are also shown.

FIG. 8 shows a series of immunoblots, probed with antibodies to phospho-tyrosine and PDGFRA. CHO cells were transiently transfected with expression vectors encoding cDNAs for wild-type or mutant PDGFRA. Transfected cells were serum starved overnight and treated with vehicle or ligand (recombinant human PDGF-AA) for 10 minutes. Whole cell lysates were immunostained sequentially for phospho-tyrosine and PDGFRA. Wild type PDGFRA displays low-level phosphorylation that is upregulated by ligand stimulation with PDGF-AA. In contrast, the mutant PDGFRA proteins display ligand-independent phosphorylation.

FIG. 9 shows a series of immunoblots, illustrating the cell signaling profiles of the indicated mutants. Whole cell lysates were prepared from snap-frozen GISTs, and immunoblots were detected with antibodies to phosphorylated and total forms of AKT, MAPK, and STATs. All GISTs express phosphorylated AKT, MAPK, STAT1, and STAT3, whereas STAT5 is not tyrosine phosphorylated.

SEQUENCE LISTING

Figure 1:
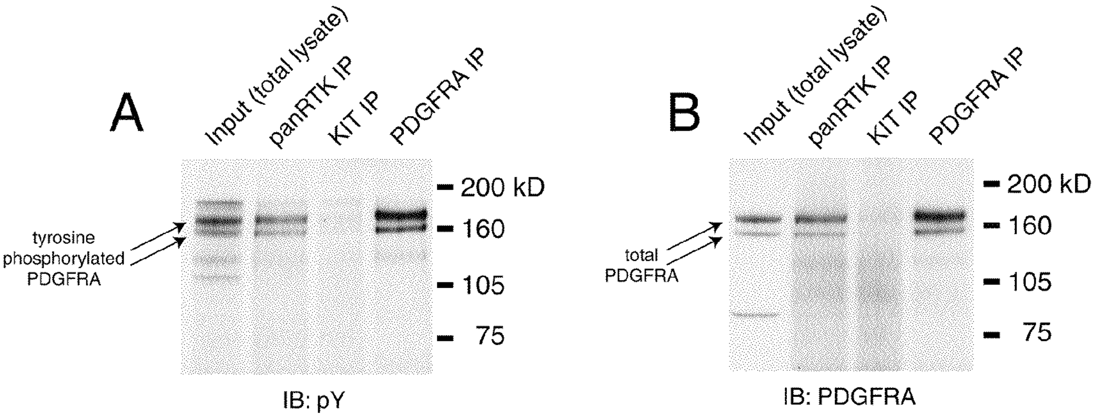
FIG. 1 (including FIG. 1A and FIG. 1B): Immunostaining for phosphotyrosine (A) and PDGFRA (B) in GIST478. A) A strongly tyrosine phosphorylated doublet at 150/170 kD is seen in the RTK immunoprecipitate (lane 2). This phosphorylated doublet corresponds to two of the stronger phosphoproteins in the total cell lysate (lane 1), and comigrates with the strongly phosphorylated PDGFRA doublet (lane 4). KIT is not demonstrably phosphorylated (lane 3). B) The strongly phosphorylated RTK (lane 2) was confirmed as PDGFRA, by stripping and restaining the blot with a specific antibody to PDGFRA.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Unless specifically noted otherwise herein, the position numbering associated with the name of a variant PDGFRA molecule is based on numbering in the corresponding wildtype molecule. Where a reference is made to positions in a variant, the numbering is based on the actual position in the specified variant. The Sequence Listing is submitted as an ASCII text file in the form of the file of ~578,000 bytes created on Dec. 30, 2011, which is incorporated by reference herein.

In the accompanying sequence listing:

SEQ ID NO: 1 shows the nucleic acid sequence of the human PDGFRA cDNA (GenBank Accession No. XM_011186); the sequence list also shows the encoded protein.

SEQ ID NO: 2 shows the amino acid sequence of human PDGFRA protein.

SEQ ID NO: 3 shows the nucleic acid sequence of the human PDGFRA D842V variant cDNA; the sequence list also shows the encoded protein.

SEQ ID NO: 4 shows the amino acid sequence of human PDGFRA D842V variant protein.

SEQ ID NO: 5 shows the nucleic acid sequence of the human PDGFRA DIMH842-845 variant cDNA; the sequence list also shows the encoded protein.

SEQ ID NO: 6 shows the amino acid sequence of human PDGFRA DIMH842-845 variant protein.

SEQ ID NO: 7 shows the nucleic acid sequence of the human PDGFRA HDSN845-848P variant cDNA; the sequence list also shows the encoded protein.

SEQ ID NO: 8 shows the amino acid sequence of human PDGFRA HDSN845-848P variant protein.

SEQ ID NO: 9 shows the nucleic acid sequence of the human PDGFRA ER561-562 variant cDNA; the sequence list also shows the encoded protein.

SEQ ID NO: 10 shows the amino acid sequence of human PDGFRA ER561-562 variant protein.

SEQ ID NO: 11 shows the nucleic acid sequence of the human PDGFRA SPDGHE566-571R variant cDNA; the sequence list also shows the encoded protein.

SEQ ID NO: 12 shows the amino acid sequence of human PDGFRA SPDGHE566-571R variant protein.

SEQ ID NOs: 13-18 are amino acid sequences of the RTK catalytic domain sequences of different families of human RTK proteins.

SEQ ID NO: 19 is the genomic sequence of PDGFRA, with introns and exons indicated. Regions where the sequence is unknown or unconfirmed have been indicated with "n" designations using standard conventions. This sequence is available in the April 2002 release of the human genome project, as provided by University of California, Santa Cruz, on their Internet website.

SEQ ID NO: 20 shows the nucleic acid sequence of the human PDGFRA V561D variant cDNA; the sequence list also shows the encoded protein.

SEQ ID NO: 21 shows the amino acid sequence of human PDGFRA V561D variant protein.

SEQ ID NO: 22 shows the nucleic acid sequence of the human PDGFRA RVIES560-564 variant cDNA; the sequence list also shows the encoded protein.

SEQ ID NO: 23 shows the amino acid sequence of human PDGFRA RVIES560-564 variant protein.

SEQ ID NO: 24 shows the nucleic acid sequence of the human PDGFRA Substitution RD841-842KI variant cDNA; the sequence list also shows the encoded protein.

SEQ ID NO: 25 shows the amino acid sequence of human PDGFRA Substitution RD841-842KI variant protein.

SEQ ID NO: 26 shows the consensus sequence produced by aligning the nucleic acid sequences of each of the identified activating PDGFRA mutants (SEQ ID NOs: 3, 5, 7, 9, 11, 20, 22, and 24), and the consensus protein encoded thereby.

SEQ ID NO: 27 shows a PDGFRA consensus sequence.

SEQ ID NO: 28 shows the genomic sequence of PDGFRA around exon 18.

SEQ ID NO: 29 shows the amino acid sequence encoded by PDGFRA exon 18.

SEQ ID NO: 30 shows the genomic sequence of PDGFRA around exon 12.

SEQ ID NO: 31 shows the amino acid sequence encoded by PDGFRA exon 12.

DETAILED DESCRIPTION

I. Abbreviations

2D-PAGE two-dimensional polyacrylamide gel electrophoresis

ASO allele-specific oligonucleotide

ASOH allele-specific oligonucleotide hybridization

DASH dynamic allele-specific hybridization

ELISA enzyme-linked immunosorbant assay

HPLC high pressure liquid chromatography

MALDI-TOF matrix-assisted laser desorption/ionization time-of-flight

PCR polymerase chain reaction

PDGFRA platelet derived growth factor receptor alpha

PDGFRB platelet derived growth factor receptor beta

RT-PCR reverse-transcription polymerase chain reaction

SSCP single-strand conformation polymorphism

TKI tyrosine kinase inhibitor

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For present purposes, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Injectable composition: A pharmaceutically acceptable fluid composition including at least one active ingredient. The active ingredient is usually dissolved or suspended in a physiologically acceptable carrier, and the composition can additionally include amounts of one or more non-toxic auxiliary substances, such as emulsifying agents, preservatives, and pH buffering agents and the like. Such injectable compositions that are useful for use with the provided nucleotides and proteins are conventional; appropriate formulations are well known in the art.

In vitro amplification: Techniques that increase the number of copies of a nucleic acid molecule in a sample or specimen. An example of in vitro amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

The product of in vitro amplification may be characterized by electrophoresis, restriction endonuclease cleavage patterns, oligonucleotide hybridization or ligation, and/or nucleic acid sequencing, using standard techniques.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mutation: Any change of the DNA sequence within a gene or chromosome. In some instances, a mutation will alter a characteristic or trait (phenotype), but this is not always the case. Types of mutations include base substitution point mutations (e.g., transitions or transversions), deletions, and insertions. Missense mutations are those that introduce a different amino acid into the sequence of the encoded protein; nonsense mutations are those that introduce a new stop codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

This term specifically encompasses variations that arise through somatic mutation, for instance those that are found only in disease cells, but not constitutionally, in a given individual. Examples of such somatically-acquired variations include the point mutations that frequently result in altered function of various genes that are involved in development of cancers. This term also encompasses DNA alterations that are present constitutionally, that alter the function of the encoded protein in a readily demonstrable manner, and that can be inherited by the children of an affected individual. In this respect, the term overlaps with "polymorphism," as defined below, but generally refers to the subset of constitutional alterations that have arisen within the past few generations in a kindred and that are not widely disseminated in a population group. In particular embodiments, the term is directed to those constitutional alterations that have major impact on the health of affected individuals.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include PNA molecules.

Particular oligonucleotides and oligonucleotide analogs can include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame (ORF): A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with the compositions provided herein are conventional. By way of example, Martin, in *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene, usually carried from one generation to another in a population. Polymorphisms can be those variations (nucleotide sequence differences) that, while having a different nucleotide sequence, produce functionally equivalent gene products, such as those variations generally found between individuals, different ethnic groups, or geographic locations. The term polymorphism also encompasses variations that produce gene products with altered function, i.e., variants in the gene sequence that lead to gene products that are not functionally equivalent. This term also encompasses variations that produce no gene product, an inactive gene product, or increased or decreased activity gene product.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation (e.g., an alteration of a secondary structure such as a stem-loop, or an alteration of the binding affinity of the nucleic acid for associated molecules, such as polymerases, RNases, and so forth).

Probes and primers: Nucleic acid probes and primers can be readily prepared based on the nucleic acid molecules provided as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other in vitro nucleic-acid amplification methods known in the art.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs (for instance, for use with polymerase chain reaction amplification) can be derived from a known sequence such as the PDGFRA or other tyrosine kinase sequences described herein, for example, by using computer programs intended for that purpose such as Primer (Version 0.5, © 1991, Whitehead Institute for Biomedical Research, Cambridge, Mass.).

One of ordinary skill in the art will appreciate that the specificity of a particular probe or primer increases with its length. Thus, for example, a primer comprising 30 consecutive nucleotides of a tyrosine kinase protein encoding nucleotide will anneal to a target sequence, such as another homolog of the designated tyrosine kinase protein, with a higher specificity than a corresponding primer of only 15 nucleotides. Thus, in order to obtain greater specificity, probes and primers can be selected that comprise at least 20, 23, 25, 30, 35, 40, 45, 50 or more consecutive nucleotides of a tyrosine kinase-encoding nucleotide sequence.

Also provided are isolated nucleic acid molecules that comprise specified lengths of tyrosine kinase-encoding nucleotide sequences. Such molecules may comprise at least 10, 15, 20, 23, 25, 30, 35, 40, 45 or 50 or more (e.g., at least 100, 150, 200, 250, 300 and so forth) consecutive nucleotides of these sequences or more. These molecules may be obtained from any region of the disclosed sequences (e.g., a PDGFRA nucleic acid may be apportioned into halves or quarters based on sequence length, and isolated nucleic acid molecules may be derived from the first or second halves of the molecules, or any of the four quarters, etc.). A cDNA or other encoding sequence also can be divided into smaller regions, e.g. about eighths, sixteenths, twentieths, fiftieths, and so forth, with similar effect.

Another mode of division, provided by way of example, is to divide a tyrosine kinase-encoding sequence based on the regions of the sequence that are relatively more or less homologous to other tyrosine kinase sequences.

Another mode of division is to select the 5' (upstream) and/or 3' (downstream) region associated with a tyrosine kinase gene (e.g., PDGFRA).

Nucleic acid molecules may be selected that comprise at least 10, 15, 20, 25, 30, 35, 40, 50, 100, 150, 200, 250, 300 or more consecutive nucleotides of any of these or other portions of a PDGFRA nucleic acid molecule, such as those disclosed herein, and associated flanking regions. Thus, representative nucleic acid molecules might comprise at least 10 consecutive nucleotides of the PDGFRA cDNA shown in SEQ ID NO: 1.

Protein: A biological molecule expressed by a gene or recombinant or synthetic coding sequence and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of human PDGFRA protein, and the corresponding cDNA or gene sequence(s), will possess a relatively high degree of sequence identity when aligned using standard methods. This homology will be more significant when the orthologous proteins or genes or cDNAs are derived from species that are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2: 482, 1981; Needleman & Wunsch *J. Mol. Biol.* 48: 443, 1970; Pearson & Lipman *Proc. Natl. Acad. Sci. USA* 85: 2444, 1988; Higgins & Sharp *Gene,* 73: 237-244, 1988; Higgins & Sharp *CABIOS* 5: 151-153, 1989; Corpet et al. *Nuc. Acids Res.* 16, 10881-90, 1988; Huang et al. *Computer Appls. in the Biosciences* 8, 155-65, 1992; and Pearson et al. *Meth. Mol. Bio.* 24, 307-31, 1994. Altschul et al. (*J. Mol. Biol.* 215:403-410, 1990), presents a detailed consideration of sequence alignment methods and homology calculations.

The NCBI Basic Local Alignment Search Tool (BLAST) (Altschul et al. *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment is performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual*, CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a human tyrosine kinase protein-encoding sequence will typically hybridize to a probe based on either an entire human tyrosine kinase protein-encoding sequence or selected portions of the encoding sequence under wash conditions of 2×SSC at 50° C.

Nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Specific binding agent: An agent that binds substantially only to a defined target. Thus a protein-specific binding agent binds substantially only the specified protein. By way of example, as used herein, the term "PDGFRA-protein specific binding agent" includes anti-PDGFRA protein antibodies (and functional fragments thereof) and other agents (such as soluble receptors) that bind substantially only to the PDGFRA protein.

Anti-PDGFRA protein antibodies (or antibodies to another tyrosine kinase) may be produced using standard procedures described in a number of texts, including Harlow and Lane (*Antibodies, A Laboratory Manual*, CSHL, New York, 1988). The determination that a particular agent binds substantially only to the specified protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given protein binding agent, such as an anti-PDGFRA protein monoclonal antibody, binds substantially only to the PDGFRA protein.

Shorter fragments of antibodies can also serve as specific binding agents. For instance, Fabs, Fvs, and single-chain Fvs (SCFvs) that bind to a specified protein would be specific binding agents. These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals.

Target sequence: "Target sequence" is a portion of ssDNA, dsDNA or RNA that, upon hybridization to a therapeutically effective oligonucleotide or oligonucleotide analog, results in the inhibition of expression. For example, hybridization of therapeutically effective oligonucleotide(s) to a PDGFRA target sequence results in inhibition of PDGFRA expression. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

One embodiment is an isolated variant PDGFRA polypeptide. Specific examples of such polypeptides comprise an amino acid sequence as set forth in SEQ ID NO: 4, 6, 8, 10, 12, 21, 23, or 25 or a fragment thereof comprising at least 10 contiguous amino acids including the variant site as set forth in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25. Also encompassed herein are the PDGFRA polypeptides defined by the consensus sequence shown in SEQ ID NO: 27, and fragments thereof, particularly fragments that overlap one or more of the noted variable regions.

Also provided are isolated nucleic acid molecules encoding such polypeptides, recombinant nucleic acid molecules comprising a promoter sequence operably linked to these nucleic acid molecules, and cells transformed with such recombinant nucleic acid molecules. Specific examples of nucleic acid molecules comprise a nucleotide sequence as set forth in SEQ ID NO: 3, 5, 7, 9, 11, 20, 22, or 24; or a fragment thereof including the variant nucleic sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2071 and 2072 of SEQ ID NO: 22, or 2916 to 2919 of SEQ ID NO: 24. Also encompassed herein are the PDGFRA nucleic acid molecules defined by the consensus sequence shown in SEQ ID NO: 26, and fragments thereof, particularly fragments that overlap one or more of the noted variable regions.

A further embodiment is a method of detecting a biological condition (e.g., neoplasia) associated with an activating PDGFRA mutation in a subject, comprising determining whether the subject has an activating mutation in PDGFRA, and wherein the activating mutation comprises the variant nucleic sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2071 and 2072 of SEQ ID NO: 22, or 2916 to 2919 of SEQ ID NO: 24, or in any one or more of the variable positions indicated in SEQ ID NO: 26. Specific examples of biological conditions contemplated herein are neoplasias that comprise a GIST.

In specific examples of these methods, the method involves reacting at least one PDGFRA molecule contained in a clinical sample from the subject with a reagent comprising a PDGFRA-specific binding agent to form a PDGFRA:agent complex. For instance, the PDGFRA molecule in some instances is a PDGFRA encoding nucleic acid or a PDGFRA protein, and the PDGFRA specific binding agent is a PDGFRA oligonucleotide or a PDGFRA protein specific binding agent. In some embodiments, the sample from the subject includes a neoplastic cell, or is prepared from a neoplastic cell or a sample comprising a neoplastic cell.

In some of the provided methods of detecting a biological condition, the PDGFRA molecule is a PDGFRA encoding nucleic acid sequence. Specific examples of such methods involve using an agent that comprises a labeled nucleotide probe. For instance, the nucleotide probe will in some instances have a sequence as shown in SEQ ID NO: 3, 5, 7, 9, 11, 20, 22, or 24, or a fragment of one of these sequences that is at least 15 nucleotides in length, and that includes the sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2071 and 2072 of SEQ ID NO: 22, or 2916 to 2919 of SEQ ID NO: 24.

Specific method embodiments involve in vitro amplifying a PDGFRA nucleic acid prior to detecting the activating PDGFRA mutation. By way of example, the PDGFRA nucleic acid is in some cases in vitro amplified using at least one oligonucleotide primer derived from a PDGFRA-protein encoding sequence, such as the specific oligonucleotide primers listed herein. Other specific oligonucleotide primers comprise at least 15 contiguous nucleotides from SEQ ID NO: 3, 5, 7, 9, 11, 20, 22, or 24. For instance, representative examples of such primers include a sequence as represented by at least 15 contiguous nucleotides shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2071 and 2072 of SEQ ID NO: 22, or 2916 to 2919 of SEQ ID NO: 24. Also included are primers that would be situated across a region including one or more of these variant positions, or any variant position indicated in SEQ ID NO: 26, so that the primers could be used to prime the amplification of a nucleic acid sequence encompassing one or more of the variants.

In other method of detection embodiments, the PDGFRA molecule is a PDGFRA protein, for instance a variant PDGFRA protein comprising a sequence as shown in SEQ ID NO: 4, 6, 8, 10, 12, 21, 23, or 25. In examples of such methods, the complexes are detected by western blot assay, or by ELISA.

Specific examples of PDGFRA-specific binding agents are PDGFRA-specific antibody or a functional fragment thereof, for instance monoclonal antibodies or fragments of monoclonal antibodies. Optionally, such monoclonal antibodies recognize an epitope of a variant PDGFRA (such as an epitope of a variant PDGFRA having an amino acid sequence as shown in SEQ ID NO: 4, 6, 8, 10, 12, 21, 23, or 25) and not (or to a lesser extent) an epitope of wildtype PDGFRA. In particular methods, the antibody is reactive to an epitope including the amino acid sequence shown in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25.

Also provided in the disclosure are kits for detecting an activating PDGFRA mutation in a subject using methods described herein. Examples of such kits are used with protein-detection methods, and include at least one PDGFRA protein specific binding agent. For instance, in specific kits the agent (e.g., an antibody) is capable of specifically binding to an epitope within a PDGFRA variant protein but not to an epitope of wildtype PDGFRA. Thus, some such agents are capable of specifically binding to an epitope within the amino acid sequence shown in SEQ ID NO: 4, 6, 8, 10, 12, 21, 23, or 25, or more particularly antigenic fragments of (a) that comprise the sequence shown in position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25. Examples of the protein-detection kits further include a means for detecting binding of the PDGFRA protein binding agent to a PDGFRA polypeptide.

A further embodiment is a kit for determining whether or not a subject (e.g., an animal, or more particularly a mammal) has a biological condition (e.g., neoplasia, such as that comprising a GIST) associated with an activating PDGFRA mutation by detecting a mutant PDGFRA sequence in the subject, which kit includes a container comprising at least one oligonucleotide specific for a PDGFRA mutation sequence; and instructions for using the kit, the instructions indicating steps for performing a method to detect the presence of mutant PDGFRA nucleic acid in the sample; and analyzing data generated by the method, wherein the instructions indicate that presence of the mutant nucleic acid in the sample indicates that the individual has or is predisposed to the biological condition. Optionally, such kits further include at least one container that comprises a detectable oligonucleotide. Specific examples of oligonucleotides (labeled or not) that may be included in these kits will be specific for a PDGFRA mutation sequence. For instance, particular example oligonucleotides comprise a sequence specific for a PDGFRA encoding sequence and containing the specific sequence shown in position(s) 2919 of SEQ ID NO: 3, 2917 and 2918 of SEQ ID NO: 5, 2927 and 2928 of SEQ ID NO: 7, 2075 to 2080 of SEQ ID NO: 9, 2089 to 2093 of SEQ ID NO: 11, 2076 of SEQ ID NO: 20, 2071 and 2072 of SEQ ID NO: 22, or 2916 to 2919 of SEQ ID NO: 24.

Another specific embodiment is a kit for determining whether or not a subject (e.g., an animal, or more particularly a mammal) has a biological condition (e.g., neoplasia, such as that comprising a GIST) associated with an activating PDGFRA mutation, the kit including a container comprising a PDGFRA mutant specific antibody; a container comprising a negative control sample; and instructions for using the kit, the instructions indicating steps for: performing a test assay to detect a quantity of PDGFRA mutant protein in a test sample of tissue and/or bodily fluid from the subject, performing a negative control assay to detect a quantity of PDGFRA mutant protein in the negative control sample; and comparing data generated by the test assay and negative control assay, wherein the instructions indicate that a quantity of PDGFRA mutant protein in the test sample more than the quantity of PDGFRA mutant protein in the negative control sample indicates that the subject has the biological condition. Specific examples of such kits further include one or more detectable antibodies that bind to the antibody specific for PDGFRA mutant protein (e.g., to be used in detection of the primary antibody).

Yet another embodiment is a method of screening for a compound useful in influencing (for instance, inhibiting or treating) PDGFRA-mediated neoplasia in a mammal, comprising determining if a test compound binds to or interacts with the polypeptide or fragment according to claim 1, and selecting a compound that so binds. In specific examples of this method, binding of the compound inhibits a PDGFRA protein biological activity (e.g., kinase activity). In certain examples, the test compound is applied to a test cell. Compounds identified or selected by such methods, whether or not formulated for use as therapeutic agents, are also contemplated.

Also provided are compositions that include at least one antigenic fragment of a provided PDGFRA variant protein, where the antigenic fragment includes the variant sequence as shown at position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25.

IV. Identification of Activating Mutations of PDGFRA

The inventors have determined that mutations in the platelet derived growth factor receptor alpha (PDGFRA) gene, particularly mutations that produce activated PDGFRA protein, are linked to neoplastic disease such as cancer, and thereby can be used to assess whether a subject suffers from or is susceptible to such a condition. The following examples illustrate this by showing particular examples of mutations that are associated with specific cancers in human subjects. Moreover, guidance is provided about finding other mutations associated with other specific cancers, both in PDGFRA and in other tyrosine kinases. Hence, in its broadest aspect, the disclosure is not limited to particular mutations, but is instead premised on the finding that activating PDGFRA mutations are associated with neoplastic disease.

The PDGFRA protein is a type III receptor tyrosine kinase with homology to KIT, FLT3, CSF1-R, and PDGFR beta (PDGFRB). Although PDGFRA activation has been hypothesized to be involved in certain cancers, most notably gliomas, evidence of genomic activation in human cancer has only recently been reported in two cases of myeloproliferative disease associated with translocation of the BCR and PDGFRA genes. We report herein several novel mutations of PDGFRA resulting in constitutive activation. These mutations were initially discovered in GISTs. Based on experience with KIT and FLT3, it is likely that mutations in other regions of the PDGFRA gene may result in constitutive activation of tyrosine kinase activity. At least in the case of KIT, the site of mutation varies between different diseases (e.g., mastocytosis vs. GIST). Finally, findings reported herein strongly suggest that similar mutations can activate related family members PDGFRB and CSF-1R, and that these mutant proteins are likely to be therapeutic targets in human cancer.

The discovery that mutations in the sequence of PDGFRA predisposes a subject to developing neoplasms also enables a variety of diagnostic, prognostic, and therapeutic methods that are further embodiments. The new appreciation of the role of activated PDGFRA in neoplastic diseases, such as cancers, enables detection of predisposition to or diagnosis of these conditions in a subject. This disclosure also enables early detection of subjects at high risk of these conditions, identification of subjects with particularly severe disease and/or tendency to progress, and in some embodiments detection of resistance or susceptibility of a subject to drug(s). Identification of the activating mutations described herein provides opportunities for prevention and/or early treatment as well as particular treatment selection.

V. Diagnostic and Therapeutic Applications

The presence of PDGFRA gene mutations in GIST strongly suggests that other human cancers will have similar mutations. When present in a cancer, mutant isoforms of PDGFRA represent a therapeutic target for tyrosine kinase inhibitors (TKIs), immunotherapy and other novel targeted approaches. Because PDGFRA gene mutations are not found in all tumors, the selection of patients for therapy targeting mutant PDGFRA isoforms would be optimized by pre-therapy analysis of cancer cells for the presence of PDGFRA gene mutations.

Such analysis can be based on PCR-based assays for these mutations, using for instance one or more of the following approaches: size fractionation by gel electrophoresis, direct sequencing, single-strand conformation polymorphism (SSCP), high pressure liquid chromatography (including partially denaturing HPLC), allele-specific hybridization, amplification refractory mutation screening, PDGFRA mutation screening by oligonucleotide microarray, restriction fragment polymorphism, MALDI-TOF mass spectrometry, or various related technologies (Abu-Duhier et al., *Br. J. Haematol.,* 113: 983-988, 2001; Kottaridis et al., *Blood,* 98: 1752-1759, 2001; Choy et al., *Ann. Hum. Gen.,* 63: 383-391, 1999; Grompe, *Nature Genetics,* 5: 111-117, 1993; Perlin & Szabady, *Hum. Mutat.,* 19: 361-373, 2002; Amos & Patnaik, *Hum. Mutat.,* 19: 324-333, 2002; Cotton, *Hum. Mutat.,* 19: 313-314, 2002; Stirewalt et al., *Blood,* 97: 3589-3595, 2001; Hung et al., *Blood Coagul. Fibrinolysis,* 13: 117-122, 2002; Larsen et al., *Pharmacogenomics,* 2: 387-399, 2001; Shchepinov et al., *Nucleic Acids Res.,* 29: 3864-3872, 2001).

In addition, mutant PDGFRA proteins may be detected through novel epitopes recognized by polyclonal and/or monoclonal antibodies used in ELISA, immunoblotting, flow cytometric, immunohistochemical and other mutant protein detection strategies (Wong et al., *Cancer Res.,* 46: 6029-6033, 1986; Luwor et al., *Cancer Res.,* 61: 5355-5361, 2001; Mishima et al., *Cancer Res.,* 61: 5349-5354, 2001; Ijaz et al., *J. Med. Virol.,* 63: 210-216, 2001). Additionally mutant PDGFRA proteins could be detected by mass spectrometry assays coupled to immunoaffinity assays, the use of matrix-assisted laser desorption/ionization time-of-flight (MALDI-TOF) mass mapping and liquid chromatography/quadrupole time-of-flight electro spray ionization tandem mass spectrometry (LC/Q-TOF-ESI-MS/MS) sequence tag of tumor derived proteins separated by two-dimensional polyacrylamide gel electrophoresis (2D-PAGE) (Kiernan et al., *Anal. Biochem.,* 301: 49-56, 2002; Poutanen et al., *Mass Spectrom.,* 15: 1685-1692, 2001). All of these approaches may be used to detect a sequence anomaly or variant of the PDGFRA protein, a relative increase in the phosphorylation of the protein, or an increase in the inherent kinase activity of the protein.

In addition to direct detection of mutant PDGFRA proteins, it is expected that various PDGFRA mutants will result in distinctive signal transduction profiles that could be detected by global gene expression profile or analysis of the activation of various signaling intermediates (e.g., STAT5) (Hofmann et al., *Lancet,* 359: 481-486, 2002).

Utility of this disclosure is highlighted by the correlative studies of response to imatinib mesylate and tumor KIT genotype in patients treated in a phase II trial of imatinib mesylate. In this trial, response to treatment was vastly superior in patients with an imatinib mesylate-sensitive KIT mutation compared with patients with no detectable KIT mutation (Heinrich et al., *Proc. of ASCO,* 21:2A, 2002).

It is believed that the nature and location of PDGFRA mutations affects the sensitivity of the resultant mutant protein to various TKIs. For example, imatinib mesylate is highly active against the kinase activity of wild-type KIT and against activating mutations involving the extracellular, juxtamembrane and TK1 domain (Tuveson et al., *Oncogene,* 20: 5054-5058, 2001; Heinrich et al., *Blood,* 96: 925-932, 2000). In contrast, imatinib mesylate has no clinically useful activity against mutations of the aspartic acid residue at position 816 (e.g., D816V, D816Y, D816F, or D816H) (Ma et al., *Blood,*

99: 1741-1744, 2002). The KIT D816V mutation is homologous to the D842V PDGFRA mutation described in this application. In addition, indolinone and tyrphostin compounds have little or no activity against KIT D816 mutations (or the equivalent D814 residue in murine KIT) but are potent inhibitors of the kinase activity of wild-type and juxtamembrane mutant KIT polypeptides (Ma et al., *Blood,* 99: 1741-1744, 2002; Ikeda et al., *Blood* 96, 99a-99a. Nov. 16, 2000; Ma et al., *J. Invest. Derma.,* 114: 392-394, 2000). However, imatinib mesylate has some activity against other KIT activation loop mutations that involve residues other than aspartic acid 816.

Based on homology to KIT, it is predicted that imatinib mesylate and indolinone compounds would have minimal activity against the D842V PDGFRA mutation but might have clinically useful activity against PDGFRA deletion and/or insertion mutations. In the absence of structural biology information concerning the structure of both wild type and mutant PDGFRA proteins and the site of binding of imatinib mesylate or other TKIs to these proteins, it will be necessary to empirically determine the activity of TKIs against the kinase activity of various mutant PDGFRA proteins. This could be accomplished by cloning cDNAs of the various PDGFRA mutant isoforms and the recombinant protein in prokaryotic or eukaryotic cells (Ma et al., *Blood,* 99: 1741-1744, 2002; Wood et al., *Cancer Res,* 60: 2178-2189, 2000). Protein expressed in such a manner could be used to determine biochemical activity of existing TKIs and could also be used in high throughput screening of chemical libraries to help identify and optimize pre-clinical development of new compounds against these or other PDGFRA mutant isoforms (Chroeder et al., *J. Med. Chem.,* 44: 1915-1926, 2001; Hamby et al., *J. Med. Chem.,* 40: 2296-2303, 1997; Druker et al., *Nature Medicine,* 2: 561-566, 1996). Prior determination of biochemical potency of specific compounds to different PDGFRA mutations would allow clinical testing of patient specimens for PDGFRA mutations and selection of the appropriate TKI based on the specific mutation and sensitivity associated with that patient's tumor.

Since the novel PDGFRA activating protein variants are only expressed by neoplastic cells, they have the potential to serve as tumor-specific antigens for cytotoxic T-lymphocytes (CTL). Indeed, it has been shown that the unique peptide sequence generated by the BCR-ABL fusion protein characteristic of chronic myelogenous leukemia can serve as the basis of an in vivo immune therapy that utilizes BCR-ABL peptide loaded dendritic cells to generate CTL with BCR-ABL specificity (He et al., *Cancer Immunol. Immunother.,* 50: 31-40, 2001).

VI. Prediction of Additional Types of PDGFRA Mutations

Based on experience with KIT and FLT3, it is likely that mutations in other regions of the PDGFRA gene may result in constitutive activation of tyrosine kinase activity. Other likely sites of PDGFRA activating mutations include the proximal extra-cellular, juxtamembrane, and TK1 domains of PDGFRA (Rubin et al., *Cancer Res,* 61: 8118-8121, 2001; Lux et al., *Am. J. Pathol.,* 156: 791-795, 2000; Abu-Duhier et al., *Br. J. Haematol.,* 111: 190-195, 2000). Indeed, it should be noted that there is one solitary case report of an astrocytoma with a large in-frame deletion of 81 amino acids involving portions of the fourth and fifth immunoglobulin domains of PDGFRA. The tumor in that report had genomic amplification of this PDGFRA mutant allele. The activity of PDGFRA kinase of this mutant isoform was not reported (Kumabe et al., *Oncogene,* 7: 627-633, 1992). Recently Baxter et al. reported a translocation having the structure t(4; 22) (q12; q11) in two cases of atypical chronic myeloid leukemia. Molecular cloning of the translocation revealed fusion of a portion of the BCR gene with part of exon 12 of PDGFRA (Baxter et al., *Hum. Mol. Genet.* 11:1391-1397, 2002). The fusion gene from these translocations is predicted to encode a constitutively activated tyrosine kinase, however no formal biochemical characterization of these proteins was performed (Baxter et al., 2002). Without meaning to be limited to a single interpretation, it is believed that fusion mechanisms of oncogenesis involving PDGFRA (e.g., the BCR-PDGFRA fusions reported by Baxter et al.) likely are a rare occurrence, while point mutation and deletion activations are expected to be more common, and that these two mechanisms are independent of each other.

In KIT, FLT3, and CSF-1R, kinase activation results from a variety of amino acid substitutions at the conserved aspartic acid in the activation loop (D816 KIT, D835 FLT3, and D802 of CSF-1R) (Morley et al., *Oncogene,* 18: 3076-3084, 1999; Moriyama et al., *J. Biol. Chem.,* 271: 3347-3350, 1996). In the case of KIT and FLT3, a number of these substitutions have been found in association with certain malignancies (Ma et al., *Blood,* 99: 1741-1744, 2002; Abu-Duhier et al., *Br. J Haematol.,* 113: 983-988, 2001; Yamamoto et al., *Blood,* 97: 2434-2439, 2001; Longley et al., *Leuk. Res.,* 25: 571-576, 2001; Ning et al., *Leuk. Lymphoma,* 41: 513-522, 2001). To date, no mutations of D802 of CSF-1R have been found in any human cancer. Thus far, we have found only a valine substitution at D842 of PDGFRA, but it can be predicted that a variety of amino acid substitutions at this position of PDGFRA would be activating. Assuming a single nucleotide change in codon 842, the most likely possible mutations of PDGFRA would be substitution of Asparagine, Tyrosine, Histidine, Valine, Alanine, Glycine, or Glutamic acid for the normal Aspartic acid. We predict that these additional PDGFRA mutations would also be oncogenic and will be found in one or more human neoplasms.

VII. Prediction of Similar Activating Mutations in PDGFRB

The amino acid sequence of the members of the Type III receptor tyrosine kinase family are highly conserved in the activation loop:

| | |
|---|---|
| DFGLAR**D**IMHDSN | Human PDGFRA |
| DFGLAR**D**IMRDSN | Human PDGFRB |
| DFGLAR**D**IKNDSN | Human KIT |
| DFGLAR**D**IMNDSN | Human CSF-1R |
| DFGLAR**D**IMSDSN | Human FLT3 |

As noted above, amino acid substitutions at the conserved aspartic acid (shown in bold) result in constitutive activation of the tyrosine kinase activity of KIT, PDGFRA or FLT3 in different human malignancies (Rosnet et al., *Blood,* 82: 1110-1119, 1993; Claesson-Welsh et al., *Proc. Natl. Acad. Sci. U.S.A,* 86: 4917-4921, 1989; Gronwald et al., *Proc. Natl. Acad. Sci. U.S.A,* 85: 3435-3439, 1988; Yarden et al., *Nature,* 323: 226-232, 1986). Amino acid substitution at the same aspartic acid of CSF-1R is also activating, but has not yet been found in association with human disease. Based on our findings, we predict that amino acid substitution at the same aspartic acid of PDGFRB would also be activating and that this mutation will be found in some human malignances.

VIII. Identification of Compounds that Inhibit PDGFRA Variants

This disclosure further relates in some embodiments to novel methods for screening test compounds for their ability to treat, detect, analyze, ameliorate, reverse, and/or prevent neoplasia, especially pre-cancerous lesions. In particular, the present disclosure provides methods for identifying test compounds that can be used to treat, ameliorate, reverse, and/or prevent neoplasia, including precancerous lesions. The compounds of interest can be tested by exposing the novel activating PDGFRA variants described herein to the compounds, and if a compound inhibits one of the PDGFRA variants, the compound is then further evaluated for its anti-neoplastic properties.

One aspect involves a screening method to identify a compound effective for treating, preventing, or ameliorating neoplasia, which method includes ascertaining the compound's inhibition of a provided novel activating PDGFRA variant or another activating PDGFRA variant. In some embodiments, the screening method further includes determining whether the compound inhibits the growth of tumor cells in a cell culture.

By screening compounds in this fashion, potentially beneficial and improved compounds for treating neoplasia can be identified more rapidly and with greater precision than possible in the past.

A. In General

Activating tyrosine kinase mutants, for instance the novel activating PDGFRA variants described herein, are useful to identify compounds that can be used to treat, ameliorate, or prevent neoplasms.

The screening or creation, identification and selection of appropriate high affinity inhibitors of activating PDGFRA mutants can be accomplished by a variety of methods. Broadly speaking these may include, but are not limited to, two general approaches. One approach is to use structural knowledge about the target enzyme to design a candidate molecule with which it will precisely interact. An example would be computer assisted molecular design. A second approach is to use combinatorial or other libraries of molecules, whereby a large library of molecules is screened for affinity with regard to the target enzyme.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth a test compound affects can be important to the discovery of a relevant target for pharmaceutical therapy. Screening assays based on this technology can be combined with other tests to determine which compounds have growth inhibiting and pro-apoptotic activity.

B. Inhibitor Screening

Some embodiments provided herein involve determining the ability of a given compound to inhibit activating PDGFRA mutants, for instance the ability to specifically inhibit constitutive kinase and/or transforming activities in the PDGFRA D842V, PDGFRA V561D, PDGFRA DIMH842-845, PDGFRA HDSN845-848P, insertion ER561-562, or SPDGHE566-571R, RD841-842KI, or RVIES560-564 deletion mutants described herein. Test compounds can be assessed for their probable ability to treat neoplastic lesions either directly, or indirectly by comparing their activities against compounds known to be useful for treating neoplasia. In particular, the compounds are tested for their ability to inhibit a neoplasia that is found to contain an activating PDGFRA mutation.

C. Determining Tyrosine Kinase Influencing Activity

Compounds can be screened for inhibitory or other effects on the activity of the novel activating PDGFRA mutants described herein using an expressed recombinant version of the enzyme, or a homolog or ortholog isolated from another species. Alternatively, cells expressing one of these tyrosine kinases can be treated with a test compound and the effect of the test compound on phosphorylation of a specific target can be determined, for instance using one of the techniques described herein. Additional detail regarding methods for determining tyrosine kinase phosphorylation influencing activity (e.g., inhibition) is provided herein.

D. Determining Whether a Compound Reduces the Number of Tumor Cells

In an alternate embodiment, provided screening methods involve further determining whether the compound reduces the growth of tumor cells, for instance tumor cells known to express an activated tyrosine kinase mutation such as a mutation in PDGFRA.

Various cell lines can be used, which may be selected based on the tissue to be tested. For example, these cell lines include: SW-480—colonic adenocarcinoma; HT-29—colonic adenocarcinoma, A-427—lung adenocarcinoma carcinoma; MCF-7—breast adenocarcinoma; and UACC-375—melanoma line; and DU145—prostate carcinoma. Cell lines can also be used that are known to express activated, mutant, tyrosine kinase proteins, for example: GIST882—gastrointestinal stromal tumor cell line expressing KIT tyrosine kinase point mutant; SKBR3—breast carcinoma cell line expressing ERBB2 amplification mutant; and K562—leukemia cell line expressing BCR-ABL tyrosine kinase fusion mutant. Cytotoxicity data obtained using these cell lines are indicative of an inhibitory effect on neoplastic lesions. Certain cell lines are well characterized, and are used for instance by the United States National Cancer Institute (NCI) in their screening program for new anti-cancer drugs. Though a compound may be identified by its ability to inhibit a specific tyrosine kinase activating mutant, its activity likely will not be limited to inhibition of only that mutant protein, thus testing in different cell lines and samples is beneficial to determine the scope of its activity.

By way of example, a test compound's ability to inhibit tumor cell growth in vitro can be measured using the HT-29 human colon carcinoma cell line obtained from ATCC (Bethesda, Md.). HT-29 cells have previously been characterized as a relevant colon tumor cell culture model (Fogh & Trempe, In: *Human Tumor Cells in Vitro*, Fogh (ed.), Plenum Press, N.Y., pp. 115-159, 1975). HT-29 cells are maintained in RPMI media supplemented with 5% fetal bovine calf serum (Gemini Bioproducts, Inc., Carlsbad, Calif.) and 2 mM glutamine, and 1% antibiotic-antimycotic, in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of test compound. Each determination of cell number involved six replicates. After six days in culture, the cells are fixed by the addition of cold trichloroacetic acid (TCA) to a final concentration of 10% and protein levels are measured, for instance using the sulforhodamine B (SRB) colorimetric protein stain assay as previously described by Skehan et al. (*J. Natl. Cancer Inst.* 82: 1107-112, 1990). In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 30% at a dose of 100 μM or below is further indicative that the compound is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the compound to be considered further for potential use for treating, ameliorating, or preventing neoplastic lesions.

E. Determining Whether a Test Compound Induces Apoptosis

In other embodiments, screening methods provided herein further involve determining whether the test compound induces apoptosis in cultures of tumor cells.

Two distinct forms of cell death may be described by morphological and biochemical criteria: necrosis and apoptosis. Necrosis is accompanied by increased permeability of the plasma membrane, whereby the cells swell and the plasma membrane ruptures within minutes. Apoptosis is characterized by membrane blebbing, condensation of cytoplasm, and the activation of endogenous endonucleases.

Apoptosis occurs naturally during normal tissue turnover and during embryonic development of organs and limbs. Apoptosis also can be induced by various stimuli, including cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc.

Test compounds can be screened for induction of apoptosis using cultures of tumor cells maintained under conditions as described above. In some examples of such screening methods, treatment of cells with test compounds involves either pre- or post-confluent cultures and treatment for two to seven days at various concentrations of the test compounds. Apoptotic cells can be measured in both the attached and "floating" portions of the cultures. Both are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (e.g., Piazza et al., *Cancer Res.,* 55:3110-16, 1995). Particular features include collecting both floating and attached cells, identification of the optimal treatment times and dose range for observing apoptosis, and identification of optimal cell culture conditions.

Following treatment with a test compound, cultures can be assayed for apoptosis and necrosis, for instance by florescent microscopy following labeling with acridine orange and ethidium bromide. Many methods for measuring apoptotic cells are known to those of ordinary skill in the art; for instance, one method for measuring apoptotic cell number has been described by Duke & Cohen (*Curr. Prot. Immuno.*, Coligan et al., eds., 3.17.1-3.17.1, 1992).

For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with test compounds. Commercial photometric EIA for the quantitative in vitro determination of cytoplasmic histone-associated-DNA-fragments (mono- and oligo-nucleosomes) are available (e.g., Cell Death Detection ELISA, Boehringer Mannheim). The Boehringer Mannheim assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

By way of example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e., cytoplasmic fraction) are transferred into a streptavidin-coated MTP. Care is taken not to shake the lysed pellets (i.e., cell nuclei containing high molecular weight, un-fragmented DNA) in the MTP. Samples are then analyzed. Fold stimulation ($FS=OD_{max}/OD_{veh}$), an indicator of apoptotic response, is determined for each compound tested at a given concentration. $EC_{50}$ values may also be determined by evaluating a series of concentrations of the test compound.

Statistically significant increases of apoptosis (i.e., greater than 2 fold stimulation at a test compound concentration of 100 μM) are further indicative that the compound is useful for treating neoplastic lesions. Preferably, the $EC_{50}$ value for apoptotic activity should be less than 100 μM for the compound to be further considered for potential use for treating neoplastic lesions. $EC_{50}$ is understood herein to be the concentration that causes 50% induction of apoptosis relative to vehicle treatment.

F. Organ Culture Model Tests

Test compounds identified by the methods described herein can be tested for antineoplastic activity by their ability to inhibit the incidence of preneoplastic lesions in an organ culture system, such as a mammary gland organ culture system. The mouse mammary gland organ culture technique has been successfully used by other investigators to study the effects of known antineoplastic agents such as NSAIDs, retinoids, tamoxifen, selenium, and certain natural products, and is useful for validation of the screening methods provided herein.

By way of example, female BALB/c mice can be treated with a combination of estradiol and progesterone daily, in order to prime the glands to be responsive to hormones in vitro. The animals are sacrificed, and thoracic mammary glands are excised aseptically and incubated for ten days in growth media supplemented with insulin, prolactin, hydrocortisone, and aldosterone. DMBA (7,12-dimethylbenz(a) anthracene) is added to medium to induce the formation of premalignant lesions. Fully developed glands are then deprived of prolactin, hydrocortisone, and aldosterone, resulting in the regression of the glands but not the premalignant lesions.

The test compound is dissolved in, for instance, DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

The following examples are provided to illustrate certain particular features and/or embodiments. These examples should not be construed to limit the invention to the particular features or embodiments described.

EXAMPLES

The PDGFRA protein is a type III receptor tyrosine kinase with homology to KIT, FLT3, CSF1-R and PDGFR beta (PDGFRB). Although PDGFRA activation has been suspected to be involved in certain cancers, most notably gliomas, evidence of genomic activation in human cancer has not been previously reported. Provided herein are novel mutations of PDGFRA resulting in constitutive activation. These mutations were initially discovered in GISTs. It is expected that other human cancers will have identical or similar mutations. Based on experience with KIT and FLT3, it is likely that mutations in other regions of the PDGFRA gene may result in constitutive activation of tyrosine kinase activity. At least in the case of KIT, the site of mutation varies between different diseases (e.g., mastocytosis vs. GIST). Finally, these findings strongly suggest that similar mutations can activate related family members PDGFRB and CSF-1R, and that these mutant proteins are likely to be therapeutic targets in human cancer.

Example 1

Activating Mutations in PDGFRA in GISTs

Methods

Three to five $mm^3$ pieces of frozen gastrointestinal stromal tumors were homogenized by 5 to 10 strokes of a Tissue Tearor™ homogenizer in ice-cold lysis buffer (1% Nonidet P-40, 50 mmol/L Tris, pH 8.0, 100 mmol/L sodium fluoride, 30 mmol/L sodium pyrophosphate, 2 mmol/L sodium molybdate, 5 mmol/L ethylenediaminetetracetic acid, 2 mmol/L sodium vanadate, 10 μg/ml aprotinin, 10 μg/ml leupeptin, and 100 μg/ml phenylmethylsulfonyl fluoride) and rocked overnight at 4° C. Residual cell debris was removed by centrifugation (14,000 g) for 20 minutes at 4° C., and the supernatant protein concentrations were determined using the BioRad™ MMT assay. Five hundred microliters (μl) of protein cell lysates (2 mg/ml) were pre-cleared with 20 μl of normal rabbit serum (Zymed Laboratories) and 20 μl of protein A sepharose 4B (Zymed Laboratories) for one hour at 4° C., followed by sequential additions of 20 μl of panRTK antibodies and 20 μl of protein A sepharose 4B with end-to-end rotation for two hours after each addition.

Antibodies used for immunoprecipitation were to KIT (Santa Cruz sc-168), PDGFRA (Santa Cruz sc-338), and panRTK. The panRTK antibodies were raised against combinations of epitopes, each epitope representing one variation of the conserved RTK catalytic domain sequence (#1 YVHRDLAARNIL (SEQ ID NO: 13); #2 CIHRDLAARNVL (SEQ ID NO: 14); #3 FVHRDLAARNCM (SEQ ID NO: 15); #4 LVHRDLAARNVL (SEQ ID NO: 16); #5 FIHRDIAARNCL (SEQ ID NO: 17); and #6 FVHRDLATRNCL (SEQ ID NO: 18)). Each rabbit was injected with three panRTK epitopes, either combination #1 (YVHRDLAARNIL, CIHRDLAARNVL and FVHRDLAARNCM) or combination #2 (LVHRDLAARNVL, FIHRDIAARNCL, and FVHRDLATRNCL). The panRTK antisera were then affinity purified using the same combinations of epitopes against which they had been raised. These panRTK antisera are expected to react with all human and murine RTKs, and with a subset of nonreceptor tyrosine kinase proteins (e.g., JAK family members, SRC family members, FAK/PTK2, ABL, and ARG) that contain the conserved epitope. The panRTK antisera immunoprecipitate individual RTK proteins with lower efficiency than specific kinase antibodies, inasmuch as they react with the entire class of RTK proteins, rather than targeting a specific kinase protein. Typically, 10-20 μg of panRTK antisera are required per immunoprecipitation, in order to purify the same amount of each RTK protein that would typically be immunoprecipitated with 2-4 μg of an optimized, specific antibody.

The immunoprecipitates were then washed three times in lysis buffer, 10 minutes each wash, and once in 10 mM Tris for one hour. After discharging the supernatant, 20 μl of sodium dodecyl sulfate (SDS)-polyacrylamide gel electrophoresis loading buffer was added to the immunoprecipitates, and heated for six minutes at 95° C. The supernatants were then collected and loaded into 4-12% sodium dodecyl sulfate-polyacrylamide gel gradient gels (NuPAGE™, Invitrogen, Carlsbad, Calif.), followed by electrophoretic transfer to nitrocellulose membranes (PROTRAN™, Schleicher & Schuell, Keene, N.H.). Ponceau S solution was used to confirm adequate protein transfer (Sigma Chemical Co., St Louis, Mo.).

The membranes were then blocked overnight using a 1% solution of bovine serum albumin (BSA; Sigma Chemical Co., St Louis, Mo.) in 0.01% phosphate-buffered saline (PBS)-Tris at pH 7.4. Protein tyrosine phosphorylation was detected by staining the membranes with anti-phosphotyrosine monoclonal mouse antibody (PY99; Santa Cruz Biotechnology, Santa Cruz, Calif.; 1:4000) in 1% BSA/0.01% PBS-Tris solution for 2 hours at room temperature (RT) and with anti-mouse immunoglobulin-horseradish peroxidase goat polyclonal antibody (Amersham Pharmacia Biotech, Piscataway, N.J.; 1:5000). The membranes were then stripped, blocked with 5% non-fat milk/0.01% PBS-Tris solution for one hour at room temperature, and restained with specific antibodies to PDGFRA (Santa Cruz) or KIT (Dako). All antibody reactions were detected by chemiluminescence (ECL; Pierce, Rockford, Ill.).

Tumor tissue was identified on unstained, 5 μm sections by comparison with H&E (Hematoxylin and Eosin) stained slides and was carefully collected using a clean, sterile scalpel blade into a microfuge tube. Dissection by this approach was straightforward and there was minimal contamination from adjacent normal tissue. Dissected tissue was deparaffinized by serial extraction with xylene and ethanol and allowed to air-dry. DNA was extracted using the Qiagen mini-kit (Qiagen, 51304) in accordance with the manufacturer's recommendations.

0.5 μg of purified tumor DNA was subjected to 45 cycles of in vitro amplification by polymerase chain reaction (PCR) using the High Fidelity PCR System (Roche #1732078). Primer pairs for each exon analyzed are listed in Table 1. Negative controls were included in every set of amplifications. In a minority of cases there was insufficient amplified DNA for screening by HPLC after single step amplification and therefore a second round of amplification was performed using nested primers (Table 1).

For the analysis of mutations in PDGFRA exon 18, the following primer pairs used were 1) PDGFRA 181634F (residues 181634 through 181653 of SEQ ID NO: 19) and PDGFRA 181874R (residues 181844 through 181874 of SEQ ID NO: 19) or 2) PDGFRA 181752F (SNP exclusion) (residues 181752 through 181772 of SEQ ID NO: 19) and PDGFRA 181874R. The locations of these primers are indicated in FIG. 7A, along with PDGFRA 181671F (residues 181671 through 181690 of SEQ ID NO: 19) and PDGFRA 181862R (residues 181842 through 181862 of SEQ ID NO: 19).

For the analysis of mutations in PDGFRA exon 12, the following primer pairs were used: 1) PDGFRA 170636F (residues 170636 through 170655 of SEQ ID NO: 19) and PDGFRA 170894R (residues 170876 through 170894 of SEQ ID NO: 19), and 2) PDGFRA 170658F (residues 170658 through 170677 of SEQ ID NO: 19) and PDGFRA 170866R (residues 170847 through 170866 of SEQ ID NO: 19).

Five to 20 μl aliquots of the final PCR reaction were screened for mutations on a Transgenomic WAVE HPLC system (D-HPLC; Transgenomic, Inc., Omaha, Nebr.) by running at non-denaturing (50° C.) or partially denaturing temperature (61° C.). D-HPLC-detected mutations were confirmed by two methods: 1) re-amplification of the exon and repeat D-HPLC analysis on a different day; 2) bi-directional sequence analysis on an ABI 377 sequencer using the BigDye terminator kit (Applied Biosciences, Inc.). D-HPLC-detected mutations were confirmed by two methods: 1) re-amplification of the exon and repeat D-HPLC analysis on a different day; 2) bi-directional sequence analysis on an ABI 377 sequencer using the BigDye terminator kit (Applied Biosciences, Inc.) (Corless et al., *Am. J. Pathol.* 160, 1567, 2002).

Figure 3:
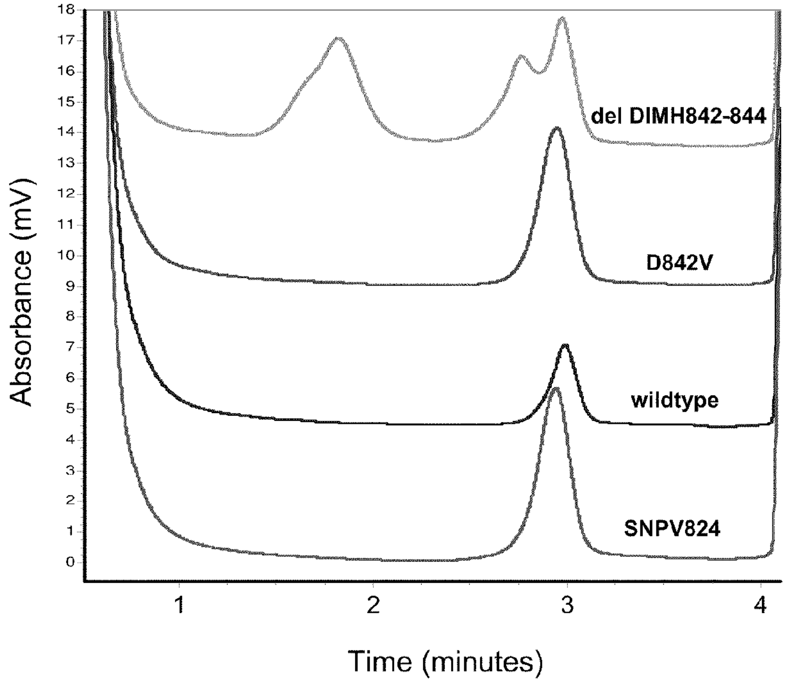
FIG. 3: Detection of PDGFRA activation loop deletion mutations by D-HPLC. DNA was isolated from GISTs and amplified using primer pair PDGFRA 181634F and PDGFRA 181874R as described herein. Amplicons were analyzed at 50° C. using a Transgenomics WAVE™ D-HPLC system. Sample 1 has the DIMH deletion described herein. The deletion mutant is readily detected due to the appearance of novel peaks representing species homozygous for the deletion and heteroduplexes of wild-type and deletion mutation.
Figure 4:
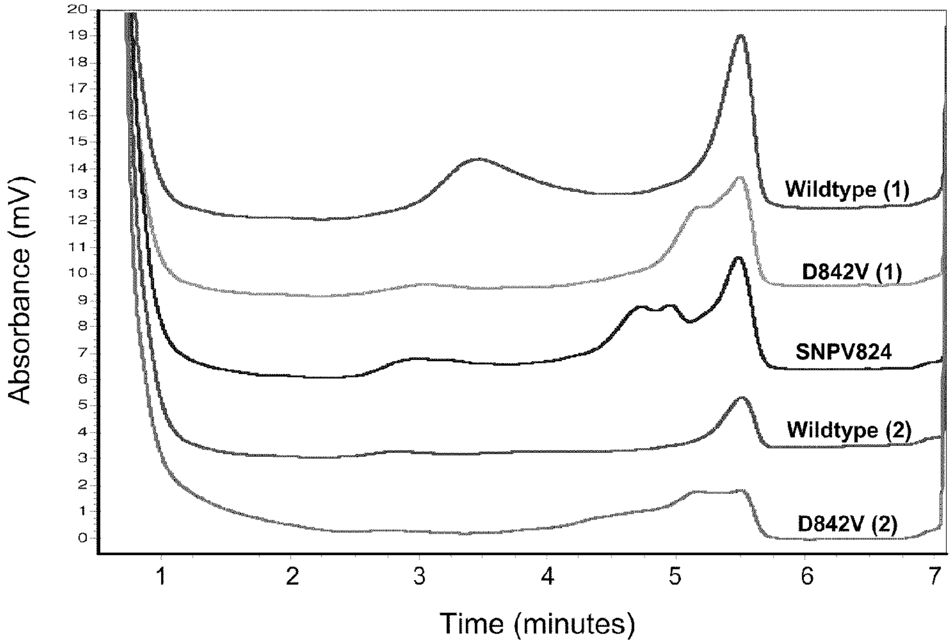
FIG. 4: Detection of PDGFRA activation loop V824V SNP and D842V point mutation by D-HPLC. Amplicons were prepared from GISTs using the PDGFRA 181634F and PDGFRA 181874R primer pair as described above and analyzed at 61° C. using a Transgenomics WAVE™ D-HPLC system. Under partially denaturing conditions, amplicons with the V824V SNP and the D842V point mutation (two examples) elute in a complex pattern. The V824V and D842V amplicons have unique elution profiles. Direct DNA sequencing was performed to confirm that the V824V and D842V amplicons contained the equivalent stretch of PDGFRA nucleotide sequence.
Figure 5:
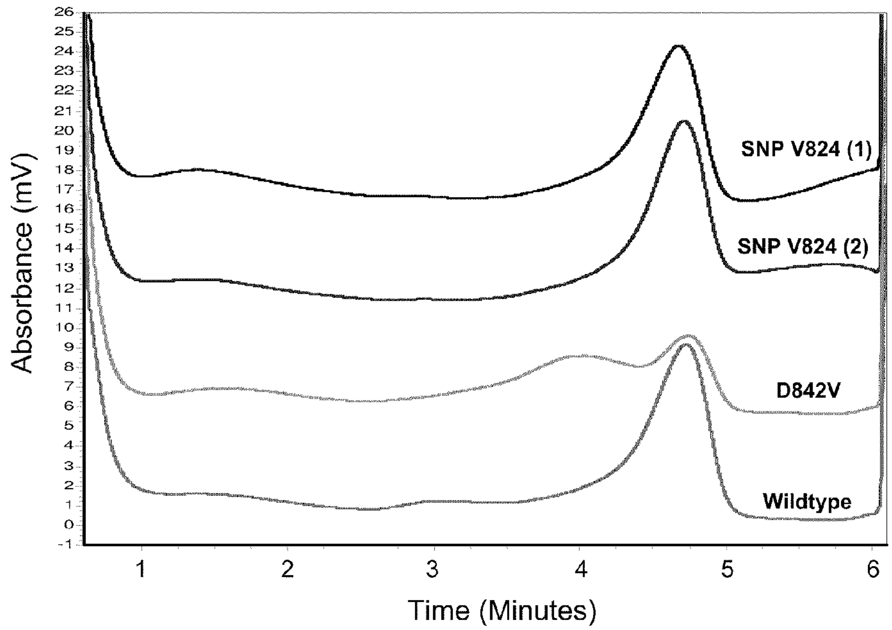
FIG. 5: Detection of D842V point mutation using a primer pair that excludes the V824V SNP. Amplicons were prepared from GISTs using the PDGFRA 181752F (SNP exclusion) and PDGFRA 181874R primer pair as described above and analyzed at 61° C. using a Transgenomics WAVE™ D-HPLC system. Under partially denaturing conditions, amplicons with the D842V point mutation elute in a complex pattern. Note that this amplicon does not contain the V824V SNP and therefore these amplicons have the same elution profile as for wild-type PDGFRA. Direct DNA sequencing was performed to confirm that the amplicons from GISTs with V824V (two examples) versus D842V contained the equivalent stretch of PDGFRA nucleotide sequence.
Figure 6:
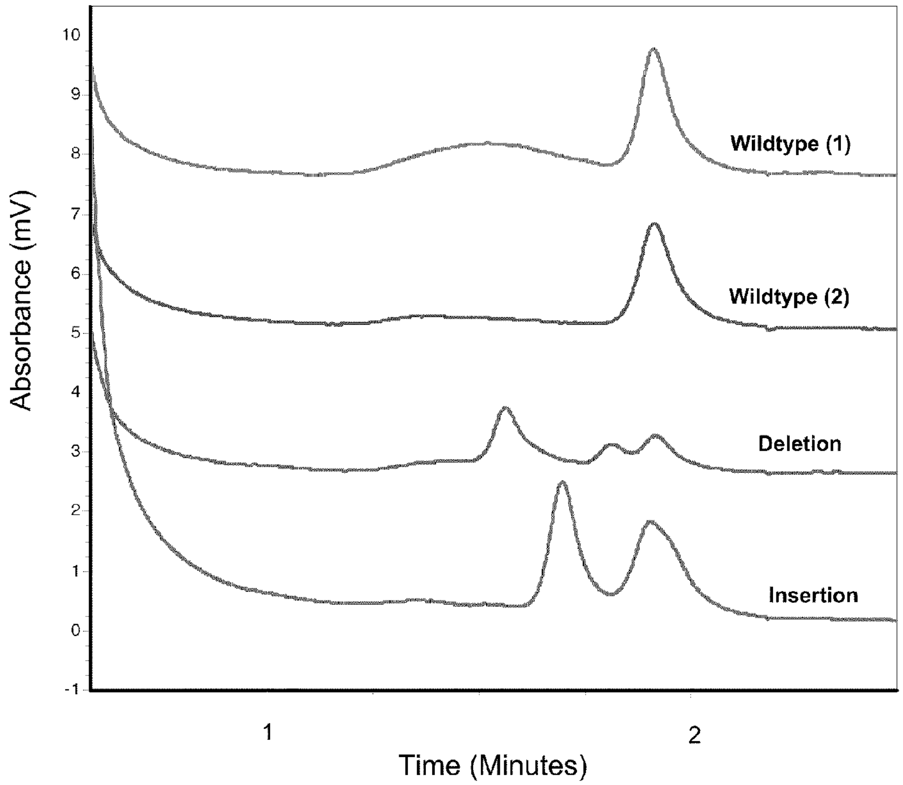
FIG. 6: Detection of PDGFRA Exon 12 Deletion and Insertion Variants. Amplicons were prepared from GISTs using the PDGFRA 170636F and PDGFRA 170894R primer pair as described above and analyzed at 50° C. using a Transgenomics WAVE™ D-HPLC system. The amplicons prepared from the two samples with wild-type PDGFRA exon 12 elute as a single peak. In contrast, amplicons from tumors with either a deletion mutation or an insertion are easily detected due to the appearance of novel peaks representing species homozygous for the deletion and heteroduplexes of wild-type and deletion mutation. In tumors homozygous for these mutations, only a single unique elution peak would be detected. These mutations would be identifiable based on the unique peak elution profile compared with wild type amplicons.

Using primer pair 1, it was possible to reliably detect the D842V point mutation as well as the deletion and insertion mutations (FIGS. 3 and 4). However, there is a fairly common single nucleotide polymorphism (SNP) in the PDGFRA gene that is detected using these primer pairs and D-HPLC analysis. This SNP is C2472T (V824V) in PDGFRA cDNA (using numbering system of GenBank Accession No. XM_011186). To exclude this SNP, the mutation detection assay was further optimized by using primer pair 2. The forward primer of this set begins immediately 3' of the SNP and thus the resultant amplicon from this primer set does not contain the SNP. Using this primer pair, the D842V activating mutation can be reliably detected and differentiated from the C2472T (V824V) SNP (FIG. 5).

To further verify the sequence of the PDGFRA exon 18 deletion mutations we cloned the amplification products into pCR®4-TOPO using the TOPO TA cloning kit (Invitrogen, version H) and the ligated plasmids were used to transform competent *E. coli* (OneShot TOP10, Invitrogen). Isolated plasmids were screened for the mutant exon insert by PCR and D-HPLC. Direct sequence analysis of cloned mutant DNA confirmed the presence of an in-frame exon 18 deletion in these cases.

Results

Activation of PDGFRA in GISTs

Using methods described above, RTK activation was assessed in three GISTs lacking apparent KIT oncoproteins. This was accomplished by immunoprecipitating with pan-RTK antibodies, and then immunoblotting with an antibody against phosphotyrosine (FIG. 1). Normally, KIT is heavy phosphorylated in GISTs and is one of the dominant tyrosine phosphorylated protein (FIG. 1).

By sequentially stripping and reprobing the membrane with additional antibodies, the predominant RTK phosphoprotein appeared to be PDGFRA. The possibility of a highly activated PDGFRA protein was then confirmed by immunoprecipitating PDGFRA, using a specific antibody to this protein. These studies revealed that the highly activated phosphoRTK comigrated with equally strongly phosphorylated PDGFRA (FIG. 1). Further, these studies showed that KIT was inactive (non-phosphorylated) in the GISTs with strongly phosphorylated PDGFRA. Therefore, the studies revealed that PDGFRA is highly activated in a subset of GISTs that lack KIT activation, and—furthermore—PDGFRA is the predominant activated RTK, and indeed one of the predominant tyrosine phosphorylated proteins (FIG. 1) in those GISTs.

Figure 2A:
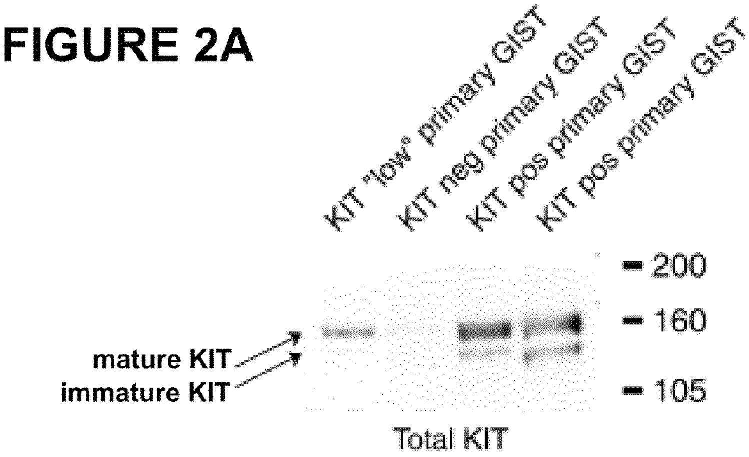
FIG. 2 (including FIGS. 2A, 2B, and 2C): Sequential staining of GIST immunoblot for KIT (A), phosphoPDGFRA Y754 (B), and total PDGFRA (C). A) The four GISTs analyzed here include two cases with a low (lane 1) or absent (lane 2) level of KIT expression and two cases with strong KIT expression (lanes 3 and 4). B) Strongly phosphorylated PDGFRA (doublet at 150/170 kD) is seen in the GISTs with low-to-absent KIT expression. C) Total PDGFRA is also expressed strongly in the two GISTs with low-to-absent KIT expression. The two GISTs with phosphoPDGFRA have D842V oncogenic mutations.
Figure 2B:
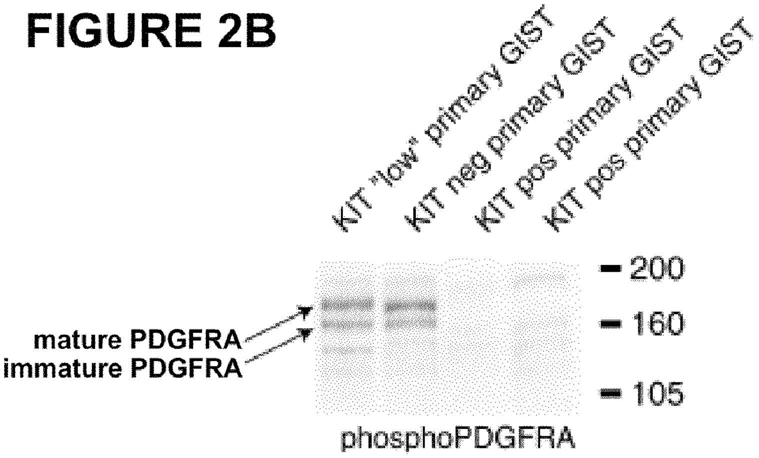
Figure 2C:
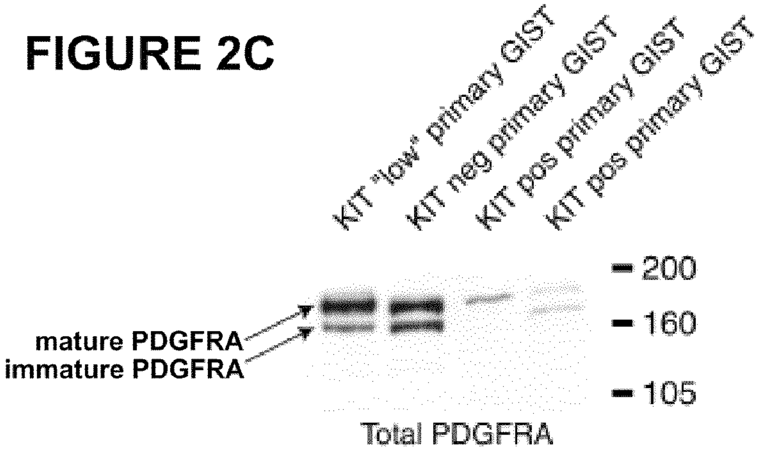

Additional studies indicated that KIT and PDGFRA oncoproteins are typically alternative, rather than synergistic, mechanisms of transformation in GISTs. Therefore, PDGFRA activation and high-level PDGFRA expression can be found in GISTs that have reduced levels of KIT expression (FIG. 2) and that lack KIT genomic oncogenic mutations.

Analysis of Genomic Mechanisms of PDGFRA activation in GISTs

The large amount of phosphorylated PDGFRA in these GISTs suggested the possibility of activating mutations in the PDGFRA gene. Clues to a possible location for such mutations came from comparisons with other related kinases. As mentioned above, mutation of KIT is common in GISTs (approximately 80-90% of cases); mutations also occur in seminoma (25% of cases), mastocytosis (95%+) and rarely in cases of acute myeloid leukemia (AML) (Heinrich et al., *J. Clin. Oncol.,* 20: 1692-1703, 2002; Rubin et al., *Cancer Res,* 61: 8118-8121, 2001; Lux et al., *Am. J. Pathol.,* 156: 791-795, 2000). KIT mutations in GIST are found most commonly in the juxtamembrane and extracellular domains, as well as the first portion of the tyrosine kinase domain, whereas mutations in mastocytosis and seminoma are found in the activation loop located in the second portion of the tyrosine kinase domain (Hirota et al., *J. Pathol.,* 193: 505-510, 2001; Lasota et al., *Am. J. Pathol.,* 157: 1091-1095, 2000; Lux et al., *Am. J. Pathol.,* 156: 791-795, 2000; Ma et al., *Blood,* 99: 1741-1744, 2002; Beghini et al., *Blood,* 95: 726-727, 2000; Tian et al., *Am. J. Pathol.,* 154: 1643-1647, 1999; Longley et al., *Nature Genetics,* 12: 312-314, 1996). Somatic mutation of FLT3 has also been associated with certain human malignancies. Mutation of FLT3 has been reported in approximately 20-40% of cases of AML and rarely in Acute Lymphoblastic Leukemia. In AML, mutations of FLT3 are most commonly found in the juxtamembrane domain and less commonly in the activation loop (Abu-Duhier et al., *Br. J Haematol.,* 113: 983-988, 2001; Kottaridis et al., *Blood,* 98: 1752-1759, 2001; Meshinchi et al., *Blood,* 97: 89-94, 2001; Yamamoto et al., *Blood,* 97: 2434-2439, 2001).

Based on the homology of PDGFRA to KIT and FLT3, we hypothesized that mutation of the PDGFRA activation loop in a subset of GISTs might result in activation of tyrosine kinase activity. Thus, we developed a polymerase chain reaction (PCR) based assay to test for mutations of the PDGFRA activation loop (exon 18) (see FIG. 7). Genomic DNA was purified from formalin fixed, paraffin embedded archival pathology specimens or fresh frozen tumor specimens that were obtained in accordance with the rules and regulations of both OHSU and the Portland VA Medical Center. Amplification of PDGFRA exon 18 was performed using primer sets described in the methods section below. Amplicons were analyzed using a Transgenomic WAVE HPLC instrument using both non-denaturing (50° C.) and partially denaturing temperatures (58° C.). Amplicons with abnormal HPLC elution profiles were directly sequenced.

Two different classes of PDGFRA activation loop mutations were identified in GISTs using this technique—point mutation and small in-frame deletions (FIG. 3). These amplicons have been directly sequenced and/or cloned into plasmids and the resultant clones sequenced. The most common mutation is a change of the conserved aspartic acid at position 842 of PDGFRA to valine (D842V). This aspartic acid is highly conserved in kinases related to PDGFRA. The homologous mutation D816V of KIT is observed in mastocytosis and seminoma, while the homologous D835V mutation of FLT3 is found in some cases of AML.

Two different in-frame deletions of PDGFRA exon 18 were identified in GISTs. The first is deletion of genomic nucleotides 53264-53275, which encode PDGFRA amino residues 842-845 (DIMH). In this mutation the conserved aspartic residue at position 842 is substituted by the aspartic acid at position 846 that is immediately 3' of the deletion. The second deletion found to date is a deletion with insertion of a single cytosine at the 3' end of the deletion—the result is deletion of residues 845-848 (HDSN) with generation of a novel proline residue that follows the normal methionine residue at position 844. Thus, these two deletions are partially overlapping. These deletions are novel; it is believed that they result in constitutive activation of the tyrosine kinase activity of PDGFRA. This is based on prior observations that in-frame deletions or insertion in the activation loop of the related FLT3 RTK are known to result in constitutive activation of tyrosine kinase activity (Abu-Duhier et al., *Br. J Haematol.,* 113: 983-988, 2001); and our observations that PDGFRA is strongly activated in protein lysates from GIST tumors that harbor these PDGFRA mutations, but not in GISTs expressing wild-type PDGFRA (see FIGS. 1 and 2).

We have also found one GIST with an acquired mutation of exon 12 of PDGFRA, specifically insertion of GAGAGG at nucleotide position 1681 of PDGFRA. This mutation results in insertion of novel amino acid residues ER between amino acids 560 and 561. Based on analogy with similar length mutations in FLT3 and KIT, this inframe insertion would be predicted to result in constitutive activation of PDGFRA kinase activity. We have also found a second example of an insertion/deletion mutation in exon 12 in a GIST: SPDGHE566-571R.

TABLE 1

| Genotype | DNA sequence (top line)<br>Translation (bottom line) | |
|---|---|---|
| PDGFRA Wild type | 2906* | GGCCTGGCCAGAGACATCATGCATGATTCGAACTATGTG |
| (Ac. No. XM_011186; | 838 | G L A R D I M H D S N Y V |
| SEQ ID NOs: 1 and 2) | | |
| D842V | 2906 | GGCCTGGCCAGAG**T**CATCATGCATGATTCGAACTATGTG |
| (SEQ ID NOs: 3 and 4) | 838 | G L A R **V** I M H D S N Y V |
| Deletion of DIMH842-845 | 2906 | GGCCTGGCCAGA------------GATTCGAACTATGTG |
| (SEQ ID NOs: 5 and 6) | 838 | G L A R - - - - D S N Y V |
| Deletion of HDSN845-848P | 2906 | GGCCTGGCCAGAGACATCATGC---------**C**CTATGTG |
| (SEQ ID NOs: 7 and 8) | 838 | G L A R D I M **P** Y V |
| PDGFRA Wild type | 2060 | GAAATTCGCTGGAGGGTCATTGAATCA |
| | 556 | E I R W R V I E S |
| PDGFRA Insertion ER561-562 | 2060 | GAAATTCGCTGGAGG**GAGAGG**GTCATTGAATCA |
| (SEQ ID NOs: 9 and 10) | 556 | E I R W R **E** **R** V I E S |
| PDGFRA Wild type | 2081 | GAATCAATCAGCCCGGATGGACATGAATATATT |
| | 563 | E S I S P D G H E Y I |
| PDGFRA Deletion SPDGHE566-571R | 2081 | GAATCAATC---------------**CGC**TATATT |
| (SEQ ID NOs: 11 and 12) | 563 | E S I - - - - - **R** Y I |

*Numbering as in SEQ ID NO: 1 and SEQ ID NO: 2.

TABLE 2

| Mutation | Cases (% total) |
|---|---|
| D842V | 10 (24.4%) |
| Exon 18 Deletion | 2 (4.9%) |
| Exon 12 Insertion/Deletion | 2 (4.9%) |
| No mutation | 27 (65.9%) |
| Total | 41 (100.0%) |

In our analysis of GISTs to date, we have found KIT mutation and PDGFRA mutation to be mutually exclusive. That is, PDGFRA mutations have only been found in GISTs without any detectable KIT mutation. Based on our studies to date, we believe that mutations of PDGFRA are found in approximately 34-35% of KIT wild-type GISTs or 3-6% of all GISTs.

Example 2

Other Activating PDGFRA Mutations

With the provision herein of the correlation between activating PDGFRA mutations and neoplastic disease, the isolation and identification of additional activating PDGFRA mutations is enabled. Any conventional method for the identification of genetic mutations in a population can be used to identify such additional mutations.

For instance, existing populations (e.g., human populations) are assessed for the presence of neoplastic or tumorous cells, and individuals within the population are genotyped as relates to a PDGFRA sequence. These PDGFRA sequences are then compared to a reference PDGFRA sequence, such as the alleles described herein, to determine the presence of one or more variant nucleotide positions. Once variant nucleotides are identified, statistical analysis of the population is used to determine whether these variants are correlated with neoplasm or tumorous growth or development.

By way of example, it is predicted that additional mutations will be identified at least in positions similar to those identified herein. SEQ ID NO: 26 shows a nucleic acid consensus sequence for the PDGFRA activating mutations discussed herein; the consensus polypeptide encoded by SEQ ID NO: 26 is shown in SEQ ID NO: 27. Explicitly contemplated herein are additional PDGFRA mutations and variant molecules that occur in the variable positions indicated in these consensus sequences, alone or in combination with one or more of the mutations described herein. Included are insertion and deletion mutations, such as examples provided herein, as well as point mutations.

Example 3

Clinical Uses of PDGFRA Variants

To perform a diagnostic test for the presence or absence of a mutation in a PDGFRA sequence of an individual, a suitable genomic DNA-containing sample from a subject is obtained and the DNA extracted using conventional techniques. For instance, a blood sample, a buccal swab, a hair follicle preparation, or a nasal aspirate is used as a source of cells to provide the DNA sample; similarly, a surgical specimen, biopsy, or other biological sample containing genomic DNA could be used. It is particularly contemplated that tumor biopsies or tumor DNA found in plasma or other blood products can serve as a source. The extracted DNA is then subjected to amplification, for example according to standard procedures. The allele of the single base-pair mutation is determined by conventional methods including manual and automated fluorescent DNA sequencing, primer extension methods (Nikiforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), Taq-Man™, oligonucleotide hybridization, and the like. Also, see the following U.S. patents for descriptions of methods or applications of polymorphism analysis to disease prediction and/or diagnosis: U.S. Pat. No. 4,666,828 (RFLP for Huntington's); U.S. Pat. No. 4,801,531 (prediction of atherosclerosis); U.S. Pat. No. 5,110,920 (HLA typing); U.S. Pat. No. 5,268,267 (prediction of small cell carcinoma); and U.S. Pat. No. 5,387,506 (prediction of dysautonomia).

Examples of activating tyrosine kinase mutations are the PDGFRA D842V and V561D point mutations, the ER561-562 in frame insertion, and the DIMH842-845, HDSN845-848P, RD841-842KI, RVIES560-564, and SPDGHE566-571R in-frame deletions. In addition to these particular mutations, other mutations can be detected that may be associated with variable predisposition to development of a neoplastic disease or likelihood of having a tumor, and used in combination with the disclosed PDGFRA mutations, to predict the probability that a subject will develop neoplasia, or have a tumor with drug responsive tyrosine kinase activity.

The activating mutations of the present disclosure can be utilized for the detection of, and differentiation of, individuals who are homozygous and heterozygous for activating and/or drug responsive variants. The value of identifying individuals who carry an activating allele of PDGFRA (i.e., individuals who are heterozygous or homozygous for an allele that contains the D842V or V561D point mutation, the ER561-562 in frame insertion, or one of the DIMH842-845, HDSN845-848P, RD841-842KI, RVIES560-564, or SPDGHE566-571R in-frame deletions, or any combination thereof, or another mutation in one or proximal to one of the variable regions indicated in SEQ ID NOs: 26 or 27) is that these individuals could then initiate customized therapies (such as specific drug therapies that inhibit the mutant, activated, PDGFRA), or undergo more aggressive treatment of the condition, and thereby beneficially alter its course.

Example 4

Mutation Gene Probes and Markers

Sequences surrounding and overlapping single base-pair mutations and deletions and insertions in the PDGFRA gene can be useful for a number of gene mapping, targeting, and detection procedures. For example, genetic probes can be readily prepared for hybridization and detection of the D842V or the V561D point mutation, the ER561-562 in frame insertion, or one of the DIMH842-845, HDSN845-848P, RD841-842KI, RVIES560-564, or SPDGHE566-571R in-frame deletion mutations. As will be appreciated, probe sequences may be greater than about 12 or more oligonucleotides in length and possess sufficient complementarity to distinguish between the variant sequence and the wildtype, for instance, between the Valine (at amino acid residue 842 in the D842V activating allele) and Aspartic acid (in the wild-type allele). Similarly, sequences surrounding and overlapping any of the specifically disclosed mutations (or other mutations found in accordance with the present teachings, including those encompassed in or proximal to the variable regions indicated in SEQ ID NOs: 26 or 27), or longer sequences encompassing for instance the entire length of exon 18 of PDGFRA, or portions thereof, can be utilized in allele specific hybridization procedures. A similar approach can be adopted to detect other PDGFRA mutations.

Sequences surrounding and overlapping a PDGFRA mutation, or any portion or subset thereof that allows one to identify the mutations, are highly useful. Thus, another embodiment provides a genetic marker predictive of the one or more of the D842V or the V561D point mutation, the ER561-562 in frame insertion, or the DIMH842-845, HDSN845-848P, RD841-842KI, RVIES560-564, or SPDGHE566-571R in-frame deletions of PDGFRA, comprising a partial sequence of the human genome including at least about 10 contiguous nucleotide residues such as those shown in Table 1 or Table 3, and sequences complementary therewith.

Example 5

Detecting Single Nucleotide Alterations

PDGFRA single nucleotide alterations, whether categorized as SNPs or new mutations (such as that giving rise to the D842V variant) can be detected by a variety of techniques. Clinically relevant PDGFRA single nucleotide alterations include those arising as somatic mutations—i.e., restricted to the neoplastic cells—as well as those that are present constitutionally in both normal and neoplastic cells in a given individual. The constitutional single nucleotide alterations can arise either from new germline mutations, or can be inherited from a parent who possesses a SNP or mutation in their own germline DNA. The techniques used in evaluating either somatic or germline single nucleotide alterations include allele-specific oligonucleotide hybridization (ASOH) (Stoneking et al., *Am. J. Hum. Genet.* 48:370-382, 1991) which involves hybridization of probes to the sequence, stringent washing, and signal detection. Other new methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*BioTechniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the mutations in DNA. Merely by way of example, see U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods.

Example 6

Detection of PDGFRA Nucleic Acid Level(s)

Individuals carrying activating mutations in the PDGFRA gene, or having amplifications or heterozygous or homozygous deletions of the PDGFRA gene, may be detected at the DNA or RNA level with the use of a variety of techniques. The detection of point mutations, or SNPs, was discussed above; in the following example, techniques are provided for detecting the level of PDGFRA nucleic acid molecules in a sample.

For such diagnostic procedures, a biological sample of the subject (an animal, such as a mouse or a human), which biological sample contains either DNA or RNA derived from the subject, is assayed for a mutated, amplified or deleted PDGFRA encoding sequence, such as a genomic amplification of the PDGFRA gene or an over- or under-abundance of a PDGFRA mRNA. Suitable biological samples include samples containing genomic DNA or mRNA obtained from subject body cells, such as those present in peripheral blood, urine, saliva, tissue biopsy, surgical specimen, amniocentesis samples and autopsy material. The detection in the biological sample of a mutant PDGFRA gene, a mutant PDGFRA RNA, or an amplified or homozygously or heterozygously deleted PDGFRA gene, may be performed by a number of methodologies.

Gene dosage (copy number) can be important in disease states, and can influence mRNA and thereby protein level; it is therefore advantageous to determine the number of copies of PDGFRA nucleic acids in samples of tissue. Probes generated from the encoding sequence of PDGFRA (PDGFRA probes or primers) can be used to investigate and measure genomic dosage of the PDGFRA gene.

Appropriate techniques for measuring gene dosage are known in the art; see for instance, U.S. Pat. No. 5,569,753 ("Cancer Detection Probes") and Pinkel et al. (*Nat. Genet.* 20:207-211, 1998) ("High Resolution Analysis of DNA Copy Number Variation using Comparative Genomic Hybridization to Microarrays").

Determination of gene copy number in cells of a patient-derived sample using other techniques is known in the art. For example, PDGFRA amplification in immortalized cell lines as well as uncultured cells taken from a subject can be carried out using bicolor FISH or chromogenic in situ hybridization (CISH) analysis. FISH or CISH evaluations of PDGFRA amplification can be performed in various cell and tissue preparations that include, but are not limited to, venipuncture, biopsy, fine needle aspiration, and cell scraping. Such clinical materials can be analyzed in various forms, which include, but are not limited to, cytogenetic preparations; touch preparations from fresh or frozen biopsies; disaggregated cells from fresh, frozen or paraffin-embedded materials; histological sections from frozen or paraffin-embedded materials; and cytological preparations including cytospins and cell smears (Xiao et al., *Am J Pathol*; Hsi et al. *Pathol.* 147:896-904; 1995; Davison et al., *Am. J. Pathol.* 153:1401-1409; 1998). By way of example, interphase FISH analysis of immortalized cell lines can be carried out as previously described (Barlund et al., *Genes Chromo. Cancer* 20:372-376, 1997). The hybridizations can be evaluated using a Zeiss fluorescence microscope. By way of example, approximately 20 non-overlapping nuclei with intact morphology based on DAPI counterstain are scored to determine the mean number of hybridization signals for each test and reference probe.

Likewise, FISH can be performed on tissue microarrays, as described in Kononen et al., *Nat. Med.* 4:844-847, 1998. Briefly, consecutive sections of the array are deparaffinized, dehydrated in ethanol, denatured at 74° C. for 5 minutes in 70% formamide/2×SSC, and hybridized with test and reference probes. The specimens containing tight clusters of signals or >3-fold increase in the number of test probe as compared to chromosome 17 centromere in at least 10% of the tumor cells may be considered as amplified. Microarrays using various tissues can be constructed as described in WO 99/44063 and WO 99/44062.

Overexpression of the PDGFRA gene can also be detected by measuring the cellular level of PDGFRA-specific mRNA. mRNA can be measured using techniques well known in the art, including for instance Northern analysis, RT-PCR and mRNA in situ hybridization.

Example 7

Expression of PDGFRA Polypeptides

The expression and purification of proteins, such as the PDGFRA protein, can be performed using standard laboratory techniques. After expression, purified PDGFRA protein may be used for functional analyses, antibody production, diagnostics, and patient therapy. Furthermore, the DNA sequence of the PDGFRA cDNA can be manipulated in studies to understand the expression of the gene and the function of its product. Mutant forms of the human PDGFRA gene may be isolated based upon information contained herein, and may be studied in order to detect alteration in expression patterns in terms of relative quantities, tissue specificity and functional properties of the encoded mutant PDGFRA protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to PDGFRA proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous PDGFRA cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci. USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, New York, 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell. Biol.*

1:486, 1981) or Epstein-Barr (Sugden et al., *Mol. Cell. Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell. Biol.* 7:2013, 1987), electroporation (Neumann et al., *EMBO J.* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Tyrosine kinase encoding sequences can also be delivered to target cells in vitro via non-infectious systems, for instance liposomes.

These eukaryotic expression systems can be used for studies of PDGFRA encoding nucleic acids and mutant forms of these molecules, the PDGFRA protein and mutant forms of this protein. Such uses include, for example, the identification of regulatory elements located in the 5' region of the PDGFRA gene on genomic clones that can be isolated from human genomic DNA libraries using the information contained in the present disclosure. The eukaryotic expression systems may also be used to study the function of the normal complete protein, specific portions of the protein, or of naturally occurring or artificially produced mutant proteins.

Using the above techniques, the expression vectors containing the PDGFRA gene sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the PDGFRA gene or cDNA sequences, for expression in a suitable host. The PDGFRA DNA is operatively linked in the vector to an expression control sequence in the recombinant DNA molecule so that the PDGFRA polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant PDGFRA DNA sequences, similar systems are employed to express and produce the mutant product. In addition, fragments of the PDGFRA protein can be expressed essentially as detailed above. Such fragments include individual PDGFRA protein domains or sub-domains, as well as shorter fragments such as peptides. PDGFRA protein fragments having therapeutic properties may be expressed in this manner also.

Example 8

Production of PDGFRA Protein Specific Binding Agents

Monoclonal or polyclonal antibodies may be produced to either the normal PDGFRA protein or mutant forms of this protein, for instance particular portions that contain a mutation and therefore may provide a distinguishing epitope. Optimally, antibodies raised against these proteins or peptides would specifically detect the protein or peptide with which the antibodies are generated. That is, an antibody generated to the PDGFRA protein or a fragment thereof would recognize and bind the PDGFRA protein and would not substantially recognize or bind to other proteins found in human cells. In some embodiments, an antibody is specific for (or measurably preferentially binds to) an epitope in a variant protein versus the wildtype protein, or vice versa, as discussed more fully herein.

The determination that an antibody specifically detects the PDGFRA protein is made by any one of a number of standard immunoassay methods; for instance, the western blotting technique (Sambrook et al., In *Molecular Cloning: A Laboratory Manual*, CSHL, New York, 1989). To determine that a given antibody preparation (such as one produced in a mouse) specifically detects the PDGFRA protein by western blotting, total cellular protein is extracted from human cells (for example, lymphocytes) and electrophoresed on a sodium dodecyl sulfate-polyacrylamide gel. The proteins are then transferred to a membrane (for example, nitrocellulose) by western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the PDGFRA protein will, by this technique, be shown to bind to the PDGFRA protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PDGFRA protein binding.

Substantially pure PDGFRA protein or protein fragment (peptide) suitable for use as an immunogen may be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the PDGFRA protein identified and isolated as described can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein (Example 7), which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against the PDGFRA protein or peptides is to use one or more synthetic peptides synthesized on a commercially available peptide synthesizer based upon the predicted amino acid sequence of the PDGFRA protein or peptide. Polyclonal antibodies can be generated by injecting these peptides into, for instance, rabbits or mice.

D. Antibodies Raised by Injection of PDGFRA Encoding Sequence

Antibodies may be raised against PDGFRA proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the PDGFRA encoding sequence under the transcriptional control of either the human β-actin promoter or the cytomegalovirus (CMV) promoter.

Antibody preparations prepared according to these protocols are useful in quantitative immunoassays which determine concentrations of antigen-bearing substances in biological samples; they are also used semi-quantitatively or qualitatively to identify the presence of antigen in a biological sample; or for immunolocalization of the PDGFRA protein.

In addition, antibodies to PDGFRA are commercially available. See, for instance, rabbit anti-PDGFRA, catalog no. sc-338, from Santa Cruz Biotechnology Inc. (Santa Cruz, Calif.) and rabbit anti-PDGFR, catalog no. 6495, from Upstate Biotechnology (Waltham, Mass.).

For administration to human patients, antibodies, e.g., PDGFRA-specific monoclonal antibodies, can be humanized by methods known in the art. Antibodies with a desired binding specificity can be commercially humanized (Scotgene, Scotland, UK; Oxford Molecular, Palo Alto, Calif.).

E. Antibodies Specific for Mutant PDGFRA

With the provision of several activating variant PDGFRA proteins, the production of antibodies that specifically recognize these proteins (and peptides derived therefrom) is enabled. In particular, production of antibodies (and fragments and engineered versions thereof) that recognize at least one PDGFRA variant with a higher affinity than they recognize wild type PDGFRA is beneficial, as the resultant antibodies can be used in diagnosis and treatment, as well as in study and examination of the PDGFRA proteins themselves.

In particular embodiments, it is beneficial to generate antibodies from a peptide taken from a mutation or variation-specific region of the PDGFRA protein. By way of example, such regions include a portion or all of exon 18 of PDGFRA, or a portion or all of exon 12. More particularly, it is beneficial to raise antibodies against peptides of four or more contiguous amino acids that overlap the mutations identified in SEQ ID NO: 4, 6, 8, or 25, and particularly which comprise at least four contiguous amino acids including the residue(s) shown in position(s) 842 of SEQ ID NO: 4, positions 841 and 842 of SEQ ID NO: 6, positions 846 and 847 of SEQ ID NO: 8, or positions 841 and 842 of SEQ ID NO: 25.

Similarly, it is beneficial to raise antibodies against peptides of 4 or more contiguous amino acids that overlap the mutations identified in SEQ ID NO: 10, 12, 21, or 23, and particularly which comprise at least four contiguous amino acids including the residue(s) shown in position(s) 561 and 562 of SEQ ID NO: 10 positions 565 and 566 of SEQ ID NO: 12, position 561 of SEQ ID NO: 21, or positions 559 and 560 of SEQ ID NO: 23.

Longer peptides also can be used, and in some instances will produce a stronger or more reliable immunogenic response. Thus, it is contemplated in some embodiments that more than four amino acids are used to elicit the immune response, for instance, at least 5, at least 6, at least 8, at least 10, at least 12, at least 15, at least 18, at least 20, at least 25, or more, such as 30, 40, 50, or even longer peptides. Also, it will be understood by those of ordinary skill that it is beneficial in some instances to include adjuvants and other immune response enhancers, including passenger peptides or proteins, when using peptides to induce an immune response for production of antibodies.

Embodiments are not limited to antibodies that recognize epitopes containing the actual mutation identified in each variant. Instead, it is contemplated that variant-specific antibodies also may each recognize an epitope located anywhere throughout the PDGFRA variant molecule, which epitopes are changed in conformation and/or availability because of the activating mutation. Antibodies directed to any of these variant-specific epitopes are also encompassed herein.

By way of example, the following references provide descriptions of methods for making antibodies specific to mutant proteins: Hills et al., (*Int. J. Cancer,* 63: 537-543, 1995); Reiter & Maihle (*Nucleic Acids Res.,* 24: 4050-4056, 1996); Okamoto et al. (*Br. J. Cancer,* 73: 1366-1372, 1996); Nakayashiki et al., (*Jpn. J. Cancer Res.,* 91: 1035-1043, 2000); Gannon et al. (*EMBO J.,* 9: 1595-1602, 1990); Wong et al. (*Cancer Res.,* 46: 6029-6033, 1986); and Carney et al. (*J. Cell Biochem.,* 32: 207-214, 1986). Similar methods can be employed to generate antibodies specific to specific PDGFRA variants.

Example 9

Protein-Based Diagnosis

An alternative method of diagnosing PDGFRA mutation, gene amplification, or deletion as well as abnormal PDGFRA expression, is to quantitate the level of PDGFRA protein, and/or to evaluate activation (phosphorylation) of PDGFRA in the cells of an individual. The oncogenic, activating mutations disclosed herein result in constitutive PDGFRA activation as manifested by PDGFRA tyrosine phosphorylation. Therefore, antibodies specific for phosphotyrosine-containing PDGFRA epitopes can be used to routinely detect such mutant, activated, PDGFRA proteins in any mammalian cell type. Such evaluations can be performed, for example, in lysates prepared from cells, in fresh or frozen cells, in cells that have been smeared or touched on glass slides and then either fixed and/or dried, or in cells that have been fixed, embedded (e.g., in paraffin), and then prepared as histological sections on glass slides. This diagnostic tool would also be useful for detecting reduced levels of the PDGFRA protein that result from, for example, mutations in the promoter regions of the PDGFRA gene or mutations within the coding region of the gene that produced truncated, non-functional or unstable polypeptides, as well as from deletions of a portion of or the entire PDGFRA gene. Alternatively, amplification of a PDGFRA-encoding sequence may be detected as an increase in the expression level of PDGFRA protein. Such an increase in protein expression may also be a result of an up-regulating mutation in the promoter region or other regulatory or coding sequence within the PDGFRA gene, or by virtue of a point mutation within the PDGFRA coding sequence, which protects the PDGFRA protein from degradation.

Localization and/or coordination of PDGFRA expression (temporally or spatially) can also be examined using known techniques, such as isolation and comparison of PDGFRA from subcellular fractions, including specific organelles, or from specific cell or tissue types, or at specific time points after an experimental manipulation. Demonstration of reduced or increased PDGFRA protein levels, in comparison to such expression in a control cell (e.g., normal, as in taken from a subject not suffering from a neoplastic disease, such as cancer), would be an alternative or supplemental approach to the direct determination of PDGFRA gene deletion, amplification or mutation status by the methods outlined above and equivalents.

The availability of antibodies specific to the PDGFRA protein will facilitate the detection and quantitation of cellular PDGFRA by one of a number of immunoassay methods which are well known in the art and are presented in Harlow and Lane (*Antibodies, A Laboratory Manual*, CSHL, New York, 1988). Methods of constructing such antibodies are discussed above, in Example 8.

Any standard immunoassay format (e.g., ELISA, western blot, or RIA assay) can be used to measure PDGFRA polypeptide or protein levels, and to compare these with PDGFRA expression levels in control, reference, cell populations. Altered PDGFRA polypeptide expression may be indicative of an abnormal biological condition related to unregulated cell growth or proliferation, in particular a neoplasm, and/or a predilection to development of neoplastic disease. Immunohistochemical techniques may also be utilized for PDGFRA polypeptide or protein detection. For example, a tissue sample may be obtained from a subject, and a section stained for the presence of PDGFRA using a PDGFRA specific binding agent (e.g., anti-PDGFRA antibody) and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating a PDGFRA protein, a biological sample of the subject (which can be any animal, for instance a mouse or a human), which sample includes cellular proteins, is required. Such a biological sample may be obtained from body cells, such as those present in a tissue biopsy, surgical specimens, or autopsy material. In particular embodiments, biological samples may be obtained from peripheral blood sample, urine, saliva, amniocentesis samples, and so forth. Quantitation of PDGFRA protein can be achieved by immunoassay and compared to levels of the protein found in control cells (e.g., healthy, non-neoplastic cells of the same lineage or type as those under evaluation, or from a patient known not to have a neoplastic disease). Detection of tyrosine phosphorylated PDGFRA (using an antibody, i.e. a phospho-specific antibody, that detects such forms and does not detect non-phosphorylated PDGFRA) could be taken as an indication of a PDGFRA protein containing an activating mutation. Detection of phosphorylated PDGFRA could also indicate activation by other mechanisms, such as overexpression of PDGFRA by genomic amplification, or over-expression of PDGFRA ligands, e.g. PDGF-A. A significant (e.g., 10% or greater) reduction in the amount of PDGFRA protein in the cells of a subject compared to the amount of PDGFRA protein found in normal human cells could be taken as an indication that the subject may have deletions or mutations in the PDGFRA gene, whereas a significant (e.g., 10% or greater) increase would indicate that a duplication (amplification), or mutation that increases the stability of the PDGFRA protein or mRNA, may have occurred. Deletion, mutation, and/or amplification within the PDGFRA encoding sequence, and substantial under- or over-expression of PDGFRA protein, may be indicative of neoplastic disease (such as a tumor) and/or a predilection to develop neoplastic disease.

Example 10

Differentiation of Individuals Homozygous Versus Heterozygous for Activating Mutation(s)

Though it is believed that the activating variants described herein are the result of sporadic mutations rather than germline mutations, it may sometimes be beneficial to determine whether a subject is homozygous or heterozygous for the mutation.

By way of example, the oligonucleotide ligation assay (OLA), as described at Nickerson et al. (*Proc. Natl. Acad. Sci. USA* 87:8923-8927, 1990), allows the differentiation between individuals who are homozygous versus heterozygous for the D842V or the V561D point mutation, the ER561-562 in frame insertion, or the DIMH842-845, HDSN845-848P, RD841-842KI, RVIES560-564, or SPDGHE566-571R in-frame deletions. This feature allows one to rapidly and easily determine whether an individual is homozygous for at least one tyrosine kinase activating mutation, which condition is linked to a relatively high predisposition to developing neoplastic disease and/or an increased likelihood of having a tumor. Alternatively, OLA can be used to determine whether a subject is homozygous for either of these mutations.

As an example of the OLA assay, when carried out in microtiter plates, one well is used for the determination of the presence of the PDGFRA allele that contains a T at nucleotide position 2919 (numbering from SEQ ID NO: 1) and a second well is used for the determination of the presence of the PDGFRA allele that contains an A at that nucleotide position in the wildtype sequence. Thus, the results for an individual who is heterozygous for the mutation will show a signal in each of the A and T wells.

Example 11

Suppression of PDGFRA Expression

A reduction of PDGFRA protein expression in a transgenic cell may be obtained by introducing into cells an antisense construct based on the PDGFRA encoding sequence, including the human PDGFRA cDNA or genomic sequence (SEQ ID NOs: 1 and 19, respectively) or flanking regions thereof. For antisense suppression, a nucleotide sequence from a PDGFRA encoding sequence, e.g. all or a portion of the PDGFRA cDNA or gene, is arranged in reverse orientation relative to the promoter sequence in the transformation vector. Other aspects of the vector may be chosen as discussed above (Example 7).

The introduced sequence need not be the full-length human PDGFRA cDNA or gene or reverse complement thereof, and need not be exactly homologous to the equivalent sequence found in the cell type to be transformed. Generally, however, where the introduced sequence is of shorter length, a higher degree of homology to the native PDGFRA sequence will be needed for effective antisense suppression. The introduced antisense sequence in the vector may be at least 30 nucleotides in length, and improved antisense suppression will typically be observed as the length of the antisense sequence increases. The length of the antisense sequence in the vector advantageously may be greater than 100 nucleotides. For suppression of the PDGFRA gene itself, transcription of an antisense construct results in the production of RNA molecules that are the reverse complement of mRNA molecules transcribed from the endogenous PDGFRA gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous PDGFRA expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Expression of PDGFRA can also be reduced using small inhibitory RNAs, for instance using techniques similar to those described previously (see, e.g., Tuschl et al., *Genes Dev* 13, 3191-3197, 1999; Caplen et al., *Proc. Nat.l Acad. Sci. U.S.A.* 98, 9742-9747, 2001; and Elbashir et al., *Nature* 411, 494-498, 2001).

Finally, dominant negative mutant forms of PDGFRA may be used to block endogenous PDGFRA activity.

Example 12

PDGFRA Gene Therapy

Gene therapy approaches for combating activating mutations in PDGFRA, or reducing the risk of developing neoplastic disease such as cancer, in subjects are now made possible by the present disclosure.

Retroviruses have been considered a preferred vector for experiments in gene therapy, with a high efficiency of infection and stable integration and expression (Orkin et al., *Prog. Med. Genet.* 7:130-142, 1988). The full-length PDGFRA gene or cDNA can be cloned into a retroviral vector and driven from either its endogenous promoter or from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Recent developments in gene therapy techniques include the use of RNA-DNA hybrid oligonucleotides, as described by Cole-Strauss et al. (*Science* 273:1386-1389, 1996). This technique may allow for site-specific integration of cloned sequences, thereby permitting accurately targeted gene replacement.

In addition to delivery of a PDGFRA encoding sequence to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

To reduce the level of PDGFRA expression, gene therapy can be carried out using antisense or other suppressive constructs, the construction of which is discussed above (Example 11).

Example 13

Kits

Kits are provided which contain the necessary reagents for determining the presence or absence of mutation(s) in a PDGFRA-encoding sequence, such as probes or primers specific for the PDGFRA gene or a highly variable region of this gene, such as those regions indicated in SEQ ID NO: 26. Such kits can be used with the methods described herein to determine whether a subject is predisposed to neoplastic disease or tumor development, or whether the subject is expected to respond to one or another therapy, such as a particular tyrosine kinase inhibitory compound.

The provided kits may also include written instructions. The instructions can provide calibration curves or charts to compare with the determined (e.g., experimentally measured) values. Kits are also provided to determine elevated or depressed expression of mRNA (i.e., containing probes) or PDGFRA protein (i.e., containing antibodies or other PDGFRA-protein specific binding agents).

A. Kits for Amplification of PDGFRA Sequences

Oligonucleotide probes and primers, including those disclosed herein, can be supplied in the form of a kit for use in detection of a predisposition to neoplastic disease or tumor formation in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of a PDGFRA mutation can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (PCR Protocols, A Guide to Methods and Applications, Academic Press, Inc., San Diego, Calif., 1990), Sambrook et al. (In Molecular Cloning: A Laboratory Manual, Cold Spring Harbor, N.Y., 1989), and Ausubel et al. (In Current Protocols in Molecular Biology, Greene Publ. Assoc. and Wiley-Intersciences, 1992).

A kit may include more than two primers, in order to facilitate the in vitro amplification of PDGFRA sequences, for instance the PDGFRA gene or the 5' or 3' flanking region thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of PDGFRA mutation(s). In certain embodiments, these probes will be specific for a potential mutation that may be present in the target amplified sequences. The appropriate sequences for such a probe will be any sequence that includes one or more of the identified polymorphic sites, particularly nucleotide positions that overlap with the variants shown in Table 1 or Table 3, such that the sequence of the probe is complementary to a polymorphic site and the surrounding PDGFRA sequence.

It may also be advantageous to provide in the kit one or more control sequences for use in the amplification reactions. The design of appropriate positive control sequences is well known to one of ordinary skill in the appropriate art.

B. Kits for Detection of PDGFRA mRNA Expression

Kits similar to those disclosed above for the detection of PDGFRA mutations directly can be used to detect PDGFRA mRNA expression, such as over- or under-expression. Such kits include an appropriate amount of one or more oligonucleotide primers for use in, for instance, reverse transcription PCR reactions, similarly to those provided above with art-obvious modifications for use with RNA amplification.

In some embodiments, kits for detection of altered expression of PDGFRA mRNA may also include some or all of the reagents necessary to carry out RT-PCR in vitro amplification reactions, including, for instance, RNA sample preparation reagents (including e.g., an RNase inhibitor), appropriate buffers (e.g., polymerase buffer), salts (e.g., magnesium chloride), and deoxyribonucleotides (dNTPs). Written instructions may also be included.

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential mutation that may be present in the target amplified sequences, for instance specific for the D842V or V561D point mutation, the ER561-562 in frame insertion, or the DIMH842-845, HDSN845-848P, RD841-842KI, RVIES560-564, or SPDGHE566-571R in-frame deletion, or another mutation identified in PDGFRA.

It may also be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of PDGFRA mRNA. Such kits include, for instance, at least one PDGFRA-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential mutation that may be present in the target amplified sequence, such as the mutations disclosed herein.

C. Kits For Detection of PDGFRA Protein Expression

Kits for the detection of PDGFRA protein expression (such as over- or under-expression) are also encompassed. Such kits may include at least one target protein specific binding agent (e.g., a polyclonal or monoclonal antibody or antibody fragment that specifically recognizes the PDGFRA protein) and may include at least one control (such as a determined amount of PDGFRA protein, or a sample containing a determined amount of PDGFRA protein). The PDGFRA-protein specific binding agent and control may be contained in separate containers Likewise, kits for detection of activated PDGFRA may include at least one target protein binding agent (e.g., a polyclonal or monoclonal antibody or antibody fragment) that specifically recognizes the PDGFRA protein only when PDGFRA is expressed in activated manner. These kits include, but are not limited to, those in which the PDGFRA binding agent recognizes, and binds specifically with, epitopes in which one or more tyrosine residues are phosphorylated. Kits for detection of activated/phosphorylated PDGFRA might include at least two controls, including a positive control with tyrosine phosphorylated PDGFRA and a negative control lacking tyrosine phosphorylated PDGFRA. The positive controls may include lysates or paraffin sections from cells and tissues expressing mutant (activated) PDGFRA, or expressing native PDGFRA that has been activated by exposure of the cells to PDGF-A. The negative controls may include lysates or paraffin sections from cells and tissues expressing non-activated PDGFRA, e.g. tissues expressing non-mutant PDGFRA, and without exposure to PDGF-A.

The PDGFRA protein expression detection kits may also include a means for detecting PDGFRA:binding agent complexes, for instance the agent may be detectably labeled. If the detectable agent is not labeled, it may be detected by second antibodies or protein A for example, which may also be provided in some kits in one or more separate containers. Such techniques are well known.

Additional components in specific kits may include instructions for carrying out the assay. Instructions will allow the tester to determine whether PDGFRA expression levels are elevated. Reaction vessels and auxiliary reagents such as chromogens, buffers, enzymes, etc. may also be included in the kits.

D. Kits for Detection of Homozygous Versus Heterozygous Allelism

Also provided are kits that allow differentiation between individuals who are homozygous versus heterozygous for the D842V or V561D point mutations, the ER561-562 in frame insertion, or the DIMH842-845, HDSN845-848P, RD841-842KI, RVIES560-564, or SPDGHE566-571R in-frame deletion mutations of PDGFRA. Such kits provide the materials necessary to perform oligonucleotide ligation assays (OLA), as described at Nickerson et al. (*Proc. Natl. Acad. Sci. USA* 87:8923-8927, 1990). In specific embodiments, these kits contain one or more microtiter plate assays, designed to detect mutation(s) in the PDGFRA sequence of a subject, as described herein.

Additional components in some of these kits may include instructions for carrying out the assay. Instructions will allow the tester to determine whether a PDGFRA allele is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

Example 14

PDGFRA Knockout and Overexpression Transgenic Animals

Mutant organisms that under-express or over-express PDGFRA protein are useful for research. Such mutants allow insight into the physiological and/or pathological role of PDGFRA in a healthy and/or pathological organism. These mutants are "genetically engineered," meaning that information in the form of nucleotides has been transferred into the mutant's genome at a location, or in a combination, in which it would not normally exist. Nucleotides transferred in this way are said to be "non-native." For example, a non-PDGFRA promoter inserted upstream of a native PDGFRA encoding sequence would be non-native. An extra copy of a PDGFRA gene on a plasmid, transformed into a cell, would be non-native.

Mutants may be, for example, produced from mammals, such as mice, that either over-express PDGFRA or under-express PDGFRA, or that do not express PDGFRA at all. Over-expression mutants are made by increasing the number of PDGFRA genes in the organism, or by introducing a PDGFRA gene into the organism under the control of a constitutive or inducible or viral promoter such as the mouse mammary tumor virus (MMTV) promoter or the whey acidic protein (WAP) promoter or the metallothionein promoter. Mutants that under-express PDGFRA may be made by using an inducible or repressible promoter, or by deleting the PDGFRA gene, or by destroying or limiting the function of the PDGFRA gene, for instance by disrupting the gene by transposon insertion.

Antisense genes may be engineered into the organism, under a constitutive or inducible promoter, to decrease or prevent PDGFRA expression, as discussed above in Example 11.

A gene is "functionally deleted" when genetic engineering has been used to negate or reduce gene expression to negligible levels. When a mutant is referred to in this application as having the PDGFRA gene altered or functionally deleted, this refers to the PDGFRA gene and to any ortholog of this gene. When a mutant is referred to as having "more than the normal copy number" of a gene, this means that it has more than the usual number of genes found in the wild-type organism, e.g., in the diploid mouse or human.

A mutant mouse over-expressing PDGFRA may be made by constructing a plasmid having a PDGFRA encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

A mutant knockout animal (e.g., mouse) from which a PDGFRA gene is deleted can be made by removing all or some of the coding regions of the PDGFRA gene from embryonic stem cells. The methods of creating deletion mutations by using a targeting vector have been described (Thomas and Capecch, *Cell* 51:503-512, 1987).

Engineered PDGFRA knockout animals are known. See, for instance, Bostrom et al., *Dev. Dyn.,* 223:155-162, 2002; Fruttiger et al., *Development,* 126:457-467, 1999; Hellstrom et al., *J. Cell Biol.,* 153:543-553, 2001; Kaminski et al., *Blood,* 97:1990-1998, 2001; Karlsson et al., *Development,* 127:3457-3466, 2000. In addition, Patch mutant mice have a congenital chromosomal deletion that includes the PDGFR-$\alpha$ gene locus.

Example 15

Knock-in Organisms

In addition to knock-out systems, it is also beneficial to generate "knock-ins" that have lost expression of the wild-type protein but have gained expression of a different, usually mutant form of the same protein. By way of example, the activating mutant PDGFRA mutant proteins provided herein (e.g., as shown in SEQ ID NO: 4, 6, 8, 10, 12, 21, 23, 25, and 27) can be expressed in a knockout background, such as the Patch mutant mice, in order to provide model systems for studying the effects of these mutants. In particular embodiments, the resultant knock-in organisms provide systems for studying neoplasia.

Those of ordinary skill in the relevant art know methods of producing knock-in organisms. See, for instance, Rane et al. (*Mol. Cell. Biol.,* 22: 644-656, 2002); Sotillo et al. (*EMBO J.,* 20: 6637-6647, 2001); Luo et al. (*Oncogene,* 20: 320-328, 2001); Tomasson et al. (*Blood,* 93: 1707-1714, 1999); Voncken et al. (*Blood,* 86: 4603-4611, 1995); Andrae et al. (*Mech. Dev.,* 107: 181-185, 2001); Reinertsen et al. (*Gene Expr.,* 6: 301-314, 1997); Huang et al. (*Mol. Med.,* 5: 129-137, 1999); Reichert et al. (*Blood,* 97: 1399-1403, 2001); and Huettner et al. (*Nat. Genet.,* 24: 57-60, 2000), by way of example.

Example 16

Demonstration of PDGFRA Fusion Oncoproteins in Human Leukemias

The PDGFRA activating genomic mutations disclosed herein involve intragenic point mutations or deletions. These models of genomic PDGFRA mutation can readily be extended to different mechanisms of activation, e.g. as might result from chromosomal rearrangement in which the promoter and 5' end of an ectopic gene are fused to the 3' end—including the kinase domain—of PDGFRA. The principle of receptor tyrosine kinase activation, in which cytogenetic rearrangement produces a gene fusion, has been established for several kinase proteins, including FGFR1, FGFR3, NTRK3, and ALK, and have been reported recently for PDGFRA, in two patients with chronic myelogenous leukemia, in which PDGFRA was fused with the BCR gene. In the PDGFRA context, the applicants have identified four leukemias in which cytogenetic banding analyses reveal translocation breakpoints in the PDGFRA gene (chromosome band 4q12) region, and in which—based on cytogenetic correlates—the putative PDGFRA fusion gene is not expected to be BCR. Therefore, these leukemias may contain novel forms of PDGFRA fusion oncogenes. FISH analyses will be performed to determine whether any of these translocations targets PDGFRA, in which case the translocation partner gene will be identified by rapid amplification of cDNA ends, and the activating nature of the PDGFRA fusion will be determined by expressing the PDGFRA fusion gene in cell types such as Ba/F3 and CHO.

Example 17

Additional PDGFRA Activating Mutations in Gastrointestinal Stromal Tumors

Using methods essentially as described in Example 1, three additional PDGFRA activating mutations were identified in GISTs. These mutations are as shown in Table 3.

TABLE 3

| Genotype | | DNA sequence (top line)<br>Translation (bottom line) |
|---|---|---|
| PDGFRA Wild type | 2906* | GGCCTGGCCAGAGACATCATGCATGATTCGAACTATGTG |
| (SEQ ID NOs: 1 and 2) | 838 | G L A R D I M H D S N Y V |
| PDGFRA Substitution RD841-842KI | 2906 | GGCCTGGCC**AAAT**CATCATGCATGATTCGAACTATGTG |
| (SEQ ID NOs: 24 and 25) | 838 | G L A **K I** I M H D S N Y V |
| PDGFRA Wild type | 2060 | GAAATTCGCTGGAGGGTCATTGAATCAATCAGCCCGGAT |
| | 556 | E I R W R V I E S I S P D |
| V561D | 2060 | GAAATTCGCTGGAGGG**A**CATTGAATCAATCAGCCCGGAT |
| (SEQ ID NOs: 20 and 21) | 556 | E I R W R **D** I E S I S P D |
| PDGFRA Deletion RVIES560-564 | 2060 | GAAATTCGCTGG---------------ATCAGCCCGGAT |
| (SEQ ID NOs: 22 and 23) | 556 | E I R W - - - - - I S P D |

*Numbering as in SEQ ID NO: 1 and SEQ ID NO: 2.

After taking into account these three additional mutations, and additional instances of other identified mutations, the total number of each of the identified activating mutations was as shown in Table 4 and Table 5.

TABLE 4

Summary of PDGFRA mutations in KIT-WT GISTs.

| PDGFRA Region | Mutation | #GISTs |
|---|---|---|
| Activation Loop (exon 18) | D842V | 15 |
| | Del DIMH | 4 |
| | Del HDSN845-848P | 1 |
| | RD841-842KI | 1 |
| Juxtamembrane (exon 12) | V561D | 1 |
| | Ins ER561-562 | 1 |
| | Del RVIES560-564 | 1 |
| | Del SPDGHE566-571R | 1 |

TABLE 5

| Mutation | Cases (% total) |
|---|---|
| D842V | 15 (21.7%) |
| Exon 18 Deletion | 6 (8.7%) |
| Exon 12 Insertion/Deletion/PM | 4 (5.8%) |
| No mutation | 44 (63.7%) |
| Total | 69 (100.0%) |

The nucleic acid sequences of all of the identified activating PDGFRA mutations were aligned to produce the consensus sequence shown in SEQ ID NO: 26; the numbering in the consensus sequence aligns with that in the wildtype PDGFRA nucleic acid sequence (SEQ ID NO: 1). In the consensus sequence, the insertion identified in variant PDGFRA Insertion ER561-562 is indicated in a miscellaneous features field in the Sequence Listing. As emphasized and clearly illustrated in the consensus sequence, clusters of activating mutations in the PDGFRA nucleic acid sequence are found in positions 2072 to 2107 and 2916 to 2937, though it is noted that positions 2087, 2088, and 2089 appear to be invariable at least in the current studies.

Example 18

Additional Characterization of PDGFRA Activating Mutations in GISTs

Materials and Methods

Reagents

Antibodies used for immunoblotting were to phosphotyrosine (Santa Cruz PY99), actin (Sigma 1PKCA4), KIT (Dako A4502), PDGFRA (Santa Cruz sc-338), phosphoPDGFRA Y754 (Santa Cruz sc-12911), MAPK (Zymed 61-7400), phosphoMAPK Thr202/Thr204 (Cell Signaling 9106), AKT (Cell Signaling 9272), phosphoAKT S473 (Cell Signaling 9271S), STAT1 (Zymed ST1-3D4), phosphoSTAT1 Y7012 (Zymed ST1P-11A5), STAT3 (Zymed 13-7000), phosphoSTAT3 Y705 (Cell Signaling 9131), STAT5 (Zymed ST5-8F7), and phosphoSTAT5 Y694 (Zymed ST5P-4A9). Antibodies to phosphorylated kinases were validated as phosphospecific by evaluation of phosphatase treated cell lysates, and by evaluation of lysates from GIST cells treated with kinase inhibitors.

Cytogenetic Analyses

Tumor specimens were chopped with scalpel blades, disaggregated enzymatically, and seeded into T25 flasks. The monolayer cultures were expanded for two-to-five days prior to metaphase cell harvesting with Colcemid. Tissue culture, metaphase harvesting, metaphase slide making, and Giemsa-trypsin banding were performed as described previously (Fletcher et al., *N. Engl. J. Med.* 324, 436, 1991).

Cloning, Expression and Characterization of PDGFRA Mutant cDNAs

PDGFRA mutations were cloned by site-directed mutagenesis of the wild type PDGFRA cDNA. CHO cells were transiently transfected with expression vectors encoding for mutant or wild-type PDGFRA cDNA. Transfected cells were serum starved overnight and stimulated with vehicle or 100 ng/ml recombinant human PDGF-AA for 10 minutes before harvesting cells and preparing whole cell lysates for immunoblotting. The membranes were sequentially immunoblotted with antiserum against phosphorylated tyrosines (PY20 Transduction Laboratories) or total PDGFRA (Santa Cruz sc-338).

Results and Discussion

Figure 8:
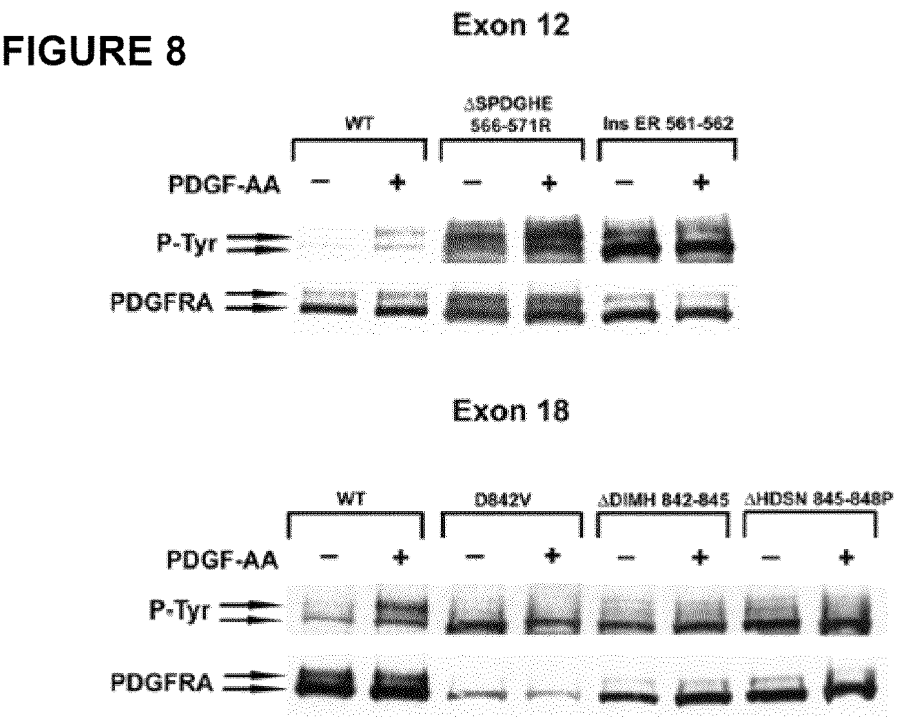
FIG. 8: DGFRA mutations in GISTs result in constitutive activation of PDGFRA kinase.

The biochemical consequences of somatic PDGFRA mutations were studied by transient expression of wild-type and mutant PDGFRA cDNA constructs in Chinese hamster ovary (CHO) cells. Baseline tyrosine phosphorylation was weak for non-mutant PDGFRA, and was substantially increased by ligand stimulation (FIG. 8). By contrast, baseline tyrosine phosphorylation was strong in all five of the tested PDGFRA mutants, and was not increased by ligand stimulation (FIG. 8).

Figure 9:
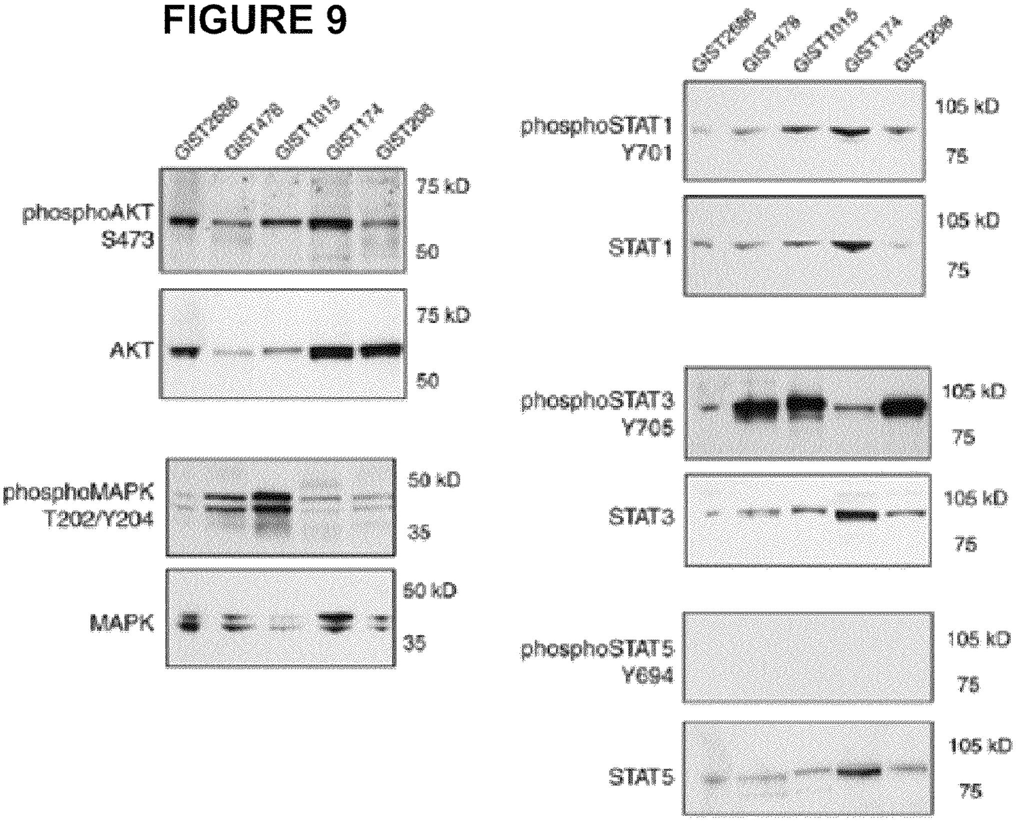
FIG. 9: Cell signaling profiles in PDGFRA-mutant (2686, 478, and 1015) and KIT-mutant GISTs (174 and 208).

Next the signal transduction pathways activated in PDGFRA-mutant versus KIT-mutant GISTs were compared. The PDGFRA-mutant GISTs showed uniform activation of signaling intermediates AKT, MAPK, STAT1, and STAT3, which are also activated in most KIT-mutant GISTs (FIG. 9). The PDGFRA-mutant GISTs lacked expression of phospho-STAT5, despite strong expression of total STAT5, which is also typical of KIT-mutant GISTs. The cytogenetic profiles of four PDGFRA-mutant GISTs and 52 KIT-mutant GISTs were also compared. KIT mutations are early events in GIST tumorigenesis, whereas cytogenetic aberrations occur later in disease progression (Heinrich et al., *Hum. Pathol.* 33, 484, 2002). Most of these GISTs—irrespective of PDGFRA or KIT mutation—featured noncomplex karyotypes with deletions of chromosome 1p, and with monosomies of chromosomes 14 and 22. Hence, these results suggest that the mechanisms of cytogenetic progression and oncoprotein-driven signal transduction are similar in GISTs expressing oncogenic forms of PDGFRA and KIT.

Activating mutations of KIT or PDGFRA appear to be mutually exclusive oncogenic events in GISTs, and these mutations have similar biological consequences. The data presented also highlight a crucial role for PDGFRA in the pathogenesis of a solid tumor. Notably, a translocation involving the BCR and PDGFRA genes has been described in BCR-ABL negative chronic myelogenous leukemia, and is predicted to result in dimerization and kinase activation of the fusion protein (Baxter et al., *Hum. Mol. Genet.* 11, 1391, 2002). PDGFRA is widely expressed in human tissues, so it will be important to determine whether PDGFRA mutations play a role in other human malignancies. Such tumors could be sensitive to Gleevec and other small molecule drugs that inhibit PDGFRA kinase activity (Buchdunger et al., *J. Pharmacol. Exp. Ther.* 295, 139, 2000; Lokker et al., *Cancer Res.* 62, 3729, 2002; Sun et al., *J. Med. Chem.* 43, 2655, 2000).

This disclosure provides tyrosine kinase protein and nucleic acid variants, particularly PDGFRA variants, which are activating forms of these molecules and are linked to neoplasms and/or the development or progression of cancer. The disclosure further provides methods of diagnosis and prognosis, using these molecules and fragments thereof, and kits for employing these methods and compositions. It will be apparent that the precise details of the compositions and methods described may be varied or modified without departing from the spirit of the described invention. We claim all such modifications and variations that fall within the scope and spirit of the claims below.

We claim:

1. An isolated constitutively active variant platelet derived growth factor receptor alpha (PDGFRA) polypeptide comprising:

the amino acid sequence set forth in SEQ ID NO: 27, wherein the sequence comprises a variant amino acid shown in one or more of positions 560 through 571 or 841 through 848 of SEQ ID NO: 27; or a fragment of said constitutively active PDGFRA comprising at least 10 contiguous amino acids including at least one variant amino acid site as set forth in one or more of positions 560 through 571 or 841 through 848 of SEQ ID NO: 27.

2. An isolated constitutively active variant platelet derived growth factor receptor alpha (PDGFRA) polypeptide comprising:

the amino acid sequence set forth in SEQ ID NO: 4, 6, 8, 10, 12, 21, 23, or 25; or a fragment of said constitutively active PDGFRA comprising at least 10 contiguous amino acids including one or more of the following amino acid variants: substitution D842V (shown in SEQ ID NO: 4); deletion of DIMH842-845 (shown in SEQ ID NO: 6); deletion of HDSN845-848P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and substitution of RD841-842KI (shown in SEQ ID NO: 25).

3. The isolated variant PDGFRA polypeptide of claim 2, which comprises one or more of the following amino acid variants: substitution D842V (shown in SEQ ID NO: 4); deletion of DIMH842-845 (shown in SEQ ID NO: 6); deletion of HDSN845-848P (shown in SEQ ID NO: 8); insertion ER561-562 (shown in SEQ ID NO: 10); deletion of SPDGHE566-571R (shown in SEQ ID NO: 12); substitution V561D (shown in SEQ ID NO: 21); deletion of RVIES560-564 (shown in SEQ ID NO: 23); and substitution of RD841-842KI (shown in SEQ ID NO: 25).

4. The isolated variant PDGFRA polypeptide of claim 2, comprising the amino acid sequence as set forth in SEQ ID NO: 4.

5. The isolated variant PDGFRA polypeptide of claim 2, comprising the amino acid sequence as set forth in SEQ ID NO: 6.

6. The isolated variant PDGFRA polypeptide of claim 2, comprising the amino acid sequence as set forth in SEQ ID NO: 8.

7. The isolated variant PDGFRA polypeptide of claim 2, comprising the amino acid sequence as set forth in SEQ ID NO: 10.

8. The isolated variant PDGFRA polypeptide of claim 2, comprising the amino acid sequence as set forth in SEQ ID NO: 12.

9. The isolated variant PDGFRA polypeptide of claim 2, comprising the amino acid sequence as set forth in SEQ ID NO: 21.

10. The isolated variant PDGFRA polypeptide of claim 2, comprising the amino acid sequence as set forth in SEQ ID NO: 23.

11. The isolated variant PDGFRA polypeptide of claim 2, comprising the amino acid sequence as set forth in SEQ ID NO: 25.

12. A kit for determining whether or not a subject has a neoplasia associated with an activating platelet derived growth factor receptor alpha (PDGFRA) mutation, the kit comprising:

an antibody specific for a variant PDGFRA polypeptide of claim 1, wherein said specific antibody binds to an epitope in said variant PDGFRA not found in the wild-type PDGFRA of SEQ ID NO: 2;

a negative control sample; and instructions for using the kit, the instructions indicating steps for:

performing a test assay to detect a quantity of PDGFRA activating mutant protein in a test sample of tissue and/or bodily fluid from the subject, performing a negative control assay to detect a quantity of PDGFRA activating mutant protein in the negative control sample; and comparing data generated by the test assay and negative control assay, wherein the instructions indicate that a quantity of PDGFRA activating mutant protein in the test sample more than the quantity of PDGFRA activating mutant protein in the negative control sample indicates that the subject has the neoplasia.

13. The kit of claim 12 further comprising a detectable antibody that binds to said specific antibody.

14. The kit of claim 12, wherein the neoplasia associated with an activating PDGFRA mutation comprises gastrointestinal stromal tumor (GIST).

15. A composition comprising at least one antigenic fragment of the isolated constitutively active variant PDGFRA polypeptide of claim 1, where the at least one antigenic fragment is at least seven amino acids long and includes the amino acid(s) as shown at position(s) 842 of SEQ ID NO: 4, 841 and 842 of SEQ ID NO: 6, 845 and 846 of SEQ ID NO: 8, 561 and 562 of SEQ ID NO: 10, 565 and 566 of SEQ ID NO: 12, 561 of SEQ ID NO: 21, 559 and 560 of SEQ ID NO: 23, or 841 and 842 of SEQ ID NO: 25.

* * * * *

SEQUENCE LISTING

```
<160> NUMBER OF SEQ ID NOS: 31

<210> SEQ ID NO 1
<211> LENGTH: 6633
<212> TYPE: DNA
```

```
<213> ORGANISM: Homo sapiens
<220> FEATURE:
<221> NAME/KEY: CDS
<222> LOCATION: (395)..(3664)

<400> SEQUENCE: 1

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgagggggg gcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                    Met Gly Thr Ser His Pro Ala
                                      1               5

ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
         10                  15                  20

cag ctt tca tta ccc tct atc ctt cca aat gaa aat gaa aag gtt gtg       511
Gln Leu Ser Leu Pro Ser Ile Leu Pro Asn Glu Asn Glu Lys Val Val
 25                  30                  35

cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
 40                  45                  50                  55

agc tgg cag tac ccc atg tct gaa gaa gag agc tcc gat gtg gaa atc       607
Ser Trp Gln Tyr Pro Met Ser Glu Glu Glu Ser Ser Asp Val Glu Ile
                 60                  65                  70

aga aat gaa gaa aac aac agc ggc ctt ttt gtg acg gtc ttg gaa gtg       655
Arg Asn Glu Glu Asn Asn Ser Gly Leu Phe Val Thr Val Leu Glu Val
         75                  80                  85

agc agt gcc tcg gcg gcc cac aca ggg ttg tac act tgc tat tac aac       703
Ser Ser Ala Ser Ala Ala His Thr Gly Leu Tyr Thr Cys Tyr Tyr Asn
         90                  95                 100

cac act cag aca gaa gag aat gag ctt gaa ggc agg cac att tac atc       751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat       799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc       847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg       895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act       943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag       991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat      1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att      1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg      1135
```

-continued

```
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat     1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat     1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt     1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat     1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc     1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa     1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac     1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt     1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct     1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc     1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg     1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag     2047
Val Ile Val Ile Ile Ser Leu Ile Val Leu Val Val Ile Trp Lys Gln
                540                 545                 550

aaa ccg agg tat gaa att cgc tgg agg gtc att gaa tca atc agc ccg     2095
```

```
Lys Pro Arg Tyr Glu Ile Arg Trp Arg Val Ile Glu Ser Ile Ser Pro
            555                 560                 565

gat gga cat gaa tat att tat gtg gac ccg atg cag ctg cct tat gac     2143
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg     2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta     2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc     2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata     2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc     2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat     2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc     2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac     2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac     2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc     2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga     2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac     2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act     2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag     2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac     2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg     2911
Val Leu Leu Ala Gln Gly Lys Ile Val Lys Ile Cys Asp Phe Gly Leu
    825                 830                 835

gcc aga gac atc atg cat gat tcg aac tat gtg tcg aaa ggc agt acc     2959
Ala Arg Asp Ile Met His Asp Ser Asn Tyr Val Ser Lys Gly Ser Thr
840                 845                 850                 855

ttt ctg ccc gtg aag tgg atg gct cct gag agc atc ttt gac aac ctc     3007
Phe Leu Pro Val Lys Trp Met Ala Pro Glu Ser Ile Phe Asp Asn Leu
                860                 865                 870

tac acc aca ctg agt gat gtc tgg tct tat ggc att ctg ctc tgg gag     3055
```

-continued

```
Tyr Thr Thr Leu Ser Asp Val Trp Ser Tyr Gly Ile Leu Leu Trp Glu
            875                 880                 885

atc ttt tcc ctt ggt ggc acc cct tac ccc ggc atg atg gtg gat tct     3103
Ile Phe Ser Leu Gly Gly Thr Pro Tyr Pro Gly Met Met Val Asp Ser
        890                 895                 900

act ttc tac aat aag atc aag agt ggg tac cgg atg gcc aag cct gac     3151
Thr Phe Tyr Asn Lys Ile Lys Ser Gly Tyr Arg Met Ala Lys Pro Asp
    905                 910                 915

cac gct acc agt gaa gtc tac gag atc atg gtg aaa tgc tgg aac agt     3199
His Ala Thr Ser Glu Val Tyr Glu Ile Met Val Lys Cys Trp Asn Ser
920                 925                 930                 935

gag ccg gag aag aga ccc tcc ttt tac cac ctg agt gag att gtg gag     3247
Glu Pro Glu Lys Arg Pro Ser Phe Tyr His Leu Ser Glu Ile Val Glu
                940                 945                 950

aat ctg ctg cct gga caa tat aaa aag agt tat gaa aaa att cac ctg     3295
Asn Leu Leu Pro Gly Gln Tyr Lys Lys Ser Tyr Glu Lys Ile His Leu
            955                 960                 965

gac ttc ctg aag agt gac cat cct gct gtg gca cgc atg cgt gtg gac     3343
Asp Phe Leu Lys Ser Asp His Pro Ala Val Ala Arg Met Arg Val Asp
        970                 975                 980

tca gac aat gca tac att ggt gtc acc tac aaa aac gag gaa gac aag     3391
Ser Asp Asn Ala Tyr Ile Gly Val Thr Tyr Lys Asn Glu Glu Asp Lys
    985                 990                 995

ctg  aag gac tgg gag ggt  ggt ctg gat gag cag  aga ctg agc gct     3436
Leu  Lys Asp Trp Glu Gly  Gly Leu Asp Glu Gln  Arg Leu Ser Ala
1000                 1005                 1010

gac  agt ggc tac atc att  cct ctg cct gac att  gac cct gtc cct     3481
Asp  Ser Gly Tyr Ile Ile  Pro Leu Pro Asp Ile  Asp Pro Val Pro
1015                 1020                 1025

gag  gag gag gac ctg ggc  aag agg aac aga cac  agc tcg cag acc     3526
Glu  Glu Glu Asp Leu Gly  Lys Arg Asn Arg His  Ser Ser Gln Thr
1030                 1035                 1040

tct  gaa gag agt gcc att  gag acg ggt tcc agc  agt tcc acc ttc     3571
Ser  Glu Glu Ser Ala Ile  Glu Thr Gly Ser Ser  Ser Ser Thr Phe
1045                 1050                 1055

atc  aag aga gag gac gag  acc att gaa gac atc  gac atg atg gac     3616
Ile  Lys Arg Glu Asp Glu  Thr Ile Glu Asp Ile  Asp Met Met Asp
1060                 1065                 1070

gac  atc ggc ata gac tct  tca gac ctg gtg gaa  gac agc ttc ctg     3661
Asp  Ile Gly Ile Asp Ser  Ser Asp Leu Val Glu  Asp Ser Phe Leu
1075                 1080                 1085

taa ctggcggatt cgaggggttc cttccacttc tggggccacc tctggatccc          3714

gttcagaaaa ccactttatt gcaatgcgga ggttgagagg aggacttggt tgatgtttaa   3774

agagaagttc ccagccaagg gcctcgggga gcgttctaaa tatgaatgaa tgggatattt   3834

tgaaatgaac tttgtcagtg ttgcctctcg caatgcctca gtagcatctc agtggtgtgt   3894

gaagtttgga gatagatgga taagggaata ataggccaca gaaggtgaac tttgtgcttc   3954

aaggacattg gtgagagtcc aacagacaca atttatactg cgacagaact tcagcattgt   4014

aattatgtaa ataactctaa ccaaggctgt gtttagattg tattaactat cttctttgga   4074

cttctgaaga gaccactcaa tccatccatg tacttccctc ttgaaacctg atgtcagctg   4134

ctgttgaact ttttaaagaa gtgcatgaaa aaccattttt gaaccttaaa aggtactggt   4194

actatagcat tttgctatct tttttagtgt taagagataa agaataataa ttaaccaacc   4254

ttgtttaata gatttgggtc atttagaagc ctgacaactc attttcatat tgtaatctat   4314

gtttataata ctactactgt tatcagtaat gctaaatgtg taataatgta acatgatttc   4374

cctccagaga aagcacaatt taaaacaatc cttactaagt aggtgatgag tttgacagtt   4434
```

-continued

```
tttgacattt atattaaata acatgtttct ctataaagta tggtaatagc tttagtgaat   4494
taaatttagt tgagcataga gaacaaagta aaagtagtgt tgtccaggaa gtcagaattt   4554
ttaactgtac tgaataggtt ccccaatcca tcgtattaaa aaacaattaa ctgccctctg   4614
aaataatggg attagaaaca aacaaaactc ttaagtccta aaagttctca atgtagaggc   4674
ataaacctgt gctgaacata acttctcatg tatattaccc aatggaaaat ataatgatca   4734
gcaaaaagac tggatttgca gaagtttttt ttttttttct tcatgcctga tgaaagcttt   4794
ggcaacccca atatatgtat tttttgaatc tatgaacctg aaaagggtca gaaggatgcc   4854
cagacatcag cctccttctt tcacccctta ccccaaagag aaagagtttg aaactcgaga   4914
ccataaagat attctttagt ggaggctgga tgtgcattag cctggatcct cagttctcaa   4974
atgtgtgtgg cagccaggat gactagatcc tgggtttcca tccttgagat tctgaagtat   5034
gaagtctgag ggaaaccaga gtctgtattt ttctaaactc cctggctgtt ctgatcggcc   5094
agttttcgga aacactgact taggtttcag gaagttgcca tgggaaacaa ataatttgaa   5154
ctttggaaca gggttggaat tcaaccacgc aggaagccta ctatttaaat ccttggcttc   5214
aggttagtga catttaatgc catctagcta gcaattgcga ccttaattta actttccagt   5274
cttagctgag gctgagaaag ctaaagtttg gttttgacag gttttccaaa agtaaagatg   5334
ctacttccca ctgtatgggg gagattgaac tttccccgtc tcccgtcttc tgcctcccac   5394
tccatacccc gccaaggaaa ggcatgtaca aaaattatgc aattcagtgt tccaagtctc   5454
tgtgtaacca gctcagtgtt ttggtggaaa aaacatttta agttttactg ataatttgag   5514
gttagatggg aggatgaatt gtcacatcta tccacactgt caaacaggtt ggtgtgggtt   5574
cattggcatt ctttgcaata ctgcttaatt gctgatacca tatgaatgaa acatgggctg   5634
tgattactgc aatcactgtg ctatcggcag atgatgcttt ggaagatgca gaagcaataa   5694
taaagtactt gactacctac tggtgtaatc tcaatgcaag ccccaacttt cttatccaac   5754
tttttcatag taagtgcgaa gactgagcca gattggccaa ttaaaaacga aaacctgact   5814
aggttctgta gagccaatta gacttgaaat acgtttgtgt ttctagaatc acagctcaag   5874
cattctgttt atcgctcact ctcccttgta cagccttatt ttgttggtgc tttgcatttt   5934
gatattgctg tgagccttgc atgacatcat gaggccggat gaaacttctc agtccagcag   5994
tttccagtcc taacaaatgc tcccacctga atttgtatat gactgcattt gtgggtgtgt   6054
gtgtgttttc agcaaattcc agatttgttt ccttttggcc tcctgcaaag tctccagaag   6114
aaaatttgcc aatctttcct actttctatt tttatgatga caatcaaagc cggcctgaga   6174
aacactattt gtgacttttt aaacgattag tgatgtcctt aaaatgtggt ctgccaatct   6234
gtacaaaatg gtcctatttt tgtgaagagg gacataagat aaaatgatgt tatacatcaa   6294
tatgtatata tgtatttcta tatagacttg gagaatactg ccaaaacatt tatgacaagc   6354
tgtatcactg ccttcgttta tattttttta actgtgataa tccccacagg cacattaact   6414
gttgcacttt tgaatgtcca aaatttatat tttagaaata ataaaaagaa agatacttac   6474
atgttcccaa aacaatggtg tggtgaatgt gtgagaaaaa ctaacttgat agggtctacc   6534
aatacaaaat gtattacgaa tgcccctgtt catgtttttg ttttaaaacg tgtaaatgaa   6594
gatctttata tttcaataaa tgatatataa tttaaagtt                          6633
```

<210> SEQ ID NO 2
<211> LENGTH: 1089
<212> TYPE: PRT
<213> ORGANISM: Homo sapiens

<400> SEQUENCE: 2

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415
```

-continued

```
Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
```

```
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                1015                1020

Asp Ile  Asp Pro Val Pro Glu  Glu Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser  Ser Ser Thr Phe Ile  Lys Arg Glu Asp Glu  Thr Ile Glu
    1055                1060                1065

Asp Ile  Asp Met Met Asp Asp  Ile Gly Ile Asp Ser  Ser Asp Leu
    1070                1075                1080

Val Glu  Asp Ser Phe Leu
    1085


<210> SEQ ID NO 3
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 3

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                      Met Gly Thr Ser His Pro Ala
                                      1               5

ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20
```

-continued

```
cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340
```

-continued

```
cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg agg gtc att gaa tca atc agc ccg      2095
Lys Pro Arg Tyr Glu Ile Arg Trp Arg Val Ile Glu Ser Ile Ser Pro
            555                 560                 565

gat gga cat gaa tat att tat gtg gac ccg atg cag ctg cct tat gac      2143
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg      2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta      2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc      2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata      2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc      2383
Met Thr His Leu Gly Pro His Leu Asn Ile Val Asn Leu Leu Gly Ala
        650                 655                 660
```

```
tgc acc aag tca ggc ccc att tac atc atc aca gag tat tgc ttc tat      2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc      2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac      2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac      2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc      2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga      2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac      2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act      2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag      2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac      2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg      2911
Val Leu Leu Ala Gln Gly Lys Ile Val Lys Ile Cys Asp Phe Gly Leu
    825                 830                 835

gcc aga gtc atc atg cat gat tcg aac tat gtg tcg aaa ggc agt acc      2959
Ala Arg Val Ile Met His Asp Ser Asn Tyr Val Ser Lys Gly Ser Thr
840                 845                 850                 855

ttt ctg ccc gtg aag tgg atg gct cct gag agc atc ttt gac aac ctc      3007
Phe Leu Pro Val Lys Trp Met Ala Pro Glu Ser Ile Phe Asp Asn Leu
                860                 865                 870

tac acc aca ctg agt gat gtc tgg tct tat ggc att ctg ctc tgg gag      3055
Tyr Thr Thr Leu Ser Asp Val Trp Ser Tyr Gly Ile Leu Leu Trp Glu
            875                 880                 885

atc ttt tcc ctt ggt ggc acc cct tac ccc ggc atg atg gtg gat tct      3103
Ile Phe Ser Leu Gly Gly Thr Pro Tyr Pro Gly Met Met Val Asp Ser
        890                 895                 900

act ttc tac aat aag atc aag agt ggg tac cgg atg gcc aag cct gac      3151
Thr Phe Tyr Asn Lys Ile Lys Ser Gly Tyr Arg Met Ala Lys Pro Asp
    905                 910                 915

cac gct acc agt gaa gtc tac gag atc atg gtg aaa tgc tgg aac agt      3199
His Ala Thr Ser Glu Val Tyr Glu Ile Met Val Lys Cys Trp Asn Ser
920                 925                 930                 935

gag ccg gag aag aga ccc tcc ttt tac cac ctg agt gag att gtg gag      3247
Glu Pro Glu Lys Arg Pro Ser Phe Tyr His Leu Ser Glu Ile Val Glu
                940                 945                 950

aat ctg ctg cct gga caa tat aaa aag agt tat gaa aaa att cac ctg      3295
Asn Leu Leu Pro Gly Gln Tyr Lys Lys Ser Tyr Glu Lys Ile His Leu
            955                 960                 965

gac ttc ctg aag agt gac cat cct gct gtg gca cgc atg cgt gtg gac      3343
Asp Phe Leu Lys Ser Asp His Pro Ala Val Ala Arg Met Arg Val Asp
        970                 975                 980
```

```
tca gac aat gca tac att ggt gtc acc tac aaa aac gag gaa gac aag     3391
Ser Asp Asn Ala Tyr Ile Gly Val Thr Tyr Lys Asn Glu Glu Asp Lys
    985                 990                 995

ctg  aag gac tgg gag ggt  ggt ctg gat gag cag  aga ctg agc gct      3436
Leu  Lys Asp Trp Glu Gly  Gly Leu Asp Glu Gln  Arg Leu Ser Ala
1000                 1005                 1010

gac  agt ggc tac atc att  cct ctg cct gac att  gac cct gtc cct      3481
Asp  Ser Gly Tyr Ile Ile  Pro Leu Pro Asp Ile  Asp Pro Val Pro
1015                 1020                 1025

gag  gag gag gac ctg ggc  aag agg aac aga cac  agc tcg cag acc      3526
Glu  Glu Glu Asp Leu Gly  Lys Arg Asn Arg His  Ser Ser Gln Thr
1030                 1035                 1040

tct  gaa gag agt gcc att  gag acg ggt tcc agc  agt tcc acc ttc      3571
Ser  Glu Glu Ser Ala Ile  Glu Thr Gly Ser Ser  Ser Ser Thr Phe
1045                 1050                 1055

atc  aag aga gag gac gag  acc att gaa gac atc  gac atg atg gac      3616
Ile  Lys Arg Glu Asp Glu  Thr Ile Glu Asp Ile  Asp Met Met Asp
1060                 1065                 1070

gac  atc ggc ata gac tct  tca gac ctg gtg gaa  gac agc ttc ctg      3661
Asp  Ile Gly Ile Asp Ser  Ser Asp Leu Val Glu  Asp Ser Phe Leu
1075                 1080                 1085

taa ctggcggatt cgaggggttc cttccacttc tggggccacc tctggatccc          3714

gttcagaaaa ccactttatt gcaatgcgga ggttgagagg aggacttggt tgatgtttaa   3774

agagaagttc ccagccaagg gcctcgggga gcgttctaaa tatgaatgaa tgggatattt   3834

tgaaatgaac tttgtcagtg ttgcctctcg caatgcctca gtagcatctc agtggtgtgt   3894

gaagtttgga gatagatgga taagggaata ataggccaca gaaggtgaac tttgtgcttc   3954

aaggacattg gtgagagtcc aacagacaca atttatactg cgacagaact tcagcattgt   4014

aattatgtaa ataactctaa ccaaggctgt gtttagattg tattaactat cttctttgga   4074

cttctgaaga gaccactcaa tccatccatg tacttccctc ttgaaacctg atgtcagctg   4134

ctgttgaact ttttaaagaa gtgcatgaaa aaccattttt gaaccttaaa aggtactggt   4194

actatagcat tttgctatct tttttagtgt taagagataa agaataataa ttaaccaacc   4254

ttgtttaata gatttgggtc atttagaagc ctgacaactc attttcatat tgtaatctat   4314

gtttataata ctactactgt tatcagtaat gctaaatgtg taataatgta acatgatttc   4374

cctccagaga aagcacaatt taaaacaatc cttactaagt aggtgatgag tttgacagtt   4434

tttgacattt atattaaata acatgtttct ctataaagta tggtaatagc tttagtgaat   4494

taaatttagt tgagcataga gaacaaagta aaagtagtgt tgtccaggaa gtcagaattt   4554

ttaactgtac tgaataggtt ccccaatcca tcgtattaaa aaacaattaa ctgccctctg   4614

aaataatggg attagaaaca aacaaaactc ttaagtccta aaagttctca atgtagaggc   4674

ataaacctgt gctgaacata acttctcatg tatattaccc aatggaaaat ataatgatca   4734

gcaaaaagac tggatttgca gaagtttttt tttttttct tcatgcctga tgaaagcttt    4794

ggcaacccca atatatgtat tttttgaatc tatgaacctg aaaagggtca gaaggatgcc   4854

cagacatcag cctccttctt tcacccctta ccccaaagag aaagagtttg aaactcgaga   4914

ccataaagat attctttagt ggaggctgga tgtgcattag cctggatcct cagttctcaa   4974

atgtgtgtgg cagccaggat gactagatcc tgggtttcca tccttgagat tctgaagtat   5034

gaagtctgag ggaaaccaga gtctgtattt ttctaaactc cctggctgtt ctgatcggcc   5094

agttttcgga aacactgact taggtttcag gaagttgcca tgggaaacaa ataatttgaa   5154

ctttggaaca gggttggaat tcaaccacgc aggaagccta ctatttaaat ccttggcttc   5214
```

```
aggttagtga catttaatgc catctagcta gcaattgcga ccttaattta actttccagt   5274

cttagctgag gctgagaaag ctaaagtttg gttttgacag gttttccaaa agtaaagatg   5334

ctacttccca ctgtatgggg gagattgaac tttccccgtc tcccgtcttc tgcctcccac   5394

tccatacccc gccaaggaaa ggcatgtaca aaaattatgc aattcagtgt tccaagtctc   5454

tgtgtaacca gctcagtgtt ttggtggaaa aaacatttta agttttactg ataatttgag   5514

gttagatggg aggatgaatt gtcacatcta tccacactgt caaacaggtt ggtgtgggtt   5574

cattggcatt ctttgcaata ctgcttaatt gctgatacca tatgaatgaa acatgggctg   5634

tgattactgc aatcactgtg ctatcggcag atgatgcttt ggaagatgca gaagcaataa   5694

taaagtactt gactacctac tggtgtaatc tcaatgcaag ccccaacttt cttatccaac   5754

tttttcatag taagtgcgaa gactgagcca gattggccaa ttaaaaacga aaacctgact   5814

aggttctgta gagccaatta gacttgaaat acgtttgtgt ttctagaatc acagctcaag   5874

cattctgttt atcgctcact ctcccttgta cagccttatt ttgttggtgc tttgcatttt   5934

gatattgctg tgagccttgc atgacatcat gaggccggat gaaacttctc agtccagcag   5994

tttccagtcc taacaaatgc tcccacctga atttgtatat gactgcattt gtgggtgtgt   6054

gtgtgttttc agcaaattcc agatttgttt ccttttggcc tcctgcaaag tctccagaag   6114

aaaatttgcc aatctttcct actttctatt tttatgatga caatcaaagc cggcctgaga   6174

aacactattt gtgacttttt aaacgattag tgatgtcctt aaaatgtggt ctgccaatct   6234

gtacaaaatg gtcctatttt tgtgaagagg gacataagat aaaatgatgt tatacatcaa   6294

tatgtatata tgtatttcta tatagacttg gagaatactg ccaaaacatt tatgacaagc   6354

tgtatcactg ccttcgttta tatttttta actgtgataa tccccacagg cacattaact   6414

gttgcacttt tgaatgtcca aaatttatat tttagaaata ataaaaagaa agatacttac   6474

atgttcccaa aacaatggtg tggtgaatgt gtgagaaaaa ctaacttgat agggtctacc   6534

aatacaaaat gtattacgaa tgcccctgtt catgtttttg ttttaaaacg tgtaaatgaa   6594

gatctttata tttcaataaa tgatatataa tttaaagtt                          6633
```

<210> SEQ ID NO 4
<211> LENGTH: 1089
<212> TYPE: PRT
<213> ORGANISM: Homo sapiens

<400> SEQUENCE: 4

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125
```

-continued

```
Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
```

-continued

```
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Val Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975
```

```
Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                 1015                1020

Asp Ile  Asp Pro Val Pro Glu  Glu Glu Asp Leu Gly  Lys Arg Asn
    1025                 1030                1035

Arg His  Ser Ser Gln Thr Ser  Glu Glu Ser Ala Ile  Glu Thr Gly
    1040                 1045                1050

Ser Ser  Ser Ser Thr Phe Ile  Lys Arg Glu Asp Glu  Thr Ile Glu
    1055                 1060                1065

Asp Ile  Asp Met Met Asp Asp  Ile Gly Ile Asp Ser  Ser Asp Leu
    1070                 1075                1080

Val Glu  Asp Ser Phe Leu
    1085

<210> SEQ ID NO 5
<211> LENGTH: 6621
<212> TYPE: DNA
<213> ORGANISM: Homo sapiens
<220> FEATURE:
<221> NAME/KEY: CDS
<222> LOCATION: (395)..(3652)

<400> SEQUENCE: 5

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                    Met Gly Thr Ser His Pro Ala
                                      1               5

ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
           10                  15                  20

cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                 100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
```

```
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat     1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat     1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt     1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat     1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc     1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa     1759
```

```
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac     1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt     1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct     1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc     1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg     1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag     2047
Val Ile Val Ile Ile Ser Leu Ile Val Leu Val Val Ile Trp Lys Gln
                540                 545                 550

aaa ccg agg tat gaa att cgc tgg agg gtc att gaa tca atc agc ccg     2095
Lys Pro Arg Tyr Glu Ile Arg Trp Arg Val Ile Glu Ser Ile Ser Pro
            555                 560                 565

gat gga cat gaa tat att tat gtg gac ccg atg cag ctg cct tat gac     2143
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg     2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta     2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc     2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata     2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc     2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat     2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc     2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac     2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac     2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc     2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga     2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac     2719
```

```
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act     2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag     2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac     2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg     2911
Val Leu Leu Ala Gln Gly Lys Ile Val Lys Ile Cys Asp Phe Gly Leu
    825                 830                 835

gcc aga gat tcg aac tat gtg tcg aaa ggc agt acc ttt ctg ccc gtg     2959
Ala Arg Asp Ser Asn Tyr Val Ser Lys Gly Ser Thr Phe Leu Pro Val
840                 845                 850                 855

aag tgg atg gct cct gag agc atc ttt gac aac ctc tac acc aca ctg     3007
Lys Trp Met Ala Pro Glu Ser Ile Phe Asp Asn Leu Tyr Thr Thr Leu
                860                 865                 870

agt gat gtc tgg tct tat ggc att ctg ctc tgg gag atc ttt tcc ctt     3055
Ser Asp Val Trp Ser Tyr Gly Ile Leu Leu Trp Glu Ile Phe Ser Leu
            875                 880                 885

ggt ggc acc cct tac ccc ggc atg atg gtg gat tct act ttc tac aat     3103
Gly Gly Thr Pro Tyr Pro Gly Met Met Val Asp Ser Thr Phe Tyr Asn
        890                 895                 900

aag atc aag agt ggg tac cgg atg gcc aag cct gac cac gct acc agt     3151
Lys Ile Lys Ser Gly Tyr Arg Met Ala Lys Pro Asp His Ala Thr Ser
    905                 910                 915

gaa gtc tac gag atc atg gtg aaa tgc tgg aac agt gag ccg gag aag     3199
Glu Val Tyr Glu Ile Met Val Lys Cys Trp Asn Ser Glu Pro Glu Lys
920                 925                 930                 935

aga ccc tcc ttt tac cac ctg agt gag att gtg gag aat ctg ctg cct     3247
Arg Pro Ser Phe Tyr His Leu Ser Glu Ile Val Glu Asn Leu Leu Pro
                940                 945                 950

gga caa tat aaa aag agt tat gaa aaa att cac ctg gac ttc ctg aag     3295
Gly Gln Tyr Lys Lys Ser Tyr Glu Lys Ile His Leu Asp Phe Leu Lys
            955                 960                 965

agt gac cat cct gct gtg gca cgc atg cgt gtg gac tca gac aat gca     3343
Ser Asp His Pro Ala Val Ala Arg Met Arg Val Asp Ser Asp Asn Ala
        970                 975                 980

tac att ggt gtc acc tac aaa aac gag gaa gac aag ctg aag gac tgg     3391
Tyr Ile Gly Val Thr Tyr Lys Asn Glu Glu Asp Lys Leu Lys Asp Trp
    985                 990                 995

gag  ggt ggt ctg gat gag  cag aga ctg agc gct  gac agt ggc tac      3436
Glu  Gly Gly Leu Asp Glu  Gln Arg Leu Ser Ala  Asp Ser Gly Tyr
1000                 1005                 1010

atc  att cct ctg cct gac  att gac cct gtc cct  gag gag gag gac     3481
Ile  Ile Pro Leu Pro Asp  Ile Asp Pro Val Pro  Glu Glu Glu Asp
1015                 1020                 1025

ctg  ggc aag agg aac aga  cac agc tcg cag acc  tct gaa gag agt     3526
Leu  Gly Lys Arg Asn Arg  His Ser Ser Gln Thr  Ser Glu Glu Ser
1030                 1035                 1040

gcc  att gag acg ggt tcc  agc agt tcc acc ttc  atc aag aga gag     3571
Ala  Ile Glu Thr Gly Ser  Ser Ser Ser Thr Phe  Ile Lys Arg Glu
1045                 1050                 1055

gac  gag acc att gaa gac  atc gac atg atg gac  gac atc ggc ata     3616
Asp  Glu Thr Ile Glu Asp  Ile Asp Met Met Asp  Asp Ile Gly Ile
1060                 1065                 1070

gac  tct tca gac ctg gtg  gaa gac agc ttc ctg  taa ctggcggatt      3662
```

-continued

```
Asp  Ser Ser Asp Leu Val  Glu Asp Ser Phe Leu
1075                 1080                1085

cgaggggttc cttccacttc tggggccacc tctggatccc gttcagaaaa ccactttatt   3722

gcaatgcgga ggttgagagg aggacttggt tgatgtttaa agagaagttc ccagccaagg   3782

gcctcgggga gcgttctaaa tatgaatgaa tgggatattt tgaaatgaac tttgtcagtg   3842

ttgcctctcg caatgcctca gtagcatctc agtggtgtgt gaagtttgga gatagatgga   3902

taagggaata ataggccaca gaaggtgaac tttgtgcttc aaggacattg gtgagagtcc   3962

aacagacaca atttatactg cgacagaact tcagcattgt aattatgtaa ataactctaa   4022

ccaaggctgt gtttagattg tattaactat cttctttgga cttctgaaga gaccactcaa   4082

tccatccatg tacttccctc ttgaaacctg atgtcagctg ctgttgaact ttttaaagaa   4142

gtgcatgaaa aaccattttt gaaccttaaa aggtactggt actatagcat tttgctatct   4202

tttttagtgt taagagataa agaataataa ttaaccaacc ttgtttaata gatttgggtc   4262

atttagaagc ctgacaactc attttcatat tgtaatctat gtttataata ctactactgt   4322

tatcagtaat gctaaatgtg taataatgta acatgatttc cctccagaga aagcacaatt   4382

taaaacaatc cttactaagt aggtgatgag tttgacagtt tttgacattt atattaaata   4442

acatgtttct ctataaagta tggtaatagc tttagtgaat taaatttagt tgagcataga   4502

gaacaaagta aaagtagtgt tgtccaggaa gtcagaattt ttaactgtac tgaataggtt   4562

ccccaatcca tcgtattaaa aaacaattaa ctgccctctg aaataatggg attagaaaca   4622

aacaaaactc ttaagtccta aaagttctca atgtagaggc ataaacctgt gctgaacata   4682

acttctcatg tatattaccc aatggaaaat ataatgatca gcaaaaagac tggatttgca   4742

gaagtttttt ttttttttct tcatgcctga tgaaagcttt ggcaacccca atatatgtat   4802

tttttgaatc tatgaacctg aaaagggtca gaaggatgcc cagacatcag cctccttctt   4862

tcacccctta ccccaaagag aaagagtttg aaactcgaga ccataaagat attctttagt   4922

ggaggctgga tgtgcattag cctggatcct cagttctcaa atgtgtgtgg cagccaggat   4982

gactagatcc tgggtttcca tccttgagat tctgaagtat gaagtctgag ggaaaccaga   5042

gtctgtattt ttctaaactc cctggctgtt ctgatcggcc agttttcgga aacactgact   5102

taggtttcag gaagttgcca tgggaaacaa ataatttgaa ctttggaaca gggttggaat   5162

tcaaccacgc aggaagccta ctatttaaat ccttggcttc aggttagtga catttaatgc   5222

catctagcta gcaattgcga ccttaattta actttccagt cttagctgag gctgagaaag   5282

ctaaagtttg gttttgacag gttttccaaa agtaaagatg ctacttccca ctgtatgggg   5342

gagattgaac tttccccgtc tcccgtcttc tgcctcccac tccatacccc gccaaggaaa   5402

ggcatgtaca aaaattatgc aattcagtgt tccaagtctc tgtgtaacca gctcagtgtt   5462

ttggtggaaa aaacatttta agttttactg ataatttgag gttagatggg aggatgaatt   5522

gtcacatcta tccacactgt caaacaggtt ggtgtgggtt cattggcatt ctttgcaata   5582

ctgcttaatt gctgatacca tatgaatgaa acatgggctg tgattactgc aatcactgtg   5642

ctatcggcag atgatgcttt ggaagatgca gaagcaataa taaagtactt gactacctac   5702

tggtgtaatc tcaatgcaag ccccaacttt cttatccaac tttttcatag taagtgcgaa   5762

gactgagcca gattggccaa ttaaaaacga aaacctgact aggttctgta gagccaatta   5822

gacttgaaat acgtttgtgt ttctagaatc acagctcaag cattctgttt atcgctcact   5882

ctcccttgta cagccttatt ttgttggtgc tttgcatttt gatattgctg tgagccttgc   5942

atgacatcat gaggccggat gaaacttctc agtccagcag tttccagtcc taacaaatgc   6002
```

```
tcccacctga atttgtatat gactgcattt gtgggtgtgt gtgtgttttc agcaaattcc   6062

agatttgttt ccttttggcc tcctgcaaag tctccagaag aaaatttgcc aatctttcct   6122

actttctatt tttatgatga caatcaaagc cggcctgaga aacactattt gtgacttttt   6182

aaacgattag tgatgtcctt aaaatgtggt ctgccaatct gtacaaaatg gtcctatttt   6242

tgtgaagagg gacataagat aaaatgatgt tatacatcaa tatgtatata tgtatttcta   6302

tatagacttg gagaatactg ccaaaacatt tatgacaagc tgtatcactg ccttcgttta   6362

tatttttttta actgtgataa tccccacagg cacattaact gttgcacttt tgaatgtcca   6422

aaatttatat tttagaaata ataaaaagaa agatacttac atgttcccaa aacaatggtg   6482

tggtgaatgt gtgagaaaaa ctaacttgat agggtctacc aatacaaaat gtattacgaa   6542

tgcccctgtt catgtttttg ttttaaaacg tgtaaatgaa gatctttata tttcaataaa   6602

tgatatataa tttaaagtt                                                  6621
```

<210> SEQ ID NO 6
<211> LENGTH: 1085
<212> TYPE: PRT
<213> ORGANISM: Homo sapiens

<400> SEQUENCE: 6

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
```

```
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685
```

-continued

```
Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ser Asn Tyr Val Ser Lys
        835                 840                 845

Gly Ser Thr Phe Leu Pro Val Lys Trp Met Ala Pro Glu Ser Ile Phe
    850                 855                 860

Asp Asn Leu Tyr Thr Thr Leu Ser Asp Val Trp Ser Tyr Gly Ile Leu
865                 870                 875                 880

Leu Trp Glu Ile Phe Ser Leu Gly Gly Thr Pro Tyr Pro Gly Met Met
                885                 890                 895

Val Asp Ser Thr Phe Tyr Asn Lys Ile Lys Ser Gly Tyr Arg Met Ala
            900                 905                 910

Lys Pro Asp His Ala Thr Ser Glu Val Tyr Glu Ile Met Val Lys Cys
        915                 920                 925

Trp Asn Ser Glu Pro Glu Lys Arg Pro Ser Phe Tyr His Leu Ser Glu
    930                 935                 940

Ile Val Glu Asn Leu Leu Pro Gly Gln Tyr Lys Lys Ser Tyr Glu Lys
945                 950                 955                 960

Ile His Leu Asp Phe Leu Lys Ser Asp His Pro Ala Val Ala Arg Met
                965                 970                 975

Arg Val Asp Ser Asp Asn Ala Tyr Ile Gly Val Thr Tyr Lys Asn Glu
            980                 985                 990

Glu Asp Lys Leu Lys Asp Trp Glu  Gly Gly Leu Asp Glu  Gln Arg Leu
        995                 1000                1005

Ser Ala  Asp Ser Gly Tyr Ile  Ile Pro Leu Pro Asp  Ile Asp Pro
    1010                1015                1020

Val Pro  Glu Glu Glu Asp Leu  Gly Lys Arg Asn Arg  His Ser Ser
    1025                1030                1035

Gln Thr  Ser Glu Glu Ser Ala  Ile Glu Thr Gly Ser  Ser Ser Ser
    1040                1045                1050

Thr Phe  Ile Lys Arg Glu Asp  Glu Thr Ile Glu Asp  Ile Asp Met
    1055                1060                1065

Met Asp  Asp Ile Gly Ile Asp  Ser Ser Asp Leu Val  Glu Asp Ser
    1070                1075                1080

Phe Leu
    1085
```

<210> SEQ ID NO 7

```
<211> LENGTH: 6624
<212> TYPE: DNA
<213> ORGANISM: Homo sapiens
<220> FEATURE:
<221> NAME/KEY: CDS
<222> LOCATION: (395)..(3655)

<400> SEQUENCE: 7

ttctccccgc cccccagttg ttgtcgaagt ctggggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                      Met Gly Thr Ser His Pro Ala
                                      1               5

ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg       511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc       607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg       655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac       703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc       751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat       799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc       847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg       895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act       943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag       991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat      1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att      1087
Leu Glu Met Glu Ala Leu Lys Thr Val Tyr Lys Ser Gly Glu Thr Ile
                220                 225                 230
```

-continued

```
gtg gtc acc tgt gct gtt ttt aac aat gag gtg gtt gac ctt caa tgg      1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa      1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag      1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct      1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag      1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc      1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca      1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550
```

-continued

```
aaa ccg agg tat gaa att cgc tgg agg gtc att gaa tca atc agc ccg      2095
Lys Pro Arg Tyr Glu Ile Arg Trp Arg Val Ile Glu Ser Ile Ser Pro
            555                 560                 565

gat gga cat gaa tat att tat gtg gac ccg atg cag ctg cct tat gac      2143
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg      2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta      2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc      2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata      2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc      2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat      2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc      2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac      2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac      2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc      2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga      2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac      2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act      2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag      2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac      2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg      2911
Val Leu Leu Ala Gln Gly Lys Ile Val Lys Ile Cys Asp Phe Gly Leu
    825                 830                 835

gcc aga gac atc atg ccc tat gtg tcg aaa ggc agt acc ttt ctg ccc      2959
Ala Arg Asp Ile Met Pro Tyr Val Ser Lys Gly Ser Thr Phe Leu Pro
840                 845                 850                 855

gtg aag tgg atg gct cct gag agc atc ttt gac aac ctc tac acc aca      3007
Val Lys Trp Met Ala Pro Glu Ser Ile Phe Asp Asn Leu Tyr Thr Thr
                860                 865                 870
```

```
ctg agt gat gtc tgg tct tat ggc att ctg ctc tgg gag atc ttt tcc     3055
Leu Ser Asp Val Trp Ser Tyr Gly Ile Leu Leu Trp Glu Ile Phe Ser
            875                 880                 885

ctt ggt ggc acc cct tac ccc ggc atg atg gtg gat tct act ttc tac     3103
Leu Gly Gly Thr Pro Tyr Pro Gly Met Met Val Asp Ser Thr Phe Tyr
        890                 895                 900

aat aag atc aag agt ggg tac cgg atg gcc aag cct gac cac gct acc     3151
Asn Lys Ile Lys Ser Gly Tyr Arg Met Ala Lys Pro Asp His Ala Thr
    905                 910                 915

agt gaa gtc tac gag atc atg gtg aaa tgc tgg aac agt gag ccg gag     3199
Ser Glu Val Tyr Glu Ile Met Val Lys Cys Trp Asn Ser Glu Pro Glu
920                 925                 930                 935

aag aga ccc tcc ttt tac cac ctg agt gag att gtg gag aat ctg ctg     3247
Lys Arg Pro Ser Phe Tyr His Leu Ser Glu Ile Val Glu Asn Leu Leu
                940                 945                 950

cct gga caa tat aaa aag agt tat gaa aaa att cac ctg gac ttc ctg     3295
Pro Gly Gln Tyr Lys Lys Ser Tyr Glu Lys Ile His Leu Asp Phe Leu
            955                 960                 965

aag agt gac cat cct gct gtg gca cgc atg cgt gtg gac tca gac aat     3343
Lys Ser Asp His Pro Ala Val Ala Arg Met Arg Val Asp Ser Asp Asn
        970                 975                 980

gca tac att ggt gtc acc tac aaa aac gag gaa gac aag ctg aag gac     3391
Ala Tyr Ile Gly Val Thr Tyr Lys Asn Glu Glu Asp Lys Leu Lys Asp
    985                 990                 995

tgg  gag ggt ggt ctg gat  gag cag aga ctg agc  gct gac agt ggc      3436
Trp  Glu Gly Gly Leu Asp  Glu Gln Arg Leu Ser  Ala Asp Ser Gly
1000                 1005                 1010

tac  atc att cct ctg cct  gac att gac cct gtc  cct gag gag gag      3481
Tyr  Ile Ile Pro Leu Pro  Asp Ile Asp Pro Val  Pro Glu Glu Glu
1015                 1020                 1025

gac  ctg ggc aag agg aac  aga cac agc tcg cag  acc tct gaa gag      3526
Asp  Leu Gly Lys Arg Asn  Arg His Ser Ser Gln  Thr Ser Glu Glu
1030                 1035                 1040

agt  gcc att gag acg ggt  tcc agc agt tcc acc  ttc atc aag aga      3571
Ser  Ala Ile Glu Thr Gly  Ser Ser Ser Ser Thr  Phe Ile Lys Arg
1045                 1050                 1055

gag  gac gag acc att gaa  gac atc gac atg atg  gac gac atc ggc      3616
Glu  Asp Glu Thr Ile Glu  Asp Ile Asp Met Met  Asp Asp Ile Gly
1060                 1065                 1070

ata  gac tct tca gac ctg  gtg gaa gac agc ttc  ctg taa ctggcggatt   3665
Ile  Asp Ser Ser Asp Leu  Val Glu Asp Ser Phe  Leu
1075                 1080                 1085

cgaggggttc cttccacttc tggggccacc tctggatccc gttcagaaaa ccactttatt   3725

gcaatgcgga ggttgagagg aggacttggt tgatgtttaa agagaagttc ccagccaagg   3785

gcctcgggga gcgttctaaa tatgaatgaa tgggatattt tgaaatgaac tttgtcagtg   3845

ttgcctctcg caatgcctca gtagcatctc agtggtgtgt gaagtttgga gatagatgga   3905

taagggaata ataggccaca gaaggtgaac tttgtgcttc aaggacattg gtgagagtcc   3965

aacagacaca atttatactg cgacagaact tcagcattgt aattatgtaa ataactctaa   4025

ccaaggctgt gtttagattg tattaactat cttctttgga cttctgaaga gaccactcaa   4085

tccatccatg tacttccctc ttgaaacctg atgtcagctg ctgttgaact tttaaagaa    4145

gtgcatgaaa aaccattttt gaaccttaaa aggtactggt actatagcat tttgctatct   4205

tttttagtgt taagagataa agaataataa ttaaccaacc ttgtttaata gatttgggtc   4265

atttagaagc ctgacaactc attttcatat tgtaatctat gtttataata ctactactgt   4325

tatcagtaat gctaaatgtg taataatgta acatgatttc cctccagaga aagcacaatt   4385
```

```
taaaacaatc cttactaagt aggtgatgag tttgacagtt tttgacattt atattaaata   4445
acatgtttct ctataaagta tggtaatagc tttagtgaat taaatttagt tgagcataga   4505
gaacaaagta aaagtagtgt tgtccaggaa gtcagaattt ttaactgtac tgaataggtt   4565
ccccaatcca tcgtattaaa aaacaattaa ctgccctctg aaataatggg attagaaaca   4625
aacaaaactc ttaagtccta aaagttctca atgtagaggc ataaacctgt gctgaacata   4685
acttctcatg tatattaccc aatggaaaat ataatgatca gcaaaaagac tggatttgca   4745
gaagtttttt ttttttttct tcatgcctga tgaaagcttt ggcaacccca atatatgtat   4805
tttttgaatc tatgaacctg aaaagggtca gaaggatgcc cagacatcag cctccttctt   4865
tcacccctta ccccaaagag aaagagtttg aaactcgaga ccataaagat attctttagt   4925
ggaggctgga tgtgcattag cctggatcct cagttctcaa atgtgtgtgg cagccaggat   4985
gactagatcc tgggtttcca tccttgagat tctgaagtat gaagtctgag ggaaaccaga   5045
gtctgtattt ttctaaactc cctggctgtt ctgatcggcc agttttcgga aacactgact   5105
taggtttcag gaagttgcca tgggaaacaa ataatttgaa ctttggaaca gggttggaat   5165
tcaaccacgc aggaagccta ctatttaaat ccttggcttc aggttagtga catttaatgc   5225
catctagcta gcaattgcga ccttaattta actttccagt cttagctgag gctgagaaag   5285
ctaaagtttg gttttgacag gttttccaaa agtaaagatg ctacttccca ctgtatgggg   5345
gagattgaac tttccccgtc tcccgtcttc tgcctcccac tccatacccc gccaaggaaa   5405
ggcatgtaca aaaattatgc aattcagtgt tccaagtctc tgtgtaacca gctcagtgtt   5465
ttggtggaaa aaacatttta agttttactg ataatttgag gttagatggg aggatgaatt   5525
gtcacatcta tccacactgt caaacaggtt ggtgtgggtt cattggcatt ctttgcaata   5585
ctgcttaatt gctgatacca tatgaatgaa acatgggctg tgattactgc aatcactgtg   5645
ctatcggcag atgatgcttt ggaagatgca gaagcaataa taaagtactt gactacctac   5705
tggtgtaatc tcaatgcaag ccccaacttt cttatccaac tttttcatag taagtgcgaa   5765
gactgagcca gattggccaa ttaaaaacga aaacctgact aggttctgta gagccaatta   5825
gacttgaaat acgtttgtgt ttctagaatc acagctcaag cattctgttt atcgctcact   5885
ctcccttgta cagccttatt ttgttggtgc tttgcatttt gatattgctg tgagccttgc   5945
atgacatcat gaggccggat gaaacttctc agtccagcag tttccagtcc taacaaatgc   6005
tcccacctga atttgtatat gactgcattt gtgggtgtgt gtgtgttttc agcaaattcc   6065
agatttgttt ccttttggcc tcctgcaaag tctccagaag aaaatttgcc aatctttcct   6125
actttctatt tttatgatga caatcaaagc cggcctgaga aacactattt gtgacttttt   6185
aaacgattag tgatgtcctt aaaatgtggt ctgccaatct gtacaaaatg gtcctatttt   6245
tgtgaagagg gacataagat aaaatgatgt tatacatcaa tatgtatata tgtatttcta   6305
tatagacttg gagaatactg ccaaaacatt tatgacaagc tgtatcactg ccttcgttta   6365
tattttttta actgtgataa tccccacagg cacattaact gttgcacttt tgaatgtcca   6425
aaatttatat tttagaaata ataaaaagaa agatacttac atgttcccaa aacaatggtg   6485
tggtgaatgt gtgagaaaaa ctaacttgat agggtctacc aatacaaaat gtattacgaa   6545
tgcccctgtt catgtttttg ttttaaaacg tgtaaatgaa gatctttata tttcaataaa   6605
tgatatataa tttaaagtt                                                6624
```

<210> SEQ ID NO 8
<211> LENGTH: 1086

<212> TYPE: PRT
<213> ORGANISM: Homo sapiens

<400> SEQUENCE: 8

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400
```

```
Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830
```

```
Lys Ile Cys Asp Phe Gly Leu Ala Arg Asp Ile Met Pro Tyr Val Ser
        835                 840                 845

Lys Gly Ser Thr Phe Leu Pro Val Lys Trp Met Ala Pro Glu Ser Ile
    850                 855                 860

Phe Asp Asn Leu Tyr Thr Thr Leu Ser Asp Val Trp Ser Tyr Gly Ile
865                 870                 875                 880

Leu Leu Trp Glu Ile Phe Ser Leu Gly Gly Thr Pro Tyr Pro Gly Met
                885                 890                 895

Met Val Asp Ser Thr Phe Tyr Asn Lys Ile Lys Ser Gly Tyr Arg Met
            900                 905                 910

Ala Lys Pro Asp His Ala Thr Ser Glu Val Tyr Glu Ile Met Val Lys
        915                 920                 925

Cys Trp Asn Ser Glu Pro Glu Lys Arg Pro Ser Phe Tyr His Leu Ser
    930                 935                 940

Glu Ile Val Glu Asn Leu Leu Pro Gly Gln Tyr Lys Lys Ser Tyr Glu
945                 950                 955                 960

Lys Ile His Leu Asp Phe Leu Lys Ser Asp His Pro Ala Val Ala Arg
                965                 970                 975

Met Arg Val Asp Ser Asp Asn Ala Tyr Ile Gly Val Thr Tyr Lys Asn
            980                 985                 990

Glu Glu Asp Lys Leu Lys Asp Trp  Glu Gly Gly Leu Asp  Glu Gln Arg
        995                 1000                 1005

Leu Ser  Ala Asp Ser Gly Tyr  Ile Ile Pro Leu Pro  Asp Ile Asp
    1010                 1015                 1020

Pro Val  Pro Glu Glu Glu Asp  Leu Gly Lys Arg Asn  Arg His Ser
    1025                 1030                 1035

Ser Gln  Thr Ser Glu Glu Ser  Ala Ile Glu Thr Gly  Ser Ser Ser
    1040                 1045                 1050

Ser Thr  Phe Ile Lys Arg Glu  Asp Glu Thr Ile Glu  Asp Ile Asp
    1055                 1060                 1065

Met Met  Asp Asp Ile Gly Ile  Asp Ser Ser Asp Leu  Val Glu Asp
    1070                 1075                 1080

Ser Phe  Leu
    1085


<210> SEQ ID NO 9
<211> LENGTH: 6639
<212> TYPE: DNA
<213> ORGANISM: Homo sapiens
<220> FEATURE:
<221> NAME/KEY: CDS
<222> LOCATION: (395)..(3667)

<400> SEQUENCE: 9

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                      Met Gly Thr Ser His Pro Ala
                                      1               5

ttc ctg gtc tta ggc tgt ctt ctc aca ggg ctg agc cta atc ctc tgc       463
```

-continued

```
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
```

-continued

```
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg agg gag agg gtc att gaa tca atc      2095
Lys Pro Arg Tyr Glu Ile Arg Trp Arg Glu Arg Val Ile Glu Ser Ile
            555                 560                 565

agc ccg gat gga cat gaa tat att tat gtg gac ccg atg cag ctg cct      2143
Ser Pro Asp Gly His Glu Tyr Ile Tyr Val Asp Pro Met Gln Leu Pro
        570                 575                 580

tat gac tca aga tgg gag ttt cca aga gat gga cta gtg ctt ggt cgg      2191
Tyr Asp Ser Arg Trp Glu Phe Pro Arg Asp Gly Leu Val Leu Gly Arg
    585                 590                 595

gtc ttg ggg tct gga gcg ttt ggg aag gtg gtt gaa gga aca gcc tat      2239
Val Leu Gly Ser Gly Ala Phe Gly Lys Val Val Glu Gly Thr Ala Tyr
600                 605                 610                 615

gga tta agc cgg tcc caa cct gtc atg aaa gtt gca gtg aag atg cta      2287
Gly Leu Ser Arg Ser Gln Pro Val Met Lys Val Ala Val Lys Met Leu
                620                 625                 630

aaa ccc acg gcc aga tcc agt gaa aaa caa gct ctc atg tct gaa ctg      2335
Lys Pro Thr Ala Arg Ser Ser Glu Lys Gln Ala Leu Met Ser Glu Leu
            635                 640                 645

aag ata atg act cac ctg ggg cca cat ttg aac att gta aac ttg ctg      2383
```

```
Lys Ile Met Thr His Leu Gly Pro His Leu Asn Ile Val Asn Leu Leu
        650                 655                 660

gga gcc tgc acc aag tca ggc ccc att tac atc atc aca gag tat tgc     2431
Gly Ala Cys Thr Lys Ser Gly Pro Ile Tyr Ile Ile Thr Glu Tyr Cys
    665                 670                 675

ttc tat gga gat ttg gtc aac tat ttg cat aag aat agg gat agc ttc     2479
Phe Tyr Gly Asp Leu Val Asn Tyr Leu His Lys Asn Arg Asp Ser Phe
680                 685                 690                 695

ctg agc cac cac cca gag aag cca aag aaa gag ctg gat atc ttt gga     2527
Leu Ser His His Pro Glu Lys Pro Lys Lys Glu Leu Asp Ile Phe Gly
                700                 705                 710

ttg aac cct gct gat gaa agc aca cgg agc tat gtt att tta tct ttt     2575
Leu Asn Pro Ala Asp Glu Ser Thr Arg Ser Tyr Val Ile Leu Ser Phe
            715                 720                 725

gaa aac aat ggt gac tac atg gac atg aag cag gct gat act aca cag     2623
Glu Asn Asn Gly Asp Tyr Met Asp Met Lys Gln Ala Asp Thr Thr Gln
        730                 735                 740

tat gtc ccc atg cta gaa agg aaa gag gtt tct aaa tat tcc gac atc     2671
Tyr Val Pro Met Leu Glu Arg Lys Glu Val Ser Lys Tyr Ser Asp Ile
    745                 750                 755

cag aga tca ctc tat gat cgt cca gcc tca tat aag aag aaa tct atg     2719
Gln Arg Ser Leu Tyr Asp Arg Pro Ala Ser Tyr Lys Lys Lys Ser Met
760                 765                 770                 775

tta gac tca gaa gtc aaa aac ctc ctt tca gat gat aac tca gaa ggc     2767
Leu Asp Ser Glu Val Lys Asn Leu Leu Ser Asp Asp Asn Ser Glu Gly
                780                 785                 790

ctt act tta ttg gat ttg ttg agc ttc acc tat caa gtt gcc cga gga     2815
Leu Thr Leu Leu Asp Leu Leu Ser Phe Thr Tyr Gln Val Ala Arg Gly
            795                 800                 805

atg gag ttt ttg gct tca aaa aat tgt gtc cac cgt gat ctg gct gct     2863
Met Glu Phe Leu Ala Ser Lys Asn Cys Val His Arg Asp Leu Ala Ala
        810                 815                 820

cgc aac gtc ctc ctg gca caa gga aaa att gtg aag atc tgt gac ttt     2911
Arg Asn Val Leu Leu Ala Gln Gly Lys Ile Val Lys Ile Cys Asp Phe
    825                 830                 835

ggc ctg gcc aga gac atc atg cat gat tcg aac tat gtg tcg aaa ggc     2959
Gly Leu Ala Arg Asp Ile Met His Asp Ser Asn Tyr Val Ser Lys Gly
840                 845                 850                 855

agt acc ttt ctg ccc gtg aag tgg atg gct cct gag agc atc ttt gac     3007
Ser Thr Phe Leu Pro Val Lys Trp Met Ala Pro Glu Ser Ile Phe Asp
                860                 865                 870

aac ctc tac acc aca ctg agt gat gtc tgg tct tat ggc att ctg ctc     3055
Asn Leu Tyr Thr Thr Leu Ser Asp Val Trp Ser Tyr Gly Ile Leu Leu
            875                 880                 885

tgg gag atc ttt tcc ctt ggt ggc acc cct tac ccc ggc atg atg gtg     3103
Trp Glu Ile Phe Ser Leu Gly Gly Thr Pro Tyr Pro Gly Met Met Val
        890                 895                 900

gat tct act ttc tac aat aag atc aag agt ggg tac cgg atg gcc aag     3151
Asp Ser Thr Phe Tyr Asn Lys Ile Lys Ser Gly Tyr Arg Met Ala Lys
    905                 910                 915

cct gac cac gct acc agt gaa gtc tac gag atc atg gtg aaa tgc tgg     3199
Pro Asp His Ala Thr Ser Glu Val Tyr Glu Ile Met Val Lys Cys Trp
920                 925                 930                 935

aac agt gag ccg gag aag aga ccc tcc ttt tac cac ctg agt gag att     3247
Asn Ser Glu Pro Glu Lys Arg Pro Ser Phe Tyr His Leu Ser Glu Ile
                940                 945                 950

gtg gag aat ctg ctg cct gga caa tat aaa aag agt tat gaa aaa att     3295
Val Glu Asn Leu Leu Pro Gly Gln Tyr Lys Lys Ser Tyr Glu Lys Ile
            955                 960                 965

cac ctg gac ttc ctg aag agt gac cat cct gct gtg gca cgc atg cgt     3343
```

```
His Leu Asp Phe Leu Lys Ser Asp His Pro Ala Val Ala Arg Met Arg
        970                 975                 980

gtg gac tca gac aat gca tac att ggt gtc acc tac aaa aac gag gaa     3391
Val Asp Ser Asp Asn Ala Tyr Ile Gly Val Thr Tyr Lys Asn Glu Glu
    985                 990                 995

gac  aag ctg aag gac tgg  gag ggt ggt ctg gat  gag cag aga ctg      3436
Asp  Lys Leu Lys Asp Trp  Glu Gly Gly Leu Asp  Glu Gln Arg Leu
1000                 1005                 1010

agc  gct gac agt ggc tac  atc att cct ctg cct  gac att gac cct      3481
Ser  Ala Asp Ser Gly Tyr  Ile Ile Pro Leu Pro  Asp Ile Asp Pro
1015                 1020                 1025

gtc  cct gag gag gag gac  ctg ggc aag agg aac  aga cac agc tcg      3526
Val  Pro Glu Glu Glu Asp  Leu Gly Lys Arg Asn  Arg His Ser Ser
1030                 1035                 1040

cag  acc tct gaa gag agt  gcc att gag acg ggt  tcc agc agt tcc      3571
Gln  Thr Ser Glu Glu Ser  Ala Ile Glu Thr Gly  Ser Ser Ser Ser
1045                 1050                 1055

acc  ttc atc aag aga gag  gac gag acc att gaa  gac atc gac atg      3616
Thr  Phe Ile Lys Arg Glu  Asp Glu Thr Ile Glu  Asp Ile Asp Met
1060                 1065                 1070

atg  gac gac atc ggc ata  gac tct tca gac ctg  gtg gaa gac agc      3661
Met  Asp Asp Ile Gly Ile  Asp Ser Ser Asp Leu  Val Glu Asp Ser
1075                 1080                 1085

ttc  ctg taactggcgg attcgagggg ttccttccac ttctggggcc acctctggat     3717
Phe  Leu
1090

cccgttcaga aaaccacttt attgcaatgc ggaggttgag aggaggactt ggttgatgtt   3777

taaagagaag ttcccagcca agggcctcgg ggagcgttct aaatatgaat gaatgggata   3837

ttttgaaatg aactttgtca gtgttgcctc tcgcaatgcc tcagtagcat ctcagtggtg   3897

tgtgaagttt ggagatagat ggataaggga ataataggcc acagaaggtg aactttgtgc   3957

ttcaaggaca ttggtgagag tccaacagac acaatttata ctgcgacaga acttcagcat   4017

tgtaattatg taaataactc taaccaaggc tgtgtttaga ttgtattaac tatcttcttt   4077

ggacttctga agagaccact caatccatcc atgtacttcc ctcttgaaac ctgatgtcag   4137

ctgctgttga actttttaaa gaagtgcatg aaaaaccatt tttgaacctt aaaaggtact   4197

ggtactatag catttttgcta tctttttttag tgttaagaga taaagaataa taattaacca   4257

accttgttta atagatttgg gtcatttaga agcctgacaa ctcattttca tattgtaatc   4317

tatgtttata atactactac tgttatcagt aatgctaaat gtgtaataat gtaacatgat   4377

ttccctccag agaaagcaca atttaaaaca atccttacta agtaggtgat gagtttgaca   4437

gtttttgaca tttatattaa ataacatgtt tctctataaa gtatggtaat agctttagtg   4497

aattaaattt agttgagcat agagaacaaa gtaaaagtag tgttgtccag gaagtcagaa   4557

tttttaactg tactgaatag gttccccaat ccatcgtatt aaaaaacaat taactgccct   4617

ctgaaataat gggattagaa acaaacaaaa ctcttaagtc ctaaaagttc tcaatgtaga   4677

ggcataaacc tgtgctgaac ataacttctc atgtatatta cccaatggaa aatataatga   4737

tcagcaaaaa gactggattt gcagaagttt tttttttttt tcttcatgcc tgatgaaagc   4797

tttggcaacc ccaatatatg tattttttga atctatgaac ctgaaaaggg tcagaaggat   4857

gcccagacat cagcctcctt ctttcacccc ttaccccaaa gagaaagagt ttgaaactcg   4917

agaccataaa gatattcttt agtggaggct ggatgtgcat tagcctggat cctcagttct   4977

caaatgtgtg tggcagccag gatgactaga tcctgggttt ccatccttga gattctgaag   5037

tatgaagtct gagggaaacc agagtctgta tttttctaaa ctccctggct gttctgatcg   5097
```

```
gccagttttc ggaaacactg acttaggttt caggaagttg ccatgggaaa caaataattt   5157

gaactttgga acagggttgg aattcaacca cgcaggaagc ctactattta aatccttggc   5217

ttcaggttag tgacatttaa tgccatctag ctagcaattg cgaccttaat ttaactttcc   5277

agtcttagct gaggctgaga aagctaaagt ttggttttga caggttttcc aaaagtaaag   5337

atgctacttc ccactgtatg gggagattgg aactttcccc gtctcccgtc ttctgcctcc   5397

cactccatac cccgccaagg aaaggcatgt acaaaaatta tgcaattcag tgttccaagt   5457

ctctgtgtaa ccagctcagt gttttggtgg aaaaaacatt ttaagtttta ctgataattt   5517

gaggttagat gggaggatga attgtcacat ctatccacac tgtcaaacag gttggtgtgg   5577

gttcattggc attctttgca atactgctta attgctgata ccatatgaat gaaacatggg   5637

ctgtgattac tgcaatcact gtgctatcgg cagatgatgc tttggaagat gcagaagcaa   5697

taataaagta cttgactacc tactggtgta atctcaatgc aagccccaac tttcttatcc   5757

aactttttca tagtaagtgc gaagactgag ccagattggc caattaaaaa cgaaaacctg   5817

actaggttct gtagagccaa ttagacttga aatacgtttg tgtttctaga atcacagctc   5877

aagcattctg tttatcgctc actctccctt gtacagcctt attttgttgg tgctttgcat   5937

tttgatattg ctgtgagcct tgcatgacat catgaggccg gatgaaactt ctcagtccag   5997

cagtttccag tcctaacaaa tgctcccacc tgaatttgta tatgactgca tttgtgggtg   6057

tgtgtgtgtt ttcagcaaat tccagatttg tttccttttg gcctcctgca aagtctccag   6117

aagaaaattt gccaatcttt cctactttct atttttatga tgacaatcaa agccggcctg   6177

agaaacacta tttgtgactt tttaaacgat tagtgatgtc cttaaaatgt ggtctgccaa   6237

tctgtacaaa atggtcctat ttttgtgaag agggacataa gataaaatga tgttatacat   6297

caatatgtat atatgtattt ctatatagac ttggagaata ctgccaaaac atttatgaca   6357

agctgtatca ctgccttcgt ttatattttt ttaactgtga taatccccac aggcacatta   6417

actgttgcac ttttgaatgt ccaaaattta tattttagaa ataataaaaa gaaagatact   6477

tacatgttcc caaaacaatg gtgtggtgaa tgtgtgagaa aaactaactt gatagggtct   6537

accaatacaa aatgtattac gaatgcccct gttcatgttt ttgttttaaa acgtgtaaat   6597

gaagatcttt atatttcaat aaatgatata taatttaaag tt                      6639
```

<210> SEQ ID NO 10
<211> LENGTH: 1091
<212> TYPE: PRT
<213> ORGANISM: Homo sapiens

<400> SEQUENCE: 10

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
```

```
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525
```

-continued

```
Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Glu Arg Val Ile Glu Ser Ile Ser Pro Asp Gly His Glu Tyr Ile Tyr
                565                 570                 575

Val Asp Pro Met Gln Leu Pro Tyr Asp Ser Arg Trp Glu Phe Pro Arg
            580                 585                 590

Asp Gly Leu Val Leu Gly Arg Val Leu Gly Ser Gly Ala Phe Gly Lys
        595                 600                 605

Val Val Glu Gly Thr Ala Tyr Gly Leu Ser Arg Ser Gln Pro Val Met
    610                 615                 620

Lys Val Ala Val Lys Met Leu Lys Pro Thr Ala Arg Ser Ser Glu Lys
625                 630                 635                 640

Gln Ala Leu Met Ser Glu Leu Lys Ile Met Thr His Leu Gly Pro His
                645                 650                 655

Leu Asn Ile Val Asn Leu Leu Gly Ala Cys Thr Lys Ser Gly Pro Ile
            660                 665                 670

Tyr Ile Ile Thr Glu Tyr Cys Phe Tyr Gly Asp Leu Val Asn Tyr Leu
        675                 680                 685

His Lys Asn Arg Asp Ser Phe Leu Ser His His Pro Glu Lys Pro Lys
    690                 695                 700

Lys Glu Leu Asp Ile Phe Gly Leu Asn Pro Ala Asp Glu Ser Thr Arg
705                 710                 715                 720

Ser Tyr Val Ile Leu Ser Phe Glu Asn Asn Gly Asp Tyr Met Asp Met
                725                 730                 735

Lys Gln Ala Asp Thr Thr Gln Tyr Val Pro Met Leu Glu Arg Lys Glu
            740                 745                 750

Val Ser Lys Tyr Ser Asp Ile Gln Arg Ser Leu Tyr Asp Arg Pro Ala
        755                 760                 765

Ser Tyr Lys Lys Lys Ser Met Leu Asp Ser Glu Val Lys Asn Leu Leu
    770                 775                 780

Ser Asp Asp Asn Ser Glu Gly Leu Thr Leu Leu Asp Leu Leu Ser Phe
785                 790                 795                 800

Thr Tyr Gln Val Ala Arg Gly Met Glu Phe Leu Ala Ser Lys Asn Cys
                805                 810                 815

Val His Arg Asp Leu Ala Ala Arg Asn Val Leu Leu Ala Gln Gly Lys
            820                 825                 830

Ile Val Lys Ile Cys Asp Phe Gly Leu Ala Arg Asp Ile Met His Asp
        835                 840                 845

Ser Asn Tyr Val Ser Lys Gly Ser Thr Phe Leu Pro Val Lys Trp Met
    850                 855                 860

Ala Pro Glu Ser Ile Phe Asp Asn Leu Tyr Thr Thr Leu Ser Asp Val
865                 870                 875                 880

Trp Ser Tyr Gly Ile Leu Leu Trp Glu Ile Phe Ser Leu Gly Gly Thr
                885                 890                 895

Pro Tyr Pro Gly Met Met Val Asp Ser Thr Phe Tyr Asn Lys Ile Lys
            900                 905                 910

Ser Gly Tyr Arg Met Ala Lys Pro Asp His Ala Thr Ser Glu Val Tyr
        915                 920                 925

Glu Ile Met Val Lys Cys Trp Asn Ser Glu Pro Glu Lys Arg Pro Ser
    930                 935                 940

Phe Tyr His Leu Ser Glu Ile Val Glu Asn Leu Leu Pro Gly Gln Tyr
945                 950                 955                 960
```

```
Lys Lys Ser Tyr Glu Lys Ile His Leu Asp Phe Leu Lys Ser Asp His
                965                 970                 975

Pro Ala Val Ala Arg Met Arg Val Asp Ser Asp Asn Ala Tyr Ile Gly
            980                 985                 990

Val Thr Tyr Lys Asn Glu Glu Asp  Lys Leu Lys Asp Trp  Glu Gly Gly
        995                 1000                1005

Leu Asp  Glu Gln Arg Leu Ser  Ala Asp Ser Gly Tyr  Ile Ile Pro
    1010                1015                1020

Leu Pro  Asp Ile Asp Pro Val  Pro Glu Glu Glu Asp  Leu Gly Lys
    1025                1030                1035

Arg Asn  Arg His Ser Ser Gln  Thr Ser Glu Glu Ser  Ala Ile Glu
    1040                1045                1050

Thr Gly  Ser Ser Ser Ser Thr  Phe Ile Lys Arg Glu  Asp Glu Thr
    1055                1060                1065

Ile Glu  Asp Ile Asp Met Met  Asp Asp Ile Gly Ile  Asp Ser Ser
    1070                1075                1080

Asp Leu  Val Glu Asp Ser Phe  Leu
    1085                1090


<210> SEQ ID NO 11
<211> LENGTH: 6618
<212> TYPE: DNA
<213> ORGANISM: Homo sapiens
<220> FEATURE:
<221> NAME/KEY: CDS
<222> LOCATION: (395)..(3649)

<400> SEQUENCE: 11

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                      Met Gly Thr Ser His Pro Ala
                                      1               5

ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg       511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc       607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg       655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac       703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc       751
```

-continued

```
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat     1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat     1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt     1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat     1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc     1711
```

-continued

```
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa     1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac     1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt     1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct     1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc     1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg     1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag     2047
Val Ile Val Ile Ile Ser Leu Ile Val Leu Val Val Ile Trp Lys Gln
                540                 545                 550

aaa ccg agg tat gaa att cgc tgg agg gtc att gaa tca atc cgc tat     2095
Lys Pro Arg Tyr Glu Ile Arg Trp Arg Val Ile Glu Ser Ile Arg Tyr
            555                 560                 565

att tat gtg gac ccg atg cag ctg cct tat gac tca aga tgg gag ttt     2143
Ile Tyr Val Asp Pro Met Gln Leu Pro Tyr Asp Ser Arg Trp Glu Phe
        570                 575                 580

cca aga gat gga cta gtg ctt ggt cgg gtc ttg ggg tct gga gcg ttt     2191
Pro Arg Asp Gly Leu Val Leu Gly Arg Val Leu Gly Ser Gly Ala Phe
    585                 590                 595

ggg aag gtg gtt gaa gga aca gcc tat gga tta agc cgg tcc caa cct     2239
Gly Lys Val Val Glu Gly Thr Ala Tyr Gly Leu Ser Arg Ser Gln Pro
600                 605                 610                 615

gtc atg aaa gtt gca gtg aag atg cta aaa ccc acg gcc aga tcc agt     2287
Val Met Lys Val Ala Val Lys Met Leu Lys Pro Thr Ala Arg Ser Ser
                620                 625                 630

gaa aaa caa gct ctc atg tct gaa ctg aag ata atg act cac ctg ggg     2335
Glu Lys Gln Ala Leu Met Ser Glu Leu Lys Ile Met Thr His Leu Gly
            635                 640                 645

cca cat ttg aac att gta aac ttg ctg gga gcc tgc acc aag tca ggc     2383
Pro His Leu Asn Ile Val Asn Leu Leu Gly Ala Cys Thr Lys Ser Gly
        650                 655                 660

ccc att tac atc atc aca gag tat tgc ttc tat gga gat ttg gtc aac     2431
Pro Ile Tyr Ile Ile Thr Glu Tyr Cys Phe Tyr Gly Asp Leu Val Asn
    665                 670                 675

tat ttg cat aag aat agg gat agc ttc ctg agc cac cac cca gag aag     2479
Tyr Leu His Lys Asn Arg Asp Ser Phe Leu Ser His His Pro Glu Lys
680                 685                 690                 695

cca aag aaa gag ctg gat atc ttt gga ttg aac cct gct gat gaa agc     2527
Pro Lys Lys Glu Leu Asp Ile Phe Gly Leu Asn Pro Ala Asp Glu Ser
                700                 705                 710

aca cgg agc tat gtt att tta tct ttt gaa aac aat ggt gac tac atg     2575
Thr Arg Ser Tyr Val Ile Leu Ser Phe Glu Asn Asn Gly Asp Tyr Met
            715                 720                 725

gac atg aag cag gct gat act aca cag tat gtc ccc atg cta gaa agg     2623
Asp Met Lys Gln Ala Asp Thr Thr Gln Tyr Val Pro Met Leu Glu Arg
        730                 735                 740

aaa gag gtt tct aaa tat tcc gac atc cag aga tca ctc tat gat cgt     2671
```

-continued

```
Lys Glu Val Ser Lys Tyr Ser Asp Ile Gln Arg Ser Leu Tyr Asp Arg
    745                 750                 755

cca gcc tca tat aag aag aaa tct atg tta gac tca gaa gtc aaa aac      2719
Pro Ala Ser Tyr Lys Lys Lys Ser Met Leu Asp Ser Glu Val Lys Asn
760                 765                 770                 775

ctc ctt tca gat gat aac tca gaa ggc ctt act tta ttg gat ttg ttg      2767
Leu Leu Ser Asp Asp Asn Ser Glu Gly Leu Thr Leu Leu Asp Leu Leu
                780                 785                 790

agc ttc acc tat caa gtt gcc cga gga atg gag ttt ttg gct tca aaa      2815
Ser Phe Thr Tyr Gln Val Ala Arg Gly Met Glu Phe Leu Ala Ser Lys
            795                 800                 805

aat tgt gtc cac cgt gat ctg gct gct cgc aac gtc ctc ctg gca caa      2863
Asn Cys Val His Arg Asp Leu Ala Ala Arg Asn Val Leu Leu Ala Gln
        810                 815                 820

gga aaa att gtg aag atc tgt gac ttt ggc ctg gcc aga gac atc atg      2911
Gly Lys Ile Val Lys Ile Cys Asp Phe Gly Leu Ala Arg Asp Ile Met
    825                 830                 835

cat gat tcg aac tat gtg tcg aaa ggc agt acc ttt ctg ccc gtg aag      2959
His Asp Ser Asn Tyr Val Ser Lys Gly Ser Thr Phe Leu Pro Val Lys
840                 845                 850                 855

tgg atg gct cct gag agc atc ttt gac aac ctc tac acc aca ctg agt      3007
Trp Met Ala Pro Glu Ser Ile Phe Asp Asn Leu Tyr Thr Thr Leu Ser
                860                 865                 870

gat gtc tgg tct tat ggc att ctg ctc tgg gag atc ttt tcc ctt ggt      3055
Asp Val Trp Ser Tyr Gly Ile Leu Leu Trp Glu Ile Phe Ser Leu Gly
            875                 880                 885

ggc acc cct tac ccc ggc atg atg gtg gat tct act ttc tac aat aag      3103
Gly Thr Pro Tyr Pro Gly Met Met Val Asp Ser Thr Phe Tyr Asn Lys
        890                 895                 900

atc aag agt ggg tac cgg atg gcc aag cct gac cac gct acc agt gaa      3151
Ile Lys Ser Gly Tyr Arg Met Ala Lys Pro Asp His Ala Thr Ser Glu
    905                 910                 915

gtc tac gag atc atg gtg aaa tgc tgg aac agt gag ccg gag aag aga      3199
Val Tyr Glu Ile Met Val Lys Cys Trp Asn Ser Glu Pro Glu Lys Arg
920                 925                 930                 935

ccc tcc ttt tac cac ctg agt gag att gtg gag aat ctg ctg cct gga      3247
Pro Ser Phe Tyr His Leu Ser Glu Ile Val Glu Asn Leu Leu Pro Gly
                940                 945                 950

caa tat aaa aag agt tat gaa aaa att cac ctg gac ttc ctg aag agt      3295
Gln Tyr Lys Lys Ser Tyr Glu Lys Ile His Leu Asp Phe Leu Lys Ser
            955                 960                 965

gac cat cct gct gtg gca cgc atg cgt gtg gac tca gac aat gca tac      3343
Asp His Pro Ala Val Ala Arg Met Arg Val Asp Ser Asp Asn Ala Tyr
        970                 975                 980

att ggt gtc acc tac aaa aac gag gaa gac aag ctg aag gac tgg gag      3391
Ile Gly Val Thr Tyr Lys Asn Glu Glu Asp Lys Leu Lys Asp Trp Glu
    985                 990                 995

ggt  ggt ctg gat gag cag  aga ctg agc gct gac  agt ggc tac atc      3436
Gly  Gly Leu Asp Glu Gln  Arg Leu Ser Ala Asp  Ser Gly Tyr Ile
1000                 1005                 1010

att  cct ctg cct gac att  gac cct gtc cct gag  gag gag gac ctg      3481
Ile  Pro Leu Pro Asp Ile  Asp Pro Val Pro Glu  Glu Glu Asp Leu
1015                 1020                 1025

ggc  aag agg aac aga cac  agc tcg cag acc tct  gaa gag agt gcc      3526
Gly  Lys Arg Asn Arg His  Ser Ser Gln Thr Ser  Glu Glu Ser Ala
1030                 1035                 1040

att  gag acg ggt tcc agc  agt tcc acc ttc atc  aag aga gag gac      3571
Ile  Glu Thr Gly Ser Ser  Ser Ser Thr Phe Ile  Lys Arg Glu Asp
1045                 1050                 1055

gag  acc att gaa gac atc  gac atg atg gac gac  atc ggc ata gac      3616
```

-continued

```
Glu  Thr Ile Glu Asp Ile  Asp Met Met Asp Asp  Ile Gly Ile Asp
1060                 1065                 1070

tct  tca gac ctg gtg gaa  gac agc ttc ctg taa  ctggcggatt          3659
Ser  Ser Asp Leu Val Glu  Asp Ser Phe Leu
1075                 1080

cgaggggttc cttccacttc tggggccacc tctggatccc gttcagaaaa ccactttatt   3719

gcaatgcgga ggttgagagg aggacttggt tgatgtttaa agagaagttc ccagccaagg   3779

gcctcgggga gcgttctaaa tatgaatgaa tgggatattt tgaaatgaac tttgtcagtg   3839

ttgcctctcg caatgcctca gtagcatctc agtggtgtgt gaagtttgga gatagatgga   3899

taagggaata ataggccaca gaaggtgaac tttgtgcttc aaggacattg gtgagagtcc   3959

aacagacaca atttatactg cgacagaact tcagcattgt aattatgtaa ataactctaa   4019

ccaaggctgt gtttagattg tattaactat cttctttgga cttctgaaga gaccactcaa   4079

tccatccatg tacttccctc ttgaaacctg atgtcagctg ctgttgaact ttttaaagaa   4139

gtgcatgaaa aaccattttt gaaccttaaa aggtactggt actatagcat tttgctatct   4199

tttttagtgt taagagataa agaataataa ttaaccaacc ttgtttaata gatttgggtc   4259

atttagaagc ctgacaactc attttcatat tgtaatctat gtttataata ctactactgt   4319

tatcagtaat gctaaatgtg taataatgta acatgatttc cctccagaga aagcacaatt   4379

taaaacaatc cttactaagt aggtgatgag tttgacagtt tttgacattt atattaaata   4439

acatgtttct ctataaagta tggtaatagc tttagtgaat taaatttagt tgagcataga   4499

gaacaaagta aaagtagtgt tgtccaggaa gtcagaattt ttaactgtac tgaataggtt   4559

ccccaatcca tcgtattaaa aaacaattaa ctgccctctg aaataatggg attagaaaca   4619

aacaaaactc ttaagtccta aaagttctca atgtagaggc ataaacctgt gctgaacata   4679

acttctcatg tatattaccc aatggaaaat ataatgatca gcaaaaagac tggatttgca   4739

gaagtttttt tttttttct tcatgcctga tgaaagcttt ggcaacccca atatatgtat   4799

tttttgaatc tatgaacctg aaaagggtca gaaggatgcc cagacatcag cctccttctt   4859

tcacccctta ccccaaagag aaagagtttg aaactcgaga ccataaagat attctttagt   4919

ggaggctgga tgtgcattag cctggatcct cagttctcaa atgtgtgtgg cagccaggat   4979

gactagatcc tgggtttcca tccttgagat tctgaagtat gaagtctgag ggaaaccaga   5039

gtctgtattt ttctaaactc cctggctgtt ctgatcggcc agttttcgga aacactgact   5099

taggtttcag gaagttgcca tgggaaacaa ataatttgaa ctttggaaca gggttggaat   5159

tcaaccacgc aggaagccta ctatttaaat ccttggcttc aggttagtga catttaatgc   5219

catctagcta gcaattgcga ccttaattta actttccagt cttagctgag gctgagaaag   5279

ctaaagtttg gttttgacag gttttccaaa agtaaagatg ctacttccca ctgtatgggg   5339

gagattgaac tttccccgtc tcccgtcttc tgcctcccac tccatacccc gccaaggaaa   5399

ggcatgtaca aaaattatgc aattcagtgt tccaagtctc tgtgtaacca gctcagtgtt   5459

ttggtggaaa aaacatttta agttttactg ataatttgag gttagatggg aggatgaatt   5519

gtcacatcta tccacactgt caaacaggtt ggtgtgggtt cattggcatt ctttgcaata   5579

ctgcttaatt gctgatacca tatgaatgaa acatgggctg tgattactgc aatcactgtg   5639

ctatcggcag atgatgcttt ggaagatgca gaagcaataa taaagtactt gactacctac   5699

tggtgtaatc tcaatgcaag ccccaacttt cttatccaac tttttcatag taagtgcgaa   5759

gactgagcca gattggccaa ttaaaaacga aaacctgact aggttctgta gagccaatta   5819

gacttgaaat acgtttgtgt ttctagaatc acagctcaag cattctgttt atcgctcact   5879
```

```
ctcccttgta cagccttatt ttgttggtgc tttgcatttt gatattgctg tgagccttgc   5939

atgacatcat gaggccggat gaaacttctc agtccagcag tttccagtcc taacaaatgc   5999

tcccacctga atttgtatat gactgcattt gtgggtgtgt gtgtgttttc agcaaattcc   6059

agatttgttt ccttttggcc tcctgcaaag tctccagaag aaaatttgcc aatctttcct   6119

actttctatt tttatgatga caatcaaagc cggcctgaga aacactattt gtgacttttt   6179

aaacgattag tgatgtcctt aaaatgtggt ctgccaatct gtacaaaatg gtcctatttt   6239

tgtgaagagg gacataagat aaaatgatgt tatacatcaa tatgtatata tgtatttcta   6299

tatagacttg gagaatactg ccaaaacatt tatgacaagc tgtatcactg ccttcgttta   6359

tatttttttta actgtgataa tccccacagg cacattaact gttgcacttt tgaatgtcca   6419

aaatttatat tttagaaata ataaaaagaa agatacttac atgttcccaa aacaatggtg   6479

tggtgaatgt gtgagaaaaa ctaacttgat agggtctacc aatacaaaat gtattacgaa   6539

tgcccctgtt catgttttttg ttttaaaacg tgtaaatgaa gatctttata tttcaataaa   6599

tgatatataa tttaaagtt                                                6618

<210> SEQ ID NO 12
<211> LENGTH: 1084
<212> TYPE: PRT
<213> ORGANISM: Homo sapiens

<400> SEQUENCE: 12

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240
```

-continued

```
Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Arg Tyr Ile Tyr Val Asp Pro Met Gln Leu Pro
                565                 570                 575

Tyr Asp Ser Arg Trp Glu Phe Pro Arg Asp Gly Leu Val Leu Gly Arg
            580                 585                 590

Val Leu Gly Ser Gly Ala Phe Gly Lys Val Val Glu Gly Thr Ala Tyr
        595                 600                 605

Gly Leu Ser Arg Ser Gln Pro Val Met Lys Val Ala Val Lys Met Leu
    610                 615                 620

Lys Pro Thr Ala Arg Ser Ser Glu Lys Gln Ala Leu Met Ser Glu Leu
625                 630                 635                 640

Lys Ile Met Thr His Leu Gly Pro His Leu Asn Ile Val Asn Leu Leu
                645                 650                 655

Gly Ala Cys Thr Lys Ser Gly Pro Ile Tyr Ile Ile Thr Glu Tyr Cys
            660                 665                 670
```

```
Phe Tyr Gly Asp Leu Val Asn Tyr Leu His Lys Asn Arg Asp Ser Phe
        675                 680                 685

Leu Ser His His Pro Glu Lys Pro Lys Lys Glu Leu Asp Ile Phe Gly
    690                 695                 700

Leu Asn Pro Ala Asp Glu Ser Thr Arg Ser Tyr Val Ile Leu Ser Phe
705                 710                 715                 720

Glu Asn Asn Gly Asp Tyr Met Asp Met Lys Gln Ala Asp Thr Thr Gln
                725                 730                 735

Tyr Val Pro Met Leu Glu Arg Lys Glu Val Ser Lys Tyr Ser Asp Ile
            740                 745                 750

Gln Arg Ser Leu Tyr Asp Arg Pro Ala Ser Tyr Lys Lys Lys Ser Met
        755                 760                 765

Leu Asp Ser Glu Val Lys Asn Leu Leu Ser Asp Asp Asn Ser Glu Gly
    770                 775                 780

Leu Thr Leu Leu Asp Leu Leu Ser Phe Thr Tyr Gln Val Ala Arg Gly
785                 790                 795                 800

Met Glu Phe Leu Ala Ser Lys Asn Cys Val His Arg Asp Leu Ala Ala
                805                 810                 815

Arg Asn Val Leu Leu Ala Gln Gly Lys Ile Val Lys Ile Cys Asp Phe
            820                 825                 830

Gly Leu Ala Arg Asp Ile Met His Asp Ser Asn Tyr Val Ser Lys Gly
        835                 840                 845

Ser Thr Phe Leu Pro Val Lys Trp Met Ala Pro Glu Ser Ile Phe Asp
    850                 855                 860

Asn Leu Tyr Thr Thr Leu Ser Asp Val Trp Ser Tyr Gly Ile Leu Leu
865                 870                 875                 880

Trp Glu Ile Phe Ser Leu Gly Gly Thr Pro Tyr Pro Gly Met Met Val
                885                 890                 895

Asp Ser Thr Phe Tyr Asn Lys Ile Lys Ser Gly Tyr Arg Met Ala Lys
            900                 905                 910

Pro Asp His Ala Thr Ser Glu Val Tyr Glu Ile Met Val Lys Cys Trp
        915                 920                 925

Asn Ser Glu Pro Glu Lys Arg Pro Ser Phe Tyr His Leu Ser Glu Ile
    930                 935                 940

Val Glu Asn Leu Leu Pro Gly Gln Tyr Lys Lys Ser Tyr Glu Lys Ile
945                 950                 955                 960

His Leu Asp Phe Leu Lys Ser Asp His Pro Ala Val Ala Arg Met Arg
                965                 970                 975

Val Asp Ser Asp Asn Ala Tyr Ile Gly Val Thr Tyr Lys Asn Glu Glu
            980                 985                 990

Asp Lys Leu Lys Asp Trp Glu Gly  Gly Leu Asp Glu Gln  Arg Leu Ser
        995                 1000                1005

Ala Asp  Ser Gly Tyr Ile Ile  Pro Leu Pro Asp Ile  Asp Pro Val
    1010                1015                1020

Pro Glu  Glu Glu Asp Leu Gly  Lys Arg Asn Arg His  Ser Ser Gln
    1025                1030                1035

Thr Ser  Glu Glu Ser Ala Ile  Glu Thr Gly Ser Ser  Ser Ser Thr
    1040                1045                1050

Phe Ile  Lys Arg Glu Asp Glu  Thr Ile Glu Asp Ile  Asp Met Met
    1055                1060                1065

Asp Asp  Ile Gly Ile Asp Ser  Ser Asp Leu Val Glu  Asp Ser Phe
    1070                1075                1080

Leu
```

<210> SEQ ID NO 13
<211> LENGTH: 12
<212> TYPE: PRT
<213> ORGANISM: Homo sapiens

<400> SEQUENCE: 13

Tyr Val His Arg Asp Leu Ala Ala Arg Asn Ile Leu
1               5                   10

<210> SEQ ID NO 14
<211> LENGTH: 12
<212> TYPE: PRT
<213> ORGANISM: Homo sapiens

<400> SEQUENCE: 14

Cys Ile His Arg Asp Leu Ala Ala Arg Asn Val Leu
1               5                   10

<210> SEQ ID NO 15
<211> LENGTH: 12
<212> TYPE: PRT
<213> ORGANISM: Homo sapiens

<400> SEQUENCE: 15

Phe Val His Arg Asp Leu Ala Ala Arg Asn Cys Met
1               5                   10

<210> SEQ ID NO 16
<211> LENGTH: 12
<212> TYPE: PRT
<213> ORGANISM: Homo sapiens

<400> SEQUENCE: 16

Leu Val His Arg Asp Leu Ala Ala Arg Asn Val Leu
1               5                   10

<210> SEQ ID NO 17
<211> LENGTH: 12
<212> TYPE: PRT
<213> ORGANISM: Homo sapiens

<400> SEQUENCE: 17

Phe Ile His Arg Asp Ile Ala Ala Arg Asn Cys Leu
1               5                   10

<210> SEQ ID NO 18
<211> LENGTH: 12
<212> TYPE: PRT
<213> ORGANISM: Homo sapiens

<400> SEQUENCE: 18

Phe Val His Arg Asp Leu Ala Thr Arg Asn Cys Leu
1               5                   10

<210> SEQ ID NO 19
<211> LENGTH: 191150
<212> TYPE: DNA
<213> ORGANISM: Homo sapiens
<220> FEATURE:
<221> NAME/KEY: exon
<222> LOCATION: (1)..(49)
<220> FEATURE:
<221> NAME/KEY: Intron
<222> LOCATION: (50)..(2330)
<220> FEATURE:
<221> NAME/KEY: exon
<222> LOCATION: (2331)..(2648)
<220> FEATURE:
<221> NAME/KEY: Intron
<222> LOCATION: (2649)..(4902)
<220> FEATURE:
<221> NAME/KEY: exon
<222> LOCATION: (4903)..(5163)
<220> FEATURE:
<221> NAME/KEY: Intron
<222> LOCATION: (5164)..(6154)
<220> FEATURE:
<221> NAME/KEY: exon
<222> LOCATION: (6155)..(6285)
<220> FEATURE:
<221> NAME/KEY: Intron
<222> LOCATION: (6286)..(8524)
<220> FEATURE:
<221> NAME/KEY: exon
<222> LOCATION: (8525)..(8696)
<220> FEATURE:
<221> NAME/KEY: Intron
<222> LOCATION: (8697)..(8787)
<220> FEATURE:
<221> NAME/KEY: exon
<222> LOCATION: (8788)..(8977)
<220> FEATURE:
<221> NAME/KEY: Intron
<222> LOCATION: (8978)..(166510)
<220> FEATURE:
<221> NAME/KEY: Unsure
<222> LOCATION: (10577)..(10676)
<223> OTHER INFORMATION: n = any nucleic acid
<220> FEATURE:
<221> NAME/KEY: misc_feature
<222> LOCATION: (10577)..(10676)
<223> OTHER INFORMATION: n is a, c, g, or t
<220> FEATURE:
<221> NAME/KEY: Unsure
<222> LOCATION: (14335)..(14434)
<223> OTHER INFORMATION: n = any nucleic acid
<220> FEATURE:
<221> NAME/KEY: misc_feature
<222> LOCATION: (14335)..(14434)
<223> OTHER INFORMATION: n is a, c, g, or t
<220> FEATURE:
<221> NAME/KEY: Unsure
<222> LOCATION: (16247)..(16346)
<223> OTHER INFORMATION: n = any nucleic acid
<220> FEATURE:
<221> NAME/KEY: misc_feature
<222> LOCATION: (16247)..(16346)
<223> OTHER INFORMATION: n is a, c, g, or t
<220> FEATURE:
<221> NAME/KEY: misc_feature
<222> LOCATION: (17457)..(17457)
<223> OTHER INFORMATION: n is a, c, g, or t
<220> FEATURE:
<221> NAME/KEY: misc_feature
<222> LOCATION: (21818)..(21818)
<223> OTHER INFORMATION: n is a, c, g, or t
<220> FEATURE:
<221> NAME/KEY: misc_feature
<222> LOCATION: (36293)..(36298)
<223> OTHER INFORMATION: n is a, c, g, or t
<220> FEATURE:
<221> NAME/KEY: misc_feature
<222> LOCATION: (36314)..(36314)
<223> OTHER INFORMATION: n is a, c, g, or t
<220> FEATURE:
<221> NAME/KEY: misc_feature
<222> LOCATION: (36316)..(36316)
<223> OTHER INFORMATION: n is a, c, g, or t
<220> FEATURE:
<221> NAME/KEY: misc_feature
<222> LOCATION: (36432)..(36433)
<223> OTHER INFORMATION: n is a, c, g, or t
<220> FEATURE:
<221> NAME/KEY: Unsure
<222> LOCATION: (36774)..(36873)
<223> OTHER INFORMATION: n = any nucleic acid
<220> FEATURE:
<221> NAME/KEY: misc_feature
<222> LOCATION: (36774)..(36873)
<223> OTHER INFORMATION: n is a, c, g, or t
<220> FEATURE:
<221> NAME/KEY: Unsure
<222> LOCATION: (59740)..(59740)
<223> OTHER INFORMATION: n = any nucleic acid
<220> FEATURE:
<221> NAME/KEY: misc_feature
<222> LOCATION: (59740)..(59740)
<223> OTHER INFORMATION: n is a, c, g, or t
<220> FEATURE:
<221> NAME/KEY: Unsure
<222> LOCATION: (59742)..(59742)
<223> OTHER INFORMATION: n = any nucleic acid
<220> FEATURE:
<221> NAME/KEY: misc_feature
<222> LOCATION: (59742)..(59744)
<223> OTHER INFORMATION: n is a, c, g, or t
<220> FEATURE:
<221> NAME/KEY: Unsure
<222> LOCATION: (59744)..(59744)
<223> OTHER INFORMATION: n = any nucleic acid
<220> FEATURE:
<221> NAME/KEY: Unsure
<222> LOCATION: (59749)..(59755)
<223> OTHER INFORMATION: n = any nucleic acid
<220> FEATURE:
<221> NAME/KEY: misc_feature
<222> LOCATION: (59749)..(59755)
<223> OTHER INFORMATION: n is a, c, g, or t
<220> FEATURE:
<221> NAME/KEY: Unsure
<222> LOCATION: (59759)..(59760)
<223> OTHER INFORMATION: n = any nucleic acid
<220> FEATURE:
<221> NAME/KEY: misc_feature
<222> LOCATION: (59759)..(59760)
<223> OTHER INFORMATION: n is a, c, g, or t
<220> FEATURE:
<221> NAME/KEY: misc_feature
<222> LOCATION: (59765)..(59766)
<223> OTHER INFORMATION: n is a, c, g, or t
<220> FEATURE:
<221> NAME/KEY: Unsure
<222> LOCATION: (59776)..(59875)
<223> OTHER INFORMATION: n = any nucleic acid
<220> FEATURE:
<221> NAME/KEY: misc_feature
<222> LOCATION: (59776)..(59875)
<223> OTHER INFORMATION: n is a, c, g, or t
<220> FEATURE:
<221> NAME/KEY: Unsure
<222> LOCATION: (82745)..(82844)
<223> OTHER INFORMATION: n = any nucleic acid
<220> FEATURE:
<221> NAME/KEY: misc_feature
<222> LOCATION: (82745)..(82844)
<223> OTHER INFORMATION: n is a, c, g, or t
<220> FEATURE:
<221> NAME/KEY: Unsure
<222> LOCATION: (96508)..(96607)
<223> OTHER INFORMATION: n = any nucleic acid
<220> FEATURE:
<221> NAME/KEY: misc_feature
<222> LOCATION: (96508)..(96607)
<223> OTHER INFORMATION: n is a, c, g, or t
<220> FEATURE:
<221> NAME/KEY: Unsure
<222> LOCATION: (147675)..(147774)
<223> OTHER INFORMATION: n = any nucleic acid
<220> FEATURE:
<221> NAME/KEY: misc_feature
<222> LOCATION: (147675)..(147774)
<223> OTHER INFORMATION: n is a, c, g, or t
<220> FEATURE:
<221> NAME/KEY: Unsure
<222> LOCATION: (157152)..(157251)
<223> OTHER INFORMATION: n = any nucleic acid
<220> FEATURE:
<221> NAME/KEY: misc_feature
<222> LOCATION: (157152)..(157251)
<223> OTHER INFORMATION: n is a, c, g, or t
<220> FEATURE:
<221> NAME/KEY: misc_feature
<222> LOCATION: (161475)..(161574)
<223> OTHER INFORMATION: n is a, c, g, or t
<220> FEATURE:
<221> NAME/KEY: Unsure
<222> LOCATION: (165240)..(165339)
<223> OTHER INFORMATION: n = any nucleic acid
<220> FEATURE:
<221> NAME/KEY: misc_feature
<222> LOCATION: (165240)..(165339)
<223> OTHER INFORMATION: n is a, c, g, or t
<220> FEATURE:
<221> NAME/KEY: exon
<222> LOCATION: (166511)..(166626)
<220> FEATURE:
<221> NAME/KEY: Intron
<222> LOCATION: (166627)..(168271)
<220> FEATURE:
<221> NAME/KEY: exon
<222> LOCATION: (168272)..(168398)
<220> FEATURE:
<221> NAME/KEY: Intron
<222> LOCATION: (168399)..(169414)
<220> FEATURE:
<221> NAME/KEY: exon
<222> LOCATION: (169415)..(169608)
<220> FEATURE:
<221> NAME/KEY: Intron
<222> LOCATION: (169609)..(170408)
<220> FEATURE:
<221> NAME/KEY: exon
<222> LOCATION: (170409)..(170503)
<220> FEATURE:
<221> NAME/KEY: Intron
<222> LOCATION: (170504)..(170718)
<220> FEATURE:
<221> NAME/KEY: exon
<222> LOCATION: (170719)..(170851)
<220> FEATURE:
<221> NAME/KEY: Intron
<222> LOCATION: (170852)..(173265)
<220> FEATURE:
<221> NAME/KEY: exon
<222> LOCATION: (173266)..(173370)
<220> FEATURE:
<221> NAME/KEY: Intron
<222> LOCATION: (173371)..(173773)
<220> FEATURE:
<221> NAME/KEY: exon
<222> LOCATION: (173774)..(173884)
<220> FEATURE:
<221> NAME/KEY: Intron
<222> LOCATION: (173885)..(174239)
<220> FEATURE:
<221> NAME/KEY: exon
<222> LOCATION: (174240)..(174393)
<220> FEATURE:
<221> NAME/KEY: Intron
<222> LOCATION: (174394)..(176193)
<220> FEATURE:
<221> NAME/KEY: exon
<222> LOCATION: (176194)..(176360)
<220> FEATURE:
<221> NAME/KEY: Intron
<222> LOCATION: (176361)..(181248)
<220> FEATURE:
<221> NAME/KEY: exon
<222> LOCATION: (181249)..(181364)
<220> FEATURE:
<221> NAME/KEY: Intron
<222> LOCATION: (181365)..(181718)
<220> FEATURE:
<221> NAME/KEY: exon
<222> LOCATION: (181719)..(181841)
<220> FEATURE:

<221> NAME/KEY: Intron
<222> LOCATION: (181842)..(183307)
<220> FEATURE:
<221> NAME/KEY: exon
<222> LOCATION: (183308)..(183419)
<220> FEATURE:
<221> NAME/KEY: Intron
<222> LOCATION: (183420)..(184676)
<220> FEATURE:
<221> NAME/KEY: exon
<222> LOCATION: (184677)..(184776)
<220> FEATURE:
<221> NAME/KEY: Intron
<222> LOCATION: (184777)..(184886)
<220> FEATURE:
<221> NAME/KEY: exon
<222> LOCATION: (184887)..(184992)
<220> FEATURE:
<221> NAME/KEY: Intron
<222> LOCATION: (184993)..(186190)
<220> FEATURE:
<221> NAME/KEY: exon
<222> LOCATION: (186191)..(186432)
<220> FEATURE:
<221> NAME/KEY: Intron
<222> LOCATION: (186433)..(191002)
<220> FEATURE:
<221> NAME/KEY: exon
<222> LOCATION: (191003)..(191150)

<400> SEQUENCE: 19

```
atg ggg act tcc cat ccg gcg ttc ctg gtc tta ggc tgt ctt ctc aca g      49
Met Gly Thr Ser His Pro Ala Phe Leu Val Leu Gly Cys Leu Leu Thr
1               5                   10                  15

gtacggagcc cagtcctctc tgagttcctt gtttgggtgt cttgtttttt taagctttgt    109

gctgcatggg tttattacca gtactctgca tacacagtcc aaaagagtga aaagaaatag    169

aaaactatag gacgttatcc agaatgacca caaaccttca gttccctttg ctgtattgca    229

cttactccat ttcaaaagga atgctctcca gtggcagttt tagtacatat ataatgttgg    289

cattgaaatg ttgttagtaa taatgtctaa atttacttac tactctcttc cttttcctag    349

gacaaggctt ctattagagc tggattagat aaattcagga atggtcagct gtgggaggtg    409

gcacatctgt tgtcccagcc ccttgagcag ctgaggtggg atgatcccct taaggccagg    469

agttcaaggg ttgcagtgca ctgtgattat gcctgtgact agccaccaca ctccagcaac    529

atagcaagac ctcatttaaa aaaaatgttc aaaggaaata aataatagaa aattcttgcc    589

caagaaatca tacttgtctt aaatcataac tctcttgagg aaagatgctt acattgcttc    649

taaatctcag agtcaccttt atcttctcta ggaatcaaat tgatagatga atgtttggct    709

cttggaaaat cttaaaaact ttcccaccaa aaggatcatt ggggtaattt gttgaagtgt    769

gtattggact gtcttagttt tcctccagat atttatgcac tgcagatgtt cgccatgaaa    829

ccagtgctct tctattctga ggagttagct cagcccgtta gtgtctttgt cttacccatt    889

tggatatggt agaattgagc aagaccagag attcaacagt tctaagctcc actaagtata    949

ccccatctac agagtaatag gtgatccaga tgtacttaca aatcctatct taacaagctt   1009

taggaattat agtggtcata tattgaagtt gggtgggagt ctcacaccag gttccaaggg   1069

agattacaaa tcactaatta ataattaagt cataaatatct cttctatcag tctcgggttt  1129

cttgttttct aagttctgtg ctccatgggt ttattatctg tactctgctt acacagtcca   1189

aaagagtgaa aagaaataga aaactacagg acgttatcca gaatgaccac aaaccttcag   1249

ttcctttgct gcattgcact tactctattg caaaaggagt aagtgcaatt tcagtctaaa   1309

taagcgagac tgaaatttga gcttcgaaga tgaacttaga gttttcactc ttgggtttta   1369
```

-continued

```
cttaccaatt gtgaattaaa atccgtatca tctggcacca ctgcactcca gcctgggtga   1429

cagagcaaga ctccatctca taaaaataaa gaaataaata aacaaataaa tccacatcat   1489

cctgctttgg ccctggaagt catgagggag agacggcatg cccgagggct ataagaaatg   1549

gaagatgtgg aattcttgag cacagatgtg ctttgtgttt tcttcagtct gtgtccttgc   1609

ctccattctt attccatgtg ggtttttttt tttttttttt tttttttttt tgagacaggt   1669

tttttttcct ttattgccca ggggggagtg caaaggctga ctgcaacctc aatcccctgg   1729

gctccagtga tcctcccacc tcagcctcca aagtagctag gactacaggt gtacaccagc   1789

acacctggct aattttttta ttttttttatt tttgggggag accaggtctc actacgttgc   1849

ccaggctggt ctcgaactcc tgagctcaag cgatcctccc acttccacct aacaaagtgc   1909

tgggattata aacatgagcc tttgcgcccc agcctttttt tttttaact aaaggaaacc   1969

tttgcagtga ttgtgaacca taaagaaccc atatgtgctt gagcccgtgc catcttggga   2029

tatttttatg gttacacata agagtctgaa atatggaatt ggaatcagac atcctctgtc   2089

tatttgagtg tttggagggg tgaatctagt ggggcttggt ggagctattt ggaacatttg   2149

ctgctctcag cagatgcagt ggctgttata atgggggagc tttcatgggc atccaggcta   2209

acggattttt gtgtagaaat ggtcattgtt catctaagct gctactgttg cttctctcag   2269

ttgtcgggat gagactgtcc tttctgactg catcctattc agagcgtgct tccttttgca   2329

g gg  ctg agc cta atc ctc tgc cag ctt tca tta ccc tct atc ctt cca   2377
  Gly Leu Ser Leu Ile Leu Cys Gln Leu Ser Leu Pro Ser Ile Leu Pro
              20                  25                  30

aat gaa aat gaa aag gtt gtg cag ctg aat tca tcc ttt tct ctg aga     2425
Asn Glu Asn Glu Lys Val Val Gln Leu Asn Ser Ser Phe Ser Leu Arg
        35                  40                  45

tgc ttt ggg gag agt gaa gtg agc tgg cag tac ccc atg tct gaa gaa     2473
Cys Phe Gly Glu Ser Glu Val Ser Trp Gln Tyr Pro Met Ser Glu Glu
    50                  55                  60

gag agc tcc gat gtg gaa atc aga aat gaa gaa aac aac agc ggc ctt     2521
Glu Ser Ser Asp Val Glu Ile Arg Asn Glu Glu Asn Asn Ser Gly Leu
65                  70                  75                  80

ttt gtg acg gtc ttg gaa gtg agc agt gcc tcg gcg gcc cac aca ggg     2569
Phe Val Thr Val Leu Glu Val Ser Ser Ala Ser Ala Ala His Thr Gly
                85                  90                  95

ttg tac act tgc tat tac aac cac act cag aca gaa gag aat gag ctt     2617
Leu Tyr Thr Cys Tyr Tyr Asn His Thr Gln Thr Glu Glu Asn Glu Leu
            100                 105                 110

gaa ggc agg cac att tac atc tat gtg cca g gtgagttggc tgggtctcca     2668
Glu Gly Arg His Ile Tyr Ile Tyr Val Pro
        115                 120

ggaccaagct tcttctcttc ctgtctctcc tgttaaatgt actaaggttt taaacatata   2728

tataaataat taatatttat tgcgggaagt ttgaaaaatg taagcgaaca cacacaaaaa   2788

tcatttgtaa tattatcaag aaatattcat tgttagcatt tcagagctgt attaagtttg   2848

gaaagtcatc tttgttatga catgtcctgt attgatactg tataaacaat ctgaaatata   2908

ctcatctcta ttcagttcat tcaagttgca cacatactca cagtgtgtcc agcactgggc   2968

taagtgttga gtacacaaaa attaataggt aagccctgtc ttggagttgc tgatagttca   3028

ttataatatc ttccaaataa acactcgatt tttcagattc actatcaaca tacatttatt   3088

cttggagagt tggaaggaat tttcttttttc cttttaaaaa agttacatat atatatatat   3148

atatatatat atatatatat tttttttttt tttggtaaca gggtctcact ctgttgccca   3208

ggctggaatg cagtggcatg atcatcatag cttactgcaa tctcaactcc cttggttcaa   3268
```

-continued

```
gcgattctcc cacttcagcc tccccagtag ctgggattac aggcatgcac caccacgccc   3328

agctaatttt tatattagtt gagacggggg tttcaccata ttgaccaggc tggtcttgaa   3388

ctcctgacct taagtgatct gcctgcttcg gcctcccaaa atgctgggat tacaggcgtg   3448

agccactgtg ccctaatttt tatttttatt tttgtagaga tagggtttca ctgtgttgcc   3508

caggctggtc tcaaactcct gggctcaagt gatccacagc cacctcagcc tcccaaagtt   3568

ctgggattac aggcacgagc cactgggcct ggcctactcc tgcattttaa ttaaaaggac   3628

aaaagggtcg agcacaagtg atggcaattt cagtatgcag ttgggtaaat taaaaaggac   3688

tatggctaga atccttggtt ttagaacaaa acctaaactg tttatgattc ttgccatcct   3748

tgctgttttg gcataggtgt gtcttcctac ctttctgcct tttctttttc agtttttaat   3808

gggctcctct ttctaccctg tataactacg agtgtcccca gggatctaga ccctctttac   3868

tttttcatga tactcttatt catatgaacc ttccttctta acaattaaaa aaaaccaaaa   3928

actttgtttt gaaaagggaa ggtatttaga atgtcactcc aacttcattc acacttagat   3988

tccttcagga aaatcctcta ggtgtggagg gattttcccc tgctgtgaag agaatggtag   4048

gaacgtgaat gtgttaaagg cacacgagtc cctgaagttt taatccgtgt aagattgtcc   4108

aaaaattttt cttgttccag cacagatgcc atccaagtag cccctgcatc gctgtctgac   4168

tgagatcttt ttattcgcaa tcatgcagac gtaggggccc tttctgcagc tgatgtttga   4228

gactgttaga acttcttacc accgtagctt aagtagctgt ttttcttttg gaaaggaaat   4288

tctcaggctc cttctccttc tttaaatttt atgtatttct caaaggatta ctttttaata   4348

aacagatttc tatgctattt ttgaatcata ctgactatag gtggtaagag tttttaaaag   4408

catttcataa taaaactcga aatatttttt cctgttttaa acagagttgg actgtattat   4468

tttattgtta atttttgttt ttagttgttt aaattttgat ttagattcct ggttagtatt   4528

tatttattta tttgtagaga cagggtctct ctatgttgcc caggctggtc tcaaactcct   4588

gaacacaagc aaccctccca ccttggcttc ccaaagtgct gggattacag gcatgagcca   4648

caactcctgt ccagtattga tatttatcat cagtattatc catcaggaga caggcaattt   4708

ggtattattc atacttaaaa atcactttgt agctgtcatg ataactaatg ccagtggggc   4768

aattcttctg gatatatgtg taaaggtgaa cttcatacct aatatcaata atgccagtgg   4828

gatagttttt ctggatttat gtgtaaaggt gaaattaatg tctaatagag tcttcattct   4888

tttttaaacc acag ac  cca gat gta gcc ttt gta cct cta gga atg acg     4937
                Asp Pro Asp Val Ala Phe Val Pro Leu Gly Met Thr
                        125                 130

gat tat tta gtc atc gtg gag gat gat gat tct gcc att ata cct tgt     4985
Asp Tyr Leu Val Ile Val Glu Asp Asp Asp Ser Ala Ile Ile Pro Cys
135                 140                 145                 150

cgc aca act gat ccc gag act cct gta acc tta cac aac agt gag ggg     5033
Arg Thr Thr Asp Pro Glu Thr Pro Val Thr Leu His Asn Ser Glu Gly
                155                 160                 165

gtg gta cct gcc tcc tac gac agc aga cag ggc ttt aat ggg acc ttc     5081
Val Val Pro Ala Ser Tyr Asp Ser Arg Gln Gly Phe Asn Gly Thr Phe
            170                 175                 180

act gta ggg ccc tat atc tgt gag gcc acc gtc aaa gga aag aag ttc     5129
Thr Val Gly Pro Tyr Ile Cys Glu Ala Thr Val Lys Gly Lys Lys Phe
        185                 190                 195

cag acc atc cca ttt aat gtt tat gct tta aaa g gtacttgtat            5173
Gln Thr Ile Pro Phe Asn Val Tyr Ala Leu Lys
    200                 205

catctccttc cttctttaaa taagagtaac aggcaaaatc ataaggtgcg tgtaggattt   5233
```

-continued

```
tttttttttt ttaaatcatc atcactggtg atcctaaatt ctgatttggg gatttaggac   5293

cccagctaat acaatgtctg tggctataat aataagctta aaattactaa aggccaaagc   5353

ttgattaccc atgcaagatt tcatgtttca tcagttgact tcaaaatact gtaaggaatt   5413

cttttcttac ataagcctct tactttcatt cacattcctg actatggcgg ccctaaaaac   5473

aaacatacac ccagggggtt agatgcctag attaatttta gtaacttaag aaaagtgatt   5533

tgaagaaagt agtttagact tcaacccttt gatgtccaca gttagtacgc ttggggaagt   5593

ataatacatg ctgaggtcaa cagatatttc ctgaacacta tattacatgg aggaatgggt   5653

agcagcaaga gtacactgtt ttaaaatcag agcacagcta attttgtgcc aggcactgtg   5713

ctaggttctg ggaaagtact gagaataact gaggagcaga gtggaagaga agaagagaag   5773

aaacaattgg atagaaacaa agtgtctaga gcagtgtgga tcagcaaatg ttggttgatt   5833

aaatgaataa atttattagt caaggagatt gtggacgagt ataaccataa ctaacccact   5893

gctgaggaat gcggtgttct gtttgattgg aatttatttt tattgttatt attttgtaat   5953

tctgtattat aactatatgc ctaattgttg tacaccatct cacaatcaag ccttgtgaga   6013

ttttccaaat tttatcttga tcaaactggt ttgcaaatta tttttcaggg ttttcttaaa   6073

aaaaaaaaaa aaaacccaaa ctttataaga tcctggctat cctgtggatt tttaggccct   6133

tgtatttgtt ctttttata g ca  aca tca gag ctg gat cta gaa atg gaa      6183
                        Ala Thr Ser Glu Leu Asp Leu Glu Met Glu
                                            215

gct ctt aaa acc gtg tat aag tca ggg gaa acg att gtg gtc acc tgt      6231
Ala Leu Lys Thr Val Tyr Lys Ser Gly Glu Thr Ile Val Val Thr Cys
220                 225                 230                 235

gct gtt ttt aac aat gag gtg gtt gac ctt caa tgg act tac cct gga      6279
Ala Val Phe Asn Asn Glu Val Val Asp Leu Gln Trp Thr Tyr Pro Gly
                240                 245                 250

gaa gtg gtaggtaccc tcaaaacgtg caatggcttg gagcagagca acagggctca      6335
Glu Val

gaagacctgc atttgagctc ggtctgtcac tgatgggcac atcactgagt ttctctagac   6395

cttagcttcc cacctctggg atgaacacat ttgattaaat ggcctttagg actccttgat   6455

caatgggaga gtttgaaatg atagttcctg gaccaggccc ttcagaatac ataaagagtg   6515

tgccgtaagc cttcttttc agaagtcaga cagaaatagg aaggttctct ggctacaaga   6575

tatcaaccaa aaaattagaa gagcaaaaaa accactggat tttactattg cggagacagt   6635

gattgattct catcgtcttg gcttctgtgc cctgaggttt gattcatctg atagtgttga   6695

ttgcccgcac cccttcctct tctgccttgt tggcacccag gacaatgtgt cttcctgttc   6755

cacctcctat gtgcctgacc tttgcatggc tcaccttcag tgaaccgtta tgatgtaatc   6815

attcagcaaa ggtttaatga agtttgctca atcccaagca ctgtaccaga agctggttca   6875

gtattgcagg aagaagggag gaggggagat ggaagtgggg aaggggagcc accatgctgc   6935

ctcttggtca ctggagattt acagagtctc agtcattcta atgcattgtc actaagtgtg   6995

taagacagcc atgtgtaaga ggctatgaat gcccaaatgc aggaatgact aatattctta   7055

tggagaacaa aaacgagata tatatatttc ttgcctccac tcctgacttg taaatttctg   7115

ctccctgttc ttttaggcat ttgacagctt tctgtccttc tatccattga tctccctcct   7175

tttatccgtt tctctctccc atgcatttgc cgctgctttt catttgtcct ggggcatctg   7235

ataggaagtt gggcattttc actattgcct cacaaacttc acacagtgaa gggacattta   7295

cagtccaaca aatgtacatc ttccctgaaa tatgaagtga tttggttctt ctgttcatac   7355

ttgattgact ttaatcctta acacataaac actgctttct atttatagga gacagcaatt   7415
```

```
tttttttcca aaccgaagta catgctattt ggcttacaaa tatataatca aagtattgtt   7475

tcatacagta tgttttttcc gattataaaa gtaatgcagg tttattgcag aaactttgta   7535

aaatatggag agacaaagga aaggctactt cccagagcat cactgtttat attttaggga   7595

gataaagctt ttatttttca tttgtatttc tttcttttt ttttcttttt tcttttttt   7655

ttttgttgtg gagatgagga tctcactaca ttgcccaggc tggtctcaaa ctcctgggct   7715

taagtgatcc tcccaccttg gcctttcaaa gtgttgggat tgattacaca tgtgagcctc   7775

tgagcttgac tgagataaag ctcttaagta tttcttatcc atagataaac attgaataat   7835

aggtgttatt ctttaaatgg taatttatta cattctttat ccttcagcag tatagcacaa   7895

acaccttata tgtgtcatta actgtccttt taaaaaatgg gctgggtgtg gtggctcatg   7955

cctgtaatcc cagtactttg ggaggctgag gcaggagagt cacttgaggc caggagtttg   8015

agatcagcct gggcaatgta tcaagactcc gtctctacaa aaatttttaa aaattagcca   8075

ggtgtggtgg catgagcctg tagccccagc tactcaggag actgaggtgg gaggatcact   8135

tgaacccagg aggttggggc tgcagtgagc catgattgtg ccactgcact ccagcctggg   8195

cagcagagtg agattctgtc tctaaaaaaa ttaaaaacaa aataaaaaat ctcatgattt   8255

tctaagcagc tagcttttat tctttaggtt ttatctttta gagcagtttt aggtttacag   8315

caaaattgag aggtacagag atttcccatg tgttccctac acccacacat gtgtagcctc   8375

ccaccttgtc aacatcccta ccatccattt gttataactg ctgaacctcc attgacacat   8435

ccatatcatc cagagtccat agtttatctt agagttcact cctaggagcg agcttttttaa   8495

aagtcggttt tcttcccctt ttgctgtag aaa ggc aaa ggc atc aca atg ctg     8548
                                Lys Gly Lys Gly Ile Thr Met Leu
                                    255                 260

gaa gaa atc aaa gtc cca tcc atc aaa ttg gtg tac act ttg acg gtc     8596
Glu Glu Ile Lys Val Pro Ser Ile Lys Leu Val Tyr Thr Leu Thr Val
            265                 270                 275

ccc gag gcc acg gtg aaa gac agt gga gat tac gaa tgt gct gcc cgc     8644
Pro Glu Ala Thr Val Lys Asp Ser Gly Asp Tyr Glu Cys Ala Ala Arg
        280                 285                 290

cag gct acc agg gag gtc aaa gaa atg aag aaa gtc act att tct gtc     8692
Gln Ala Thr Arg Glu Val Lys Glu Met Lys Lys Val Thr Ile Ser Val
    295                 300                 305

cat g gtacattccg ctttctaaaa tgtcagttgt ccatgctgct cgggatccat        8746
His
310

atgtggtaat cattatttaa tggaaactct tccctgtaca g ag  aaa ggt ttc att   8801
                                              Glu Lys Gly Phe Ile
                                                              315

gaa atc aaa ccc acc ttc agc cag ttg gaa gct gtc aac ctg cat gaa     8849
Glu Ile Lys Pro Thr Phe Ser Gln Leu Glu Ala Val Asn Leu His Glu
                320                 325                 330

gtc aaa cat ttt gtt gta gag gtg cgg gcc tac cca cct ccc agg ata     8897
Val Lys His Phe Val Val Glu Val Arg Ala Tyr Pro Pro Pro Arg Ile
            335                 340                 345

tcc tgg ctg aaa aac aat ctg act ctg att gaa aat ctc act gag atc     8945
Ser Trp Leu Lys Asn Asn Leu Thr Leu Ile Glu Asn Leu Thr Glu Ile
        350                 355                 360

acc act gat gtg gaa aag att cag gaa ata ag  gtaaagaaac tctctgccca   8997
Thr Thr Asp Val Glu Lys Ile Gln Glu Ile Arg
    365                 370

agtatgcctt tttttagtgt gcatcagagg cggactgagg tttgtgtgtg tcttacaacc   9057

cagacccaaa gtcagtctag aaaatgtaac aatctgagtt aagagatgct tgaaatcaca   9117
```

```
tccctttaat gataacattg caaagtggta ttagtatgct ggtaagtatt taatgagaag   9177
atgagaagaa agaactaaaa gctctggccc ctggggaaag acaggtcact ggattcagct   9237
agggtggaag aaaggaagta aaattggact caccaggatt gaatagattg aatatattcc   9297
ctgatgttca tcatccatat cgcaagtaga cagatatggt gattacaccc atgaggcagt   9357
tatcacatca ccttacgtga aagttaacgt cataggctta atctggaacc catttgccct   9417
aattgaggac tccacaggaa agaagagtag agcctggcta atcaggagag agatgtgcag   9477
tgagttgctt ggatccctac cttttaatca gaatggtaga ttgctctcat ctcttaattg   9537
gtggtggagt tttgaatgag tcacccctca gccacagttt cctcatctac aatgtaggat   9597
aaacaatacc ttatgtcctt caaggcaagg aattggatca gatgatatca tgaggcctct   9657
taaggtttta agctgtgatt agaacccaag agtcagaaga tacatctcac agcacccagc   9717
taaccagccc tatacttttg tcagaaatca tctcagaaag acaaagtcag tcctgtattt   9777
caagccttca ggaggaagaa cagagccttt ctcatcagtt ccattcacct caggatttgc   9837
tttcttcttt gtgaactaaa ttccacgtgt aattgagaag caatgtctga gaaaatggaa   9897
ttttacagcc tctatagaat agtaaaggaa aaatgaagtg ggatactgaa tctggaaggc   9957
tttctgttga cacaaaatga aggtgtacaa caaggagggc agctttccac gaggaacttc  10017
catgaggctg tgcagccaga gaggaatagg gtaacaaccc tggtacagct aacacctcca  10077
acacgtgtgt gagcactgtc tgcaagccat aatccatagc agtggcagga caggctcgcc  10137
aactgagtgg ttctggaaag ctgccttttc cttttagtga ttcaaggatg cttcaacgtg  10197
gatttttag ttcctgttat gagccagtga atacaaagat gaacatggta gatgggggat  10257
ctggcttcct ggagcttaaa actccaggat gggggatctg gctttcctgg agcaagaaaa  10317
ccagtggttt tcttggccga agaagtgaag agaacaaaca gcagaggata atttggtaat  10377
cagcatccta gtgtgcccca gggtactctc ttaaggaaat ccagtcctgg agcacaccca  10437
gtatggtcca gcctgctgtc ttcgtaggtc tgagtgcccc agtatttgca aagtgttttg  10497
gagcctatga aatgctttca cacatacaat ctcctttaat taactctcac aatgactctg  10557
tgctatgtgt acaattatcn nnnnnnnnnn nnnnnnnnnn nnnnnnnnnn nnnnnnnnnn  10617
nnnnnnnnnn nnnnnnnnnn nnnnnnnnnn nnnnnnnnnn nnnnnnnnnn nnnnnnnnng  10677
tatgaaaccc acttgatcat agtggattat ctttttgata tgttgttgga ttgaggtagc  10737
tagtattttg ttaaggattt tagcatctat gttcatcaag gatttcagcc tgtagctttc  10797
tttcttggac gtgtcctttt ctggttttgg tattagggtg atgttggctt cacagaatga  10857
attaggaagg gttccttctt tctctatctt gtggaatagt gtcaaaagga ttggtaccaa  10917
ttcttctctg aatgtctgtt aggattctgc tgtgaatcca tctggtcccg gacatttttt  10977
tggttggtaa tttcttaatt accattccag tcttgctgct tgttattggt ctgttcagga  11037
tatccagtgc ttcctgattt aggctaggag ggttgtattt ttacaagaat ctatctatct  11097
cttctaggtt ttctagttta tatgtgtaaa ggtgttcatt atagccttgc attatctttt  11157
atatttcagt agtgtcactt gtaatatcgc ctgtttaatt tcttagtgag gttatttgga  11217
ttttctctct tcttttcttg gttaatcttg ctaatggtct atctatttaa tttatctttt  11277
caaaaaacca gtttttgtct catttattat ttgtgtgttt ttgtttgttt caatttcatt  11337
tagttctgct ctgacctttg ttatttcctt tcttctgctg ggtttgggtt tggtttgttt  11397
ttgtttctct aattccttga ggtgtgacct tagattgtca gtttgtgctc tttcagactt  11457
tttgatgtag gcatttactg ctttgaactt tcctcttagc actgcctttg ctgtatccta  11517
```

-continued

```
gaggttttga taggttatgt cattattatc attcagttca aagaattttt taatttctac  11577
cttgattttg ttttcgaccc aatgctcatt caggagcagg ttatttaatt tccatgtatt  11637
tggatggttt tgaaggtttc ttttggaatt gatttccagt tttatttcac tgtggtccga  11697
gagagtgctt gatatatttt caattttctt aaatttatcg aggctcattt tatggcctat  11757
catatggtct atcttggaga aagttccatg tgctgttgaa tgtgtactct gtggttgttg  11817
gataaaatgt tctgtatata tttgttaggt ccatttgctc caagaaacaa tccaatgttt  11877
ctttgttaac tttctgtctt gatgacctgt ctagtgctgt cagtggagta ttgaagtccc  11937
ctactattat attgctctct atctcatttc ttaggtctgt tagtaattgt tttataaatt  11997
tgggatctcc agtgttaggt gcatatatgt ttaggattgt gacattttcc tattggacaa  12057
ggccttttat cattatataa tgtccctctt tgtctctttt taccattgtt gctttaaagt  12117
ttgttatgtg tgtacttttg tttttttgtt tttggttttt gctttataac ttgtattttt  12177
gtttcatagg tcctgtgtga tttatgcttt aaagaggttc tgttttcatg tgtttccagg  12237
atttgtttca agatttaggg ctcctttttg cagttcttgt agtggcggta atggcaaatt  12297
ctctcatcat ttgtttgtct gaaaagacct gtatctttcc ttcatatatg atgcttagtt  12357
tcactggata caagattctt ggctgataat tgttttgttt gaggaggctg aagataggcc  12417
ccgaatccct tctagcttgt agggtttctg ctgagaactc tgctgttaat ttgatagatg  12477
tacctttata ggttacctgg tgcttctgtc tcacagctct taagattctt tccttcatct  12537
taactttgga taaccttatg acaatgtacc taggtgaaga tctttttgca gtcaatttcc  12597
caggtgttct ttgtgcttct tttatttggt tgtctaggtc tctcacaagg ccagggaagt  12657
tttcctcaat tagtccccca gatatatttt gtaggctttt agaattctct tctttttcag  12717
gaacattgat tattcttagg tttggttgtt taacataatc ccagacttct tggagccttt  12777
gttcatattt tcttattatt tttttctttg tctttgttgg attgggttaa ttcaaagact  12837
ttgtctttga gctctgaatt tctttcttct acttgttcaa ttctattgct gagactttcc  12897
acagcatttc gcatttctaa aagtatgtcc aaagtttcct gaatttatga ttgtttttc  12957
tttaagctat ctatttcctt gaatatatct cccgtcactt cttctattat tcttggattt  13017
ccttgcatcg tgctttgtct ttctccgatc cctccctgat caccctaata actaacctcc  13077
tgaattcttt ttcaggtaaa tcagaaattt cttcttggtt tggatccatt gctggtgaac  13137
tagtgtgatt atttgggggt gttgtagagc cttgttttgt catattacca gggttggttt  13197
tctgattcat tctcatttgg gtaggctctg tcagagggaa ggtctaaggc tgaaggctgt  13257
tgttcagatt cttttgtccc acggggtgtt cctttgatgt agtactctcc cctttttccta  13317
tggatgtggc ttcctgtgag ccgaacttca gtgactgttg tctctcttct gaatctagcc  13377
acccagcgag tctacctggc tctaggctgg taccaagggt tgtctgcaca gaatccagtg  13437
atgtgaacca tctatgggtc tctcagtcat ggataccagc acctgttcca gtggaggtgt  13497
tggagggtgc aatgaactct gagagggtcc ttagcttcgg tggtttaatg ctctattttt  13557
gtgctggttg gcctcctgcc aggaggtggt gctttccaga aagcattaac tgcagtagtg  13617
tgaagaggaa ccggcggtga gctgggccct agattcccaa gattacatgc cctttgtctt  13677
cactactagg gtgtataggg aagtaccatc aggttggggc agggctaggt gtgtctgagc  13737
tcagactctc cttgggtgga tcttgttgca cctgctgtca gggatggagg tgagattctc  13797
aggtcactgg agttgtgtac ctaggaggat tatggctgcc tctgctgagt cttgcaggtt  13857
gtcagggaag cagggtaaag ccagcagtca caggcctcac ccagctccca tgcaaactga  13917
```

acggccagta ttacttccac cgtgaccccc aaccagtatc cctgagtata tttccaggta 13977
gagggcgaga agggcttgaa aacttgcctg aggctatctg tctccaagct gtgggggaaa 14037
aaaagggctt aagttcttcc cctgcctatg aagtctgtac tccagatttg caccctcccc 14097
cgagttctgg ccaggaggct tcccgcccgt tccaattgtt acaaagttca gctagagaat 14157
tctttctccc tgtggagttt taccacctgc ccctctggcc gccctcccta tggatccccg 14217
tggtgccagt caggaattgg ctgcttgggg acccagcgag ctcccagggc ttttctgctg 14277
cttactacta ccccctgtat ttgctcagct gtctacttga ctcagtttca ggtaaagnnn 14337
nnnnnnnnnn nnnnnnnnnn nnnnnnnnnn nnnnnnnnnn nnnnnnnnnn nnnnnnnnnn 14397
nnnnnnnnnn nnnnnnnnnn nnnnnnnnnn nnnnnnnatt aggaaaagaa ggaagtcata 14457
ttgtctctgt ttgcagatga catgattgta taattagaaa accccatcgt ctcagcccaa 14517
aatctcctta agctgataaa cagcttcagc aaagtctcag gatacaaaac tcaaaatgca 14577
aaaatccaag cattcctata caccaagaac agacaaacag agagccaaat catgagtgaa 14637
ctcccattca caattgctgc aatgagaata aaatacctag gaatccaaat tataagggat 14697
gggagggaac tcttcaagga gaactacaaa ccactgctca atgaaataac agatgacaca 14757
aacaaatgga agaacattct gtgctcatag atgggaagaa tcaatattac aaaaatggcc 14817
atattgccca aagtgattta tagattcaat gctattccca ccaagcttca cagaattgga 14877
taaaaactac tttaaatttc atatggagct aaaaaagagc ctgcatagcc aagacaatct 14937
taagcaaaaa gaacaaagct ggaggcatca tgctacctaa cttcaaatta tactacaagg 14997
ctacagtaac caaaacagca tggtactggt accaaaacag atatatagac caatggaaca 15057
gaacagaggc ctcagaaata acaccacaca ccacacatct acaaccatct gatctttgac 15117
aaacctgaca aaaacaagca gtggggaaag gattccctat ttaataaatg gtgctaggac 15177
aactggctag ccatatgtag aaagctgaaa ctggatccct tccttacacc ttacacaaaa 15237
attaactcaa gatgaattaa agacttaagc atgagaccta aaaccacaaa aaccctagaa 15297
gaaagcctag gcaataccat tcaggacata ggcatgggca aagacttcat gactaaaaca 15357
ccaaaagcaa tggcaacaaa agccaaaata gacaaatggg atctaattaa actaaagagc 15417
ttctgcacag caaaagaaac tgtcatcaga gtgaagaggc aacctacaga atgggagaaa 15477
atttttgcaa tctatccatc tgacaaagga ctaatatcca gagtatacaa agaacttaag 15537
caaatttaca agaaaaaaac aactccatca aaaagcgggc aaagaatatg aacaaacact 15597
tctcaaaaga aaacatttat gcagccaaca gacacatgaa aaaatgctca tcatcactgg 15657
tcataagaga aaagcaaatc aaaaccacaa taagatacca tctcacacca gttagaatgg 15717
cgatcattaa aatgtcagga aacaacatgc tggagaggat gtggagaaat aagaacactt 15777
ttacactgtt ggtgggagtg taaattaatt taatcattat ggaatacagt gtggtgattc 15837
ctcaaggatc tagaactaga aatattattt gacccagcga tcccattact gggtatatac 15897
ccaaagaatt ataaaacatg ctgctatgaa gacatatgca catgtatgtt tattgcgcac 15957
tattcacaat agcaaagact tgaaacaaac ccaaatgccc atcaataata gactggatta 16017
agaaaatgtg gcacatatac accatggaat actatgcagc cattaaacag gatgagttca 16077
tgtcctttgt agggacatgg atgaagctgg aaaccatcat tctcagcaaa ctatcacaag 16137
gacagaaaac caaataccac atgttctcac tcataagtgg gagttgaaca atgaaaacac 16197
atggacacag gaaggggaac atcccacacc agggcttgtt gggggtgggn nnnnnnnnnn 16257
nnnnnnnnnn nnnnnnnnnn nnnnnnnnnn nnnnnnnnnn nnnnnnnnnn nnnnnnnnnn 16317

```
nnnnnnnnnn nnnnnnnnnn nnnnnnnnna aggtatgtag ggtatctagt aggaaaagca  16377
ccctgggagg ctaaagcagg aggatcactt gagctcagga gttcaagact agccttggca  16437
acacattgag atgctgtctc tacaaaaaaa attaaacatt agccaagtgt ggtggtgcat  16497
acctatagtc ccagctactt gggaggctga ggcagaaggg ttgcttgaga ccagggggtg  16557
gaacctgcag taagccatga ttgtgccact gtactccagc ctgcgtgaca aagagagaac  16617
ttaaacaaac aaaaacctca tagattctga caaaaaagac acgatgcaaa ataatactgg  16677
tgtgaggggc aattacggga gacactcatt tatgttttgt cttctctgtt taggaggtgt  16737
ggtgtaagga gtgacatttc ggcccctcac actgtttatt cttttgcagg tgggtgagat  16797
agaagtctat aaaggggaaa gagaagaagc tgatgctgaa acttaagaga tatttctcca  16857
agactagaga aagacaagaa gaaaggagcc tctgagagtg ataagaggcc caaggtttgc  16917
atgcatggag caccagtaag agatggcttc aggaagccag agagctaggc cggggacaca  16977
gataccttgg gaaccacagc gagagtgtcc gtgggctgag gcagtggtca gtggagagac  17037
ccattgagag gtgacaacat gctagtagcc ctgcctcgct ctcggcacct cctcaagcca  17097
cggtgtccac tctggccgcg cttgaggaac ccttctgctt gcagggaggt gtggagggag  17157
aggcgcgggc gggaaccggg gccgtgcccc gtgctcgccg gccagcgcga gttccggatg  17217
ggcgtgggct cggcgggccc cgcacttgga gcggccggcc ggcgccaccg caccagtcag  17277
tgaggggctt agcacccggg ccagcatctg cagagggtgc gccgggtccc tcagcagtgc  17337
tggcccaccg ggtcggcgct cgaattctcg tcgggcctca gctgccttcc tcccccggct  17397
cccccgactc ccatggctgg cgactggcag cccgccatgc gcgagccccc ggagccccgn  17457
cgccccgccc cctccccacc ccctgctccg cggcgcccgg ccccatcgat gcccaacggc  17517
tgaggagtgc gggcacatgg cggggcactg gtgggcagct ctgccagcag ccttggggcg  17577
ggaatccact aggcaaagcc agctgggttc ctgagtggag tggggacttg gagaactttt  17637
atgtctagct ggaggattgt aaatgcacca atcagcactc tgtgtctagc attggtgggg  17697
ggcaggggtt cgtagacgca ccaatcagca ccctgtgtca agctcaaggt ttataaatgc  17757
accaatcagt gctctgtgtc tagctaatct agtagggact tggagcactt ttatgtctag  17817
ctagaggatt gtaaatacac caatcagcac tctgtgtcta gctcagggat tgtaaacgca  17877
ccaatcagca ccctgtcaaa acggaccaat cagctctcta taaaacagac caatcagctc  17937
tttgtaaaat ggaccaatca gctctctgta aaatgggcga atcagcagga tgtgggtgga  17997
gtgagataag ggaataaaag cagggtgcca gagccagcag cggcaatctg cttgggtcgt  18057
ctaccatgtt gtggcaggtt tgttcttttg ttcttcctaa taagacttgt ggctgctcac  18117
tttttggagc cttgctgcct ttatgagctg tgacactcac ctgaaggtat gtagcttcac  18177
tcctgaagct agtgagatca tgaacccact gagaggaatg aacaactcca gtgctgcctt  18237
aagaggtgta acactcccag cgaatgtctg tagcttcact cctgaagcta gtgggaccag  18297
gaacccagca gaaggaagaa actccgaaca cgtccaaaca tcagaaggaa caaactccag  18357
tcacactatg tttaagaact gttaacagtc accatgaggg tctgcagctt gattattgaa  18417
gtcagtgaga ccaagaaccc accaattacg gacataccat gggaacagtg tccctcagcc  18477
tgctgaaaga atccctgtgc aagggcaggg agggctggtc tgagtaacaa agtcctgtag  18537
cagagcagac tgaggcaatg aaacccaatg cttccagtta agactgggcc ccgcccccact  18597
ggctggatag gacaacgacc cttcccaact tcgattatat tttctgtatt tatttattta  18657
ttttgagatg gagttttgct cttgttgccc aagctggact acaatggcat gatcttagct  18717
```

```
cactgcaacc tccacatcct gggttcaagc gattctcctg cttcagcctc ctgagtagat  18777
gggattacag gcaagcgcca ccaggcccag ctaatttttt gaatttttag tagaaacggg  18837
gtttcaccat gttagccagg ctggtctcaa attcctgacc tcaggtgttc tgccctcctt  18897
ggcctcccaa attgctggga ttacaggcgt gagccactgc gcccagctta ttttgaagag  18957
gaactactca gactgtgttc tctccctttt actctcccca aggaagcgaa gaaaattatc  19017
aatagaaaat ggcaggccga gcatagtggc tcatacctgt aattccagca ctttaagaga  19077
ctgaggcagg tggaatactt aaggttagaa gttcaagacc accctggcca acagagcggt  19137
tttcatttaa aaaaaaaaaa aaagcaagtt tattaaggta aatgaataaa acaatggcta  19197
ctccataggc agagcagctg aaaccctgtc tctactaaaa tacaaaaatt agccaagcgt  19257
ggtggcacat gactatagtc ccagctactc aggaggctat ggcaggagaa tcgcttgaac  19317
ccgggaggca gaggttgcag tgagctgaga tcgcaccact gcactccaga ctgggcaaca  19377
gagtgagact ctgtctcaaa aaaaaaaatc aataagtaaa atcttaaagt agcaaatgac  19437
agttgcagcc aagtaattcc aaaagccagc ttcactcgga gaaccctgtg cttcctctta  19497
tttccagcga tccacatatt tagagaaact tttccagtaa taaaccatag aaattatacc  19557
tggaagtaga gtcttcaact tggattttta ggtgacccta acaaaagggg gaaatttccc  19617
aaaacatatc cgaaatggac tttctcactg ctttggctag tcgaggttaa gaatcagagg  19677
taattttaga acatatagat gaggtgacaa ctcatacacc caagtatgta gagcaactca  19737
tatctacccc actgcatttg gagggaaagt gtttccctgg tgaacttgtg agtataaata  19797
gatggaagaa gatgtactca aaacagcaaa cttctaatta tacaaaatgt tatatttttct  19857
gcttagtgaa gccacatcca tgtagattat gatgctctaa tcattacacc tgtcaacaca  19917
atgaaatagc tcaaatctct gaaaaacttt gcttcactct taatgatgtc aaaaattaca  19977
actcaaatta aatcttcatg tctctaatga aacctcaact ctgcaaattt ccttatttaa  20037
aaatgctgtt ttagccaaag aaatgtttca aaaattctgt attcaggcca ggcacggtgg  20097
cttacgcctg taatcccagc actttgggag gccaaggtgg gtggattgct tgaggtcagg  20157
agttcgagac cagcctggct gacatggtga aaccccgtct ctactaaaaa tacaaaaagc  20217
cggatgtggt ggtgcatgcc tgtagtccca gctactcagg agactgaggc aggagaatca  20277
cttgaacgca ggaggcggag gttgcagtga gccgagattg tgccactgca ctccagcctg  20337
ggtgacagag cgacgctccc tctgaaaaaa gaaaaaaaaa ttctgtattc acaaatagct  20397
tgatactagc aatcacttgt ttacattgta aataggcagc aggctgaaaa tttttgatga  20457
cttaattgca ggttcacagc tatgaaggca agccaaaggg ctaccttgcc aggtctgtaa  20517
aactgatgta catagtatga gctgcttgat ctttgagtaa tcacaaaaga caaatcaggc  20577
tgggcatggt ggctcatgcc tgtaatccca gtgctttggg aggccgaggc aggtggatta  20637
cttaaggtca ggcattggag accagcctgg ccaacatggt gaaatcccat ttctataaaa  20697
aaaacaaaag ttagctgggc atggtggtgt gtgcctgtag tcccagctac tcaggaagca  20757
gaggcaggag aaccgcttga acccgggaag tggagtttgc agtgagccga gatcatgcga  20817
ctgcactcca gcctgggaga cagagtgaaa ctctgtctca aaagaaaaaa aaaaaaggaa  20877
agaaataaaa gacaaatcag caaaaagagg aattcataaa aagagaataa agctttgcaa  20937
aaaaagaacc tgtctttgga tcttcagaag tgactaaaat attttaatag gtccctttta  20997
gtgcctcttt ttgcttgcct atgaaatatt gacagatctt cccaactggg ggaaaaaaaa  21057
cccaaaattc attaaactca ctgtgtctta tttggttaaa taaaaagagg tagaaagact  21117
```

attatgagaa aagagaagca atagaaactg tggaaattgg agttccaaac atcaatctta 21177
atttgattga atagtagaaa gtatataaac tatggaaatt gatgttccaa acatcaatcc 21237
gcattcctga gcaattttca aattggtcac cagctctcca ctcctcctgt catgagtcac 21297
ttatacctta aaaagtatat cctctgagaa ttctgaaagg tatccagacc ttccattaga 21357
caacttccaa tccatatgtg cctcaaagtt gtgtcttcat tttcctcctg ttccatttcc 21417
ttcagatttc caccaagata tgcatgttga gctttgtttt gagactacat ccagatgtca 21477
cctacctctc ctgtggcctt aaaaagattc tataagcaca gagagatcag cctgagacat 21537
ctgaagacct aagcctgcat ccttcctggt ttttggatta agggaatgta aagatgagag 21597
gaaaatgagc aaggcgaggt gataactcat ttctaaataa aacaggaata tttttaaaaa 21657
tctgacactg ctaaaggcca agtcatacag taggattccc accaggccag gctgtaaata 21717
ttgattctcc tctctgcaac cccagtgttc aggcttcaga gtaacagtct tagttcctcc 21777
aaccacattt ctaaccacaa ggtcactgca cacttcacca nctggcctct tctttagcac 21837
aacaattgta agtttagaga tgttatcatt tatttgcagt cgtcccacag atgttgggac 21897
ttggaaaaac ctcctttata atcaaatagt tccggtgttt tgtagtttga aaagcactgt 21957
tcgaaagtta tctcatttaa tctttacaac tgttgacttt acagataaag aaaactgcag 22017
gatcagaaaa gttaaataaa tgcccaagga cacacaactt gtaagaaaag aagccagggc 22077
taggctaggc cggctgcagt ggctcacgcc tgtaatccca gaaccttggg aggccaagac 22137
aggcggatca tctgatgtca ggagttcgag accagcctgg ccaacatggt gaaaccccgt 22197
ctctaccaaa aatacaaaaa ttagctgggt gtggtggtgg gaacctgtaa tcccagctac 22257
tcaggaggct gaggcaggag aatcacttga acccaggagg tggaggttgc agtgagccaa 22317
gatcgtgcac tccagcctag gcaacaaaag tgaaactccg tttcaaaaaa gaaaaaaaaa 22377
aaaagaagcc agggctaaaa cccacctgtg cccttcatct tctagttctg ggttcttttc 22437
atgccaccaa ttgcacttca aagaagtgga aacattttga agtttttgat aagactagta 22497
gcaaggctta ttttcaaata gtctatgaat ttttatagct tgtagaaggt ctgaggaaga 22557
tataatttca tttgtatcac ttcagaagca atacaaaaaa aagtattatc ctatttcttt 22617
attttatatt ctaggcctat tagagaacaa taaattagat aaactcaaaa tccacttagg 22677
ccttcatgta tccttttttt tttttttttt tttgagacca agtctcactc tgtcacccag 22737
gctggagtgc aatggcatga tctaggctca ctgcaacctc ctggtttcaa gcgattctct 22797
caactctgcc tccggagtag ctgggactgc aggcacgtgc caccatgccc agctaatttt 22857
tgtattttag tagagatggg gtttcacagt gttggccagg ctggtcttga actcctgacc 22917
tcaagtgatg agcctgcctc agcctcccaa agtgctggga ttatagacgt cagccaccac 22977
accccacctg ctctgatatt tattatttct tttcttctgc taattttgag tttggtttgc 23037
tcttgctttt gtagttcttt aacacgtacc attaggttat ttatgattat tagattagtt 23097
tttcttcttt ttaaatgtag atacctataa ttataaaatt ccctcttagt actgcttttg 23157
ctgtattcca tagttttggt atgttctgtt tccattatca tttgtttcaa caaatttttc 23217
aatttccctc ttaatttctt cattgaccca ctggtcattc agaagcatat tgtttaattg 23277
ctgtgtattt ttatagcttc caaatctctt gttttgttac attgtggtca gagaagatgc 23337
ctgatgttat ttcaattttt ttgaattttt taaagccttg ttttgtgatt taacatatgg 23397
tctattcttg agaataatcc atgtgctgag gagaagaatg tgtattctgc agccttcaga 23457
tgaaatgctc tgtaaatatc tattaggtcc atttgttcta tagtgcagtt taagcctgat 23517 gtttccttgt tgattttctg tctagaagat ctgtccattg gtgaaagtgg gatgttaaaa 23577
tctccagcta ttattgtact gagggctgtc tttttacctt aaataatatt tgctgcttca 23637
tatatctgga tgctccagtg ttgggtgcat atataattgt tatatcttct tgctaaactg 23697
actccttgat tattatataa tgaccttctt tgtttctgcc gcctatagag acaaagaagg 23757
ttattatata atgatgaaag agtccagttt tttgttgttg ttgtcatttt ttgagatgaa 23817
gtctcactct ttcacccagg ctggagtgca gtggcacaat cttggctcac tgcaatctct 23877
gcctctaggt tcaagtgatt cccctgcctc agcctcccga gtagctggga ctacaggtgc 23937
ccactaccac acttggctaa tttttgtatt tttagtagag acagggtttt caccatgttg 23997
gccaggctgg tctccaactc ctcatatcaa gcgatccgtc cgtctcagcc ccccaaagtg 24057
ctgggattac aggcgtgagc cactgtgcct ggcccattgt atgtttttca atttggggtt 24117
accatgaggc ttgcaactac tgtttcataa cccattgttt caaactgatg acaacttaac 24177
actgattgca taaacaaaca aataagcaaa aagaaaacta ataaaaactc ttaacttcat 24237
cctcctgctt tttaactttt tgttgtttct cttcatgtct tattgtactg tctgtcatga 24297
caaattgctg tagttattat ttttgattag ttcattgctt agtctttctg cttaagagta 24357
ttttgaacac cgtaattaaa gtgttataat attctatgtc tttctgtgtg ctattaccag 24417
tgagttttgt agcttcacgt gacttcctat tgctcatcaa tgtccttttc tttcagatgt 24477
aagaactttc tttagcattt cttttttttt ttttgagatg gagtctcact cttttgccca 24537
ggctggagtg cagtagcatg atctcagctc actgcaacct ctgcctccca tgttcaagca 24597
attatagtgc ctcagcctcc caagtagttg ggtctacagg catgcgccac cacacccagc 24657
taatttttgt atttttagta gagacacctg accatgttgg tcaggctggt ctggaactcc 24717
tggcctcaag caatccaccc gcctcagcct cacaaactgc tgggattaca cgcatgagcc 24777
accacgcttg gcctccttta gcatttctta taggacaggt ctagtgttga tgaaaatccc 24837
ttagcttttg tttgtctggg aaggtcttta tttccccttc atgcttaaaa gatatatttt 24897
gctgaatata ctattctagg gttaaagttt tttttttccc ttcagcattt aaaatatgtc 24957
atgctagttt ctcctggcct ataaggtttc cactgaaaag tctgaggcca gatgtattgg 25017
agctctatta tattttattt gtttcttttc tgttgctgtt tttaagatcc tttctttatc 25077
tttgaccttt gggagtttga ttattaaatg ccttgaggtt gtctttttttg gattaaatct 25137
gcctgatgtt ctataacttt cttgtacttg aatattgata tctttctctg ggtttgggaa 25197
gttctttgtt attatccctt tcaataaact ttctatcccc atctcttcct caacctcctc 25257
tttttggcca atagtgctta gatttgccct tttaaggcta ttttctatat cttgtagaca 25317
tgcttcattg ttttttactc tttctttttg tctcctctga ctgtggattt tcaaatagcc 25377
tgtcttcaag ctcattaatt ctttcttctg cttgatcacg tctgttatta agagacccag 25437
atgcattctt cagcatggca gttgtacttt tcagcactag aatttcattt ctttttaata 25497
acttcaatct ctttgttaaa tttgtctgat agaattctga attcctggcc aggcgcagtg 25557
gctcacacct gtaatcgcag cactttggga ggctgatcac ttgaggtcag gagttcaaga 25617
ccagcctagc caaaatggca aaactccatg tctactaaaa acataaaaat tagttgggtg 25677
tggtggcaca tacctgtaat tccagctact taggaggctg aggtgggaag atcacttgaa 25737
cccaggaggc agaggttgca gtgagccaag atcgtaccac tacactccag cctgggcgtt 25797
catctcaaga aaaaaaaaaa agaattctga atttctgttt tgtgtttctt ggatttcttt 25857
gagtttcctc gacacagcta ctttgaattc tctgtctgaa aggtcacata tctgtttctc 25917

-continued

```
caggattggt ccctggttcc ttatttattt tgtttggtga ggtcattttc tcctggatgg  25977
tcttgatgct tgtagatgtt cgttaatgtc tgggcattga agagttaggc gcttattgta  26037
gtcttcacag tctgggctta tttgtgccca tcctccttgg aaaggctttc cgggtatttt  26097
gaaggaactt gggccccaag tccaataata ttatgtttct tgcagactca tagaggtgct  26157
gctctggtag tcttggataa gatctggaag aattctctag attaccaggc agacactttt  26217
atttttttct cttatttttt cacaagcagc gtctctccct gactctgtgc tgagtctcct  26277
ggaactggag gtggagggac acaagtaccc tgtagccacc accaccagga ctgtgctggc  26337
tgagacatga aaccagcaca gcactgggcc ccacccaagg cctgctgtaa ctactatctg  26397
gctaccacct aagttcactc taggacctag ggctttatga tcagcatatg gcaaagccag  26457
tctgatttat gtccctccat tcagggcagt gagttcctcc agacctaggt tggtccagag  26517
atgttgtctg agagccaggg atttaagtca aataccttag aaatttaccg ggtattctac  26577
tctactgcag caaagctggc actcaaacca taagacaaag tccttcccac ttttctctcc  26637
ctgtggccac caccataagc accccacgag gggttctgcc aggctaccgc tgatgttcac  26697
ttaaagccca agggcccttt tgtcagcttg tgatgagtgc tgccagacct gacactcact  26757
cttcagagta gtgggcttcc ttctggtcca tggcaggtcc agaaatgcta accaagagcc  26817
taggcttgga cgtggggacc tgaagagtct gcttattgct ccaccccact gtggctgagc  26877
tggtacctga agtgcaagac ggagtcccct ttactttccc ccctgttttt ctcaaacaga  26937
aagatctttc gctgtagcca ccacagctgg gaatgtgctg ggtcacactt gaagccagca  26997
tgtctcagag cccaaggccc atagtgtatt acctgggtat tgctggtggt tattcagggc  27057
ctaggggctc ttttgtcagc aggagatgaa tcctgccagg tctccactgt gagacggcag  27117
cactaagttc aatgtaaagt cccccggttg ctgtgctctc cctctcccaa gcacaaagat  27177
ttctctgcac cacatggcca ctgctggggg gtgagggaag ggtgacaaaa gcaccctccc  27237
aagccacccc ggctggtgtc tcagtaggtt tcatgcctgc ccagtccact ggctctgagc  27297
ccagctcagc actaggactt gcctaggaat tgcactcctt gtgacctaga ctgaccctta  27357
agttcactta gtgccccaga gcactccagc ccacggtaat gaggcttgct ggaactcaag  27417
ctcccaccag tgggatggac aatttctctc tggctagagc tgggccaaat gaacatcagc  27477
tgagtagaac ctggttctgc tttccactgt aacaggggag cactgggttc aatgaaaagc  27537
ctcacaattg ctgcactttc cctctcccaa gcacccagat tctctgtgct acatggccgc  27597
tgctggggga tgaaggaggg gtggcgtcag tgcttcaatg ctgtctttcc tgccctcttc  27657
aatgtctctt tcagtgatat aaagttaaaa tcaggtacta tgattgctca cctgattttt  27717
ggttcttatg atggtgcttg ttgtgtgtag ttagtagtta aaatttggtg ttgctatgtg  27777
gaggatgaac agtataagcc tctatcagcc gtcttgctct accccattct ctgttaattt  27837
ctcaggcacc aataagtgtg tgtaactgta atatgcccat tacccaatgt gcacagcaag  27897
tcaacgtgct gatatattgg attgcagcag agaaagaggt ttaagcgaag ggttgctgaa  27957
tgaggaaatg agagtaaacc taaaatccat ctccctgaga aatttggggc taggattgtt  28017
aagggttttg gagttggctg aagtgtggag atattgattg gtcgaagagt gcagggtgaa  28077
atcatggccc aggaagatga aaaaatgtgt tttcatgctg attcagttct gctgtggggg  28137
tcttcaaact ggttggcatc agccattcca ctggaattca gagtctgctt aagcaattct  28197
taaacaagtc ttatgaatct aatgtcagaa atcctatcta taggaaaaac agggttgcaa  28257
attgtgagta tctagtgcta tgtgactttt ggttacaaag aagtgggtca aaatatagca  28317
```

```
tgattaatgc ttaattatag ctatatttct gtccaaaatt cttattaacc ctgtgagaat  28377
ggctttatta gtaattggta agtcaagtct gtgctttcta gcaatagcac tgggtatttc  28437
taccctagta gaaggcacgc acatatagcc aatgtcttat ccttgcttct ctgctcttct  28497
atgtgttgaa ttaattttag ctgggctggg aacagtgacc ttcagcatgg ctccaatcac  28557
tttatactta ccagggaagc tttttaaaca tttcattcct aggctttgct ttatatgtac  28617
ataagtcaaa gttcctggag gtggtggtct aaaatctgta tctttatctt tatcttcctg  28677
aataatttta ggaccatatt tagcatttga aaacctctgg cataggctat gcaaacagaa  28737
actctcttat ccgacctcta cttaactggc ttttcaattt tgtaaaatgt aagaaatgag  28797
gctcacagca tgttgctacc cttcctgtat tctccagtgg taattattgc ttagtgtgta  28857
ttctttcagg ccacttctaa tgtacttcaa tggataaata tgtgcttatt aaatatatat  28917
agtagaaaat atgcttttaa gaaaatggca tgcctgatga atccttctgc aacttgcttt  28977
ttacacctac caatggaatt tggagatctt cccagataag aatacatggc tccatctcat  29037
ccttattaat agctgcctag tttttcaaag ttggacctgg tttatttagg tggtcattta  29097
ttgatggaca ttttaagctt aacatctctt cctattttaa acaatggtcc aatgaatatg  29157
cttgtacatt tttccttgtg tgcatggagg ttaaaatgca gtcattgagt gtgcatttta  29217
aacatttcag tagaatctgt caaattccgc ttacaggtta ctgcaccaat atatattccc  29277
accagcagag catgaaatat ctattttatc catgggcttg ccagtatttg ataatatcaa  29337
acttgattat ttatttattt atttgacaca gggtcttgct ctgtcaccca ggctggagtg  29397
cagtggtgcg atcactgctc actgcagcct caatcttcca ggttcaagtg atcttcccac  29457
ctcagctttc caaggagccg ggactacagg tatgcaccac tatgtccagc taatttttgt  29517
atttttttgc agagatgggg ttttgccgtg ttgcccaggc tggtctcaaa ctcctcagct  29577
caagcaatct gcccacctca gcctcctaaa gtgttgggat tacagacata agccactgca  29637
tttggcccaa acttgatttt tttttcttg ccgatatatc taataagtgt tacttcattt  29697
taataaaaat ttgcattttg ccatttttaa tgaggctgtg tttttgcata tgtttattga  29757
ccatttctat ttccactttt ttgaactgcc tgttgatgca ttcttataca taattgtgtc  29817
agtaatattt ttgtttttga aaattaaact tttctcttaa tttttaattt ttaaaaatgt  29877
acatttgggg catatgtgat aatttaatac atttatatta tttgtaaaga tcaaatcagt  29937
gtaattgaga tatccattac cttaaatatt tgtcttttat ttatgctaga aacacttgca  29997
ttattgtttt ctagctattt tgaaatatgc aataaactat tgtaagctat agtttacaaa  30057
tatagtcact ctactgatct agcaaacact agatcctatt tcttctatca gactgtatat  30117
ttgtacccat taacccagct ttcttcattc ccctcaccct tcctggcctc tggtaatgac  30177
aaatttattt tcatcttcat gagatccact ttttaagctc ccacataaga atgagaacat  30237
gtgatatttg cctttctgtg cttggcttat tttgcttaac atagtaacct ctagttccat  30297
ccaagttcct acaaatgaca ggatgtcatt ctgttttata gattaacaat attccattgt  30357
gtatatatac cacattttct ttatcctttc gcccaatgat gggtacttag gttgattcca  30417
tagtttggtt attgtgaata gtgctccagt aaacatgaaa gtgcagatat ccctttgaca  30477
tattgatttt gcttcttttg tatatatacc cagtagtgaa attgctggat catatagcag  30537
tttttagtta tttgagaaac ctctatatag ttttccataa tagccgtact aatttacatt  30597
ctcaccacca gtgtatgagt gttcctcttt ctccacattc tcaacagagt ctgatattcc  30657
ctgtcttttt aataaaagcc attttaactg acttgtgata attcattgtg gttttgattt  30717
```

-continued gcatttctct gataatgagt gatgttgaac atttttttat atacctgttg gctatatgta 30777
tgtatttttt tttgagaaat gtctattcag attgcttgcc cattaaaaca attgaatcat 30837
ttgtgtgggt ttttaaattt aaattaattt aatttttttt tttttttacc attgagttgt 30897
ttgagctcct tatatattct ggttattaat ttcttgttag gtggatagcc gtaaatattt 30957
tctcccattc tgtgggttgt ctctttgctc tgttgcttgt ttcttttgct gtgcagaagc 31017
cttttcagct tgatataatc tcatttgtca atggcagctt ggttggcctg tgttctggag 31077
gttcttacac aaaaatcttt gcccagacca atatcttgga gagtttcccc aatgtttttct 31137
tccagtagtt tcatgtctta gatttaagtc tttaatctat tttggttagt tctgttgtat 31197
acggtaagaa ataggggtct agtttcattc ttttgcatat ggttatccag ttttcccagc 31257
accatttatt gaagagactg tcctttacct aaggtatgtt cttggtgcct ttgtcaaaaa 31317
tgagttggct gtaaatgtgt ggatttatat ctgggttccc tattttattc cactggtgta 31377
tgtgtttgtt tttatgccag tactatgctg atttggttac tatagctttg tagtacattt 31437
tgaagtcagg taatgtgatg cctccagctt tgttctcttt aattaaaaaa aaaatttaga 31497
ggcaggttct ttctctgtca ctctggctgg agtgcagtgg tgctatcatg gctcacggca 31557
gcctcaacct tctgggctga aatattcctc ctgccttggc ctgccgaagt gctgagatta 31617
caggttcaag ccatcacacc tggcctagct ttggtttatt ttgctcacga ctgctttgcc 31677
tatgtaaggt cttttgtggt ttcatgtaaa ttttaggatt ttgtttctat ttctgtgaag 31737
aatgtcattg gtattttgat tgagattgca ttggatctat aaattgtttg gagtaagatt 31797
atcattttca taatattaat gatttcaatt catgagcctg gaacatcttt ccactctttg 31857
tgtcctcttc aatttcttta atcagtactt tatagttttc cttatatata tatctttaac 31917
ttctatggat atattggttc ctagatattt tatattcttt gtagccattg taaatgagat 31977
tgcttttttg atttgttttt cagattgtta ctgcccactt acagtagctt atgtaagtgc 32037
tactgatttt tgtatgttga ttttgtatcc cacaattgta ctgactttgt tatttctaac 32097
aatgtttagg tgaagtcttt aggtttttct aagtataaga ttatattggc taggcatggt 32157
ggctcatgcc tataatccta gtactttggg aggccaaagt gggtggatca cttgaaccca 32217
ggagttcgag accagcctgg gcaacaaggc aaaatcccat ctctatgaaa aatacaaaaa 32277
ttagccagac ataatggtgt gggcctgtag tcccaactac tcaggaggct gaggcaggag 32337
gattgcttga gcctggaagg ttgaggctgg tgtgcagtta caccactgta ctccagcctg 32397
ggtgagacag agagggagac cctgtctcaa aaaataaaaa ataaaaatga aaataaaatt 32457
atgtcatctg tgaaccagac tgagttgact tcttcctttg ccatttggaa gccctttatt 32517
tctatctctt gcctaattgc tctggccaaa ataaaactct ttttaacctt agagaaaact 32577
gagcagccat agtctaccaa tgagttaggc tttggagatg gtgtgtcctg tgttctgaat 32637
atttgcatcc ctcaccaaat ccaaatgttg aaatcctaat ccctaaggca atggtactag 32697
gtggtcaaag cctttaggag gtgattatat tacaaaagtt gaaccctcat gaatgagatt 32757
tgtgtcctta taaaataggc ctgagacccc ttacttccac cttgtgagga catagtgaga 32817
agtttccctc cattaggaag gtggccctca accagacacc aaatctgctg ttgccttaat 32877
cttggacttc ccagtttcag aactgtgaga aataaaattt ctgttatcta taagcgaccc 32937
agtttatgat attttgtgat ggcagcctga gtgaactaaa atggtggggt atgacatctt 32997
tgagctcatc aggatatgct gcagtacagt taagactgat tgaatttgca acagtaggac 33057
tgatccattg attacgtggc ctattgcagt atgcagaaag acaaaggggt agaatccctc 33117

-continued

```
accttacacc aattagtacc tgtcagggtt tagtgcagga aaaagctatt ttaatcagga  33177
aggaacttag tagagaaagt tagatgctta caaaaccatt gaaagatggt tttgaaagga  33237
gcaaaaattg gtcactagga ctaggctttt ggcttcaagg tgatacattg ccacttctgg  33297
ggtccagagg tcaggaagcc actgtggcag tagaataggc aatgttgccc agcactgccc  33357
acactcacat ctattggagc ctacatgtgc tcctgcacct ccacaggaat acaatggggc  33417
tccacctctc ttccgctttc ttttccttcc ttcgtccctc cctccctccc ctctctctct  33477
ctttctctct ctgtttttct ttctttcttc tttctttctt tctttctttc tttctttctt  33537
tctttctttc tctctctctc tctctctctc tctctctctc tatttctttt ttgacaaggt  33597
ctcactatgt tgccaaggct ggtctcagac tcctaagttc aagtgatctg cctacttcag  33657
cctcccaaag tgttaggatt ataggcgtga gccaccgtgc ccagcctagc cactgtgcct  33717
cactttcttc tattttcaaa tgtcatgtaa ctgcctcaag ggcagagact acatctaaac  33777
tcctagctgc aagggagcct ggatactgta gtttttagct atcaatgcaa aaaatagagc  33837
atgtgaagag aatagcagta gatgctgaat atcaaaagtc tccatccttc caaaatacag  33897
tcatgtgcca cataaccatg ttttggtcaa tgatgaacca catgtatgat ggtgatacca  33957
taagattata atggagcaca tatagaaacc tgatacctgg cacaagatac tggcactgca  34017
cattaagtgg gggaaaagat tgatattcaa taatggtgat agggcattta gttttccatg  34077
tgaagaatat atataaataa taatatatat accttctagg tctgtggaag tacatgctac  34137
gatctttgca caatgacaaa atctagtgat gcgtttctca gaatgtgtcc cagttgttaa  34197
gctccgcatg actgtattga aacttaagtt gccatctggc acttactagg tgcctacctc  34257
ctgcaaagca ttctcattta tctaatagat gaatgaataa tcacttaata ggtagaattt  34317
ccattaagtg tatcaaactc tgctgataga cagtactcag tatctgtagt actctgcaaa  34377
tctccccatt ccccatttaa ggtatcaggg tctggcaggt gcagaagtga aatgggaggc  34437
aacagaagct ctcttagtcc cttcctctct caaatcagat ccctttacag ctgctcatct  34497
tcaggtcaga ggcagtgcaa ctgtataact tgaaatcatg atagtctatt ttctaacatt  34557
ttattatcag tagatcatgt tttctttact caaacacact atgtgtaata gtcctcttct  34617
agccactctc atggcatatt actctatgaa acactttaat caaagataaa atgtgactct  34677
ttttgacatc ttaaaggcat ctacccccaa aaggtatcta cagcaaacat ttattgctgg  34737
tgaaatcttt ctagtagatt acagttaata cattattggt ttattatcat ttgcatatgt  34797
atgggcaaca ctacgttttt tcaaaaaagg caacctagaa ataccatttg acccagccat  34857
cccattactg ggtatatacc caaaggacta taattcatgc taccataaag acacatgcac  34917
acgtatgttt attgcggcac tattcagaat agcaaagact tggaaccaac ccaaatgtcc  34977
aacaatgata gactggatta agaaaatgtg acacatatac accatggaat actatgcagc  35037
cataaaaaat gatgagttca tgtcctttgt agggacatgg aagaaattgg aaatcatcat  35097
tctcagtaaa ctattgcaag aacaaaaaac caaacaccgc atgttctcac tcataggtgg  35157
gaattgaaca atgagaacac atggacacag gaagggaaac atcacactct ggggactgtt  35217
gtggggtggg ggtagggggg agggatagca ttaggagata tacctaatgc taaatgacga  35277
gttaatgggt gcagcacacc agcatggcac atgtatacat atgtaactaa cctgcacatt  35337
atgcacatgt accctaaaac ttaaagtata ataataataa aataaaataa gaaaattaaa  35397
aaaataaaaa taaaaaaata aaataaaata agatcatatc attaaaaaaa aaaaaaaaaa  35457
ggctagcttg gaacccaggc accacacgcc attactggct tcctgagtac acatccttta  35517
```

gctcttacct acaattctct cctagaaatt attgtttgaa tgctgtgtcc agaaggtaac 35577 atatatatgt gtatacacac acacatacac acatgtatga aaaactaaat tgctgcttag 35637 acatatagaa aagttttcca aatttttgaa ttcataaagt ctatcaacct gatagcattt 35697 ctcaaaaaat tttttcaatg ggtagaggac ttgtgctttt cttttattct attgagaaat 35757 tctcaaacct ctaagaaatt gtgcaaagga aatttaaatc atatgaagga catagtcaaa 35817 atgtgtagct acaaggacta cacatttcaa ttgttgagaa acagtttact ctcaataatt 35877 tgtgaatgtt tgttttaatc tgccaaattc tgaggaagat agtgtaaaaa gatataattt 35937 ttaaggtatt tttaataaat ctggtaactt tttgatcaga ggacattcaa ataaaatgta 35997 gagtatagag cagaaattca gatgcagttt ttttaaaatg taatgtatgg gccgggcttg 36057 gtggctcaca cctgtaatcc cagctaggag ttcaagacca gcctggccaa catggtgaaa 36117 cccagtctct actaaaaata caaaaattag ctgggtatgg tgacgtgcac ttgtaatccc 36177 agctacacaa gaggctgagg caggagaata gcttgaaccc aggaggtgga ggttgcactg 36237 agccaaaatc acacctctgt gcctcctgag tgacacagcc agattctatc taaggnnnnn 36297 ntttgggggg gcccccnana aaaaattctg gccccagtgg gtggtttttt tttggcccga 36357 aaattccaaa aatttgccca aaaaaaaagt gggtttttg aaattttaaa ttgggcggtt 36417 ttttttcccc cctcnnggtt gtggggaggg gggccccccct tttttcttct cccctttgaa 36477 aagggggggt ttcccccctgt tttccccgaa ttttcccggg tctttttggg tatctcttgc 36537 caccggtttc ccccccccctt ggaaggttta agggggggtg gggtaaaatt ttttaaagcc 36597 cttttcaacc ctccttcccc gggttttggg cccttggggg ggagtcctaa aactcttgcc 36657 cggcccccct tcccctattt tgtgtggaac taaaaggccc gtctttctat agggggtctc 36717 cccgccgggg taaaaagccc ccacacccca aaaaactctg ttgtgtggtt ggttttnnnn 36777 nnnnnnnnnn nnnnnnnnnn nnnnnnnnnn nnnnnnnnnn nnnnnnnnnn nnnnnnnnnn 36837 nnnnnnnnnn nnnnnnnnnn nnnnnnnnnn nnnnnnacag ccttttaaaa ataatattct 36897 aatattgtca tgcacacatt aattatttct tgattaaaag aatcaaaatg gtttcagttt 36957 ctttattcaa tttctataca tatagtttta caatttattt ttaatatttt tagggaggaa 37017 aaaaaacagg ttgtcctggg atattgatcg tgaagctgat cattcctctt gctgtgtgaa 37077 gagcttttat gacaaaatgc attctcccaa aacaaagtac ataatgatta taaatgcagc 37137 aaaattgcac actatgaaaa accaaaatgc aatgagggat gaaaaaagaa accctttttca 37197 acatttaaac aataatgtag caaaaccctg tgtacattat aaggagcagc tttactaagg 37257 atttgtaaga attctaactt gtgatatgac aaagataaac agaaaagtgg acagtctact 37317 tagtacttgg ttcagttagt ccttaggata aaatgatact ggggttggtc aagtatccaa 37377 cttcaacctg gttgatctca tcgtccctct gcctgcttag tctcccttat tcttctgaat 37437 gaagagattc agaagattca tgttatagga taatgtggat attggttcac atagcccggc 37497 cagtattcat tcactcttct tggagttaag taaaggtgtc cttcctttct cttgggaaat 37557 tttgtcccct gcccattgtc agtccctgta gctgagtaag tggggtcaac cacattctca 37617 gctccttttg ttgactgtta actaagacca gaccaatcgg agcatccctt cccttagcca 37677 cagtgactga ttcaggaatg gcacccaccc aatcagaccc actctgaacc aatcccacaa 37737 ctattgctga agggaccaga aaagaggtat tattttttttt gttgctggat gaaagttgtg 37797 aagattaggc cagctgttct gctgggcttc acctttctga cgatgacctt ccagagagta 37857 aagtgtacat gagggaaatt ctagccaaga gatggacctg actcagtaac ataattgaat 37917 cccgaaatcc ggctgtgtgc aaactggtct gtgttaaaag ccagtagaga tccccatttt 37977 gctatgggaa attttattaa tagagttttt ctagcctttg caactacaag aatccaaaca 38037 aagagaagga aaggggaggc caagttgcat gccttgaaga gaaagagcac atttctctat 38097 gcccattcaa atctcactag ggtagggaca gtgccattgg tttcatcata ttccctacac 38157 tgcaaagaca ttattttcta gaaatttgat acacgtatat taatatgact taacagcaaa 38217 gcaagtgaaa gcagccattc acagtccatg tggtatgcag tgaagatcta ggtagttggt 38277 taatacgggc aaagtgcaaa aatgagataa gaaaatgcaa tgtccagatg cccctgcagt 38337 ttctgtacct gccagctaat aattctgccc cagccaagca aaaggatctc cttccactgg 38397 gtaggagagg cactctctga tgatccagac tggttagctg cttctttctt gtgaggaaac 38457 acaacacaaa gcatttttc aacttttatt ttatgttcag gagatacatg tgtaggtttc 38517 ttacttgaca tattgcatga cactgaggtt tggggtacag atagtcccat cacccaggta 38577 gtaagcatag tgctctatag gtcattttcc aggccttgcc tctctccatc tgtccttcta 38637 gcagttgtca gtgtctactg ttcccatctt tatgtccata tctacccaat gtttagcttc 38697 catttaaagt gaaaacatgc agtatttggt tttctgctcc tgtgttaact tccttaggat 38757 catggcctcc aactgcatcc atattgctac aaaggacatg atttcattct tttttatggc 38817 tgtattgtat tccatgctgt atatgtatca cgttttcttt atccagttca ctgctgatgg 38877 gtatctaggt tgattccata tatttgctgt tgtgaatagt gctgtaatga acatacaagt 38937 gcctgtgtct ttttggtaga acaatttatt ctcttttgga tatataccca gtaatgagat 38997 tgctggatgg aatggtagtt ctatttttag ttctttgaga aatctccaaa ctgctttcca 39057 tagaggctga accaatttac attcccacct tcagtatata agcattccct tttctccgca 39117 gcctctccag catctgttat tttatgtttt ttgagaccaa gtttcgctct tgttgcccag 39177 gctggagtgc aatggcatga tctcggctca ccacaacctc tgccttcctg gttcaagcga 39237 ttctcctgct tcagcctccc tagtagctgg gattacaggc atgtaccacc acgcccggct 39297 atttttgtat ttttagtgtt tgcgggattt ctccatgttg gtcaggctgg tcttgaactc 39357 cccacttcag atgatctgcc tgcctcagcc tcccaaagtg ctaggattac aggcgtgagc 39417 tgctgcaacc agccagcatc tgttattttt tgtcttttta atagtaacca ctctactggt 39477 ataaggtggt atctcattgt ggttttgatt tgcatttctc tgaagattag tagttttgag 39537 catttttca tatgtttgtt ggccacttgt atgtcttctt ctgagaagtg tctgttcatg 39597 ttctttgctc atttttaat aaggttgttt tttgcttgtt aagttcctca cagattctag 39657 acattagact tttgtcaaat gcatagtttg caaaaatttt ctcccattct gtgggttatc 39717 tgtttagtct gttgagagtt tctttgctgt gcaaaacctt tttagtttag ttaggttcca 39777 cttgtcaatt tttttttatt gcaattgctt ttgaggactt aatcaaaagt tctttgctaa 39837 ggccaatgtc cagaatggta tttcctaggt tttcttccgg gatttttatt gtttgaggta 39897 ttacacttaa atttttaatc catcttgagt taatttttgt atatgatgaa agggagggat 39957 ccagtttcat tcttctgcat atggctagcc agtaattcca gcacctttta ttttattaaa 40017 tagagaatcc tctccccatt gttgtttttg tcaactttat tgaagatcag atggttgtag 40077 gtgtgcagct ttatttctgg ggttttcatt ctgttccatt ggtctgtgtg tctgttttta 40137 taccagtgtc atgctgtgtt ggttctttct aaccttatag tataatttga agttgtataa 40197 tgtgatgtct ctggctttgt tctttttgct taggattgct gtagctattc aagctttttt 40257 tttcttttgt tttttttgg ttccatatga atttgagggc cgggcacagt ggctcacacc 40317

-continued

```
tgtaagtgtg cctcagcctc agacgccgag gtgggtggat cacctgaggt caggagttca  40377
agaccagcct ggccaacagg gtgaaacccc gtctctacta aaaatacaaa aatttgctgg  40437
gcatgttggt gggtgcctat aatcctagct acttgggagg ctgaagcaga aaaattgctt  40497
gagtctggga ggcagaggtt gcagtgagct gagatcacac cattgcactg agcgagactc  40557
cgtctcaaaa aaaaaaaaaa agaaaaaaga aaaaaaagaa ttctgggata gtttttttct  40617
aattctgtaa aaaatgacat tggtagtttg ataggaatag tgttgaatct gtagattgct  40677
ttgggcagta tggccattcg aatgatatta attcttgcaa tccatgagca tggaatgttt  40737
ttccatttgt ttttatcatc tatgatttta aatatttttt tagaacaaag gaatcattgg  40797
atgtcctgcc aaaaccagat gggagaaagc catgtgtatc tatcaattgt gactttgcat  40857
tttttcttgt gaagttgctc ttgtgttgta aagaagaaaa aggaaaagga aataaaaaag  40917
aatcatggtt ttgactatta caactgaaac agagcttcat aatcattttg ttccatcttt  40977
tttccatccc tccctttctt ttcttcctcc ttccctcctt cctttactcc ctttctccct  41037
tcatcactct ccctttcttt ccctctcttc ttctcttttt tcgcccaccc ttccctccct  41097
ccctccttcc ttccttcctt ccttcctttc ctctctctct ctctctctca atcactcact  41157
ctctctccct cccttccttc ctcttctgag gtctgacagt gagatacgcc caagggcaca  41217
tagctaactt gttggcaggg ccaggactca agtgaactca gctgaccact gattctgtta  41277
cattgttttc tccatatttt gacagacact aaggaccatc aaaagctgtt ctaaatgtgc  41337
aaatcaacca gtctgttggt ttatatccta atggtataaa agagtaagga actggctggg  41397
cgccatggct cgcacctgta atcccagcac tttgggaggc tgagaggggc agatcacctg  41457
aggtcaggag ttcgagatca gtctggccaa catggtgaaa ccctgtctcc actaaaaata  41517
taaaaaatta gcccgcgtgg tggtgcatgc ttgtagctcc agctacccag gaggctaagg  41577
caggagaatc tcttgaaccc aggtggtgga ggttaaaatg ggcaaagatc acaccactat  41637
actcctgcct gggtgacaaa aggagactct ttcaaaaaaa aaaaaaaaaa aaggaaagaa  41697
aataaagaaa caaaaaagaa aagaaaggtc aggtgtggtg gctcactcct gtaatttcag  41757
cacttcggga ggctgaggtg ggtggatcac ctgaggtcag gagttcaaaa ccagcctgac  41817
caacatggag aaaccctgtc tctactaaaa atacaaaaca ttagccaggc atggtggcac  41877
atgcctgtaa tcccagttac tcggtaggct gaggcaggtg aattgcttga acctgggagg  41937
cggaagttgt ggtgagccaa gatcatgcca ttgcactcca gcctgggcaa caagagcgaa  41997
actctgtctc aaaaataaat aaataaataa ataagaaata aaacaataaa aaaaaagtag  42057
ggaatagtcc agtatgatat gtgagttgaa agattactaa acttttcaac acaggacaaa  42117
ccatgatttc acctttccct taattcctca gagctgatga ttcccagaag aaaaatctgg  42177
gctctactca gagttcccca tacctcacgc atttctctag gaaatgttgt caggccactt  42237
acctttttagc acccatttct tttcttgcaa gatacaaagt gtcttgatct aagcatatac  42297
ttcccttcct gtctcatggg gctcagagta agcttggcta ccaggtgtta tgaaatgtat  42357
tcaaccacag gaaaataagg ctatttgtgt ttgctggtca ttgaagggct gcagatgaca  42417
agcattgtag aaattacaaa tatttattat gggtgggttg tggtggctca cgcgtgtaat  42477
tgcaacactt tgagaggctg aggcaggagg atcatttgag cccaggagtt agagaacagc  42537
ccgggcaata tagtgagacc ctgtctcaac aaaacatcaa aaaaaaaaag aaaattagct  42597
gggtgtggtg gcatgcgctt gtagtcccag ctactcagga ggctgaggtg agaggatggc  42657
ttaagcccag gaggcagagg tttcagtaag ctggcgttgc atgctgcact ccaggctgga  42717
```

```
tgacagagca agctcctgtc tcaaaaaaaa aaaaaaaaaa attactgtat gaactagttt  42777
cattttaagg tctagactaa tgggttgttg tcatatccaa ctgtgacaag aatttttgta  42837
acttaatttc tgccttggca tgttacataa gcttaataac caaaacaaat cttaaatatt  42897
aaaatatttc acaggcagtt tccaaagaaa atcgtattta ttaactgttg agagacttct  42957
tagaatgtca agacatttga aaaatactac ccactgcctt ttttcctgtg cagagtttag  43017
ttctcttttt cctctgattt ttttttcag tgttatggtg tttgagagta ctatacatcc  43077
accttataat tccatttgct gaagctgccg cttgtttttt gtgttgttgt ggttttgaga  43137
caggttcttg ctttgttgcc taggctgggt ctccaactac tgggctcgaa cgatccttct  43197
gcctcagcct tctgagtagc cgggactata gatatgcacc actgcacctg gccatatcca  43257
tccttacgaa tgggattatt gttcttataa aaaaaaaata agggggtgct gggcacggtg  43317
gctcatgcct gtaatcccag cattttggga ggtggaggca ggcagatcac ttgaggtcag  43377
gagttcgaga ccagcttggc caacatggtg aaaccctgtc tctactaaaa atacaaaaat  43437
tagcctggtg tggtggcagg cgcctgtaat cccagctact tgggaggctg tggcaggaga  43497
atctcttgaa cccaggaggc agaggttgca gtgagccaag atcacgcctt cagatttcag  43557
cctgagcaac tgagggagac tccatcaaaa ataaaaaggt tgaagagagc accctagtct  43617
cttttgtcta ccatcacttc caccacatga gaacatagtg ttcattccct ctggaggatg  43677
tagcaacaag gctgctgttt ccaagcaaca tcttggaaaa cagagacagg gtccctacaa  43737
gacaccaaat ctatctgagc ctttaacctg gtcttccaga tatatatatt tggaacagca  43797
ttgtatgacc acacatttga aaatgaagat ggaaatggga aatagcagcc ctttgattca  43857
aaatacatga acagggaaag gagaaccatc tcttatcaga taaaaagatt aagaatttga  43917
agaagccaag agagtagagg aactaggaaa aaatgaaaaa gggaagagaa aaaaagggaa  43977
cagaacagga agggtaaata caaaatgcac ctcagtgtca ttaatctatc caataaaaat  44037
atgcggagca ccatctaagt gcctggcact gttagattct gggatacaat gctgtgcaaa  44097
atcagtgttg agcctcacct ttgcagaact tatgagtaac aaggaagaca taaataatcc  44157
aaataatcac ataagcagat gtaaaggaag tgctactcag tacccagaag gtccatcaga  44217
gatagtggga gaaaaggcag aaaaaccaac aaagtggatc catcacccgc cctgagttcc  44277
agggtggaat ggaggctggc acgatagagc tgccaaatag aggtactgac tggactggca  44337
caatgtccaa gaaacacaac ggatttggct ctcagggttt tgttcggaaa tggtcagctc  44397
ctgtgacttg caatccaggt aggctaaatg agagggaatc cagccgcaga cactacacag  44457
agggcaggtg aggccagggg atctggaact caatcccctg atctgcaggg caaaactcca  44517
gtgccctatg gcaggactgg caagaggaaa gcaaagcagc aggagctcaa ttctaggcag  44577
ggatttggag cagggtttca gtcagtaggg cctgaaccag taggggccag gatcccagat  44637
acagacagga aaggatcaga ggtggaggat agagactggg agcactgtga ggccagccca  44697
tccctcaggc cactgagttc aggactttag atacttaggg gttccaggag ggtgaggcca  44757
agacaggcgg atcacctgag gtcaggagtt tgagaccagc ctggccaaca tagtgaaacc  44817
ccgtctctac taaaaataca aaaattagcc tggaatggtg gcacacgcct gtagtcccca  44877
ctacttggga ggctgaggca ggagaatcac ttgaacctgg gaggtggtgg ttgcaatgag  44937
ctgatattgt gccactgcac tccagcctgg gtgacagagc aagactctgt ctcagaaaaa  44997
aaaaaaaaaa agggtaataa taatacctac ctctagaaga ctgtgagaag taaatgtcaa  45057
gtgcttagaa cagtgaacag tacctggcac agagaaaaat actaagtaag tgtctgttga  45117
```

-continued

```
atgaatggat gaatgaacaa atacatagat aatatgggca gaggcttcca aatgtaaatg  45177
gatgaagcct taagaaagtc tcagaatgac tctggactaa cgggagttta gggatgggag  45237
caaatggaaa aggaagtaac taaacagctg agctgagtca ttaaagcatt ctagggtcat  45297
tctagaaatt gcatccaagt cttaacagtc ttactgcttc cccgttgccc tctctaatcc  45357
attttctggt ctgcagtcac atcatcttta aaacataggt cagattatgt catctcaatg  45417
aattcccata aaacttgagg gaaaaaatcc aaactatggg ccatatgagg caccaaataa  45477
aagactgtaa actagtgacc ccccccaagt cataaagagt tcacaaatgg agttaaatac  45537
tcagtttggg tttttttgtt tttgtttttt ttcaaggcag ggtctcactc tgtcacccat  45597
gcttgagtgc agtggcgcca tcatagctta ctgcagcctc aacctttccg gctcaagcaa  45657
tcctcccacc tcatcctccc aagtagctgc agccacagac acatgccacc acacctggct  45717
aatttctgta ttttttgtaa agacggggtt ttgccatgta gcccaggcta attttttttt  45777
ttttgaggtg gagtcttgcc ctgtcacccc aggttcaact gattctcctg cctcagcctc  45837
ccgagtagct gggattactg gtgcacacca ccacgcccgg ctagtttttt gtacctttag  45897
tagagatggg gtttcaccat gctggccagg caggtcctga cctcatgatc tgcctgcctt  45957
ggcctcccaa agtgccggga ttacaggcgt gagccacgac gcctggccac ccaggctaat  46017
cttgaactct tgaactcttg aactcaaggg atccacccgc ctctgcctcc caaagtgctg  46077
agattacagg cgtgagccac tggccctgt caatttactc agttttttt tttttaatct  46137
ttccaaataa gtgaccaaaa tttaaaaatt gggagagttc atgttaaaaa gtgggtttat  46197
ggcttctcct gaaaccctat gagacaagta ttatgtttaa cctccatttt atagatgaga  46257
caactgaaaa attgaactcg aagcttacat gaaatcacag cgttagcaga ggcagagtgg  46317
agacttgaac caggtcaatc tggttcctga gtctgtactc tttaactccc atgtcatatc  46377
cctgccagtt agatggggtt agtgctctcc agccctcctc tctccctgtc cccccatcct  46437
gggaccctct catacacaca gttctctctt tcctgggaca ctccctctac tctaaggctg  46497
cctggctctt cctcatcttt ctgccaactt taatgtcacc tccttggaac acacttctct  46557
gggcaaacac agagagtcct acctaatttt tctctgttgc tgacatttgt gcttccttga  46617
taaaacctat cactgtttct aattaattct tgtttgtgac tctattttat ctgtgtcggc  46677
tccaaaaagg taaacaccat tcctgtgatt gctatggttt gaatgtgtcc ctccaaaatt  46737
catgttggaa cttaacccct aaggcaatga catcaatagg tggggcttgg gccaggcttg  46797
gtggcacatg ccagtaattc cagcattttt tgggaggcca aggtggaagg tttgcttgag  46857
cccaggagtt caagaccagc ctgggcaaca tagtgagacc cccatctcta caaaaacaat  46917
ttttttaaat tagccaggta taatggtgca catctgtagt cccagctact caggaaattg  46977
aggtaagagg atcgtttcgg tttgagactg cggtgagcca tgatcatgcc actgcattcc  47037
agcctggttg acagaatgag accctgtctc aaaaaaaaaa aaaagaggtg gggctttggg  47097
gaggtgatta ggtcatgagg gctctatgaa taggataaat ctccttataa aaaaagctca  47157
agtgagttgc agagcccctt ttttgtcctt ccaccatgtg cagacatggt attcatcccc  47217
tctggaagat acggcaacaa ggcaccatcc gaaagcagag agcagccctc gccaggcact  47277
gaccctgcca gcaccttaat cttggacttc tcagcctcta gaactgtaag aaataaattt  47337
ctcttgttta taaattacct agttttggat attttgttat agcagcacaa atggactaac  47397
agtgatttac tctgagcctc tggcagacaa tagaccttca acaagtaact gttgaataaa  47457
gcaataaatg gtctcattta actggatgta caggtgagga atatcataga tgcagcgtta  47517
```

aagagctggg atgtcatccc attaggggca gattctcaag actagttttt cccctttcct 47577 aattaactga actctaggca aaagtcctca gaggcaggaa agggttttcc ttctttaaca 47637 catgaaatca gcgacatcca gcaggctttg aggtatggac cttatgagaa gggaagagaa 47697 atgaaaatat ctacatataa gattcccact tgcctatgat ttgaatgtgt gtttttctcc 47757 aaaattcatg ttggaaccta acacccaatg tgataacagt aagaggtggg ggccttttgg 47817 gaagcaatta agtcataagc actccatcct taggaatgag attagtgttc ttataaaaaa 47877 ggttgaagac agcatcttag tctcttttat cctacaatcc tttccaccag gtaagaacat 47937 agcgttcatc ctctctggag gatatagcaa caaggcgcta tcttggaaac agacagtggg 47997 tccccaccag acaccaaatg tgtctgagcc ttgaacttgg actccccagt ctccaaaact 48057 aggagaaata aatttctaat atttataatt actcagtctg tggcatttta ttacagcagc 48117 aggaatgcac taagacacgt ccccccatca aaaataacat aatctttaaa agttttacca 48177 tcttttcttt tgagtactgg gtgttacctg aatagtatcc tctttttatt ctatttttat 48237 tttatgtatt tatttttatg tatttttttt tttgagacag gatctctttt tgtcactcag 48297 gctggagtgc ggtgaacaat catagctcac tgcagcctcc aactcctggc ctcaagcaat 48357 cctcccacct taacctccca agtagctagg atcacaggca catgccacca tccctggcta 48417 ttttgtgtgt gtgtgtgtat tttttgtaga gatgaggttt caccatgttg cccaggctgg 48477 tcttgaactc ctgggctcaa gagaatcacc caaagtgcta ggattacagg cataagccac 48537 tgtgcctggc cttgaatact atcactttat tctccagaca tccattcttc accaatcatc 48597 caggctttgg gaagtagacc atgtactgca gcaatttcct gactcctgga acaccgtctt 48657 caaggtaggg gtctatatgt acccattgta aatttgaatt gcaaaaaaaa ttctaattca 48717 ttagggcctg acaatttttc ctaacattcg gtagtttaaa aacatccaca catgtgaata 48777 ctgcagacaa attcatgaaa agactaatgg tttctctaga gtgacagaaa aatcaattgt 48837 gaaaatcatg agttatcacc tacaaggaat ttatgtgatt ctttagggga tcattggtca 48897 atgtggaaat gtcaagtata agccctttc agttccccta ggtaaggtta gctattcttt 48957 ttctgtctgt ggctccacta aagccattat catattgaat tgcaataatt tgcctttgtg 49017 tctatatccc catgtgagca acttaaaagc agtgagcaca ccacaaacca atttgtaacc 49077 ccagcagagg gccaaaaaca ttccagaggt actcagtcac tatggaatga ataagtaaat 49137 gacatagtcc ctgactccag gaatgtacaa tctagctgga aactaagaca tagaaaagtg 49197 gaaaaataat tccaagacag ttatttgcta agaagtaaaa gagagattta caataattac 49257 taaagagaga aaagagagac atcagtgtgt gctgcaatcc acaggaagat gtgtaggagg 49317 agatagtgaa gagagagaga aaggctgtcc agatatagga aatcgcatgg ccaagatatt 49377 caggcaggaa aacacaaggc atttaatgag tttaatagat acagatggag tggagtggat 49437 ggttgactct gttgagatta atcaactgat atggaaacta aaaatgtcgg ctagtgctgt 49497 ggtttgaata tttgcatccc tccaaaattc atgtcaaaat gtaatctccg gctgggtgcg 49557 gtggctcatg cctgtaatcc caacactttc caaggctgag gcaggtgaat catttgaggt 49617 caggagttca tgaccagctt gaccaacatg gtgagacccc tgtctctact gaaaatacaa 49677 aacttagcca gccgtggtgg catgcacctg taatcccagc tactcgggag gctgaggtag 49737 gagaatcgct tgaaacggga ggcagaggtt gcagtgagct gagatcgtgc cattgtactc 49797 cagcctgggc aacaagagtg aaactccagg ttgaaaaaaa aaaaaattaa tcctcatcgt 49857 ggtggtatta agaggtgggg catttgggaa agtgattaac tctcaaacaa tggaattaat 49917 aatggccttt tacaagtcca ttagagagct tcctggcctt tccatctctt ctgccatgtg 49977 atggcacagc atttgttccc acttttgccc ttctgccatg tgaggacaca gagtttgccc 50037 cttccaccgt gtgaggacac agcaagagat gtcatctatg aaccagaggg taagccttta 50097 ccagactcaa atctgctagt gccttgatcg gggacttccc agccttcaga actgtggaaa 50157 aatacgtttc tcttatttat aatttaccca gtctaagata ttttgttata gtattccaaa 50217 caaactaaga gtaaggaata gatcaagagg gcctctgaca tttagctaag aattttagaa 50277 attatttaat aagctagagg gtattggaaa ggaaagtgac agaagatatt ttaagtttag 50337 tttagcaaga tagaacagta tgaattggag gtagaggtaa aaatattaag agtctaagtt 50397 ggaataatga caataaaaga gatgaaaagt aaaagctacc ttatatttct taagcctgag 50457 ttactgagga gtaggagttt catacagaag gactgatcag ccatagcaca actaagaaaa 50517 gtatccacta cagctggaag tgtggagatg gagcttagaa gagaagtctt tatacgagat 50577 gttagaaaag aaactttggc caggcacagt ggctcacgcc tgtaatccca gcactttagg 50637 aggccgagac gtgcggatca cttgaggtca ggaattcaag atcagcctgg ccaacatgat 50697 gaaactccat ctctactaaa aatataaaaa ttagcagggc atggtggcag gcgcctgtaa 50757 tcccagctac tctggaggct gaggcaggaa aatcacttga actcgggagg tggaagttgc 50817 agtgagccga gatcatgcca ctgcactcca gcttgggcaa ccgagtgaga caccatctca 50877 aaaataaata aataaataaa ataaaaatac aaaagttagc cagatatggt ggtacccacc 50937 tgtaatccca actacttggg aggctgaggc aggagaatca cttgaatccg ggaggcagaa 50997 gttgcagtga actgagatca cgccactgcc ctccagccta ggtgacagag tgagacctta 51057 tctgaaaaaa aaaaaaaaat catagagtca aaaagtggaa tggtggttgc caggggcttg 51117 gagaaggaag gaatgggaag ttactgttta atgggatgga gtttcagttt gggaagataa 51177 aagttctgga gatgtgtgat ggtggtgatg gttgcacaat aatgtcactg aaatgtatgc 51237 ttaaaatggc taaaatagta cattttatgt tatatataaa atacacaatg ttacatataa 51297 gaacacaaac atagtaagat gatagttcta ccaaccatct ttatgaaagg aatcattgat 51357 cccacgggag aggtgagagc tctgaggaag aaaattagga gcaagaaaag gacagagtct 51417 tagggatgcc cacattgagg ggaaggagaa ggaagtgggg tttagtcaaa ccttccaaga 51477 tttgacatcc ctaccaatca aagttctacc ctacaagtta agaggaaaat ctgagtccta 51537 ttgattattc ctgagatgtc cagtgaagca ctgaaatgca aaattgctgt gggatagcaa 51597 ggatggtagt gattttaaac tactttccaa gttgttagag tggcaagcta tgaatatgtt 51657 ttgaacaaat accagtagct acttggcaag aaaggagtta ttaatggtca ctggcttcta 51717 gacagttttt cttgcagaac ttggagagaa aaataaatac atcatgaaac atattcattt 51777 cagtcagttg taaatttgtg gttctgtgca tgagggaggt agaaaaggat gagtatatgt 51837 ttagatgtga agaggaatat aagacatggg atgattttag gctttaatta caaaataaaa 51897 cacccagcac ccatgattat gtttatttag aaaaagtttg tctagggaag caggagtatt 51957 aaaatggttt agttcagttt tcagcaagaa aagctggttc tttgtcactc caaccaggta 52017 ggcagctaaa acaataggcc tctataaata gcaaataagg ctttcatatg aaaagatgaa 52077 aaaattgtca atttaaaata caacaaattt ttcctggaaa acatactcat agctgtattc 52137 tctggcagat cctattgcta gagaagcaag ttgtagggag aaaatggttg tgtttctcca 52197 agaatacagg gcaaaattcg tatatgtttg tgtgataaaa acattagaac ttgtatgttt 52257 gagttgtttt gtctatttcc ttaattatct ggagataata ctaatacatc tgtctttgca 52317 gtggaaaatc tacacttaga cataactgtc ctctaaaatt aatccaccat gtctcattct 52377 actggatgaa ctgtttttat attttctttt ctttctttct tttttttttt tctttttttg 52437 agatggcatc tcactctgtc aaccaggctg gagtgaagtg gcacaatctc ggctcactgc 52497 aacctctgcc tcccaggttc aaacgattct cctgcctcag cctcccaagt agctgggaat 52557 acaggtgccc acgaccatgc ctggataatt tttttgtatt tttagtagag atggggtttt 52617 accatgttgg ccaggctggt ttcaaactcc tgacctcaag tgatccaccc acctcgggct 52677 gccaaagtgt tcggattaca ggcatgatcc tagccctttc taactttggc aaaatatctg 52737 attaaaacat cttataataa actggcaatc aaatttaaaa ttgtattaac ttttaagaat 52797 tgatttttct tagcttcagg aagtcctctt ttctttttat ttatttttag ttactttact 52857 tatttattta ttttgataca gtcttgctct gtcgcacagg ctcctggagt gcagtggcgc 52917 gatctcggct cactgcaacc tctgcctccg aggctcaagt gattctcatg cctcagcctc 52977 ccaagtagct gggattacag gtgcgcacca ccacacctgg ctaatttttt gtaggaagct 53037 gtcttttctg aactgagtta ggttaagtac tgtttgggcc ttattaccta acacgaagca 53097 gctggatgac attggagact gaaaactagt ggtccatgga ctgaattaag gaaaaagata 53157 tattttgtca ggcctgagct gtgctttgaa agatttttaa atgattagcc aacagaaaat 53217 actgggaaat acacataagg atctgaattt caggattctt ttagaaaaga aaaggaaaat 53277 ctgacaacca ggactcaaat tcttgaatgg tgtcagtaga atagagttga tttgtggttc 53337 cccctgccct ccagatcaca atagtcccca tctggctgac tttacttgtt aaaattacct 53397 gcttgactct cgtgaaacaa gaaactgatg actgggctgg aaagcatagg gatctcatga 53457 tgctaaaatt tcaaagccct atcagagaaa agaaactgga tcatgcctaa gacatacaat 53517 accataagtg gattgaactg aaatcaacaa aagtggcaac cccaagttct gattagactg 53577 aagagattac ccccaaccaa acctagcttc ctgatagagg aaagggaatc atcttggtgc 53637 agtggggagc aggggtggtg gtggtaaata ttatttataa atactcatac acacacggaa 53697 gtctaaaaca agaaatgcaa aatatgtaaa aaaaaggggg ggaaatatga cccataatga 53757 aaagaaaaaa aactcaataa aagcagactc acaggtaacc ctagtgttag aattagcaga 53817 caaaaatttt caaataacta ttacaaatat gttaaacaat ttagataaaa agatgagtga 53877 aacaagagat aagagaatct cagctaaaat aagaaaatga actaaaaaaa taacaatatc 53937 taaaatgaag tattgattgt ataagtttaa taacaaatca atatagcaga aaaaagaata 53997 agtgaactgc aagataggtc agtaaaaatt attcaaattg aaaacagaat aaaagaatga 54057 ggaaaacaaa aatggggaac aaagaatcag agactaaaag taaatattag gcaactgagt 54117 tgtcttttag tctgttttat gctgctataa cagagtaccc atgactgcat aatgtataaa 54177 taacagagat ttatttctta catttctgaa gtctgggaag tccaaggttg aaaggcctgc 54237 atgagttgag gaccttcttg ctgcgttatt tcatgacaga aggtgaaagg gcaagagagc 54297 aggtatatgc atgagaatga cagagagtga gagagctaaa attgatttcc tcataaacta 54357 atgctcacta taataaaccc actctcatga ttatattagt ccattcacaa gggcagagcc 54417 cttgcgactt aatcaccttg taaatattct acctctcaac attgttgcat tggggattaa 54477 gttttctatt ttcttttttt ctttttgaga cagagtctca ctctgtctct gaggatggag 54537 tgcactgaca cagtctcggc tcactgcaac ctccgcctcc caggtccaag cggttctcct 54597 gcctcatcct cctgagtagt tgggactaca ggcatgcacc accacaccta gctaattttt 54657 gtatttttag tagagatggg gtttcactat gttgggccag tctagtctca aatttctgac 54717 cttgtgatcc atccaccttg gcctcctaca gtgctggtat tacaggcatt agccactgtg 54777
cccagccaag gattaagttt tcaatacgtg aactctggag gacacattca aaccatatat 54837
ctagcataca ggtaattgga atccaggaac agaggagaaa ctggggcaaa ataaatattt 54897
taaaagatag tggccaagag ttttctaaaa ttgatgaaag atatgaaccc atatatccaa 54957
taatcacagt gaacactaag ctagatttaa aaaaaaaaaa ctatacctag agatatttta 55017
aaagaagcca gggcagggga aaggatctat tatgcttatg aatagaaaaa taagaatgtt 55077
ggttaacttc ttaagagaaa aaaaacggaa gacagaaaat gatggaacga catctggaaa 55137
acaaacaaac aaacaaaacc tgtcaaccta gaaatctata ccttcaaaag caccctttaa 55197
aaatgaaagc taaataaaaa cagaaacaga aaaaaattgt cacttgcaga ccagcattat 55257
gagtaacact caacgaagtt tttctccagg aatctgtgaa cgccaccaga atgggcaaag 55317
atgtgaaaaa acataaagta ctctttagaa actttcttta ggagactatt gaccatttaa 55377
agcaaataga atagcaaaat aatcgataat gaaaaaatac atgacatttg cacaagggca 55437
gaagggtaat aaaattatac tgtagtaagt ttcttacatt gtttatgaaa tgataaaata 55497
aggaaaaggt aagaacacat attgtaatct ttagtaacca ctaaaaaaat accaagagat 55557
attactagaa aaacaatagg taagataaaa tagaatactg gctgggcaca gtggctcatg 55617
cctatacttt cagcactttg ggaggctgag gtaggcagat cacttgaaac caggggtttg 55677
agactagcct gggcaacaaa gtgaaacccc atctctaata catacatata tatatatata 55737
cacacacata tacatgacta ctgaataatc cttatgtaac atataatata taatactgat 55797
atattgagaa tagtgaataa ttcttaattt ttactttttt ttaccttttt ttttttttga 55857
gatgtagtct cgccctgttg cccaggctgg agtgcagtgg cgcgatctcg gctcactgca 55917
agctccgcct tccgggttca cgccattctc ctgcctcagc ctccctagta gctgggatca 55977
caggcgccgg ccatcacgcc cagctaattt tttgtatttt tagtagagac ggggtttcac 56037
cgtgttagcc aggatggtct caatctcctg accttgtgat ccgctcgcct cggcctccca 56097
aagtgctggg attacaggcg tgagccaccg cgcccagcct attctcatcc atccttaaga 56157
ctggactctt tggtcattgt taactgactt tttcgtatag gataaattct taaacatgag 56217
atagtagtca attctgccaa cattcagttg ttgtttctga atttcccaca ttgcttaagg 56277
tcaactccac catgacgcta taaaaacact tttctccatt ttttcatata tttgtatagg 56337
tttgttttta catttaagtg aattttaaag ataaaactta cctatctata tggaatgagg 56397
aaggaaacct cttactttca tatacataac caattatgtt acactattta ttacataaac 56457
catactttat caatgattgc agtgccatct ttgtcatata ttaagtccta acaaatacct 56517
aaatatgttc ctacaatctc tattctattt acagatctac ttgacagctg tcgaaccaat 56577
acatgccatt ctgaccataa tacctttaag ataagtttga ccatttaaca taagaagtaa 56637
taaccagacc gggctcagtg gctcacgcct gtaatcccag cactttggga gtccgaggtg 56697
ggtggatcac ctgaggtcgg aagttcaaga ccagcctgac caacatggga gaaaccccat 56757
ttctactaaa aatacaaaat tagctgggcg tggtggcaca tgactatagt cccagcaact 56817
caggaggctg aggcaggaga atcgcttgaa cccgggaggc agaggttgca gtgagctgag 56877
atcgcaccac tgcactccag cctgggcaac agagtgaaat tgtctcaaaa aaaaaaatca 56937
ataagtaaaa tcttaaagta gcaaatgaca gttgcagcca agtaattcca aaagccagct 56997
tcactcggag aaccctgtgc ttcctcttat ttccagcgat ccacatattt agagaaactt 57057
ttccagtaat aaaccataga aattatacct ggaagtagag tcttcaactt ggatttttag 57117 gtgaccctaa caaaaggggg aaatttccca aaacatatcc gaaatggact ttctcactgc 57177 tttggctagt cgaggttaag aatcagaggt aattttagaa catatagatg aggtgacaac 57237 tcatacaccc aagtatgtag agcaactcat atctacccca ctgcatttgg agggaaagtg 57297 tttccctggt gaacttgtga gtataaatag atggaagaag atgtactcaa aacagcaaac 57357 ttctaattat acaaaatgtt atattttctg cttagtgaag ccacatccat gtagattatg 57417 atgctctaat cattacacct gtcaacacaa tgaaatagct caaatctctg aaaaactttg 57477 cttcactctt aatgatgtca aaaattacaa ctcaaattaa atcttcatgt ctctaatgaa 57537 acctcaactc tgcaaatttc cttatttaaa aatgctgttt tagccaaaga aatgtttcaa 57597 aaattctgta ttcaggccag gcacggtggc ttacgcctgt aatcccagca ctttgggagg 57657 ccaaggtggg tggattgctt gaggtcagga gttcgagacc agcctggctg acatgggga 57717 aaccccgtct ctactaaaaa tacaaaaagc cggatgtggt ggtgcatgcc tgtagtccca 57777 gctactcagg agactgaggc aggagaatca cttgaacgca ggaggcggag gttgcagtga 57837 gccgagattg tgccactgca ctccagcctg ggtgacagag cgacgctccc tctgaaaaaa 57897 gaaaaaaaaa ttctgtattc acaaatagct tgatactagc aatcacttgt ttacattgta 57957 aataggcagc aggctgaaaa tttttgatga cttaattgca ggttcacagc tatgaaggca 58017 agccaaaggg ctaccttgcc aggtctgtaa aactgatgta catagtatga gctgcttgat 58077 ctttgagtaa tcacaaaaga caaatcaggc tgggcatggt ggctcatgcc tgtaatccca 58137 gtgctttggg aggccgaggc aggtggatta cttaaggtca ggcattggag accagcctgg 58197 ccaacatggt gaaatcccat ttctataaaa aaaacaaaag ttagctgggc atggtggtgt 58257 gtgcctgtag tcccagctac tcaggaagca gaggcaggag aaccgcttga acccgggaag 58317 tggagtttgc agtgagccga gatcatgcga ctgcactcca gcctgggaga cagagtgaaa 58377 ctctgtctca aaagaaaaaa aaaaaaggaa agaaataaaa gacaaatcag caaaaagagg 58437 aattcataaa aagagaataa agctttgcaa aaaaagaacc tgtctttgga tcttcagaag 58497 tgactaaaat attttaatag gtccctttta gtgcctcttt ttgcttgcct atgaaatatt 58557 gacagatctt cccaactggg ggaaaaaaaa cccaaaattc attaaactca ctgtgtctta 58617 tttggttaaa taaaaagagg tagaaagact attatgagaa aagagaagca atagaaactg 58677 tggaaattgg agttccaaac atcaatctta atttgattga atagtagaaa gtatataaac 58737 tatggaaatt gatgttccaa acatcaatcc gcattcctga gcaattttca aattggtcac 58797 cagctctcca ctcctcctgt catgagtcac ttatacctta aaaagtatat cctctgagaa 58857 ttctgaaagg tatccagacc ttccattaga caacttccaa tccatatgtg cctcaaagtt 58917 gtgtcttcat tttcctcctg ttccatttcc ttcagatttc caccaagata tgcatgttga 58977 gctttgtttt gagactacat ccagatgtca cctacctctc ctgtggcctt aaaaagattc 59037 tataagcaca gagagatcag cctgagacat ctgaagacct aagcctgcat ccttcctggt 59097 ttttggatta agggaatgta aagatgagag gaaaatgagc aaggcgaggt gataactcat 59157 ttctaaataa aacaggaata tttttaaaaa tctgacactg ctaaaggcca agtcatacag 59217 taggattccc accaggccag gctgtaaata ttgattctcc tctctgcaac cccagtgttc 59277 aggcttcaga gtaacagtct tagttcctcc aaccacattt ctaaccacaa ggtcactgca 59337 cacttcacca tcctggccat cttcctttag cacatacaat tgtaagttta aaaattttat 59397 cttttatttt cagtcctccc acagctgttg ggacttggac aaacctacct tataatcaaa 59457 tatttgcggt gttttctagt ttgaaaagca ctgttcaaaa gttatctcat ttaatcttta 59517 caactgttga ctttacagat aaagaaaact gcagatcaga aaagttaaat aaatgcccaa 59577
ggacacacaa cttgtaagaa aagaagccag ggctaggcta ggccggctgc agtggctcac 59637
gcctgtaatc ccagaacctt gggaggccaa gacaggcgga tcatctgatg tcaggagttc 59697
gagaccagcc tggccaacat ggttaaaccc cgtttttacc ccncnnnccc cnnnnnnncc 59757
cnnggggnng ggcggggcnn nnnnnnnnnn nnnnnnnnnn nnnnnnnnnn nnnnnnnnnn 59817
nnnnnnnnnn nnnnnnnnnn nnnnnnnnnn nnnnnnnnnn nnnnnnnnnn nnnnnnnntt 59877
tttctttttc cttttttttt tttttttttt tgagacggag tctcgctgtg tcccccaggc 59937
tggagtacaa tggcatgatc tcggctcact gcaacctctg cctcccaggt ttcaagcgat 59997
tttcctgcct cagcctcccg agtagctggg attacaggca cccaccaccg tgcccagcta 60057
atttttgtat ctttaataga gatggggttt caccatcttg gccaggctgg tcttgaactc 60117
ctgacctcat gatccaccca cctcagtctc ccaaagtgct gggattacag gcatgagcca 60177
ccatgcccgg ccccaaaact atttctaaga gaagtgttga aagtgaggct tggctccttc 60237
cgactgctta tagtaaaata acagaagaga gaaatgactt aaatatgaaa ttgttaggta 60297
aaaaaggaag cagaacgtaa agatttagaa aattcttaga ctatccatat tgcaaaacaa 60357
gataacagta aagatgtgac caagcaacca tttgctaatg aaatttgtat ggatcagcca 60417
tctcaacaga agccaggtat gatcctctaa gacaatggaa gaatgacccc aaagatgatt 60477
ccagagatca tcagggctgc cttccttggt ttcaaaaggg aagaccatca ttgcacaatc 60537
agccagatct cctccaccca aaatagtgac agcaggactg ccaaaaggct tggagcctaa 60597
gccctgcctg acagagccgt gggagcagaa cctctaacct agcagttctt gaaggcagga 60657
gtcccactgt agtgggcctg gaaggagcat caagccaaaa aagatttttc tcaagcctta 60717
agatctcatg gagtttggct tgtagcctgg acttacatgg gatttgttac ccttttcttc 60777
tttgctattt ctccctttg gaatggatat gtctattcta tccctgtccc accactgtat 60837
tttggaagca tatggcttat ttggtttcac agtgtcacag ctagggagca atttgcctca 60897
agatgaatca tatcttgagt ctcacccata tctgatttag atgatattta ggtgagactg 60957
tgggttttaa attttaggtt gatgctggaa tgaatcaaga ttttgaggac tgttgggatg 61017
caatgtcttt tgcttgtgag aaaaacataa attttgggag gcaaggggtg gcaggctatg 61077
gattgaatat gtatccccca aaattcatat gttgaaatac taatctccaa tgtgctggca 61137
ttaggaagtg ggcactttgg taggtgataa ggccatgagg gcagagtcct tatgaatgga 61197
attagtgctg ttataaaaga gactctggat agcaccccta cttcttctat catgtgagaa 61257
cttagcaaga cactatctgt gaacctggaa gaaggccctc accagacacc aaatctgctg 61317
gcactttgat ataggaattc ccagtctcca gaactgtgag aaataaatct gttactacaa 61377
gctacctagt ctatggtagt ttgtaatagc agttccaaca gactaaggca aatgtctatt 61437
aaattttttg ttcatttttt aaatggttta tctttttatt ggtcagtttt aagagttcct 61497
tatctattct gaatactaga ctgttacctg atatatggtt tacaaatatt tttccagctc 61557
ttttaattgc cttttcgctt tattgctagt gtcctttgaa gcaaaaagtt tctaattttg 61617
atgaagtcca attgtgctga actgttttga accacaaaat ttctttatga aaattttcat 61677
catgatgcag gtaactaaaa ttaaaatgca gggcttttta taattattca tttgacaaat 61737
aactgaatat ggaatcagct tacaatttct ctgctggtac aaaagtcaaa tttctttaat 61797
ttgtaaaaga gacaaataac tataaagtag gcaaattaaa tatttaatag tcaaaagata 61857
ccaaattaat tttgtcatga ggcattcata acaaaagatt tttttctata caggctagga 61917 aaaaattgct tgaaagggat caaaataaat ataatcaatt tcttgccaat ggatagaggt 61977 taaggccatc tctagatgtc ccgtttgtag aatttctata ttcttaaatt agttttggaa 62037 tctacatctg gactaaatgc taatattatt aattcacaga acatgtttgc ttgccatcat 62097 ttcttaagat gtgaagttat acaaacatat ttcccctgca gcatttcaaa acatactcaa 62157 ccattaaaag gaaattaatt ttaaagacat ctgtgccaaa atgtatgata tatttgcttc 62217 ttctgcagag agctacaaaa gacagaactt tgctttggta ataataaaat gtgttgactt 62277 ccaagcactg catagttttg caatggaaaa caagctggag aagcttttga aggtttgtca 62337 gaaactatga tgtctgggtg gcaagtggga tttcactaat ccccagggac attgcaaaac 62397 tgtcttccca accatctgtt gctaggactc tagtcaaaaa gaggatgaca agtgaaaact 62457 attttggcaa cagaacaaaa aataagaaat ccaaaacaaa cctctcacaa acagttgggc 62517 tttctattag attcaaatca tacatgacca catttttaga aatgcacata ttcaactcac 62577 tgaaaatgcc aaaagagata gaatggaaaa ggaaaggtaa ccaggagggg acacctcttc 62637 tggaagaaac ctgtctatta atacttgttc atatgacaga aaagttcatt gagggcagtg 62697 attgtattct tagaatgtca gtgctggcta aatgaatatg tgaagagaga gtacaagaaa 62757 ggatcataag atccagatag gaaagaaatc agcttgaaaa tatccacagt atgtgacttg 62817 ggataaggaa agaacactga gcatggcagt ggtattctca agtgggatct ttagtaacca 62877 ttcattcact tattcaacaa atatttgtga aactacaatg ggtaccatct tagacactag 62937 ggatgcagct aaacaaaaca gactagatcc ctgccctcat ggagcttaca ttgaaaagct 62997 aataattatg gagcactgaa gtgtgccaag cattgtgttc agagcttcat atatattctc 63057 tctgatcttc acaccacccc tatgggataa gcactatcat cattcccatt ttacagagga 63117 gacaattgaa gtttacataa agggacttgt ttacgtccaa gaattgataa caaacacagg 63177 tctgcctaac cactgaaact ctaatcttca ccactgcaca actcccctca cagattcatc 63237 acatgactct aagatcatac ttctatatta ataactgcta tgccatgttg tttatttttg 63297 gatggcaatt atgcaaatgg gtgttatacc atttcatact atattatact attatagtca 63357 ttcacagatg agagaaaaat cttccatatt ggtaaagttt aaatctatgg gctgaagaaa 63417 ggaaattttt tgtctctgaa gattgctgaa agaggagaca gtgaggagat acaaagttaa 63477 aagagatgca catagcagaa aggaataatg ctatgagttt ttctaagatg gaagagagct 63537 gtctcccact agagataaag aattaactct cagcacccag gcaaaagagg aaactaggtt 63597 aaaaaaaaaa aaagaactct ggcaactctg tgctaggatg gtgtgtaagt cttaaagtaa 63657 ttattaatga gattcagaat attaaaaaac taagaaaatc atttgagtat atattgtctc 63717 tgatgatttt ccagtaattc agaatctaga aaataacata taaaatatta acatgaccct 63777 ccagggatat ctacataaat cttattgcta aataagttaa ttatgactta ttattccata 63837 aaatgtcaat ttagctcaac tttcaactgt tcaaattcag aacacctaaa gtctctccag 63897 agtcctgtag atacaacttt catagaaact gcttaggtga cctgtgatat aacacaggca 63957 gacatgaaga tttctgggag gagagatgca ctctgaaaaa tagggctatg gagtctgttc 64017 cttctacatt cattttagca atgctacatc ttcactatta gacactctag atcatgctca 64077 cttcccactt ccaataattt atagcttttc ttttaaaaat aattttatta attgatatta 64137 tgctggaata tcaaaactct taaaagattc aattactaaa cacttaaaga aatataaatc 64197 ttccagagtc aatatcagta tcactgtgag tttttaggca gatgtgacag aaaagaagac 64257 gtcaaaatta gaacaggaag caaaataatc tcattaaatc aaagctatat tagaaattgt 64317

```
catatgacat attgtgcaaa ttacagtgca tatttgtgct tcatttcatt caataaatat  64377
ttacagaata caataggcca agccttgtgc tagaagcata tatacaggac aaaatgacat  64437
agtctgagct tttggtggat ttacattata atttgcctga taaaacacgt catatgacac  64497
ataacaggtc gtattttta acatcttgta agaaaaaaat tttaggtcta aggaaataac  64557
ctcaaaattg ttagttgaaa tgtataatgg tacagccact ctgaaaaaca gttgggcaat  64617
ttctttaaaa aataaacata cacttaccaa acaaactagc aattacactc tcatgcattt  64677
aactcagaga agtaaaaatt tacaactcca caaaaacatg tacatgaata ttcatagtag  64737
ctttattttt aaagccccca aattggaaac aacctacatg tccaataaga gataaatggt  64797
taaacaaact gtgctacata tataccacgg aatactactc aacaatataa aggaactgat  64857
tgatatatga tataaaaaga actatggata tatgaaacaa ccttgacaga tctcaagggt  64917
atttaagggg aaaaaagcta acctcaaaag gccacttaat gtatgattcc atttatataa  64977
caatcttgaa atgacaaaat tattaagaga gaaaacagat taatgatttc catgaggtag  65037
gtagggatga tgaaaataaa aatacagtat gtcagatggt aatgttatca aaaaaataaa  65097
gcagactaaa aaaacaaaac agagggccca aatggggaag gagattattg ctactgtaca  65157
taggttggtg agaaaggctg ctctgaagga ggtacaagag tgagtcacgt ggatattcga  65217
agcagagagg acagaagagt agtgtccatg gctggagtgt gcacagtgcc tttcagaggg  65277
ctcagtgtgg ttgaatgagg gaggacagag gagcaggaga tactgttaaa acattgggaa  65337
aaagaggaga gttgatcata agtggtcttg taggcaactg tatggatttt gactttttt  65397
tgctgactga cctagggaag ctgctgaaaa gtttggagca cagggtttat accagtgccc  65457
aaaacagtga ctgcaaatga taggtgttca gcaaatagtt gttcaaggga tggcatgttt  65517
tgacttatat ttttaaaaaa ggatcaccat ggctgctgaa agaagaatga aatgtgttaa  65577
ggcaagagtc tgaagaaaca gtattgatgt gagagtaaat cagtgcaatt tccattgaga  65637
gcaatttggc aataatttgg caatatctgt caaaaaatatc aatatatata acttttgatc  65697
caggaattct tcttctagga atatatccta cagatgtact cacacatgtg tgaaataatg  65757
tatctggaag gcttctgtgt aatagcaata gattttaaac aacttcaatg gccactgtga  65817
gataagttag agaaactata gaatacccat acaacagaat accacgcaac cataaaaatt  65877
taatagaaag ctctttacat gctgatataa aacagtctcc aagatatata ttaaatgaaa  65937
aaccaaggca gatttcaatg ctatgatttg tattttaaaa ggtaatagaa aaaaaatatg  65997
tatttgtgtg tgtgtagaga tgtatatctt tgcaggagca ctcaagaaac ggtagcatca  66057
gtcatctcca ggaagaatag cagggtgaag gggctaggga tgggtggggg ccaggatgga  66117
gggaaaacat ttcactgtat gtaattttta aacttttgga ttttgaacta tgtaactaaa  66177
aaatgaataa cattgaaatt ttctttaata tttttaaaat agattattta tataccttag  66237
ttaggaactg gggaaagaaa cacgagactt aaagttacaa ggatgtaggt ttaagaccac  66297
ttccagcatt agtaggggta taacattaga aaagtcacat aaccttttga gcctcagttt  66357
cctaactggt gaatggaatt gttgtagagt agcctaactc ttaaccaaag ttcatctttc  66417
cactgtgcat cacattccat cctttctcct ctactcaatt atgtggcttg tattagtttg  66477
ctacggatgc cataacaaat atcacagaca ggtgccctaa acaacagaaa tttatttcct  66537
tacaattctg gagtctagaa gtccaagatc aaggtatcaa cagggttgtt tttctaagtc  66597
tctgtctcct tggcttgtag gtggccatgt gtctccccat gatctttcct ctgtgtatat  66657
ctgtgccctt atttcataag gatggtatga gataccaatc tcattggatt atcgcccacc  66717
```

taatgacctc atgcagccat cattaacctc tttaatgacc ctatctccaa atacagttcc 66777
attttgaggt actgagggtg aggactttaa catataacat caggaggatc acaattcagc 66837
ccataacaaa gtattggcaa ctctgctctt tttcccaatg tcatcaattt ctttaatctc 66897
tgttggacca ttttcatcag tgtacaatgt gcttttattt cttttatctt aaaaaaaaaa 66957
atctctgact ccacttctcc gttcagcaac caccctattt tctgggtctc ctttacagca 67017
taagtcttcc aaagagttgt ccatattcac tgtctcaaat tcctctttta ttctcttaca 67077
ctcattccaa caaagctttt gccccctcac tccactgaag ctgctattgc ttttgtcacc 67137
aatcaactct atgtcacaaa atacaatggt caaaactcag tcctcacctt aacttgtcct 67197
gttagcatta ctgatgtact tttacttggc tttaaagaca catattctat tagttttcct 67257
cctaattcat tggttgctgc ttctcaattt ccatttctgg tttctttctt cttcccctct 67317
attgaacgtt acttcttgaa cttctttctt tctctaacta tactcaatcc cttagtgata 67377
tcattgtctc atgactttga ataatgtcta cattccaata gctcttgcat ttttgccttg 67437
gatgttcaat agatgtgtta cattcagcat gccccaaagt gaacttatgt tcttccctta 67497
aaaaccggct cacacatagc ctcccctatt ccagctgact ttaactccaa tccctctagc 67557
tgctcaagtc aagtaatctt tgacatcgtt cttttcctta tatctcacat ctaatcctcc 67617
agagaatgcc taaggcataa tctgctatat atatatataa tctgatctct ttttacctcc 67677
ttcaccacta ccatcctggt tcaagctttc atcacctctc acttagatta ctctaaaagc 67737
ctcctaacaa gagtccatgc tcccagtctt actcccctct tcagtatctt cttgacatga 67797
tagacactgt gatcctttaa aaatgtatga cagataattt cactcctctg ctgaacacac 67857
tccaacagct ctacatttca ttcagggtta aaacctaagt gcttaaaata ccctaagact 67917
cttcatgacc tactactaca tttttctctc ttgctcattt ttttttatt atactttaag 67977
ttctagggta catgtgcaca acgtgcagat ttgttacata tgtatacatg tgccacgttg 68037
gtgtgctgca cccattaact cgtcatttac attaggtata tatcctaatg ctatccctcc 68097
ccccatcccg accccacaac aggccccggt gtgtgatgtt ccccttcctg tgcccaggtg 68157
ttctcattgt tcaattccca cctattagtg agaacatgcg gtgtttggtt ttttgtcctt 68217
gcggtagttt gctgagaatg atggtttcca gcttcatcca tgtccctaca aaggacatga 68277
actcatcatt ttttatggct gcgtagtatt ccatggtgta tatgtgccac attttcttaa 68337
tccagtctat catagatgga catttgggtt ggttccaatt cactatttgt gaacagtgcc 68397
tcaaaaaaca taagtgtgca tgtgtcttta tagcggcatg atttataatt ctttgggtat 68457
atacccagta atgggatggc tgggtcaaat ggtatttcta gttctagatc cttgaggaat 68517
cgccatgctg tcttccacaa tggttgaact agtttacagt cccaccaaca gtgtcaaagt 68577
gttcttattt ctccacatcc tctccagcac ctgttgtttc ctgacttttt aatgattgcc 68637
attctaactg gtgtgagatg gtatctcatt gtggttttga cttgcatttc tctgatggcc 68697
agtgatgatg agcatttgtt catgtgtctg ttggctgcat aaatgtcttc ttttgagaag 68757
tgtctgttca tatcctttgc ccactttttg atggggttgt ttttttcttg taaatttgtt 68817
tgagttcttt gtagattctg gatattagcc ctttgtcaga tgagtagatt gcaaaaattt 68877
tctcccattc tgtaggttgc ctgttcactt tgatgatagc ttcttttgct gtgcagaagc 68937
tctttcattt aattagatcc catttgtcaa ttttggcttt tgttgccatt gcttttggtg 68997
ttttagtcag gaagtccttg cccatgccta tgtcctgaat ggtactgcct aggttttctt 69057
ctagggtttt tatggtttta ggtctaacat gtaagtcttt aatccatctt gaattaattt 69117 ttgtataagg tgtaaggaag ggatccagtt tcagctttct acatatggct agccagtttt 69177 cccagcacca tttattaaat agggaatcct ttcctcattt cttgtttttg tcaggtttgt 69237 caaagatcag atggttgtag atgtgtggta ttatttctga gggatctgtt ctgttccatt 69297 ggtctatatc tctgttttgg tatgagtacc atgctgtttt ggttactgta gccttgtagt 69357 atagtttgaa gttaggtagc gtgatgcctc cagctttgtt cttttggctt aggattgtct 69417 tggcaatggg ggctctcttt tggttccata tgaactttaa agttgttttt tccaattctg 69477 tgaagaaagg cattggtagc ttgatgggga tggcattgaa tctataaatt accttgggca 69537 gtatggctat tttcacgata ttgattcttg ctatccatga gcatggaatg ttcttccatt 69597 tgtttgtgtc ctcttttatt tcattgagca atggtttgta gttctccttg aagaggtcct 69657 tcacatccct tgtaaattgg attcctaggt attttattct ctttgaagca attgtgaata 69717 ggagttcact catgatttgg ctctcttttt gactgttatt ggtgtataag aatgcttgtg 69777 atttttgcac attgattttg tatcctgaga ctttgctgaa gttgcttatc agctgaagga 69837 gattttgggc tgagacgatg gggttttcta aatacacaat catgttgtct gcaaagagag 69897 acaatttgac ttcctctatt cctaattgaa tacactttat ttctttctcc tgcctgattg 69957 ccctggccag aacttccaat actatgttga ataggagtgg tgagagaggg catccctgtc 70017 ttgtgccagt tttcaaaggc aatgcttcca gtttttgtcc attcagtatg atattggctg 70077 tgggtttgtc ataaatagct cttattattt tgagatatgt ccaatcaata cttaatttat 70137 tgagagttgt tagcatgaag ggctgttgaa ttttgtcaaa ggccttttct gcatctattg 70197 agataatcat gtggcttttg tctttggttc tgtttacatg ctggtttacg tttactgatt 70257 tgcctatgtt gaaccagcct tgcatcccag ggatgaagcc cacttgatca tggtggataa 70317 gctttttgat gtgctgctgg atttggttta ccagtatttt attgaggatt tttgcatcga 70377 tgttcatcag ggatattggt ctaaaattct cttttttgt tgtgtctctg ccaggatttg 70437 gtatcaggat gatgctggcc tcataaaatg agttagggag gattccctct ttttctattg 70497 attggaatag tttcagaagg aatggtacca gctcctcctt gtacctctgg tagaattcgg 70557 ctgtgaatcc gtcaggtcct ggactttttt tggttggtag gctattaatt attgcttcaa 70617 tttcggagca tgttattggt ctattcagga attcaacttc tttgtggttt agtcttggag 70677 ggtgtatgtg tccaggaatt tgtccatttc ttctagattt tgtagtttat ttgcgcagag 70737 gtgtttatag tattctctga cggtagtttg tatttctgtg ggattggtgg tgatatccca 70797 ttttgttctt taaacattcc agactcactg ctgctttaga gactgctcta actgttccct 70857 ctctctggaa agctcttccc ctagatagcc acttggttat ctcctcagta ctttaagatc 70917 aatgagcctc ttccctgaca tctctattta atacttccta catgcatgtg tgtgtgcaca 70977 cacatacaca cacactctct ctgactccct taatgactat atgattactc acacacacac 71037 atgcacgcac acattctgac ttccttaacc actatatgat tattttttc ttagtctcat 71097 caactccctt aaaactgtaa tattatttgt ttccatagac ctattcttct aacatactct 71157 atcattcatc tagctttgta tgtacctatc tatcaatcat gtttactgtt tattggctgt 71217 ctcctccagc taaactgtaa gctctgtaag ggaagtgaat cattgtctgc tttgttcact 71277 ggtatatctc aaacacccag aacagtgtct ggcgctcagt aagtattcaa aaactgtttg 71337 ttaagtgaat gaatacaagc actggtacta ttgcttctat cacttctacc accaccattc 71397 atattagaaa tatacaaaca gtaaacaatg acaagtcttc gccagttttc caaatcacta 71457 aggatgtcta taagactact tctacaatct ccttttgtca catgaggtca caaaatttca 71517 caaagcggag agttgaaaga gaaaagagta agttatcatt acattccttt taacttgtaa 71577 ccatcaaacc cataattatt agcccatttc ctcattaaat atcctctaat gggtagtaat 71637 cttttgaggg catcttagcc tactttgtgt tgctatgaag gaatatctaa ggctgggtaa 71697 tttatcaaga aaagaggttt attttgctca aggttctgca ggttgtacaa gacgcatggc 71757 gccagcatct gcttggcttc tggtgagggc ctcatgctgc ttccattcat ggtggaaggt 71817 gaaggggagc cagcatgtgc agagatcaca ttgtgagaga ggaagcaaga gagtctgagg 71877 agaggtgtca gcctgttttt aacaagcagc tctagaagga actattagag caagtactta 71937 ctccccctac ccacttaggg agggcattag tcttattcat gaggtatctg tccccatgcc 71997 tcaaacaaac acctcccatt agggactacc tccaacaccg gggatcaaat ttcaacatga 72057 ggtttggagg ggtcaaacat ccaaaccata gcagaggatt tttgtcctta attttttaaa 72117 aaattattta tgggtaagag gtatgtgaaa gtttataaaa tactggaaaa gacactgaat 72177 tgaacctcat tctagttcag tggacaagga aaatatgaac aaaaaactaa tttggaagtc 72237 tcataaatac caataaataa tggtataagc aaactaaaag gaaatcagaa tggacatcag 72297 gaaactgatg aagaaaacaa taataataat agcaatctgt tgcttgtcat gttagtaatc 72357 ttagccttca cttcttctaa ttgttactca tgtggtagtt aagagctcag gaattaaatt 72417 gccaacattt actacctggt tgaacttggg caagttattt aatttgcctc agttctctca 72477 tctgttcaat gtaggataat aatagcaact acttactagg gcttctaaga agaataaata 72537 ccttgtttat aatagtgtct ggcacctagt gatggtcctg aagtcaataa tcagaagtac 72597 catcatagtt atgaaatact aaataaatta tacaaacaaa aaataaatgt gtacacatgc 72657 atgtgtgcat atgtgaatga atggatagaa atggtttcat aacgtgatta tttaattagc 72717 cataagaacc acttcctatc cacgctagat agcaaaatta cattaccttt gttaaattag 72777 gtgttgaaag gtcattagtt ctatattaca aattcttatt attaaaaagt tgcttttata 72837 actattccaa caaagcgtac tgtaagaata aaatctggag caggaaagaa tgaacagaca 72897 cataaggctc cctatggaat cagcccaaac ccagtaagtg ttcaagatta cagaaactga 72957 atttctggct ttacttcagc attattctgg gtcccaaaaa tttgctttct ttttaagtat 73017 ttttcagtat ctctttttta gtgaatgtag gatataacca acgttagaag taaattgtaa 73077 aaaatggttt gcaagttttc attaaaatct catgactatg caaatactca gaatttttgc 73137 ataaataatc accacgaccc ccaaatgatg ttttcgaatg aatcatgcaa acccacagtt 73197 gagagattaa gtataaaaaa agacagatat ccacctctgg cacaacttca aatgcgtcga 73257 tggagacaga aaaatgtcaa acacaaagat tacatgaagc actgcagctt ccatggacag 73317 ggaagaaact accaatactt tctgtatggt aaaatactta aacacacttc agctttcatg 73377 cattataaag aggattgact tgtagaaact caggaccagt ggctttatgg atctgcaaca 73437 gggaccccta tgctgtatat gaacctagtc aaagagctgc acttccaaat gctgacatac 73497 tgctaaggag attggggctt ctctctggtc ctgttcctct ctttgactct ttgactctct 73557 ttgattcaaa gagcaactca gagttttcag aatgatattc taatttgata gtagttgatc 73617 ttttaaattc tagatagtga agggttccag tagattctag ttaacagtaa tgtgtgaagt 73677 ttaaaatgta tctgctgata gagaggaaat tactcatgga agaaatatct ctgatgcata 73737 acacacagtc tggctgtact gagatagttg tttcaaatgg aaaagaatgc agttggtagt 73797 gcttttaatc agaactttaa gaaccactgg gtgacttaaa agatataatg gtagagaaaa 73857 acctcatttg caacaacaat ggaaaaaaga gataatactt ggaaataaac tccaaatgtt 73917

-continued

```
tcaaacctat aggaccaaca ctttaataaa acactctgca aaacacaaat gtagacttga  73977
acaaatggaa agacattcct ggttcttgat taggatgtct caatgtcatc aaaagatgtt  74037
tgtactcact aagtcaattt ataaattttg tgacatccca attaaaaaaa aaccaataag  74097
ctttttctcc cctgggaaat aaacaaatga actttactac acatgaattt tcacatgaaa  74157
caatagccaa aagagaatat caagaaaaac aatgaaaaga aagagttgtg aggagataac  74217
agccacatca gatattaaaa cctaccacaa aatctgtata agtaaaacgg tgtggtcctg  74277
gaacatgaat gcacatgcaa atcaatgaag cagaacagca agtccagcaa aagacctgac  74337
cacaggtgga aattattcta gtatatgata caggtgcaac tcaaaatgct ggggcagcaa  74397
agaacatttt aataagtgct gttgggacaa ttggaaagcc atttccaaaa gataaatttt  74457
catccattcc tcatgtcatc cagtaagcac aaacttcaaa tagatcagat ttttaataag  74517
taaaagtata caagtaattt ttgatggata aattcctcta taattcctct ataatctgag  74577
ggtagaaaag gccttctgtg actaaaaatc cagatgcagt ttttaaaaat tgacatattt  74637
gactaaaaaa aattgaatgg caaaaacacc ataagcaaaa tgataggaca aataaattag  74697
aagaaaatat ttgcaaataa tataaagaac taatattcat aatttataaa gaacttttaa  74757
aagttgatga aaggagatca aaagtactct agaaaatggg caaaagacag gaatagaaaa  74817
tacacaaaaa agatataaaa ttacattaaa atatgaaaat atgttcaatt ttacataaaa  74877
ggaaaattca tattaaaatt atattgaaaa caatttctca tccatcagtt tgacaaaaaa  74937
acaaaagctt gttggtgagg ctgaagaaaa acaggcccat ttttatacat gattttcagg  74997
aaggcaaaag ggtgtaaatc ttatgtaggg gaatttcaca atgtctaaca aaaatatagg  75057
aaccagcttg caggagctct tacttgacaa atgtaaaaca ataaggtacc caaattcatt  75117
cattacaact cattgaatta agaatccatg agtctatact tataataaat aaatacatac  75177
atacataggc agacagctgg agagaaggaa aggctcttcc ttctggtaga atgtcaactg  75237
atgagtgcag ggtgtaatgg aattgaaaat cacccttac aaccatcact gtaagattgt  75297
gggaagaatc aatggggaaa agtttgatga gaagcaggat gtttgtatgg tctcaaagaa  75357
aatgaccaca cattgcttat ttcttgcaag ggagaacata ataaatataa atcaatgtct  75417
tgactgggtg atcaaaatta acataactga agggagatga ttagcaaagg gctctggata  75477
taacacccca agaaggctac attacttagt attgtgggtg agtaggggtt gggagtctga  75537
actgaatcta aacaaataaa tggatggaga attatgggag ccaagttttt cactgttggt  75597
gtggaagtgt gcagatgaac aaggacataa ggctataatc catctattca cacagaatgc  75657
tccacctggt aatggattac agctgaagac attagtataa acaaatgttt agcttaatct  75717
ggatatagaa tgtttcataa aaatatttat agatatctat attttcatgg tttttatata  75777
tattatatat aaatatatat ataattttct tgctctgtca actaagagga tgtagaagaa  75837
caatgacatt ccagtagcaa tgagcatatc tagtaccaga tcttgatttt caatatcctc  75897
cagtgaaagg aagcagggtt ccctgaagaa atagctgatt ctaggacaaa ggcaggaaat  75957
atacatgagt ctgggtcttg tagttccaga aagtaaggaa gtaaaaaaaa aaaaaaaaaa  76017
aaaaggcatg gggtagggga tgggagaaaa gaaaaaaaaa tgccgtaagg gttgacaaca  76077
cagatgccac tgaaagagct cccaatggcc aaagctggaa caatatgagc taaaaaaaaa  76137
aaaaaaaaaa gaaaatgacg tattggagta taacccaaaa tacaaaataa atatgtatca  76197
gtccatactg atataaataa ataattgatt aagtaaataa agggagaaga gaaaactatc  76257
ttgtgcagaa gaattcctaa taattatgct gaggttttat agatgttatg tatgtatatt  76317
```

gccttcaagg aggtggagca taactcctta tttattaagt gtgggctact tcctaaagag 76377 ttgagtatga aagcaggagt agtgggggaa gagtaattgt acagtagaga aaactgaaaa 76437 atgcttcttc agccaggtga taaaggtcaa catcatgtca atggtatata ctcttgatac 76497 gatgtaatga aaatgacact ttacctctgc agtctttctc cccaaaattt atatcaccaa 76557 tctaataatg agaaaaacat cagactcatc ccagctaaga gcatacaaaa tgctaaatag 76617 tgttcctcaa tactgtcatg gtcaccaaaa ataaagaaag tctaagaaac tgccataacc 76677 aagagaagcc aaaggtgacg tgatgagtaa atgtaatatg gcaccctgga tggaatccta 76737 gaacagaata aggatattag gtagaaacta aggaaatctt taaaaagtcc acactttagt 76797 taataatact gtattgttac ttgtaaatgt accatactaa cgtaagatgt aaataataag 76857 aaaaactgga tacaggttat atggaaactc tgtattagct ttgaattatt ctgtacatct 76917 aaaaccattc taaaaaacaa agtttattta aactaaaaac aaatccatgt cagctgaaca 76977 gcttgtgcta atcattactg cagaatatca tcacaaaaca cagatgacct gacgtttcct 77037 cacagttagt tctccacagc tcatggggtc atacagcgca gcctaattaa gagatttggt 77097 agtaaaaaga gaattagaga gtggctggca agatggctga ataggaacag ctccggtctg 77157 caggtcccag tgagatcaac acaaaaggaa ggtgatttct gcatttccaa gtgaggtacc 77217 tgcctcatgt cattgggagt ggtcagacaa tgggtgcagc tcacaaaggg cgagctgaag 77277 tggggtgggg cattgcctta ccccagaagt gcaagcggtc ggggaactcc ctcctctagc 77337 caaggaagcc atgagggact gtgccatgag gaatggtgca ctccggccca gatactatgc 77397 ttttcccaga ttcttcacaa cctgcagacc aggagattca cttccgtgcc tacaccacca 77457 gtgccctggg tttcaagcac aaaactgcgc ggccgtttgg gcagacaccg agctagcttt 77517 aggagttttt tttcataccc cagtggcacc tggaatacca ccgagacaga gccgttcact 77577 cccctggaaa gggggctgaa gccagggagc caagtggtct agctcagcag atcccacccc 77637 catggagccc agcatgctag gatccactgg cttgaaattc tcactgacag cacagcagtc 77697 tgaagtccac ctgggaccct cgaccttggt cgggggaggg gtgtttacca tttctgacac 77757 ttgaaaaggt ggttttcccc taacagtgta aacaaagcca cagggaagtt caaacaagat 77817 ggagcccact gcagctccgc aaagccgcag tagtcagatt gcctctctag attcctcctc 77877 tttgggcagg gcatgtctga aagtaaggca gcagccccag tcaggggctt atagataaaa 77937 ctcccatctc cctgggacag tacacctggg ggaaggagcg gctgtgggcg cagcttcagc 77997 agacttaaat gtccctgcct gcaggctctg aagagagcag cagaagtcct aacacagtgc 78057 tcgtgctctg ctaagggaca gactgcctcc tcaattgggt ccctgacccc cccaccccccc 78117 gcctcctgac tgggagacac ttcccagcag gggttgacag acacctcaca caggagagct 78177 ctggctggca tctggtgggt gcccctctgg gacgaagctt ccagaggaag gaacaggcag 78237 taatctttgc tgttctgcag gctccactgg tgatacccag tcaaacaggg tctggagtgg 78297 acccagtcaa acagggtctg gagtggacct gcaaacacta gcagacctgc agcagagggg 78357 cctgactgtt tagaaggaaa acaaataaac agaaaggaat agcatcaaca tcaacaaaaa 78417 ggatgtccac acaaaaaccc gatctgaagg tcaccaacat caaagaccaa aggtagataa 78477 atccatgaag atgaggaaaa accagcacaa aaaggctgaa aattccaaaa accaggacac 78537 ctcttctcct ccaaacggtc acaactgctt gccagcaagg gaacaaaaat ggacggagta 78597 tgagtttgac gaattgccag aagtaggctt cagaaggtgg gtaataagaa actcctctga 78657 gttaaaggag catgttctaa cccaatgcaa ggaagccaag aaccttgaaa aaaggttaga 78717

```
ggaattgata actagaataa ccgtttagag aagaacataa atgatctgat ggagctgaaa  78777
aacacagaga acttcgtgaa gcatacacaa gtatcaatag ccgaatgatc aagaggaaga  78837
aaggatatca gagattgaag atcaacttaa tgaaataaac agtgaagaaa agattagaga  78897
aaagagaatg aaaacaaaca aacaaagcct ccaaggaata ggggactatg tgaaaagacc  78957
aaacctacat ttgattgtac ctgaaagtgt acctgaaagt gatggagaga atgaaaccaa  79017
gttggaaaac actgttcagg atattatcca ggagaacttc cccaacctag caagacaggc  79077
caacattcaa attcagaaaa tacacagaac accacaaaga taccccctcga gaagagcaac  79137
cccaagacat gtaatcatca gattcaccaa aattgaaacg aaggaaaaaa tgttatgggc  79197
agccagagag aaaggtcggg ttacccacaa agggaagccc atcagactaa cagcagatat  79257
cttggcagac accctaaaag ccagaagaga gtgggggcca atattcaaca ttcttaaaga  79317
aaagaatttt caacccagaa tttcatattc agccaaacta agcttcataa gcacaggaga  79377
aataaaatcc tttacaaaca agcaaatgct gagagatttt gtcaccacca ggcctgcctt  79437
acaagaactc ctgaaggaag cactaaacat ggaaaggaaa aaccggtact atccactgca  79497
aaaacatacc aaattgtaaa caccattgac actatgaaga aactgcatcc agtaatgggc  79557
aaaataacca gctagcatca taatgacagg attaaattca cacataacga tattaacctt  79617
aaacataaat gggccaaatg ccccaaataa aatacacaga ctggcaaatt ggataaagag  79677
tcaagaccca ttggtgtgct gtattcagga gatctacctc atgtgcaaag acactcacag  79737
gctcaaaata aagagatgga gggatattta acaaacaaat ggaaagcaaa aaaaagcagg  79797
ggttgtgatc ctagtccccg attaaacaga ctttaaacca acaaagatca aaaaagaaaa  79857
gaagggcatt acatagtggt aaagggatca atgcaacaag aagagctaac tatcctaaat  79917
atatatgcac ccaatacaga agcacccaga ttcataaaat aagttcttac agatctgcaa  79977
agagacttag atgcccacac aatcatagtg gaagacttta acaccccact gtcaatatta  80037
gacagatgaa tgagacagaa aattaacaag aatattcagg acttgaactc agttctggat  80097
caagtggacc taactgacat ctacagaatt ctccacccca aatcaacaga atataccttc  80157
ttcacagcac cacatcgcac ttattctaaa attgatcaca taattggaag taaaatactc  80217
agcaaatgca aaagaacgga aatcagaaca acagtctttc agaccacagt gcaatcaaac  80277
tagaactcag gattaagaaa ctcactcaaa accccacaac tacatgaaag ctgaacaacc  80337
tgctcctgaa tgactactgg gtaaataatg aaattaaggc agaaataaat aagttctttg  80397
aaatcaatga gaacaaagac acaatgtacc agaatcaacg ggacacaact aaagcagtgt  80457
ttagagtgaa atttatagca ctatatgccc acaggagaaa gtaggaaaga tgtaaagttg  80517
acatcctaac atcaccatta aaagaactag agaagcaaga gcaaacaaat tcaaaagcta  80577
acagaagaca agaaataact acagcagaag tgaaggagat atagagacac gaaaaaccct  80637
taaaaaatca ataaatccag gaggtgcttt ttttaaaaga ttaacaaaat agataagtga  80697
ctagtcagac taataaagaa gaaaagagag aagaatcaaa tagacacaat aaaaatgata  80757
aagggaatat caccactgat cccacagaaa tacaaactac catcagagaa tactataaac  80817
acctctacac aaataaacta gaaaatctag aagaaatgga taaactcctg aacacataca  80877
ccctcccaag actaaaccag gaataagttt aattcctgac tagaccaata acaagttctg  80937
aaattgaggc agtaattaat agcctaccaa ccaaaaaaag cccaggacca gacagagtca  80997
cagctgaatt ctaccagagg tacaaagagg agctggcacc attccttctg aaactattcc  81057
aaacaatgga aaagagggac tcccctctaa ctcacttgat gaggccagca tcatcctgac  81117
```

-continued

```
accaaaacct ggcagagaca caacaaaaaa agaaaagttc aggccaatat ccctgatgaa  81177
catcgatgag aaaatcctca ataaaatact agtaaagcaa atccagcagc acattgaaaa  81237
gctcatctac catgatcaag tcagcttcat acctgggatg caagactggt tcaacatatg  81297
caaatcaaca aatgtaatcc atcacataaa cagaaccagt gacaaaaacc acatgattat  81357
ctcaacagat acagaaaagg ccttcgataa aattcaacac cccttcatgc taaaaactct  81417
ccataaacta ggtattgata aaaagtatct caaaataatg agagctatct atgacaaacc  81477
cacagccaat atcatactga atgggcaaaa actggaagca ttccctttga aaaccagcac  81537
aagacaagga tgccttctct caccactcct attcaacata atattggaag ttctggccag  81597
ggcaatcagg caagagaaat aaataaacgg tattcaaata ggaagagagg aagtcaaatt  81657
gtctctgctt gcagatgaca tgattgtata tttagaaaac cccatcgtct ctcagcccaa  81717
aatctcctta agctgataag caacttcagc aaagtctcag gataaaaaat caatgtgcaa  81777
aaatcacaag cattcctata caccaataat agaaaaacag agagccaaat catgagtgaa  81837
ctcccattca caattgctac aaagagtata aaatacctag gaatacaact cacaacgaat  81897
gtgaaggacg tcttcaagga gaactacaaa ccactgctca aggaaataag agaggacaca  81957
aacaaatgga aaaacattcc atgcttatta ataggaagaa tcaatatcat gaaaatggcc  82017
atattgtcca aagtaattta tagcttcaat gctataaatc aagctatcac tgacttcctt  82077
cacagaatta gaaaaaatta ctttaaattt cacatggaac taaaaaagag cctgtatagc  82137
caagacaatc ctaagccaaa aaaaataaat aaataaatct ggaggtatca cactacctga  82197
cttcaaacta tactacaagg ctacagtaac caaaacagca tggtactggt accaaaacag  82257
atatacagac caatggaaca gaacagaaca gaacagaaca gaggcctcag aaataacacg  82317
acacacctac aaccatctga tctttaacaa atctgacaaa aacatgcaat ggggaaagaa  82377
ttccctactt aataaacagt gttgggaaaa ctggctagct atatgcagaa aactgaaact  82437
ggatcccttc cttacacctt acacaaaaat taactcaaga tggattaaaa tattaaatgt  82497
aagacctaac accataaaaa ccctagagga aaacctaggc aatagcattc aggagatagg  82557
catgggcaaa gacttcatga ccaaaacacc aaaagcaatg ggaacaaaag ccaaaattga  82617
caaatgggat ctaattaaac taaagagcac agcacagcaa aagaaattat catcagagtg  82677
aatgggcaac ttacacaatg ggagaaaatt tttgcaatct gtccatctga caaagggcta  82737
atatccannn nnnnnnnnnn nnnnnnnnnn nnnnnnnnnn nnnnnnnnnn nnnnnnnnnn  82797
nnnnnnnnnn nnnnnnnnnn nnnnnnnnnn nnnnnnnnnn nnnnnnnggc tgaggtggca  82857
gaattgcttg agccctggag gtctaggttg cagtgagtca tgatcatgcc actgcactcc  82917
aaactgggca acagagtgag accctgtttc aatttattta tttattttaa agaagagtga  82977
tattgttttg aatgcaggtt aatagtcctt aatcccctga ggtcggtgtt gcccagtgcc  83037
ataactttag gactaccttc tttcacaaaa tagatgagaa aggaaaaaac agagtggctc  83097
acgcctgtaa tccctacact tgggaggctg aggcaggtgg atcacttgag gtcaggagtt  83157
caagaccagc ctggccaaca tagtgaaacc ccatctctac taaaaataca aaaattagcc  83217
aggcatggca acaggtatct gtagtcccag ctacctggga ggctgaagca ggagaatcac  83277
ttggacctgg gaggcggagg ttgcagtgag ccaagattgc accactgcac tctagcctcg  83337
gcaacggagc gagactccat ctcaaaagaa aaaaaaaaaa agaaagaaag aaagaaagaa  83397
aagaaaggaa aaaacagaaa aaaatatcct gaagaactca gaacagtctc taagtgctta  83457
gttgtgtatg ttcatagcca tgctgatgct gacaacaaat ccaaaaggat cacaccaaac  83517
```

-continued atttttttcaa ttaaaaatta taataaataa cgtaaggtaa tacataggct aattagcttg 83577
atttagccac tccaaatttc aaaacattat gttgtatgcc ataaatatat acaattttta 83637
tttgtcaatt aaaaaataga agataaaata attaggtaaa taggctcaaa aacatttaag 83697
aaattacacg tgaatggggc ttcattaaaa aaaattccat cctagccagg cacggtggtt 83757
tatgcctgta atcccagcac tttgggaggc caaggcgggt ggatcacccg cggtgaggag 83817
ttcgagacca gcctggccaa gatggtgaaa cctcatctct actgaaaata taaaaattag 83877
ccgggcgtgg tggtgggcac ctgtaatccc agctacttgg gaggctgagg cagagaactg 83937
cctgaacctg ggaggtggag gttacagtga gctgagatcg tgccactgca ctccagcctg 83997
ggtagtaaag caagacatca tctcaaaaaa aaaagaaaaa aaaattccat cctaagtaaa 84057
tctttgggaa taaaggctag gtttttttccc ccctgctttt atgtctattg agtttcttcg 84117
ctttagaatg agcctctgca ttaataagat cctctgggat catatccaca aaagggtatt 84177
aaatccttga agggttgtta taaatcttct gtcttggcca cactaataga aatccagcct 84237
aggaacacct tcctcacccc tgagcccctt ctctaaggaa ctctacagtg tcagtcagtc 84297
atccaaatca atgactttac ccatcaccta caggcagcca gtctgcctgg ctgaaccatg 84357
gcagtcattc tgcctcagaa ataactctga tggacaaccc gggcagggag gaatacggga 84417
aattataaga aggacctagg catggaggta gaccagctga aagttttcca ggaacatttg 84477
aaacactctt ttttacactt gagacaagtg acatggtttt cttaatgagc acatgcagcc 84537
aaaatcccag ttcatatact ggaaggaaaa gtctcataga acaagcagca gacctctgag 84597
gaatggattc agaaacaatt ccagacccag aatgtgaaaa gttagcttta aataccctgc 84657
tctcagacca cccaggaatg gtatccagac ctcatcctgg cctctagaga attcccaggg 84717
ccacctgtca aagtggcttg tcaggcatgg ataaaaatgc cattggggga aggaaaatgc 84777
aacataaagc cttctagcag aggaaatatg aagaatagta ttttctacac gactgcgcta 84837
aagggttcat ttaaagaaaa aaacacttct aactattagg gaaaattcca ggttaactat 84897
acttaaaaaa aaaaaaaaag cccaaaaatc tagtaaatat tttgctggga aattcacact 84957
taaagaaatg gtctttcagg cccctgggga gaaggcatta agctgacaca tttttcaaat 85017
caaaatggct gctctaaaaa cataaacctt caaaatgaac accacagaga gcccctttct 85077
tcctgtgctg agcacgctca ctacccactc agagcgccct gtgccaaggc gaagtcaaac 85137
cccatagaaa cctgatcccc actgtggaga aaactgtgca gcgcccttgt tttctgtcgt 85197
gctttgtttt gtatttcaga tgtgctggtc acatctgttc tttatctccc ctcttccact 85257
gtgattttgt ttacaggatc ccagaacaat ggggactgca gaatctccac acagatgaca 85317
ggagacaagg ctctcagggg gtagtcactg tctgcaaaac gtggagccaa aggcgtggtt 85377
ttcagagtag ctgccaacac tccaagttac tcaggctcat ggaccaggaa tgactggaaa 85437
ggagactgcc ttgtctgggg aagatccaga cccacagatg caattttttg aaagtaatct 85497
ctttacaatg gcctgcccat ctcctctctc tgcttagaag tttttgtgtt ctgtaaggag 85557
ccttctaatg ggcttctgtc tgcctgggct tctgtccctt tggttctccc agtctgctct 85617
ctgtctcttt tgtttctttc atccctggat tccaggaagt caaggtcagg gcagcttacc 85677
agtccctaaa caccattatt ttggcaggat gctttggcag tggaatgaat gcctgcagaa 85737
ggcctcacct agtcacccac aaattcatga acacagctgt gacttttcga agcagaagcc 85797
agactcttag tctttgtttt ttatcttttt tttctttttt tttttttttt gagacggagt 85857
ctcactctgt cgcctaggct ggagtgcggt gacaccatct tggctcactg caacttctgc 85917 ctcctgggtt caagcagttc tcctgcctca gcctcccgag taggtgggat tacaggcacc 85977
caccactaca cctggctaag ttttgtattt ttagtagaga tggggtttca ccatcttggc 86037
caggctggtc ttgaactcct gacctcatga tctgcccacc tcggcctccc aaagtgctgg 86097
gactagaggt gtgagccacc gcacctggcc tgtttttcat cttattttta aaagtcatat 86157
gtcgagcaag aaaaaatcta gactacagtg ttactcaaac tgtgggttgc taacagacag 86217
tgctcctcat ggctcttact actggtcagt ggagaaacga agaaattgag agaatgcatt 86277
tagaaaattt catagtgctt tcacagaata atcttatgtc tcttgaatct aataataaaa 86337
attggggagc ctatatttta catgtctttg gtttgctatt tcacttttct atttattcat 86397
ttttagtata tttataagaa tgtcagtcca taatggcatg gaaataattc aagaagaagg 86457
aaaccctatc acacatagta tgaaaagcaa accacagacg atacaaaaaa agaaagaaaa 86517
aaaacccacc aaacactcat ttagccatta cccagccttt gtcaaaactt aacattttat 86577
catgtttgcc tttgcttttt taatttttat tgattggttg attgattgag acagactctc 86637
actttatcac ccaggctaga gtacagaggc ccacatggct cattgcagcc tcaacctcct 86697
gagctcaagg gatcctcaca cctcagcctc ccaattagct gggactaaag ctcatgccac 86757
catgtttggc taattaaaaa tttttttttg tagagacagg gtctcactat gttgtccagg 86817
ctggtctcaa actcatgtga tcctcccacc ttggcctccc aacgtgctgg gattataggc 86877
atgagccatc gcacctggac attgcctttt tttctttttt tttttgaga cggagtttag 86937
ctctgtcacc cccaggctgg agtgcagtgg cccaatcttg gctcactgca acctccgcct 86997
tcctagttca agcaatactc ctgcctcagc ctttcgagta gctgggacta caggcatgca 87057
tcaccatgcc cagctaattt ttgtattttt agtagagaca gtgtttcacc atgttggcca 87117
ggctggtctt gaactcttga cttcaagtga tccgcctgtc ttggcttccc aaagtgctgg 87177
gattacaggc gtgagccacc atgcccagcc tagccattgc ctttttttaaa gagattaaaa 87237
attacacatt tttcctcacc tttcctctct tccacccttc tctttaccct tccctccctc 87297
ttcattctct ttcttttccc cctcttcctc ctctcttcca ttctccttct acccacccca 87357
cttctcttct attccctccc ctccctcctt catctgcctt ccacttctca cttccctaca 87417
cttctacctc ccttctctct tctccccctc cctctaattt ttaggtaaat tgagcatggt 87477
agacctccaa ggttgggaga cagaggaatc cacagtggcc cagcatgagg aagcagagcc 87537
tgggcaggat gcataagtgg gatgccaggt gaagggatgt ggggtgtcag cacccaggag 87597
aggtgagcaa gttgtccatg aagcagggca gcctctggca tgggaagtca ggactcaaac 87657
aggagagaaa gcctgtcaca tgggagaatg agatgggata ttagccgtac tccagaggat 87717
tgatcaaata aataaatgcg ataagaataa tgacagccag gtctctatgg aaataaggaa 87777
aactaggata aattctgaat tgttgaacca gaattagatg tgttggtgaa aacttaaagt 87837
ttatcatata tagagatcaa cgaataatat agttttaaat gtgtatatat gcatatacat 87897
ttctattccc tagctccgtg tgccgagagc agcgacaccc catgagcaat gaacacacct 87957
agtgctcaga tctggtttct aaatattgtt tttcactaaa aggaatgagg acttcttgga 88017
gagctggcag attctagagt taagactgag aatgcacacg atgagcctgg aacatcttgt 88077
accagaaatc aagacagtac tccaacaatg atgaggatct gtcaaaggac acagaagtga 88137
acttgaatgg gcttcccctg gccggtgtgg tcaggatttg aacattaaat taaataatta 88197
tagtaacaaa ttataatcta tttgctaaaa tagaaatcat gagcccattc agatgtacat 88257
taaaacatga gtaaattaag agtttgaagg gatgggacat ttacatagtt attcattata 88317

```
aaggaaaaga gagtctcttt acagtgaaaa agcgggcaga caccacagta atcatgtgat  88377
ccagctgaac atcatcattg cttgagccca agagtttgag cctgcagtga actgcgatca  88437
tgtcactaga ctccagcctg agtgacagac caagatccta tctctaaaac aacaacatta  88497
ttctggtttc ttagagtgtg ttaaaaaaat tatacaaaat gaacatcatc agtgttaatt  88557
aaataaaact taataggagg gcattggttc agactgggct cctaccctag gcctaacaga  88617
ccaaaatgga gttaaaccaa gccaaaacta agttgtttat ctgaccttcc aagaaatcag  88677
gaaagaaaaa tagccaaatc cctaaacagg ccagttttat acagcatgat aaggaagtcc  88737
cctctgcttt aacccttaca aaaaggtaat ctggactggg tgtggtagct catgtctgta  88797
atttcagcac tttgggaagc cgaggtgggt ggatcgtttg agaccaggag tttgagacca  88857
gcctggccaa catggcgaaa ccccacctct actaaaaata caaaaattag ccgggtgtgg  88917
tggcacacac ctgtagtccc agctactgtg gaggctgagg catgagaatc gctggaaccc  88977
aggaggagga ggttgcagtg agccaagatc atgccactgc actccagctg ggctacagag  89037
tgagactttg tctcaaaaaa aaaaaaaaaa aagaaagaaa gaaaagggaa aaaagtaacc  89097
tgaagtaact tgacattggt caatcagctt tatttctatt gttctgtttc cttgttctca  89157
ccttacaaaa cccacttctc ttttgccccc tgccaatcta ttcttctatt ttgtagaata  89217
gaggctatct taactcataa attccaaata aaagccaatt aggtctataa ctaaactcat  89277
gattttgtct tttgacatca gtaatgggac aaattgaaac tgtgcaccat tggtaccata  89337
caatgagaag tacacgacat cacttctgtg atcatcctgc tacatgaatc taatcacaag  89397
gaaatatcag aaaaacccaa attgaagggc attttacaaa ataagctaac tacaagcttc  89457
aaaattatca gggtcataaa agtcaataga agaccaagga atctttcttt tttatgtata  89517
tattctccaa tttaaaactt ttaattaaaa agtaaacttt aatgtcgaaa atgcaaactt  89577
ggggaagaca gaaaagatca cacacaaggc tgtcacttca cacttggaag gttgcacaat  89637
ggccggacag aggcgctcct cacttcccag atggggtggc tgggcagagg cgctccttac  89697
ttcccagacg gttggcagcc aggcagaggc gcctgctcct cgcttcctag acggttggca  89757
gccgggtaga ggcgctcctc acatcccagt cagttggcag ccagacagag gcgctcctca  89817
cttcccagac ggggcagtgg ccaggcggag gcgctcctca cttcccagac ggttggcggc  89877
cggggcagag gcactaacca aggaaacttt ctataatgga gtaggttaaa ggaacatgat  89937
aaactaaaca taatgcttga tttggcattg aatccttttg atctaagtgg caaaacttga  89997
atggggtatg aatatgagat actagcaatg tcaatattaa tttcttcttt ttttttttt  90057
tttctgatga tggagtctcg ctctgttacc caggctggag tgcagtggtg caattttggc  90117
taactgcaac ctctgcctcc cgggtccaag agattctcct gcctcagcct tctgagtagc  90177
tgtgactaca ggtgcccgct accatgcctg gttaattttt gtatttttag tagacacggg  90237
tttctccatg ttagcaaagc tggtctcgaa cccctgacct caggtgatct accagctcag  90297
cctcccaaag tgctgggatt acaggcatga gccatgcacc cagcctattt atttatttga  90357
gatggagtct tgctctgtca cccaggctgg tgtgcagcag ggcaatttca gctcactgca  90417
acctccacct ctggggctca agtgatcctc ctacctcagc ctcccgagta gctgggacca  90477
caggcgcatg ccaccatgcc caactaattt ttgtattttt tggtagagat ggagtttcac  90537
catgttggcc aggctggtct caaactcctg acctcaactg atctgcctgc ctcagcctcc  90597
caaagtgctg ggattacagg tgtgagccac tggacccagc cctcagcctc gtttttttctt  90657
ttcttttctt ttctttcttt cttttttttt tttttttttt tagaggtgga agcttggcta  90717
```

-continued

```
tgttgtccag gctggcctca aacccctggg tttgaactcc tgggctcaag ggatcctcct  90777
gcctcagccc ctggagttgc tgggaccaca gggatgtatt accacacaca gctcattttc  90837
ttaatctcct cacctttaat aattttgtct ctaccctatc ttaaccatac actcccatgg  90897
gcctctctgg attttgtctt tcttaatatt ttcttaagcc tttttctata gcctcaatca  90957
agcatcccat tttcatattt ccagctcatt cccattcctt tccatattca gacctgcatt  91017
cttctggttg ctcagatcaa atactttgga accattcttg atccattcct tgtggcagag  91077
gagaggaaat gtgtaaagga gggtgaggcc ctacagtcaa gaggtgggat agcatgaatg  91137
caaagaagag tagcactggg gccagccaca gtggctcaca cctgtaatct cagcactttg  91197
agaggccaag gcatgcagat cacctgacca gtctggccaa catgttgaaa ccccatctgt  91257
actaaaaata caaaaattag ccaggcatgg tggctcgaac ctgtaatccc tgctactcag  91317
gaggctgagg cagcagaatc acttgaacct ggaaggcgga ggttgcagtg agctgagatc  91377
gcaccactgc actccagcct gggtgacaga gtgaggctcc gtctaaaaaa aaaaaaagag  91437
tagcattgga tttgggaatg taagcttata ggtgaacttg caaacaggaa tgttattgga  91497
aggtggggac aaaatcctga ttttttcaat gttttggaga tagtctgtca ctaaggctgg  91557
agtacagtgg tgcaatcatg gctcactgta gcctcaaaat gttgggctca agctatcctc  91617
ctgcctcagc ctccagagta acagggtcta caggtgcacc accacacctg actaattttt  91677
attgtttatg gatatggggg tctcactatg ttgccaaggc tggtcttgaa ctcctggcct  91737
caagcagtcc tccctgtctt ggcttccgaa agtattggga ttacaggcat gcccagccaa  91797
tcctgatttg aattgaggaa ataatcatag tatttctcaa ggaattgctt gaatctgaat  91857
actcaagaag cacttattaa gcaatcaaat gatgtgggct aagtcatttt cgaaagtctt  91917
gaacctttag ccttgaaagt cggaccaatg agtttgtgcc ttatttgttt ctgaaggtct  91977
ttttgagtct tgcgttagga aattaatccg gcaaaagcag gcacaaaaga tcttgtgggt  92037
tgaggagtca gtaaaaagac tactggaata gcccgggtac aagcttatga gacactgaga  92097
tgggagccgg ggggttaggg ggtgggcaga agcgggaaga gcagtggcac tgggaatcaa  92157
tacaagagga aggaaaatca acaaccatac catagaaaat gagtcagatt tggaactgat  92217
tagatgtgga tggggagaca gaagaatcag agaataagtc aaagctagcc aggagtgttt  92277
caacctggat tcctgagaat cctgttacct aggaggagac actgtttctt agatttagtt  92337
tgaggagaag atgatagctt tggtcttaaa ttgctttttt tttgttgttt ttttttctcg  92397
agatggagtt ttgctctgtc tccggggctg gagttcaatg gcatgatctg ggctcactgc  92457
aacctccacc ccctgggttc aagtgattct cctgcctcag cctcctgagt agctgggatt  92517
acaggcatgc accaccacgc ctggctaatt ttttgtattt ttagtagaga tggggtttca  92577
ccatgttgac caggctgatc tcgaactcct gacctcgtga tccacccgct tcggcctccc  92637
aaagtgctgg gattataggc atgagccacc gcgcctggcc ttaaattgtt tttttgtttg  92697
tttttcagac agagttttgc tctgttgccc aggctagaag ctcagtggtg ccatcttggc  92757
tcactgcaac ctccgcctcc tgggttcaag cgattctcct gcctcagcct cccaagtagc  92817
tgggattaca ggtgcatacc accacacccg gctaattttt tgcattttta gtagagacgg  92877
ggtttcacca tgttggccag gctagtctgg aactcctgac ctcaggtgat ccaccccccct  92937
cggcctccca aaatgcaagg atcacaggtg tgaaccactg tgcctggcaa aaaatatttt  92997
taattttaat tttttaaatt tgtttttgag acaggaactc actctgtcac ccacactgga  93057
gtgcagtggc atgatcacag ctcactgcag cctcaacttc ctgggctcat gcgatcctgc  93117
```

```
tatccacccg agtagctgga ataacaggtg tgtgccacca tgcctggcta atttttaat  93177
tttttgtaga gatgaggtct cattatgttg cccaggctaa tctcaaactc ctgagctcaa  93237
gggatccttc caccttggcc tcccaaagtg ctgggatgag agacgtgagc cacctcatcc  93297
tctagtattt ttcactgata gagctagaag acaacctggg aaaggcagca attagaaatt  93357
aggtcataga agtagaaaga gtacttgagg ctgcagtctg tcaagctgca tggaaatgaa  93417
agttgaagcc ctaagatatg atgaaccaca gtcataacta taacttcctt ttaataaggc  93477
ttgctttctt ccaacagctg ccttaaatat ttgaaatatt tctctcccag tcgttatggt  93537
acagtgtaag taagtgttgt taactcagta ctgcagacca gaaagctaag gttcagggga  93597
atcaaataac ttgtcatgtt aacagaactc acaagtaaag aactagatct tgaacccaga  93657
tccacctgat cccatgcagt ttgatgtcag aatttggtag tcaaaggagt caatgaaaca  93717
gacagagaag aatttgttag gagaaagaaa attatgtatt tattttaatt ttatttattt  93777
ttatttttat tttttgaga tggagtcttg ttctgttgcc caggcgggag tgcagtggcg  93837
caatcttggc tcactgcaac ctctgtctcc tgggttcaag tgattctcct gtctcagcct  93897
ccatagtagc tgggactaca ggcgtgtgcc accatgcctg gctaattttt tttgtatttt  93957
taaaagagac agggtttcac catattggcc aggctgccct cgagctcctg acctcgcgat  94017
ccacccacct cagcctccca aagagctgag attacaggcg tgagccaccg aacccagctt  94077
atatatttat ttatttattg tatttattta tttattttga gatagagtct cactctgtca  94137
tccaggttgg agtgcagtgg tgtgatatcg gcttactgca acctccacct cccaagttca  94197
agtaattatc gtgtctcagc ctcctgagta gcacagaaac accccaccat acccggccat  94257
accgtacacc ataccattac agaagcaccc caccataccc agccatactg tacaccctac  94317
cattacagaa gtaccccacc atacccagcc atactgtaca ccctaccatt acagaagtac  94377
cccaccatac ccggccatac cgtacaccat accattacag aagcacccca ccatagctgg  94437
ccaattttg tatttttagt agagacacag ttttgccata ttggccaggc tggtctcgaa  94497
cttctgacct caagtgatcc acctgcctca atctcccaaa gtgttgggat ttcaggcatg  94557
agccacctag aagaaataaa attataactt tgtggggcta ctgagggtga agaaagaaac  94617
caaggaattt caagaaggaa aagttcacca gtcaaatgct ccagaactaa gaaaacacaa  94677
caaaacccac tgagtttagg tgttagtgtt ggtttcagtg gatggaggag aaaggcagat  94737
tcctaaggtt aaatctgaac ataagcccag agtaaggaga ggatcctctt ggtattatgg  94797
tcaccaactg tcctaatgcg tctaggactg tccccttttt agcacagaaa gtcacacatt  94857
tcaggaaact cctatgtcct gggtaaccca gggccaccct acccatggca gctagtgtaa  94917
ccaccctacc cccggcctct cctttttct gagacagagt ctgctctgtg acccaggctg  94977
gagtgcagtg caacctccac cacccaaatt caagtgattc tcctgcctca gcctccttag  95037
tagctgggat tacaagcgtg tgccaccatg cctagctcat atttgtattt ttagtagaga  95097
tggcgtttca ccacattggt caggctggtc tcgacctgac ctcaagtaat ctgcccatct  95157
tggcctccca aaatactggg attacaggcg cgaaccatgg cgcctggcct tggtgtaaac  95217
cccttttaag agaggttgag caaggaagag ctgaaagata agggggttgc ttccaagtgt  95277
agcaaggtca aggaaaggtt ttttattttt tttgataaag aaaacttgcg tctgttaata  95337
aactgggaga ggagattggg aagtacaatc gtcgttggac ttgatcccag aggaagcgaa  95397
actgcattgt tctgaaaggc aggcggcagt gtcccatgtt tctcacagcc ctcactgtgc  95457
tggctcagag ttgccctgtc ctgggactct gaacaggcag tgagtgctgg attccagcct  95517
```

ctgtgcatgc cttcacccga cagcgctgcg gagcagagtg ttggataaaa gtcggacaca 95577
ttagggttct gcactactgt gactgtggct gtcacacctt tctgggcctc agtttcctca 95637
actgtaaaag ccaatattac cagataaaag tggggagcac agtgcctaac acatgacagg 95697
aacaggtaga gtgtccctta ttcctttatc caaaatgctt ggtactggag tgggtttttt 95757
gttgttgttt ttgtttttgt ttttgagatg aagtcttact ctgtcaccca ggctggaatg 95817
cagtggcaca atcttagttc acggcaacct ccacctccca ggttcaagcg attctcctac 95877
ctcagcctcc cgagtagctg ggattacaga tgtgtgctac cacacctggc taatttttgt 95937
atttttagta gagatggggt ttcaccatgt tggccaggct ggtctttaac tcccgatctc 95997
aggtgatctg cctgcctcgg cctcccaaag tgctgggatt acaggcatca gccaatgagc 96057
aagaaataaa ttctttatca gatacatgtt ttacaaagaa tttctcccag tcttgtcttt 96117
tcattccctt aagagtcata ctgtggccag acacacctgt aatcccagca attttggaag 96177
ctgaggtggt ggattgcttg ggcccaggtg tttaagacct gtttggcaac atggcaaaac 96237
cctgtctcta ccaaaaaaaa atataaaaag acaaaaacaa aaaacaaaaa tttaccgggc 96297
atggtggcac acgcctgtaa tcccaactac tcgggaggct gaggtggcag aattgcttca 96357
gccctggagg tataggttgc agtgagtcat gatcatgcca ctgcactcca aactgggcaa 96417
cagagtgaga ccctgtttca atttatttat ttattttaaa gaagagtgat attgttttga 96477
atgcaggtta atagtcctta atcccctgag nnnnnnnnnn nnnnnnnnnn nnnnnnnnnn 96537
nnnnnnnnnn nnnnnnnnnn nnnnnnnnnn nnnnnnnnnn nnnnnnnnnn nnnnnnnnnn 96597
nnnnnnnnnn gtgaaaccct atctctaata aaaatacaaa agttagctgg gcatggtggc 96657
ttgttcctgt aatcccagct actcgggagg ctgaggcagg agaatcgctt gaacccagga 96717
ggtggaggtt gcagtgagcc gagatcatgc cactgcactc tagcctgggc cgtagagcaa 96777
aactctgctt ccaaaaaaaa aaaaaaaatc tattgggttt taaattatac aatcattcta 96837
gaaaatgtct tacaatacaa tgttgtataa gctaagtata aaaagtaaaa agagtaaaaa 96897
tggccaggcg tggtggttca cacctgtaat ccaagcactt tgggaggcca acgtgggcgg 96957
atcacaagct caggagttcg agaccaacct ggccaatatg gcgaaaccct gtctctacta 97017
aaatacaaaa attagctggg cgtggtggcg cacacctgta gtcccagcta ctcaggagac 97077
tgaggcagaa gaatcgcttg aaccggggag gcagaggttg cagtgagctg aggtcacacc 97137
actgcactcc agcctcggtg acagagtgag actgcatctc aaaaaaaaag gaagcgtaaa 97197
aatttacaaa atccacttcc ttccagcccc aattctacaa agcaaaggcc accactgctg 97257
ttgatatgta tatataagct tcatgagggt ttgtctgttt tctttaacat tatatcccta 97317
atttttggca gtgtctaatg catagtaatc attcaataaa tattcattga ttaaatgatt 97377
aaagtaatgt tctgcatgta tattttttac tttagtatca catttagtgt gtatatataa 97437
gattacattg tattctatat aattaatata ttatacatta tttaaccaat gcctgaactt 97497
ttaggctgtt tataattttt cctatagcaa acaatgctga tacaatcaac cttttatgca 97557
catctttgta cttgtgtgat tctttctgaa gaacaatttt tagaactgga attacagtgt 97617
caatgtgcaa acatattaaa cttttttttag tatttctttc ctctattttt ctatttaggg 97677
ggcttttttt ctaattacaa aagtagtgca tgttgtctgt aacaagtcta attataatgc 97737
taaaagttac caaacattta ttgtgtacca gtcactatgc caggattttt tgtgtattac 97797
cttatgtact ggctggctag gccaagggag ggtagcccat ggaaagcccc aaagtaagga 97857
aaattaaaaa aaaaattctt ccgcatgaga acagatgagg aaatattgtt tcaatgacaa 97917 tacagcaaga attacatgtt ctagaatgca gccatttggt tcggggatga tgtgcctttc 97977 caaggatggt tactttttac aatagtaagt ataattttgg gagctgacct tcttgaggat 98037 ataaaagacc taaattctac attgttgtga ttctctcacc aggcagacat ctcattctat 98097 atctatgcta acaactaatt gttagcatct ctgacctttg gagacttttc cataaaaaga 98157 caaaggaggc aatgggaaac cacatctacc tacttgcatt tttatcttac atagaccttc 98217 aaggtaactt agtttaagca gacttaaaca gaatccagat cattattctc attcatcttt 98277 ttgtttttgt ttttgttttt gttttttttc tgagatgtag tctcgccctg ttgcccaggc 98337 tggagtgcag tggcgcgatc tcggctcact gcaagctccg ccttccgggt tcacgccatt 98397 ctcctgcctc agcctcccta gtagctggga tcacaggcgc cggccatcac gcccagctaa 98457 tttttgtat ttttagtaga gacggggttt caccgtgtta gccaggatgg tctcaatctc 98517 ctgaccttgt gatccgctcg cctcggcctc ccaaagtgct gggattacag gcgtgagcca 98577 ccgcgcccag cctattctca tccatcctta agactggact ctttggtcat tgttaactga 98637 ctttttcgta taggataaat tcttaaacat gagatagtag tcaattctgc caacattcag 98697 ttgttgtttc tgaatttccc acattgctta aggtcaactc caccatgacg ctataaaaac 98757 acttttctcc attttttcat atatttgtat aggtttgttt ttacatttaa gtgaatttta 98817 aagataaaac ttacctatct atatggaatg aggaaggaaa cctcttactt tcatatacat 98877 aaccaattat gttacactat ttattacata aaccatactt tatcaatgat tgcagtgcca 98937 tctttgtcat atattaagtc ctaacaaata cctaaatatg ttcctacaat ctctattcta 98997 tttacagatc tacttgacag ctgtcgaacc aatacatgcc attctgacca taataccttt 99057 aagataagtt tgaccattta acataagaag taataaccag accgggctca gtggctcacg 99117 cctgtaatcc cagcactttg ggagtccgag gtgggtggat cacctgaggt cggaagttca 99177 agaccagcct gaccaacatg gagaaacccc atttctacta aaaatacaaa attagctggg 99237 cgtggtggca catgcctgta gtcccagcaa ctcaggaggc tgaggcagga aaatcgcttg 99297 aacccgggag ccggaggtta cagtgagctg agatcgcacc attgcactcc agcctgggca 99357 acaagagtga aattgtctca aaaaaaaaaa aaaaaaaaaa aatgtgggga aaaaaatctt 99417 cctcagctga agaaagaaaa aaaaaacaaa tctgacgtgg tagacaaaat agtctaaagg 99477 aattccctac tacaaaataa tgagatcctg cacaaaacaa aatgtttatt gctgggcttc 99537 caggaaataa ggtaaacctc tgacagtagg tccaaacctt gaactgacac cagaatagaa 99597 gtcctaagat gcttaaaaag tcagcttgtc ctgcaggcat atgtgatatc agctctgcaa 99657 tgtagagttc aaattttggg tcaatagaaa aaaaatagaa gctgaagctg agctttcctg 99717 attaaagaaa gggaacaaaa gtgactccta gcagaagcta ttccgctcac agtttcattc 99777 gacggatttt ctacaagtta aggttaatga aatctgactg ccaagcatac gtgttaatga 99837 gtttcttctg agtgagagcc agctgaaatc acaaacaaca gatttggaca cccttaatta 99897 ttttaattat gtataagatg ttttaaataa ataggagatc ttttttgtag ttcataaatg 99957 cgatgattgg gttttcatgt ttatgtgtga gatgtgcttc cctcaaacct tgttatgatg 100017 tcagtacgtt atccatctga tgtggaagaa aaagaaaaca aacaagaaga aataaatagg 100077 agtcataaag caataaatta cagaaacaca aatatgagga ataaaagatt atccaaagtg 100137 gccagacttt agaagaagcc aaagtgaatt tttagttttt aaaaattgtt gaagtaaaaa 100197 tttgaatata tggataaaaa ttagatacag cttaaaacag aattagtaaa ctggaagttg 100257 ggtagaataa attatccaga atacagccct ctcactccca aatggatagt atgataagag 100317

```
atagaagtgt atatatctaa ttcaaatcca gaagtagaga acagataaga ctgagaagtg 100377
gcaatatttg aagctatttg ccaggcacgg tggctcacgc ctgtaatccc agcactttgg 100437
gaggctgagg tgggtggatc acatggtcag aggttcgaga ccagcctgac caacatggtg 100497
aaaccctgtc tgtactaaaa atacaaaaat tagctgggca tggtggcagg cacctgtaat 100557
ccaagctact caggaggctg aggcaggaga attgcttgaa cctgggaggc ggaggttgca 100617
gtgagccgag atcgcgccac tgcactccag cctgggtgac agagcgagac tctgtctcaa 100677
gaaaaaaaaa tttgaagcta ttatggctga gaattttcca gaagcaatgt atgacattga 100737
tccacagata cagatggaaa atgaatacca aggaaaacaa atagaaagaa atctacactt 100797
aaacatattt ctgtgaaata caaaacacca atgcccctcc ctaccactcc cctcacacac 100857
acagaatgca actactgaga taaaatagat taccaataat ggaatgacaa ttagagtgat 100917
aacagacttt ttcataatgt gggaaggcag gagatagtgg aataatatct tcaaagtgtt 100977
gagaaaaaat tctgtcaatc ttaaattgta tacccagaaa aactatctaa ttttaggaaa 101037
tgcattgtga agtatttaga ggtaaagtac ttaagagtac tataaatctg taacttaact 101097
tcaaacattt aagaaaaaaa atacataaat aaatatatgt gtacacacat atatatttaa 101157
agagagagag aagcaaataa gataaaatgt taacatttgg agaatcttag tgaaggggat 101217
atttgggaat tctttatgct atttttacac ctttaggagt ataaaatgat ttcaaaattt 101277
caaaagataa aacttacaat agcagtaata aatataagta cctagaaata aaagatatga 101337
agaagactac aaaggagaaa cacactgcat tgatgagaga acacttagta ttatacaatg 101397
tatataatta tacaattaca cactacactt cacaacatcc cccacattta cctacagact 101457
caatgctttt cctataaaaa tcccaaaagg agtatttgag taacttaagc tgactctaaa 101517
atttatgtaa cagataaaag accccaaaat aattaaaata gccctgaaga acaacaacaa 101577
caaaaaacat gagtgaggac atgccctgtc agatagcaag acttatcata gatgacatag 101637
tacttaacac agcttagtat cagttcagat agacaaagta atcatctgaa caaaattgaa 101697
agcctgaaaa aaaaggccca cacttacgtg gacacttgat ttatgacaaa aatggtgaac 101757
tattcagtaa atggtgttgg gacaataggt tatgaaaaaa aacaaagaaa atcatatact 101817
tatatatcat acacagaagc agtctctgct gtattatata caaaacttga attctcttag 101877
agaacgttat aggataaatat ttttataacc ttaaggtagg gaagtatttc ttaaacaaga 101937
ttgaaaggca cagataaatt cagctacatt aaaattaaga acttttagcc aggcacggtg 101997
gctcacgcct gtaatcccag cacttgtgag gcggagacgg gcggatcact tgaggccagg 102057
agtttgagat cagcctggcc aacatggtga aaccccatct ctactaaaaa atacaaaaac 102117
tgagtatggt ggtgcacgcc tgtaatccca gctactcagg aggctgaggc acaagaatca 102177
cttgaaccca ggaggtggag gttgcagtga gccaagatca cgccactgca ctgcaccctg 102237
ggtgacagag tgagactctg tctcaaaaaa agaaaaaaaa aaagaacttt tgttctttaa 102297
aaggcaccat agagaaataa agaagctatt tgctacactt ataatcattg aagggttagt 102357
atccagaata tccaaagtcc aaaaaattag taatccataa aacagtaaat cagtaaaaca 102417
cacatgatgc aatatagttc tggacaggaa gtatgagcag gcatctcaca aaagagaaaa 102477
tatgaatggt gaaaagagat atgaaagttc ctcaaactca ctagtaatta gcaaaataag 102537
accataagga attatatttt acacccactg gattgccaaa agttaagaag cctgagtcta 102597
cagagttggt gaaattttag atcaactgta actcatatat acaattgttg gggctgggca 102657
tggtggctca cacctgtaat cccagcactc tgggaggctg aggcaggagg attgcttgag 102717
```

cctagacatt caagaccagc ttgggcaaca tagcaagacc ctgtctctac aaaacaaaat 102777 aataataatt taaaaagtaa ctgggcatgg tggtgcttgc ctgcattccc agctacttag 102837 gaggctgagg tggaagaatt gcttgagcct gggagattga ggctgcagtg agctgtgata 102897 atgcctctat acctcagcct gggtgacaga gtgagacctc atctcaaaaa caataaatta 102957 attaattaaa taaataaaac ctcatcttgg taagcttctt ctcaatacac aggtgactat 103017 atttccagat ttttaaaaaa atgtggtttc ttggccaggt gtggtagctc acacctgtaa 103077 tctcagcacc ttgggaggct gaggcaggtg gattgcttgg gctcagcagt tcaagaccag 103137 catgggcaac atggtaaaat gccgtcccta caaaaaatac aaaaaacaaa acaaaacaaa 103197 acaaaaaaat tacccgatca tgttggcacg tgcctgtagt cccagctact cagaagactg 103257 aggtagaaga atcgcttgag cccaggagct taaggctgaa gtgagccatg atcatgccac 103317 tgcactccag cctgggggac acagtgagat cctgtctcaa aagaaaataa tatatatatg 103377 tttctttaaa gatatctttg gattctttga ggtttttaca aatactaaca taatcttcat 103437 ctctttagca aggctatcca cattgactct ggatatatat ccaggagtaa tttttaaag 103497 tttacttaca atcataaaac tgtgtttgca ttgctcagta gccctgcata gtttactaaa 103557 acagttcaaa tcatttcgac atagtaacac cagctaatta tcacaaacta atcacacttg 103617 gaagaattgt ttccttgact aacaattgcc atatctcaga accgttactt ctcaataata 103677 taagctcttg gtcattagga ttgaaaaaag aggagatgag ctcatcatca tctttggaga 103737 gacaagcagg gggcaaaagc aacaagactg catgtcctgg ctattttccc cagaatagat 103797 tccagtttgc ctttctccta atatgctcag aatataaacc aacacttcac atttggtcta 103857 tttcttgctt cagtcattac gctttcatta gtggactttt tagttccttt aattctttat 103917 ctctcactag cactactttt taatatttca ttttatagtc tttattagct tattggttgt 103977 atctcttttt atttgttctc ttttgtctgg gtttgtggct ttggggtcta cagtgtacat 104037 tcctcacttg ttcttttttc tctttctttt ttacagacat gatctcactt ccatcaccca 104097 gactgcagtg cagtggtgca atcgcagctc actgcagcct ggaattccag agctcaagcg 104157 atcttcccac ctcagcctct caagtagctg ggactatggg tacacacaac tacaccctgc 104217 aaagtctaca gtgtaccttc ttaacttatc agtctctttt caaataatat tagactacct 104277 ttttattgat ttattttta atcgagacgg agtcttgctc tcttgcccag gctggagtgc 104337 agtggtgcaa tcttggctca ctgcaacctc tgcctcccgg gttcaagtga ttctcctgcc 104397 tcagctccca agtagctggg attacaggtc tgtgccacca cgcccagcta atttttgtat 104457 ttttagtaga gacagggttt caccatgttg gccaggctga tctcgagctc ctgatctcaa 104517 atgatccacc caactcagcc tcccaaagtg ctgggattac aagcgtgagc caccacacct 104577 ggcctagacc accttttgta gaagaatttg gcctattata taaaagcctt acaacagtgt 104637 gcttccattt ttctctccca gtttctgtgc tattgttgcc ttttacttta cttctgtata 104697 cactttattc tcattattta cagattctat atttgtaaag tcacctactt gctacaattt 104757 atttgtaact ccaaaatcta tatggtaatt ctgtaattat ttgtgaacat gctcagagca 104817 gcaaaatctt tgagtccctt gaggttcaca atccaatcag aagaaataag gcaatgcctg 104877 tcttctttgt ttcagctctt ctaatgtaaa taagtgtcct atttttggtc tagttattgc 104937 cacattgttt atatgttgtg ctttccatgt agatgatttc actgtttaaa gtggcccccc 104997 aaaagacttg tatactgaaa actatgaaat gttgttgaaa gaaataagta aatggaaaga 105057 catctggtgt tcatggaaga cttggtattg ttaggatgtc aatattaccc aaagtgatct 105117 acagatgcaa tgcaattcct atcaaaatcc caatgacatt ttttttgca aaaatagaaa 105177 agtccatctt aaaattcatg tagaatctca aggaaccacc aaatagccaa aacaatcttg 105237 aaaaagaaga aagttagaag tctcatattt tctgatttaa aaattttctg caaaggtatg 105297 gtaatcaaaa tagactggta ctggcataaa gacagatata gagactagtg gaagaaaata 105357 gagaactcag aaataaaccc tctcatatgg tcaaatgatt ttcaacaagg cttccagcca 105417 tactcaatag ggaaaggaca gactccttaa caaatagtgt caagaaaact ggatgtcagg 105477 ccaggcgcgg tggctcacgc ttgtaatccc agcaccttgg gaggccaaga caggcggatc 105537 acctgaggtc aggagtttga gaccagcctg gccaacatgg tgaaaccccg tctctaataa 105597 aaatacaaaa gttagccggg cgtggtggca catgcctgta atcccagcta cataggaggc 105657 tgaggcagga gaatcacttg aacccaggag gtggaggttg cagtgaacct agatcatgcc 105717 actgcactcc agcctgggcg acagagcgag actctgtcaa aaaaaaaaaa cagaaaaaaa 105777 gaaagaaaga gaaaactaga tgtccacatg caaaagaata aagttggacc tttatcttat 105837 accatataca aaaatggact caaggccggg cgcggtggct cacgcctgtt atcccagcac 105897 tttgggaggc cgaggcgggt ggatcacgag gtcaggagat cgagaccatc ctggctaaca 105957 cagtgaaacc ccgtctctac taaaaataca aaaaattagc cgggcgtggt agcgggcgcc 106017 tgtagtccca gctactcggg aggctgaggc aggagaatgg cgtgaacccc ggggggcgga 106077 gccctgcagt gagccgagat cgcgccactg cactccagcc tgggtgacag agcaagactc 106137 cgtctcaaaa aaaaaaaaaa aaaaaaaaaa atggactcaa aatggattaa agatctaaac 106197 atgaggccta gacctataaa actcctagaa gaaaacatag ggaaaaagct tcatgatgtt 106257 ggatttggca atgatttagt ggatatcact ggataatgat aaatattaga taatgatttc 106317 ttcctttgga tatgacacca aaagcacgag caacaaaaga aaaaaaagac aaatggaact 106377 acatcaaact caaaaacttt tgctcatcaa aggacacagt ccacagagtg aaaagggaac 106437 ctatggaatg ggagaaaata ttttgaaatc ctatatctga taagggatcc agaatatata 106497 aacaactaca actcaacaac aataaaaaaa tcaaataacc cattttaaaa gtgggtaaag 106557 gcatggaata ctgtgtggct ataaaaatga gtgagatcgc cgggtgcggt ggctcatgcc 106617 tgtaatcgca gcactttggc aggcagataa tgaggtcagg aattcaagac cagcctggcc 106677 aacatggtaa aaccctgtct ctactaaaaa tacaaaacag ctggctgtgg tggcaggtgc 106737 ctgtaatccc agctactcag gaggctgagg aaggagaatg acttggagcc gggaggtgga 106797 ggttgcagtg agccaagatc atgccactgc actccaccct gggtgacaca gcgagactct 106857 gtctcaaaaa aaataaaaat aaataagatc atgtcctttg cagcaacatg gatggagcta 106917 gaggccatta tcctaagcaa atacagaaac agaaagccaa atactgcatg ttctcactta 106977 taagtgggag ctaaacaatg agtgcacatg aacacaaata agggaacaac agacaccagg 107037 acctacctga gggtagaggg tgggaggagg gtgaggatgg ccaaactacc tatctggtac 107097 tatgctgatt atatgagtga caaaataatc cgtacaccaa actcctgtga gacacagctt 107157 acctatatca caaacctgca catgtagccc tgaccctaaa ataaaagtga aaaaaatgga 107217 taaaggatct gcttgagtag acatttctcc aatgataata cacaaatgac catcaagcat 107277 atgcaaagat gctcaacatg actaatcatc agagaaaagc aaatcaaaac cacaatgaga 107337 tatcacttta cacctcttag aatatcaaaa acaacaaaca agcaaaaccc cagaaaacag 107397 caagtattgg caggaatatg gagaggcctg gacccttgaa cactgttggt atgactataa 107457 aatggtacaa ccacggtgga aaacagtatg gtggttcttc aaaaagttaa aacagaacta 107517 ccgtatggtc tagcaatccc acttctgaat atatctccaa aagaactgaa atcagggttt 107577 tgaagagaga tttgcaaacc cctatatcta gcagcactat taacaatagc gaagagttgg 107637 gaacaaacta aatgtccatc catggatgaa tcaatagaca aaatgcaata tgtatgcaca 107697 atggaatact atgcagcctt aagaaggaaa gaaatcctgt cacatgcaac agcatagatt 107757 acccttgagg acattatgct aagtgaaaca agccagttac aaaagaacaa acaccgtgtg 107817 attcttccta tataaggtat ccaaaatagt cgaattcatt gatatagaaa gtagaatggc 107877 tgttaccagg ggatgaggga aagggaaaat ggggagatgt tgtttaatgg atatagaatt 107937 tcagttctgc aagatgaaaa agtactggtg atctatttca taacaatgta aatatgctta 107997 acactactga accgtatact taaaaaaggt taattatggg ctaggcgtgg tggttcatgc 108057 ctgtaatcct agcactttgg gaggccgagg tgggtggatc acctgaggtc aggagttgga 108117 gaggagcctg gccaacatgg tgaaacccca tctctaccaa aaatacaaaa attagctggg 108177 caaggtggtg cgcacctgta atgccagcta ctcgggaggc tgaagcagga gaattgcttg 108237 aacacggaag gtggaggttg cagtgagcca ggattacgcc actgtactct agcctgggcg 108297 acagagctgg actcaatctc caaaaaaaaa aaatattgtt aacatggtaa cttttatgat 108357 ttgtttttta accacaattt ttaaaatctt attttagtgc atatgtataa ctaagatata 108417 cagaaattcc tggctcagtg acccttccag atgctttgcc tttgggggag aaatcaagta 108477 gaagttcgga ggggctaata cagttacaca gatcataaaa tatgctgtga gagaaaagag 108537 gcagagttgt ttgtctattt tgtgttttgg gctcacattt gctcaagagc tttatgttta 108597 tcaatcagat aattaaagaa tatttgctta aatatcactt tggtttgctg aaatcaacac 108657 agcctaagga taaaaaccta gtttttcctc aaattttgtc atgactggtt gaattaagtg 108717 atcccctcag attcacacat tgaagtcata cccccccagt cccttaaaat tgatacattt 108777 tatgttgtgt tttttccccc caaatgaaaa tttttaaaac tatttttaaa aaataaataa 108837 actcaaaagg gatcaaagcc ccaactataa aactataaat ttttttttaaa agaaaacata 108897 aaactgggcg tggtggttca tgcctgtaat ctcagcactt tgggaggcca agaagagtgg 108957 attgcttgag tccaggagtt tgagaccagc ccaggcaaca tggggagacc cccatctcta 109017 taaaaataca aaaattagcc aggcgtagtg gcggacgcct gtagtccctc ctgttcagga 109077 ggctagggtg gaggatcact tgagcctggg aggtagaggc tgcagtgagc tgtggtcaca 109137 ccactgcact ccagcctggg tgacagagta aaaccttgtc tcaaaaaaaa aattagggaa 109197 gaagctttat gacattgggt ttgacaatga tttattggat atgacatcaa aagcataggc 109257 aacaaaagaa aaaattgata agatggactt cttcaagatt gaaaactttt gtgcatcaaa 109317 gggcactatc aacagggtga aagggaatcc acgaaatggg agaaagtatt tgtaaatcat 109377 atatctgata agagattgat attcaagata tatagagaac tctcttaaaa tgcaacaacc 109437 aaaaaaacca acctgatttt aaaatgagca aaagattcaa ataaatgatt ttcaaaaaaa 109497 atacaaatgg ccaataagta catttaaaaa tggtcaaaat gaggccaggt gcagtggctc 109557 acctgtaatc ccagcacttt aggaggctga ggtgggaaga tcacttgagg ccaaagttca 109617 agatcagcct ggtcaacatg gtgaaatccc atctctacta gaaatacaaa aaaaaaaaaa 109677 aaaaaaaatt atctgggcat ggcagtacat gcctgtggtc ccagctactc atgaggctga 109737 ggtaggagga tggcctgagg ccaggaggtg gaggttgcaa tgagtcaaga ccatgccact 109797 gcaatccagc ctgggcgaca gagcaagacc ctgtctcaaa aaaataaata aataaaaaat 109857 aacatcagta agcattaggg aaatgaataa caaaacacag taaaatacca cttcacatac 109917 acccattaga atggctatta cttattattt taaaaaatga caacaacaaa taatgtgttg 109977
gtgaaaatgt ggagaaacag gaacccttgt gcattgctga ggaaaaatgt aaaatggagc 110037
agctgctgtg aaaaacagta tggcaatttc tcaaaacatt agacatagaa ttaccataag 110097
atccagcaat tccacttctg ggtgtatacc caaagaacta aaatcaaggt cttaaagaga 110157
catttgtaca cctgcgttca tatcacactg tgattatagc attattcata ataaccaaaa 110217
gatagaagca accccagcgt tcatcaatga atgaatgaat aaacaaaatg tggcgtatac 110277
atacaaggga atattattca accttgtcac aaaaggacaa atattgtatg attccactta 110337
tatgagtgtg ggaacaagag tgacttctga ctaaccctga gtccaaaaat gcctccataa 110397
tgtctaggtg tcagtacttt ttgtgtagaa acagctagtc actgtaagtt tcctccaaaa 110457
caacacttaa tgctgttaca aacatcatag gctaggattc ctgtagcacc tatacattcc 110517
ttccagagca catattttta tacttttccc caagacatca gcctccctaa ggatctggga 110577
ggttgtggtg ctaagatcta cctgtcttgc agcccccaag accatgcttc tgtccataaa 110637
ttcccctgat aaataatctc ataccaacaa actggatttg tctgcttcct tctttgattt 110697
cttcacttct ttggtatttg gggatctctt tgcatataca gccctttcac agaacaatga 110757
ggtacctaga gtactcaaat tcatagagac aaaaagtaga atggtggttg tcagggcaga 110817
aggcacagga caggggagtt attgtttaat gggtatggag gtttcatttg agaagatgaa 110877
aacgttctag agatgggtaa tggtggtggt ggtggttgca gaataatata aaaatgctta 110937
atggcactga attgtacact gaaaaataat taaaatagta aattttatgc catatatatt 110997
tttcaccata aaaaaatggc tcccaggggc aattgtaaaa ttatatctgg tattcctagt 111057
acgagaagac atggatgtgc cttatgtgtg tgttagatga gctttgttca gacatgttgg 111117
ctgtgagctc catgttaata aatcaatgat ttgtattaca taagctgact ttaagtagag 111177
acacacataa aacaaggtta tgtgttgatt gcttgacaaa agtgttgcaa ccagaggttt 111237
acagaatcta actctgtatt tcccctgtga acaatgttca gtgttcacta attcatcatt 111297
ttcaacaact ttacagagca taactatcat gactaaaaag aatcagctga gacagacaca 111357
gtggctcaca cctgtaatcc cagcattttg ggaggatgag gtgggatgac tgcctgagtc 111417
caggagttca aaatcagcct gggcaacata gtgaaacccc atctctaatt tttttttaaa 111477
aagtaaaaaa aaaaaaacca acaaaaaaac tgtatgttat aaactccaca atatattact 111537
atttttgctt taaaatattc aattatcttt aaaagagatc ttttaaaaac atcttttata 111597
tttacccaca tattttttat ttgcaggcat gttcccatct acgtctttgc acttgtttct 111657
acctctgtct ggaattctct tgctccagca agccatgtga tcagttctcc acattctctt 111717
taggtctcta ttcaaaagtt actttttcag ttagaccttc catggctact ttatctaaat 111777
agctatatat cttcacatct atttccttat ttaactatca atgtccttat ttaattctca 111837
actattaatt atccttattt tacaaatgag gcaagtggaa gtcagaggga tgaagtgaat 111897
tgcccgaggt cacactgcta gtaaatggta aagcacgtag attgtctcca gaaacttctc 111957
aatatattta ccttatgtac atgatattta gcctatataa acatttacat atatttatca 112017
tgtgtataca cacacctata gatatatccc atcttcaagc tatatttcat catagctgtt 112077
tctaagtcct ccatgattga tgcaactggt agagacttgg aagtaagatg atgcactgac 112137
ccagctagca tttactgggc atctgctagt aggtgctagg cattgtgatg aatgctaagg 112197
atatagagat gaaagatgca gttgctgtca tcaatgtcct cacagttggg aatagggaga 112257
agacagacac ttagaagttc catggagaaa gaactaggta ggacccaatg gataaaaaat 112317 actgaatgaa gattctaatc caacacaaga aagtttctaa tggtcaaagc tgtctgaaaa 112377 tgaaatgggt tagagggtgg agttcctctc acaggagttg tcccagcaaa agtatggtga 112437 cagttgagct ggctgttata gaagggattg acttaaacat aacatggctg atcaggagcc 112497 aggtaaccaa tgtgagctag ggtttttaaa gacacttttc aacaaagcga ctatttgcag 112557 agatgtgtgt agggctaatg gaactaacaa gaattttgat gcacccaggg gactagcaga 112617 aactagaagg catttccact tcatgcctga aggcacaggg ggagtctgat taaaagccag 112677 agcctaggaa aataggctct caaagagaaa aagaatttct agagaagcag caactgccag 112737 aactggaaca atataacatt cccagaaaca atatacctgc agttctctat ccttaggttg 112797 ttcggttatt tgcagtgcca cttattcacc aaatgcaaat ggaagccaga ggcaagcgcc 112857 tgccagtgac gcagttgata aaggaactaa tactgtccac aaaggtcagt gtccgagggc 112917 acccagcagg gcagaagagg gcgaaatgga tccagatgga aaacgcagga taatcagcag 112977 agttgttttt aagggccctt tatttattca gaggcaaaat tttctttccc tttagactct 113037 acaaatgaac aatcgggaag cgaacctcaa ctgtggggtg agtggcgctt ggagaaaatt 113097 ggagctgagt ggataatccg gctatgccct tcccacgtct ctttcccacg cagcgtcacc 113157 gtcgtgctct ccagtgcaca ccaccagcca tccctgccct ggcgcccgga cgaagctcac 113217 gggctgggga gcctctttcc tgcgccggtg atcaagggcg tcccagccca ctgagggcca 113277 ggaggcgagg cttgggcaca cgtcccttcc cgcccggacg ctggtgcccg cgaggtcctc 113337 ttggccctgc tgggagcgca ggggtcgcgg caaccattca gaaccccggc tgccagacaa 113397 gcgaggcttt ccacgtgggc agaggcgacg ttgttcaggt ggcaaggatc caaggctgag 113457 ccttcctccc tctgcgtcca cccaccgccc ctccccaccc ccgacctaga aaaggacacg 113517 cacacaaaaa actttcgcca cactattaat atattcgcgt ttcctcccac tttcccaatg 113577 ggctaccagc tgcagaactc ctgaatagaa agcttaattg tgctttgtca tgcagagtac 113637 ctcgattttc tatagaaggt tacaaagggc catttgaagt atttctttct cgcctaatag 113697 tgaaccattt gcatacggca cctctgcgcc tgccagaccc aggtagctgt gccgaagctc 113757 cgggggcccc ggagtaacaa aacccagggc ggtttccaaa gggcgcccta ccccgcctct 113817 cgcccagcgt ttggactttt ctctccaatt ccctcgggtc acggcccgcc ctaggcagct 113877 gatttggagg acgcgaaata tggcctgcag gccgcgggtg cccagccggt ccgtctgata 113937 tcttggaggc ctcgggccat ccaggccctt ctagcctgga cccgagcctt ttttaggccg 113997 ggtctaccga acccaggtgg tgtttttcat ctactatctg caggtccaga gaccaggcct 114057 ttgcccacgc ggggtcctcc acccacttgc ttctcacgta aggcccaagt gaggcgctga 114117 agaactggaa ggtgattatg atttcgatac cacgctgttc gtttctcctg gttgattgac 114177 agggctgcgt tcagaatatc ttttcttgtt gcttgttttg acagttcaaa tccaggtctg 114237 tgtgacatat aaagctaata aaattctaat ttcattgtta atcttatttc attgcagtat 114297 aggtttttac cctcacacct gcatggcagg gtgtaattcc attaataaaa aaaatcaaca 114357 tattcattgc atgtcttttc cctgatgata tattgtgagc agtgtgagtt gagaaagagc 114417 catttattcc caccgtgaat gagcctgcat ggggcgggag cttcacctgc ccctcagtca 114477 attaggaatg tatcgaaaag tctagcagaa aacgagttaa attaaccgtt ggctaatttc 114537 cttatgtccc tcctacataa tcccccccttt tcagcttgcc ccagaaatta ccacatgttg 114597 caaggttcaa atagtgccta atgaaacagt gactaaacgc ttctccctcc ggcgccaccg 114657 acgggggagc cctttcgccg gccttcaaag cttgcaggat ttcgtggttc tggttcccgt 114717 atccaagaaa aaaaaaaaga aaaaaagaga agaaaagaaa gagaaagaaa tttttgacaa 114777 gcagaaaaaa gaaaatctaa gctgtcaata actctcgatc cagcgagtga aactacatta 114837 atgcccaccc acttcctgcc accgatgatg cagtgggatt ccgagatgcc tgtgcccgca 114897 gtagataccc aagtaggaat ggcagcttta gcatcctcct ctttccccgg agagctagga 114957 ggattgagcc atggccaggg gagactggat ggggaaaacg gccaggagaa caaagggtgg 115017 gggtgggggc ggatatcaag gcagaaggag atggagacaa gacagagaaa tgcagacaga 115077 gaaagatcac tggggaagca gatgcaaagg caaaaaaaaa aaaaaaaaaa aaaaaagaca 115137 gagtgacagc aaacacacct ctaaagtctc aactccctta tcccaagtta aaactacatg 115197 tatggcttaa gcaactcatc agcctctagc caaaggcatt ttgaagcctt gacattcaaa 115257 atcctaataa ttaatcattc ttattaatta attaaggagg aaaggaggaa ggtggctggc 115317 tgctgcttga ccccaaacaa tctaaattag ggtttgtgaa ggaagtctcc aaaagcatgc 115377 actccctctc cttcgtattc tttcttttc acactctcaa aaatttccat tataatcctt 115437 caaggtctgg ggcaggcaga gcttctcacc ctgctccatc ccttcgcagc aaactgagac 115497 caagctggct tctgctcctt ggagccggct gccactcata ggcagggagc tctttcccat 115557 cgggagcaac tcccacctgc cttttttct ctgcacctgc tgtgggtggt ttctccttga 115617 acttcagaaa ccaagtagtt gcctagaatt actttcgcca cagtgctcac aggctaaata 115677 ttactacatt ctctctctct ctctctctct ctctctctct ctctctctct ctctcttgtc 115737 ttctctctcc tctctcccct tgcctccctc tcactagaga cttgagtccc ctatttgaaa 115797 tggtgcagct aatacaaagt catcaaagca ctatggttct tgtcttaaag tgacagcctg 115857 ctttatgaga ctgtttgaaa tactcccctt gcttttcaat gtctctctat ccatctttgt 115917 ctgctcttca gaaaagggga caatataaag cccagcctgg cgagctcccc acgctcaggc 115977 ctgggcagtg ccaacctccg cctttaagca gattgaaatt gtcactgctt cattaatctg 116037 aaactagtta ctttcctaag cacacagcat acacttccga tctgttagga ttcactcagg 116097 ggagcccctg gggccttcct gggtttggga tttagaaggc tcaacaaaga tacagcaagg 116157 gttcaggaaa acatagggct cagcttgaag aaaagcagtg tccagtaccg aagggcggca 116217 ttgacatcag tatattaaga gagcacaaaa cactattttc agagacaatg ggatgcccag 116277 gattttggag ggtacacttg agaataagta gtctggctat ggcaacagac aaggttatct 116337 attgccacat ggagcagcac tagaggtctc acaggcctca gaattttttt ccccaaacag 116397 aagaaactgg aatccaaatt tctttgcaag ttggagtttt gctgactttc ttttttttta 116457 gttttttttt ttttttaatc tgagttctga ttcaagtctg attctaagag atgtcttaag 116517 ttctgtgctt ctttggcccc tcccttagtt ccagcctgtg ttgcccactc caagtgccag 116577 atgttggatg tagaagcctc gggtccttat agaatttcta tgagacaagt tgcccctttt 116637 cttcataccc ccaccattaa caaaagacaa tacaaaggat tctattactt ttaatatttc 116697 tagctggctt agaatagcaa gtttttgggt tctattctat gtagtttagg gaagagatgt 116757 gggcattttt taagagaagc tcaattttca gtaatgtgag cctaaagatt tataaaatag 116817 atttatatta aattatgtta atagacgcct agtaaatgca ccatttaatt gcatggaaaa 116877 aaatgttccc ttttaaaagg tctgtcacct taacaggtac attcaaagat ttcctgtgaa 116937 taatgaaaat aggaacaatt gctttgatgc actgaactgc attcatcgtc taggacagct 116997 ttgggctgtg tttggagaag atgggaggag ctcttttgaa aggagtgatt gctcctttaa 117057 acttgatttc ctctagcaaa taggttctat tggagtgtca ttctcctccc ctctctcaca 117117 cccgtaaggc tgggcttgag atcatgcccc agagctcttc tccatgtctc ccctccatgt 117177 tcagactgtt tttcctcccc acaacccaac actgagcacc tccccatctc cctcaaagaa 117237 atctctcaag gagtgccatt aaaagcgagt ggaacctgca ggaaaggtat aagtgggaaa 117297 caaaaagaaa aagaaaacct ggttaaaaat tactcttttc cacctacatc accaccatca 117357 aaggaccctc tctgtctctt tcacacacac atgtgcctca tgcatgcaca cactacacac 117417 atgtacatac aaagcccctg ttgccctctg tgactgcttt tagttagaac caccaccttt 117477 ctggcaattg tctgaccaca gttagagtgt gccaagcaaa ctgcatttct aatcctgacc 117537 agatataact ggacagaact ggtggggcgt tgtgggttag cggggtggtg gttggcaatg 117597 aggagacgga ggcggaggtc agaaatcaaa gacttcacat ccccaagtgt tttgtctctc 117657 ctaaaattat tagatattct ttaggggagt ggggaaggga ctgagctatg atgaccactt 117717 cagaataagg accctagagg aaaagaggtc tatgggcacc agtgtctcca tcatgcaggc 117777 ccactgacac cctaaggatg ggctactggg tcacttttgc ttttggccta gtttgctatc 117837 agtatcaggc ccttggcctt aggcatttgt tggtggctga gtgggagagt gaaggggaaa 117897 agtctctgtt cctcctctat gctctgaatg tctgggctgg gccagggcac atgggtgaga 117957 ggtcatcctt cctgctctcc actctgcctt ccacccccag ctcttttcct gtttaaaact 118017 aacatgagac ttgttctcaa aaagatggac tcaaccacac tcacagcggg tgctacccac 118077 tgattttctc ttggtggagc aagttcctgt tttctaattc tcattctcat tttcattctc 118137 tttctttcca ttctttcttt ctttccatga cctctctaag aggtcatgct ctgggggaac 118197 atagttctgt ttctgttttt caattggggc ataatggaaa ctagtatcta gtgcttccca 118257 ggtagagaaa ttgtcaaggg tgaccccata catcttaaac tttcctctta aatgggtgtt 118317 tgatatcaag attatttagc tgagaatgtg agtttctgag ggttggctta aatgctctta 118377 aactaaagtg aaactgttgg tctttagaat cagaccgact ccaaaatacc aaagcattat 118437 tccgatttga aaacttcaaa aacatcaact gatatttttt gaggagtggg gatagggaaa 118497 catgtaaaac ttattctagc atagtaggag acctcatact ccattttgaa agtgaccaaa 118557 ggagtccact ttgcatcgga tgtcctagaa ggaagacctc cctgggaacc ctggagaacc 118617 ttttttttta tggagagtgt cccaacattt aaataggtat cgctacgctt tttttttttt 118677 tttttttttt ttttttttgc ctctgggcag aaatactttg tttattctcc tttccctagg 118737 gaacttcccc aaagatcgaa gcaagagggg ctggggccat ccaagcagat ccaaaccatc 118797 taaacagggt tggcactgcg gctatctgcg gcatggcaga gctgggtcca ccgcgcgcgg 118857 tacctggtgt tccaagtgct tggctccgca gggcctggga gccgggggcc gggagaggct 118917 taagagactg tgatcggggc tagtcatgga catagggggag ggctaaaccc aagcgctgag 118977 ccccagaggg gccgggctgg gtagatggaa cggggaccag aggagtctcc ccacagccca 119037 aaggaagctt aactttgggc aaaaaacgcaa agagctgcag caggcgctct ttgtgcttct 119097 tatttcccct ggtggaaata gactgcttaa actcctgttc tttgcgcctg caaactcccg 119157 tcctcccacc tctgttctcg cgcgcggaga ggcctgcttc ttgggaagaa gggagacaga 119217 atcttttgga aaggcagccg gcctgcgcct cctccctttc gtggcgggca gggcgaagag 119277 cccggagctc tgcgcgtgag agacaggagg aaagagatcc agaggcctga gcttcccagg 119337 ccaggcagta gtgagccggc tgtctgggac ctctgcgcag gacagagctc agcacattgc 119397 acaaagcgcc ggcagctccc ttttcagcct cacacagtgc gggccctcct ccctatgtcc 119457 cttgacggaa cgaagaggga ttttccttct gagcctactg tgtgtgtgtg tgtgtgtgtg 119517 tgtgtgtgtg tgtgtgtgtg tgcgcgcgcg cgcgcgcgct aaagacaaca ctcagggaaa 119577
accgtgtcca gttttagaac cccagccgta cctggtgagg ttcagtccga ccggcctcta 119637
gtaactcaga cctaaagccc ttgtgtatgt gtgttgtcat taactcctgt ggcttgaacc 119697
tattgggtgg cgtctttata gaacctaatc agaaatcaca ccggttgagg attagtgggg 119757
ctcagcttgc agggaatgag atctcttcgt tttcctgttt ccagtttctt cacttctctc 119817
cctaagataa caagcccagg ccgcactgag gagagagcca gttgccctgc tgagggaaga 119877
gctagaaata agtcttctct gggaccaggc ttaaaggaag tgattctgct aggctatggg 119937
aagggggggtg ggctggaagg gactagaagg gagccaaatt aactgaatat tagggtgacc 119997
gggaaaaaaa gccccaaaac tcaaagctct aaaggcatct ctgggctgct ttgaaaaagt 120057
gagattataa atctttgaac agaatacttc ctgtccctga ctttttgttt tcttaacatt 120117
gagggaaacc cgctaattct gcttgtagca tcgttattaa gtttccactg tttgcttctg 120177
acctgtttga tggattgttg ctcttcctaa aactattctg actctacaaa ttccttcaca 120237
taattcaagt tttcgtactg agagaaatga ggaagtagaa agaagaaaac aaaaactaga 120297
tgggggattt ttacccttcc ttgctaaata aaggtttacc tgtcgttaat ggtcagtgtc 120357
attccaaatg gagtgatttg tcctatcaac tgtgaggagg ttgcctattt taaggatgga 120417
gaggcactgc ctggtagatg ccatcatgac taaaggtgtc tccttggcga aagttctgtt 120477
acatagaaaa cccattgagc cacaaactcc ctcagtcaag agacccacat taccaagttc 120537
ttactcaaca ttttcctcga attcctcaga cagctttttc ctgcatatgc ctttctctag 120597
acattggagg agggggcagg agaagatagg gagagcaaac accacagatt taaaattctg 120657
gtttttgttt catttattta aataaatata aatataaatt ttatataaac ctattcacat 120717
acaaagggac ttccagcgac ttagatttta aattctcccc aggcgaaatt tcagaaagca 120777
agacctacaa ggtctaattt tctaaattat tttcaacttg ggtgtttttg tttgaaaacg 120837
acaacagaaa ataatcaata aatcctgtgt tcttatcgag ttctgaaaga gagtagggat 120897
ggggaactga catgtgcttt caaaaacccc atacagtgtt aaacttaaac caaccctgtt 120957
tttcctctgt tatacgacaa gaatgagttg aattataggt tatttacatt ttttaaaaaa 121017
atctgtaact tcaagttgga gtcctagata aacaggtcaa gaaggagacg cgaagggtca 121077
ggtcccggct tgtccattcc agaacttcca ggttcgtttc ttctccagat gggaccactg 121137
caatgagcaa ggattctggc ccctgggtgc cccacgcctt ggcgttgcct ggtctgccag 121197
gagcggggga tgtgagggag gaggccctcc ctcataaggg ggaaatctcc ttgtcatcgt 121257
tggctgaggc cggcgacagg gagtcctcat cctcggagcg cgcgtagtgc acctggctcc 121317
cgacgcactt gcagcccgcg tgactgttcc tctgcgtgcc cttcccctcc ttcttgtgct 121377
tcactcggcg gttctgaaac cagattttca cctgcttctc cgacaggttc aggtaagtgg 121437
cgatttcaat cctccggagt cgagacaggt acatgttgga agagaattct ctctccagct 121497
ccaggagttg cgtgctagtg aacgccgtcc tcatcctctt gccattgggt acctggctgg 121557
cgtcagagcc tcctgcggac cggcgaagag agggtagaga ggtaaggctc gggcaaggtg 121617
ctcccacccc atgtgctaac caggacgcat ttcagggacc cacccgggga agcccagccg 121677
aacatctgta tccctttccc atttcaaggc acgtggttgc ttagcgggga agaaaagaga 121737
cgtgcaaagc aaataaaggt cttcgatgcg caggatgcga agtcacagga ttaaagaggg 121797
atgggggctt gcactatctg atcgcctccc tttgagccaa gcggagaagc gcgcaggctt 121857
agccaaaaac gtcaagacgc tttagccgcc ccgacgcggg gatgccacac aggttcaaac 121917

-continued acacccaccc caaatcccaa gcagttaacc tctggtttat ccgccgtgac gttcgaggtc 121977 cctaaggccc cagtattaat aaggcaatac tcgagcacct actactagga gtaaaacgca 122037 ccaggctgag tggagaagct ggcaaactaa cttccacttt cgtggaactt ctgtggctga 122097 ctctacggtt acactaaaag cccgtcctct ctcttcaccc tgtccccggg ctcccacttc 122157 ctccactgga ggtggaaagt ttgctccagg agcgcgaaag gcgcggagcg caggtgcccc 122217 aagaccccgc cctacccatg gtgaggcagt ggaatctccg cgggtccgcc acgttgtagg 122277 tggtggcggt gcagacaggt gcgtggtgct gcgggtgccc caaggccgcc gcggccgccg 122337 ccgccgctgc tgctgctgcc gccgccgcgg ccgagccagg ctgctggggc tgatgatggt 122397 gatggtggtg ctgcggcggg tggtggtgat gatgcgcatg gttcacccgc gggcaaaact 122457 gcgcgtcccc aggagccgaa gagaactggc ccttaagcag aggcagtgcc cctgcggccc 122517 ctgccacccc actgcctccg gccccggtaa ccccggcccc tgcgccccg ctgccggcgc 122577 ccacagaccc ccgagaggag tgcaggtgcg aagtgacgca gagagggcac acgcagaacg 122637 cgccgctctt gcgggacggg cagccggggc cggacacgga catcaccaat gggggcggca 122697 tgccaagcgg gatgaagaaa tccggcccgg ggtgcggttc aggcagcgag ggcgcaggcc 122757 gtgaggtgtc cttgatgatg agcgagtcga catagaagga gcgcgacatg tcgagagggg 122817 tgggtggctg gaagccccgg cagttcgcgg cgacccctct cctctagtgt tctaagctct 122877 gccctgggag ccgcgcagac acgggcagtc aagcccttgg ggacgcagag gtgttggcgt 122937 ctgggctggg aacaaagggg tccccggaga gggctggtcc tcacgtcccc cgcccggcgc 122997 cccggctcgg gtattttata gccccccacc ctggcacgtg atgctgcgga gtaccgctcg 123057 gctcaggctc ctcggcagct ccgcaccctc gggataggct gcccgagtca caacagaagc 123117 cgcgaggagg ggcgggcgcg cggcggggaa gaactcgggg gagggggatg ggggagactt 123177 tgcaaagtgt aggttttgtt aatttcccgg ggaggccggc ctcctccccc tctttctcca 123237 cgctttactg agaaatcaca gcgctgcatc ctccatccca ccccctctcg ctaccctggc 123297 cgcagcccaa ctcttcccca cgccccaccg caaagcgtac caggtgggga cttggaggct 123357 tatttaatag gaatgctcag tgtttccagc tcctctgtgg taggggtggc tgcggcgcgg 123417 tgaagtgtga ggcctgcggt ttggagcagg attgtgcggg cgacggactg gcagtcgtcc 123477 agtccctgag cgcagctctg gccacggtta cacctacccc tgtccacagc ttttggactt 123537 ggcagaggtc attcaggtgg ttagttcagg actgtccggc gcagaactgt gaggcctccc 123597 agctaagaaa ccgtcaagct tttcatgctg atgttcgaca aggtctgaag tgtctttgta 123657 cttggggccc tcctggggcc actcagacca acgacccttc cttgtttccc tttctgatcg 123717 gcacctccca cttccgcaga gagagagaga tgttgaagag tcacccttt ctttctccaa 123777 gtagtaacac catggcattc cagggcaatc ctacaaactc catcctgaag attttggagg 123837 gaggacctca aacaccaagc cctcctaaag acgcagcagg gattagatag accttcgctc 123897 tgggtctgag gatttcctgt ccctcatttt taccaatcat gggcagctta gcaaggctaa 123957 ccaggaagca ctctttcctc tgcatcttaa gaacctaaaa aggatgaaga ggattcagcc 124017 atccagggaa tcttgcctct gattggcaga agtggctttg taagggaact ctctctggtc 124077 catggaagtc ttgcacaccc cttactgccc gagagagggt ggctgccaaa ctattgggac 124137 tatttatctt cggagaaggc aaggcagcag aggtggccat tttctctctt catttccccc 124197 tgcagaaaag cgggctgggg ccatgtggtt gggcaatagt tagaagtctg atcctttttc 124257 cagagcagct aacttcaatc ctgagttcat gatggtgcta agaaacttag agacaggact 124317

```
ccctccacct gagagaacaa ggtgcccaaa tccaggagag cactagctag aggcacggct 124377
ctatctttcc atcctctgtc ttcccctctc catctctgtg acagtctctc ttgcctgcta 124437
gagaagtgta attgggttgt agggatgccc ggctctgggg agcccaggat ttatggatgg 124497
caattaaagt tttatgaatt gcagctgagg ctggttattg agctatttga atgtgattag 124557
aattcaatta gaaagcggtt agtggacggt gggtctctgg agtgtaaaca gacagctatt 124617
ccagaaatgt gctaatccaa catcttgtga caacaattaa ggagtctcag ggcttaacat 124677
ggggcagctc agctgtaact acttttgtac cacaaggtct gcagacgctc aggctcaccc 124737
cagcccgccc ttgttcatga ctggaggatc taggcaatcc ccgaaatcat ttcagcccca 124797
agaagaaggc ttggagccac tgatggagaa tggcaataaa aaacataccc tgctgaatgg 124857
caggatattt tttacagtcc taaactgtcc aaatagatga ctcgattccc cccattcact 124917
ttgcaactat acaagcatat atagatatag atacagatac tctttaagaa taatagcttt 124977
ctctcttttc ctcctctggg ttaggtccca ggttatccac agtctgtttt gggctgatgg 125037
tttgagtcac aatgttccca gcagtttggg atgtgttcag aggaagagct cctatgctaa 125097
agtcctagaa atcgcaccca tgtgcagacc attttacctt agagaatctt aactatgcaa 125157
gaggcttgtg catcttattc aatttgtgtc tgactgtgga aactttcatt tttcagtgcc 125217
aaggagtttt gagaaatgtg aggggctcat ggggtttcct aaagacttca aggggagcag 125277
tggtttcaga ccaggctgag gctgaaagca agaccatgtc tgaaaaactt gacccttagg 125337
gtacttggtt aattccttca gcccaccaag agcaagtata ctggaatccc atttcttgca 125397
cagtttctgt ccactctgac tcacttctct agttctcttt ggatctctca gtgtctgcca 125457
gtctctctcc ctccttctct tctgagtcca gcccctatct ggccctacct gcctatcccc 125517
tcctcaaagg aagcctaccc tccatgcccc cggggcagca ctgcccaccc cccaccccag 125577
ccctgcccag ccctactgtt ccccagagtg cagtgccctg aaccagcagg agaccccaag 125637
ttcagctttc ttttcctgag agggaacaga cagaccattg gcgtgtgccc atggtgtctg 125697
agccgccaca caattttatt tctcagtgat tctgtccgat aaaatttcat cgtccattaa 125757
gtaatcccca aaatgagagc tcttatgagc ctataatgag ctctaattgc cacaactcca 125817
ggagccacgt ggaaggattt attctgtatt aagcagtcgg gtacagagta caggctgtta 125877
cctaagccat tactttcata attcaaggag aaaattagtt cttttaaagg aaaggggaaa 125937
tctttttatt atctccctct tgcttgggac aatagagtat ggttttgtct tccttgagtg 125997
caagacagtg tcacatatgt gatggtaaca aaattgttct ttgtacctcc tcctggccaa 126057
ggcactccac ccttaccctc aacttacaaa aaaaaaatca aagcttttct agaaagaaca 126117
gcagaggcat ggccttcttg tctctcgatt ctccaagttg agcctgggtg agcagtttcc 126177
tttcagccca accctgagat ttggattctc agttctagct tccaaaaggt ctccagtact 126237
tcttcccagc tctggaatgg cacctgacct gaaccccaca ttcctgtctc acttctcttt 126297
cttcctgttt gctttcatgg gcaaagtcag gacaagtaaa gggcagggac ttagcattgc 126357
ttattcaaca ggccccagag ttctgacccg ttcctgtgct tagctgtttt tttcaggctg 126417
taactcccac tttgcccctc cctctgtgtc ctccaaacct ccccacctcc cccaccacca 126477
ctttcatccc cagtcctttt ttctcttagt ttcagcattt gcccacatgg ttctccagct 126537
ccaaatggag gctgcaggca gggcgggaca gccggggagt tggcggggcc gcctcggatt 126597
tatttgctcc tcttacattg atttcatatt agtttccaaa gcgatgaatg atctcaaagc 126657
tgggttttgt tagccgaaca caaacaggag acaggactta cttgccccca gctcccttta 126717
```

atgaggtcat tatcaaagcg tgaacaagtc tatgaatgtt ttattgaaag tgcatcgtta 126777 acttgtatcc atccttttct ccgagtggca ttgtgatatt gctgtctgtg gcacatctta 126837 cccgatatag cccgagattt ccccattctc tgtaaccagg caaccctttc tgaataccca 126897 aaaattgaaa agaaccgctt agtcttcaag aaagtcctca ataatagtgg aaaagaacaa 126957 agatccagga gacaacaaaa tgccacaggg gtgacttttc atgagcaatt atctctcatt 127017 aatcagaaga acagctgcaa tattaatttt ctctctttct tcctctcttt tcacagtccc 127077 caacatttga ataatcataa attttgattt tatgaaggag tcacattttc aggggctgga 127137 ggaaagcagc tacctaggtg aagacaagaa gaaaatgctc tcattttatt ttattttttg 127197 tttgggtaaa gctgccaaca aagcaaaatg gaaaaaaataa aaataagaaa tgccagagaa 127257 aatgcccccc cccctttctt cttctagatg gctgttgaga ataaggactc tcttctcccc 127317 caccctctgc tcacaactac ccctcctttc tttcctcccc ccgcccagac ccattcccca 127377 gttttgctct gagcagggcg gagggaaacg tccctggcgt ctggcgtggg agtttcagcc 127437 gggtttctgc ccgtttaact tgcaaacgtg aagccaagcg ttgtcgatct gaccaaagag 127497 acactctttg ggcgtaactt gcattgtggc catcaaaagc ccgccagcct tggatgaact 127557 gagaagtgta ttcagcagaa atggggcgct cgctctcctt tcaggctctg gagaggcaat 127617 tgttcacagg atgtgtagcc agggtggaaa acgtgggtcc ccagataagg ctataacctg 127677 caaacgagct tgggggagtt aaaagaatct cattaaagcc ccggctgcaa ttagcaaata 127737 cacactcata gagaactcaa gctcctcttg aaaagctgtg ggtcaagatg aaagagggca 127797 gttgggagct agtccccaca ttcttgtact gcttgagtga tggggggctc aggagccagg 127857 ctattccttc agctgcccca atattgttag ttttaatgca aggccaggga aggcctttct 127917 agagggaggg caggctgtgg gccctgtgtt catgcaccac caaaaataat cttgcttctc 127977 cctggtgttt attcagaacg gatgggcttt tgagaaacct gaattcgcct ttgtgctcac 128037 cacagttgca agagttcaat tcggccctct gagaagaagc agcggggaga ggggggtggg 128097 gggtggtagt ggaggtcttc tgagaaataa gtgaggggtt tggcttagaa tttcaggaac 128157 ggcccagttg gaaaaaagtt gtgatggcac tgaatgcctg ccacacagcc cctctgctcc 128217 ccacttcact ttaattaata ttcgcccacc cccaaatcct caagccgaac aaggcatccc 128277 tctcccaccc tcagagctct cctctgtcat cagaataaaa tttatcgagc gcctactctg 128337 tgcccagcgt gtgctaggca ctgcagggag caggcctgaa aaggccaaga cagtatccaa 128397 tagaatattg tttcatttca gtaacaatgg cctgaggtgg ggaacaatta tccggataat 128457 tgaagcaaat gcttcacctc cctccctccc tctccagttc tcctggcact tactattttt 128517 tactacccta ttcagagatg tggtttttgt attggagggc gggcgggga ggcaggagtg 128577 tgtaagagga gggttgaatt attcacatgc ataccaattc cccacttccc ttggcctaaa 128637 ttttctgaaa gcttggagcc aaaatagctg cttagttatg ggagcaaaga cttaaaaaaa 128697 aaaaagtcac taaaataaga gcaattcttt ataattttta gcagcccagc ccttctggtt 128757 tttgatcttg gtcatctaca aaaatcacct ggagagcttt ataaaaatac tgattaccta 128817 agggatttcg atttaatgat gtgaggctgg aacacggcgg ggtgtagatg gagggggaga 128877 cagaagtcaa ccagaattct gcatgcggtt ctgatgtagt tgagaaataa ctgataaatc 128937 ctgcccccta cgccctccta ccatggaatc tgaagagagc aacgtaactt ttttgagcct 128997 tatctggtca tttgatagtt ggaaagtgtg tattgagcgc ctattatacc ccaggctgcg 129057 cgcaaggaa ttcagtagca caagacccgc ccccggggag tttccaggtt aagcgaatca 129117 acaaattaac tcggagctgg tgagttaaaa aggtcgtgtg aatatgaaag aaaagctcaa 129177
ggggctctgg gtgatgataa aaccgaagct tgaagtgaca tttaaacgga gacctgcaag 129237
atgtgcgggt gttggcctgg gaaagaggga tggggaatgc gttcccggcc acctaagggt 129297
gctcacggga gcctccgaga gtttctcttg gttaattgca aaaactgaaa ggaggcctag 129357
gaaagtggag aaagaatttc agtttctgca tctgtaaaat agagaaaatg ccatcgtctt 129417
cgagtttttg tgaggaattc aggactgcct aacaccgggc ctggtgcctg gtaaggctcg 129477
tggcttctct tgttggtttt attattatct gagacctgca gctccatagg ctcttgaagc 129537
ttgtaaatta ggtatcagag tccctgggct tggcaactag gagccaggaa gccgctgcac 129597
aatcatctct ccgtcccccc gcgccttttc ccggccgagt gttgccctct aaggctcctc 129657
cacagcctgg cgctcgcacc ctgaaggcgc ccagtgtggg gcctttctat ccctcggttt 129717
ccgggcatat gtttgttcag cagttacatt aacctcgcca ctccccaccc ccgtcaaagg 129777
ctctggcgtc ctggccgtcc ctacttggga ctgcgcccta aatttcaaaa cgttcctatg 129837
atattagaaa cctcccagct ttgctgcaca cccacctgct ttgcatagga ggaaaacagt 129897
cgcctttcga gtatatgaca atactcgtag gtacattttc tgagctctca ctgtgtggca 129957
gttcttgaac caagagcctt gcctgcatga cctcattaat ccgcacaaca gccctcccag 130017
ataaaatgcc attattttct cctcattatg tttgcggaga accctatttg aactactgaa 130077
gttcaaagac tgaaccaagg tcacacagct agtgatggca gagcctttta ggcactaagc 130137
aatactaacc acctgataac acctagcatt tattgaacac ctactatatg cctggcagtg 130197
gctgaagact ttaatgcctc ctttatttct cacagcaacc ctgtgaggta ggtgctttta 130257
ttacttcctt atttgttggc tgtccatttg ttggttagtg tggttggttt tcctacatat 130317
taaaggttct gagggccagt ccaatgtacg gactgaaatt agaatgagga cagggaacat 130377
gattgttttt attcacctgt gcccagaaca cagtaagcgc tgaaaaacat ttggagtgga 130437
tgaaagcaat attttattat ttaattcaaa agccctcttc ataatcaatc cgtatgcttg 130497
ttgactgcaa actgctcctg ggcagaaact gggtctgttt tatgtattca ccagtgtatg 130557
ccaaatgtcc agaccagagg tgacatatat taggatggca attaatattt gttgaatgaa 130617
tgattcctta tttcagatag gaaacggagg ctccgagaca acggtaaact ggccaaggcc 130677
acatagcaag tggcaggggg agaattccaa ccatagtttc taacgctgag tccctttttc 130737
agcctcctgc cctgtgtccc cggggcatag ggacagggcg cgggaaccct gtgctgcgcg 130797
gccgaggacg gttgtaagtc tgtcctcact cgcccgcgtc ccacacctgg gcgagggcaa 130857
gggaggcaga agaaatgaga cgctggagaa gccgctccga ggaagagggt aaacaaacag 130917
gctctggggc tgcgcgaggt gctctctgcg cgacagctcc tacccggcgc tcttgctccc 130977
acggctctaa aacctcaacc tactcccttc ctccagtctc ggtctccctg ggtctccgcc 131037
tctctctctt cctggctaac ttatttctca ctgggaaacc aaggaaatct aaacgatcgc 131097
actgacccca cagcctcaaa acaagcccat ccgcaaaggc caccaaacac ccgctcccac 131157
accaggcaca aagtcctctc cgcgacggat gcgcatgcac gagcgcgagt gaggaggcag 131217
agttagcgtg tgcgcctgtg cgcatgcgtg agtgtaagtg ggtagggagt ccttgagtgt 131277
gtctgcgcgc aagctcgtgt aaagagcgaa ggcgaggtgg gggcgagtgt gcatgagcgc 131337
gagcataagt gtactgtcaa cagtgagatt aaggtacgtg ggcgtgatgg tgtgtgaaga 131397
ggtgaaaagt gaattagaat gagggtaggg aatgagattg cttttccttt tttattttta 131457
aattatttca atagtttttt gaggaacagg tggtgttagg ttacatggat aggttcttta 131517 gtggtgattt ctgagatttt ggtgcaccca tcacccaagc agtgtacact gtacccaatg 131577 tggtctttga tccctgtgcg cggagctgtg tgagtgaagc gtgtttggga gcatgggtgt 131637 gtgtgaatat atgagtgtat gaatgtgtga atgtgaggaa tacgagaaac tggggatgtg 131697 cacagggtga gtgcggtgtg aatgagagtg tgagaacgtg cgtagagaga gcaggagtgt 131757 gtctgcgtgt gcccggcccc tggagccccg cctccccact aggcacgcct tcctcttggt 131817 ggggtgcgct acgggcgcag cccagtgcct ctgtccgcgc agacccgctc tgctggtcct 131877 ggagcctggc gtgggctgag gcttgaaact ggcgtcactc agcgagccag aaaggagtgg 131937 gcgggagtgt ctggggggtg cgctgtctcc ccatgtagaa gcctggacac tctaagcagg 131997 aggggctctg gcagtattgc ctcgaggtcc tccctttcac ctgcccccag tattgttcac 132057 ccacctgtgg atcatcttta tgttcatgta ctcagggagc acccatggtg tgcctatagt 132117 atgccaggct ctacttgggc ttgggaaacc gtgagaacaa gatagcttag atctcatttg 132177 ttttggaact tccactgggc cttttattaa tgtgtaacca gcttgcaaaa tgccagtcat 132237 acacaagttt tgtcgcctct gtcctcaagc agaggggcat ggagattatg agacaaacac 132297 tgatcgtaat aagacgatgc attgaaatca gtgcaaatcc atttcatctc caacccaacc 132357 tcaccctttc actgcaccac tgagtttggg attgggttta ggaggtcctg gatgtgaatc 132417 caccttctct ctgaccatgg aaataataat gaccctcttc tcacaggatg gttgtgagca 132477 ttaagtgagt taagcctgac atcccttggc acaacgcctt gcacatactt agcactcagt 132537 atacaaacta tgacgacgtt gatgtgtgat gacgttccct gagtctgatg gaatgttgtg 132597 gggaaagagg gaggatgcgt ttgtgagcta caaaatttaa gggattattt ctggatttag 132657 gttaaattag gccggttgtg gtggctcatg tcaataatcc tagcactttg gcaggccgag 132717 gcaggcagat tacttgaggc tagaagttcg agaccagcct ggccaatata gtgaaacccc 132777 atctctacta aaaatacaaa aattagccag cgtggtggta cacgcctgta gccgcagcta 132837 cttgggaggc tgagacagga gaattcttga acctgagagg tggaggttgc agtgagccga 132897 gattgcacca ctgcacttca gcctgggcca tagagcaaaa cttcatctaa aaaatatata 132957 tatataaaat aaaataatta aattgtgtat aatttataca gattgagtat ccttcattag 133017 aaatgcttgg gaccagatgt gtctgaagat tttggatttt ttatggtttt ggaacatttg 133077 catgtatata atgagatatc ttggaagagg accctagtct aaacacaaaa ttcatttata 133137 tttcacatac agcttattca gtgtacatag cctaaaagtt ttttatacaa tattttaaat 133197 gatttttgc atgaagcaat atgttttaag tacttctgtg tggaattttc cacttgtgat 133257 gtcatgttgg tgctcaataa gttgcaaatt ttcaatattc agcctgtatt acattctcct 133317 ctagcatcag gctagtgtta tagtatcaga tactccatct tcatccttta ctatgacttc 133377 ttttcttcca ccaatgttat caaaagtact gttaccaagg gaaataaaaa tgcagcaaga 133437 acctatagga gctgaatatt cttttaggca gctttggaag catttttagt cctgttaaaa 133497 tggaagggaa tattttcaca gtggcacaaa atgaatgctg taatttaacc ttgtgagcaa 133557 aatttctgat taaatacaac ataggaaata tgtttcctga ttagccatgt acctccctgg 133617 aacaaggtat tgtataaaca attgcaagac atacttattt ttattttaga gaagctgact 133677 tattaaaaac atttttgat attttgatca aatattttga tcactatata tgtgtgtgta 133737 tatatatata tatatatata tggaatgtgg tggtgggatc atagctcact gtagccttga 133797 actcctaggc tcaagctgat cacaatataa ttttgtttaa aaccaaaatt tttaaagatt 133857 ggatttcatt attgagatgt tttcccaagg aaaaaaaatc aaaaagaagg cttgaaagat 133917 tggagaaccg attgcagatc taggttcttg aatttaacag caagaaagga attctgtcct 133977
tatgtaactg acctatctca tgttataagt agggagactg aggtctcaag ggatgaaatg 134037
gtcttagtgg tcagtctctc ctacagtcac caaataggac catatcagct ttgttcctct 134097
acctacagtt ttatacactt gcaggaagat gccctggaaa ctaggagaag agaaggtaca 134157
ggagttccag gttcctgcat taccctcagg tctctgttgc tggcacctcc atcttctggt 134217
ggctcttgcc caaatccttt gaatcttctg tgactcctct cttgctcttt ctctaatcct 134277
gtacatttaa cccatcatga agtcctgaag gctttaactt caaatgtaac tggaaactga 134337
ccacttctta acactccaac tactatcgca cgggtccaag ccatcaccac tgcataggga 134397
tgactgggtt cattcttcct atacttgcct ctacaatctg ttctcaacag agcagccaga 134457
aggatcgttt tgaaatagaa gtctgatcag gtcagaccaa gaacaaaagg ccctccatga 134517
tgccaccatg gctgtctctg accactccaa ccactggcct acttgctccc tctgttttcc 134577
ttgctggtct ggccctctct agccttcccc tctgttgaga actcttcccc tacaagctca 134637
cacgtcttac ttcctcacct ttaggtcttt cctccaaaga cactttctta ctgtcttttt 134697
tctttttgc tttgaaattt agaaacaaat tttatttaag atctgaaatg taattcctaa 134757
aatatcaact ttttcagaaa actgtggctt acacaataat gcattgcctc tatcacgtta 134817
caacatgcat tagactcaaa tgcaaaaacc atgaaacaaa cgaccaccct tcaacaattt 134877
gcgcaaagac agaatgccta aggaacaaca tagacggatt tgcagaggat gggctgtttt 134937
acttcaagca tcattaaaaa aaagagaaca aatgcatggg tttttgggta tatatatcaa 134997
attgaatgtt tggcactagg agtcagggca ttttgtcatg tagcattaac acatattaga 135057
aaattgtgta gtgtcaaagg ggtagaacca ccagcattca agcaatgttg tcaactaggc 135117
aataaaatgt tccactgaat atttcttctt tgttctaatt actgcatacc ctggtagcaa 135177
ctttgaaatg agaaaaggag cttacactcc ttttattttc tgtttaaaac agaacagaaa 135237
acaaactgaa acataagccc tgttttacat taacaatgtt aaagaatatc cattttacaa 135297
gaaaaagact aagaacaaaa agtgtttcca gatctcaggg aaataacagt gaatggtctg 135357
tagaccagca cagggctttg tggtggtact tagcagaagc tactttgtaa tcaccgccag 135417
taaaaagaga tgcagaattc tttgccagat attttaggaa atcatgcaaa tggcccaaca 135477
ataacgcaag gctcttctca tcaagggata tataggccaa catttctcct attcttacaa 135537
ataacctcag taggtgtgtg ccccttaaac ctgggacaca ggagcatcag ggtgagccaa 135597
gaggatttct gcatacaggg gcctctcaaa tttgtagagc agctgagtgc ctaacatcac 135657
gtcgaaatat tcttttattc ttgtcacaat ttcattaact gcctatgcct tattatcgac 135717
gtttccctgc gatgttttac aatttgcata ctcctttaga attgcatcta catttttgctt 135777
agcagggagt taaaacagct gcttctgctt ggtaactaag ttccagtccc cagcaagcca 135837
tggtttcgat tcttcaggca tcttcacttt aacttccatt ctgttcttaa atgcgtcctc 135897
gctttcaaca gtgaggtctg cccaggctct ttccttccct ggggtctgag gtgctttgct 135957
ggtactgccc ccatatctgt ttccaggagt cctctgtttg ttctttctgg tcttcctcac 136017
ggatcctgaa gctaagaagt tctctgcaga gcgaccccac atcttcctga gagaggtggt 136077
tcaagatttt tctgctgtgg accagctgcc ttctttcctg aggaggcccc tctcatctct 136137
gcatgttgct tctagttggt tttttgaagt tgtcttcttc tgcagattgt tgtccatgag 136197
attgagaacc cggctttctg gaactcattc aaccctttt attccaacca acaatctttc 136257
ttctttccaa gaactcctag ggatttccca aaaggactct tatagatctt gcaggatggt 136317 ctaggaggat acagtgggag atacaatcca agattctgta atcagaggtt tctacaatca 136377 ggatcagatc tcctgagcct tactgtacag caaacttagc ttttctgaat ggtgacctga 136437 aatgagaatc cagatctttc tagctgccgc tttctcactc tttttaaaat atcaaagctg 136497 ctactgtgcc ttctgcactc ccaatccctt ttccatgctc tattttttc tcccatagca 136557 gtcatcactt tccaactata tgctacataa tatcttctgt ttatgtttat cgtctgaatc 136617 tccctgctag aatggaagct cctgcaggat atttatgtct actgggttca ttgagaacaa 136677 ccaccctatg agaagagggc cattattatt tcaaagagag ggtgaattta catccaggac 136737 ctcctaaacc aaaccccaaa ctcaatggtg cagtaaaagg gtgaggttgg gatggagatg 136797 aaatggattt gcactgattt caatgcatca tcttattact atcatcatct gtctcataat 136857 cttctccatg cccctctgct tgagggcaga gcccaaaact tgtgtatgac cagcattttg 136917 caagctggtt gcacatgaat caaaggccta gtggaagctt caaaatgaat gagatctaag 136977 ctatcttgtt tacatgcttt cctaagcata taaagcagaa cctggcagag gagatgctca 137037 ataatttatg aaggattgaa agaagaatgt cagtgttcta ggtggatgct tcctcaccat 137097 tctattttac ctgtatacag gactgcagtt tataaagact ctaaccagtt atgtccttgg 137157 gttagcacaa ttatttaagc tagataggac tttttgtttt tttttaact gttatttcca 137217 caataagata ttgagaggtt aaacgacttg ccaaaatcag atcctggatt tagacttgca 137277 atcaaagtat cattttgttt ttggtgggag acaagttccc tttccagacc tcctggctaa 137337 atgaggaaaa ctaataagtt actggattta ctgtggatgc ttctaaatcc agtggccctg 137397 agattagggc taaggttctc cctccactgt cggcctgtgg aattctttag ctgctcacat 137457 cacagctaca tgaacagttt ttgggaaaca caccataatg gccacatcct cttgttttta 137517 taatttacac agggttgaaa acaagagata ttgtcttgtt gttagctaga gctcatttgg 137577 agtctgccct gagtctctgg acttggctcg atgcccttcc tcatctgact gctctgggca 137637 aaccaactac tgtcttagtc attgtattac tctgtttgga ttctctgtca gtccatcaga 137697 tttagctgat gagctcattg actgaaaatt gattgagcaa gacagtgtcc ctaattctgt 137757 atgcatacac agcaccattg tcttccacag atacttcgta ataattggca tccccctacg 137817 agatcattgg tatctcaata attaaaatca atagctgttg ttaaggcaag aatttatcat 137877 agtaacctac aaaagtggta aaaaggtaat ataattcaga agatagatgt aaatataaaa 137937 ttaccaattc tgaacaggtt tttaaagata atacttgttc cttaaggaca ttcatattta 137997 ataaaataaa tgagttattt ctttatcatt tgaatgacat aaattgttac tttttatgt 138057 gagtggggaa aatatagcac tttaacattt tgagataagg agtagaacac tttatttata 138117 tcaattcagt gtttagcttt tcacagattt tgtctctatg ctacctgttt gatttttttt 138177 tttttttttt tttttgagac agagcaaggc tgtgtctccc aggctggagt ttagtggtga 138237 aaccttggct cattgcaacc ttcgcctcct gagttcaagt ggttctcatg tgtcagcctc 138297 ccgagtagct gagattgcag gtatacacca ccacgcctga ctaatttttt atactttttt 138357 gagtatactc taattttttg ctttctgggg ttttaccatg ttggccaggt tggtctcaaa 138417 ctcctggcct caagtgacct gtctgccctg gcctcccaac gtactgggat tacaggtgta 138477 agccactgtg cttagcctgt tagaatttaa taggtctcag ttatacacta tttcactatt 138537 ctgggtgctc taaagcatca gtgacaataa ttatgaatgt agaaggtgca ttggtagcca 138597 aagttaacta tgtcattgct gtccttgaga ggggttttta cctgtgtttt cttttttttt 138657 tgtaattttt ctgagatcag acaagttagt tagattccaa acaatatggg cctaatataa 138717

-continued tcacaattcc atttaaattg gccaaagaat gacccttatc cagacaggac tcttagtgta 138777 cttagctgtc aacaaaatat aaaacttatc agaataatgg ctacttttaa atataaggcc 138837 tgcatcatat tgttagagga acttctggaa ataggagaca gttgctatta aaattcaatt 138897 tagtttaatt caccattatt tactgagtgc ctacatatgt taggtactag ggctacaaag 138957 atgactagac cccgggctgg gcacagtggc tcacctaacc atagccatca atgaattcaa 139017 gtaagtgtgt gatagtggca tgcaacaact gtggaaccat ggaggagaga tctgttcttt 139077 cttcctgctg gcatcatgga ctctgagact gaggcttgaa ctatttctag gagatgctca 139137 gagtaaaaac aacagcagga gaagagactt ctaggccaaa gtttcaagag tgagcacagg 139197 cccagaggat ggatatgcat taagctgcat gcaggagaca gaagcaggaa gggctgctta 139257 gtggcagaaa gcaaagagtg tgagtggcag gtgaagaagt atgaaggcct ctgtagtaag 139317 atgaatggtc tttgaaggat gctaagcaga aaattgaaat gattatattg taatcattgt 139377 aaaggatggg attggaagag agagaaacca gagacagtta gtgtccagta ccaaagtcca 139437 gacttgaaat gataagtgtc acattaatca gtagtggtgg gaatggagag gagagaataa 139497 attcaagagt aatttggaag gtagcaccaa tgagccttgg ttactaatta gataggacag 139557 gggtacagaa agacaaatgg gtcagtgggg acttgggttt ctagctcagg tgtctgtatt 139617 gaatatgatt gtgttaacaa atatagtggt tacagatgaa agataagcag tttttgttg 139677 tttcagatga gactgtagat agagtgaatg gaacagaaaa aagataaatt ggttgtaaac 139737 attttgagtt ttaagtgcta taagaatagc caagaggaaa tttttgatgt agagtagcag 139797 ttggaaatat ggatctgaat ttaacagaaa ttgagattgg agttgggcgt ggtggctcat 139857 gcctgtaatc ccagcacttt gggaggctga ggtgggtgga tcacctgagg tcaggagttc 139917 gagaccagcc tgaccaacat agtgaaaccc cgtctctact aaaaatacaa aattagctgg 139977 gtgaggtggc acatccctgt aatcccagct acttggctgg ctgaggcagg agaatcgctt 140037 aaacccggga ggcagaggtt gcagtgagcc gagatcactc cagcctgggc aatagagcaa 140097 gactcagtct caaaaaaaaa aaaaaaaaaa aaaaaagaaa gaaagaaaaa agaaagtgag 140157 agtagaaata aaaatggcat cagcctatat tatttaaagc atatataata tttgaagcaa 140217 tatgatgaga tgaaattacc cagggttggt gtcatggtta ggatggtggt caggaaagtc 140277 attgttttgg tgtagtactt agagtagttt gaatatatta tgtgatatat ttgttggatg 140337 ctgagtctct tctacagtct cacttccctc ctctaaggac ttgtataatc ttttggtgag 140397 tctatctagg gataatccag tacttactat ttgacagtgg aactggaata cacctgggaa 140457 accaaattaa ggttgtaaga caggttggtg taaatatggg attggattta gaaacgactg 140517 gtatgaatat gagattagag ttacaaatag ccctgaccac cagatgactt gaaaaggtgg 140577 ctgagtactc tttcctcatc cctctcatct aatagaaata gagtggagta gggaaatcct 140637 gatggagggt tcagacaccc tgccttcttt tctttccaaa agactttctt ttccatgtag 140697 accgtagatg ttttctgact gagtcaactt tatatccaca aggtctgttg acatttaaca 140757 tgccaaagat ccatacagtg gagcagccag atgtttaggg cctggtcctg gcttattgcc 140817 atgagcattg ctcagattcc cagtctgagt cagaatcctg agtgacagat cacaggatgt 140877 ttgtgtttcc tgaaggactt aaagggcttg caaaatgttc tgtcttatcc acctccagag 140937 agaagattgc tcatttttga gatccatgta gatggaaaaa gaaaggaaaa atggtatatc 140997 aatgcacaaa atcatataca gtatcaccat tcatcatcag ctatcactct tgattttcca 141057 tcagtcactt ccttacctat ctaatgccct catcccatta tgttcgggat caaccttttt 141117 gcttcgacca ggctagcctg tttgtggtcc atggcacaca tagttatctt accatatgtg 141177 gggtttccca ttgacacctt tctccacctc tatcatctat ttttcatctt taaattgcta 141237 ttcaaaacta tggcttctcc acaaaacatt tgcttcccaa tggtaaaaac ttaggctggg 141297 tgctatggct cacacctata atcccagcac tttgggaggg caaggcagga ggctcactta 141357 agaccaggag ttcgagacca tcttgggcaa catagtgaga cctcatctct aaaaacaaca 141417 acaacaacaa caacagcaac aagcaaccca aaacaagcac atcaaatcat cccaaattca 141477 ccagtggttt cctatatggc aattaaagtt ttatctcccc atagaaatta taccagaggt 141537 aaaatttata ctcatttggg cataaagtac ttatttatac atgtctaggg cagattcctg 141597 atctttccat agcagtatgt tacagagtag ccctcactta gagaggtaga taagtagaat 141657 agaatatttg actacatcaa attgaagtat cttagatgat gagaataata gcgataataa 141717 gtatcattca tcaagtgtct gccatgccag acactctact aagcattttg taatgttatt 141777 acatttaact atcacaataa agattaagaa gggtatcatg cccatcttat agactagaaa 141837 acaaagattc aaagaagtaa tttgaagcca ggcacagtgg tgtgtgcctg tagtcctagc 141897 tacttgggag gctaaggcag gaggatccct tcagctcagg agttcaaggc cagcctgggt 141957 aacatagtga gaccctgtct ctgaaaaaag aaaagaaaca aataaaggac taatttgccc 142017 aaggtcttaa tttataggca gtggaatctg gattcagacc taagtctttt ttttccccag 142077 ctttttgaga tattaatcaa ataaaatttg tatatattta attgacaaat aaaaattgta 142137 tatatttaag gtatatgtgt gatgatttta tatatatata tatatatata tatatatata 142197 tatatatata tacacacaca cattgtgaaa tgattaccac aatcaagcta attagcacat 142257 ccattatctg acatagttac catgtgtggt gagaatactt aagatctact ctcacagtaa 142317 atttcaagta tacaatgcag tattaaccat tgtcaccatg ctgtacatta gagaccccag 142377 tacttttttt tttttttttg agacagagtc tcactctgta gcccaagctg gagtccagtg 142437 gtgcgatctc ggcctccacc tcctgggttc aagcaattct catacctcag cttcccaagt 142497 agctgagact acaggtgtgt gccaccacgc ccagctaatt ttttgtattt tagtagagat 142557 ggggtttcac catgttgctc aggttggtct tgaactcttg atttcagatg atccacctgc 142617 ctcagccttc caaagtgctg ggattatagg catgagccac tgcacccagc cgagacccca 142677 gtgctcttta atctttcaac agaaagtttg taccccttaac caacatcttc ccatctcttc 142737 cccttaccct gcaccccaaa cccctgcctc agctcctgga aaccactatt ctactttctg 142797 cctctgtgag ttcaattttt ttagattcca cctataagtg agattatata gcatttgtct 142857 ttctttgtct gtcttatttc acttagcata atgtcctcat tgtcacaaat ggtagaattt 142917 tctttttttt aatggctgaa tatatatata tatacacata tatatacaca tatatataca 142977 catatatata tacacataca tatacacata tatacacata tatatatgta tatatatata 143037 ccaaattttc tttatccatt aactgtggat gaatacttaa gttgatatca taacatgcaa 143097 taaacatgag aatgcagata tctctttgag ataccgattt cattttgttt gactacatac 143157 ccagaagtgg gattgctgga tcatatagga gttctatttt taattttttg aggaactgcc 143217 gtactgtttt tcataatggc tataccaagt tacatttcct ccaacagtgt ataagggttc 143277 cctttctcca tacccttgca gacactcatc ttttatcttt tggataatag ccattctatt 143337 ttaaaaaatt tttatttttt aatttgtttt tttttatttc tgagacctct cagggatgaa 143397 aatattaata attgccattc taacaggtgt gaagtgatat cccattgtgg ttttgatttg 143457 cacttacctg atgattagta atgctgagga ccttttatat acctgctgga cattggtaca 143517

-continued tcttctttga aaaaatgtct attctggtcc tttgcctatc tttaaatcag gtttttgtc 143577 tttcactatt gagttgtatg acttcttttt ctatattaaa tactaacccc ttctctgata 143637 cgtggtttct aaatatttc ttctattctg tgggttttct tttcatttgt tgcttgtttt 143697 ctttgctgtg cagaagcttt ttgatttgat gcagtgtact acttctttat ttttgtttct 143757 attgcctgta cttttggtat cacatccaaa aaaaatcatt gccaataaca acgtcaagga 143817 aattttcccc tattttttgt tctaggagtt ttgtggtttc agactttagc ttaagtctga 143877 aaggataaaa gttttctgga aggggaagtt ttgttgttgt tgttgtttct ttgtttgctt 143937 taaatggagt ctctgtcacc taggctcgag tgtgcagtgg cgcaatctca gctcactgca 143997 acctctgcct tccaggttca agcaattctc ctgcctcagc ctcctgagta gctgggatta 144057 caggcaccca ccaccatgcc tgcctaattt ttatattttt agtagaggcg gggtttcacc 144117 atgttggcta ggctggtctc gaactcctga cctcaagtga tctgcctgcc tcagcctccc 144177 aaattgctag gattacagcc atgagccacc gcacccggct ctgtaagggg aagttttaac 144237 actaacatgg aaaagaaagt atatagtaaa atttcaaaga ttgtataatt taatgtcatg 144297 taggaaaaca taaagataat agttaacaaa tcataagaga ggccgggaac ggtggctcac 144357 ttatgtaatc ccagcacttt gggaggccaa ggtgggcaga tcacttgagg tcaggagatc 144417 gagaccagtc gtgaccaaca tggcgaaacc ccatctctac taaaaataca aaattaacgg 144477 ggtgtggtag tgcatgcctg taatcccagc tacttgggag gctgaggcca gataatcgct 144537 tgaacccagg aggcggaggt tgcagtaagc caagatcgtg tcactgcact ccagccctgg 144597 ggacagagac agactctgtc tcaaaacaat aaataaataa ataaatcatg agagatcttt 144657 taaggttgta tgacagaaaa atgaaaggcc agctcaatac agacaaacta attcaagctt 144717 tattaataag gttgttccta tattatttta attatgatcc agaaacaaaa gaggaattag 144777 aaaagattgt ggaactgttc tctaatggca tgatcctaat atgactggat taaatctgac 144837 tggactgctc tgttcaacac aaccatcaaa atgttgattt tgaccatcct agcaacgaga 144897 ataaaaagca acatctgacc ctttgacagt ggcatttata aaaatgaaat ctcacatata 144957 catgagggta gggtcctgag ctacctaaag tttgtaaact catttcagta acttgaagaa 145017 acctctatta gtaagcacta attatagaat cccacatgtg agacacatta cattcatggg 145077 ttgattggca tcattctcag ttgatctgag attatcatca aaaaaatttt gacttaggat 145137 ttctttgcca agttacatca ttcctaaagc atctaaaatc aggcagggca gaatagaacc 145197 acatgctgat gtcacagggt gtaggtgggt ttgaatggtc tctgatttag tcaacattca 145257 tgctgtaatt gtgaatgata gctgctctgt gatactaata agaatgctca cctgctcaag 145317 tgatacgccc ttgaacaaca ggtcctcaca gttggcagcc gggtggcagg agggctgcta 145377 tagaaatgaa gttatagaga cctaacagaa ccactggcag agtgggatct ttgagccaaa 145437 gtgggatcat gtctaaggtg agtagtagcc tcaacagcct tgcaagtaca ttttgaggaa 145497 gcatattctt gtggagaaac ctcttacagg ctagtgacta tgctcatcct cagcaaaata 145557 acctgtctgt tccttagatg ataggtgcat agatagtgtg aactattcat ttgattctca 145617 gaaaacaata aaatcatgct ggctgttctt tccagttcag ccattgaact cttaaattgc 145677 cagacagcca tgtaagtctg aatgaatgac cattcatata ccctttccac tgcactgcaa 145737 tatggctctg ctcagaatgg caaggagaaa gactggaaga gaaaaatggt tgcaggatct 145797 tcttgtgttt ctacaaggct ttgacggtgc tgagaacata atccattctg gtgaattttt 145857 tctgtgaagg aggcaactag aaaggaatat tgtcttcatt ctctagaaaa aaagaactga 145917

```
aggaagagaa tttatagttg gctgattata acagcatgaa aacgcatatc ttctactctt 145977
tatctagaat tttgtccatc ctgattaaaa taacaacacc ctcaataaca actaacgttg 146037
agtacttgtc atatattgta tcattttaat cctcccaaca actttatgaa tgagtactat 146097
aattagctgc attacacaga tgataacaag gatgacaatt gttgagttaa cccagtttcc 146157
tcagtttctt tttttaaatt tttaattgtt tatttatcag tacaaatgat tccttagccc 146217
acatattcat gtttcatagt tcaggaacat aggtcagtga caaacttctg aggaactcaa 146277
tcccaaaaca ttcttaacat tccaaaatca ctttgcactc tgaaaggtac cagccctctt 146337
cacctcctca aaatctttca tggaatcata gtttctgtag aaatctacat atatctgctt 146397
tcttggttca gcaatgtaaa ctttaagaga gctgcaaccc ccagcattac aagaaatgct 146457
ctgacaatat gaaatcacag acacctggcc aaaaggctat gcatctgaaa tttcttcaaa 146517
acactggaag ccgtggtagt tattgtcctc aacaccaatg tccttcctgg ctgatggaga 146577
aatgcccagt ttcttaaata tcatcatggg attgtaaaat ctttggggaa gcatatagac 146637
ttttaaaata accactcaac aattgctaat tatactgagt aaaaccagtt agctttattt 146697
tctcattgct tatatttttt ccttcttatt tatcttttct cccttgcagt agaaacattt 146757
acctacagca gaagtcttag accttagttg tatttcagct tttaggggcc atctgagctg 146817
agtaagtcat ttttaaaaat taatttaatt aattaattaa tttttttttt gagacagatt 146877
ttcactctat tgcccaggct ggactacagt ggcatgatca tggctcactg tagtcttggc 146937
tttcctggct caagcaattc tgcctgagcc ccccaaataa ctgggactac agctgtgcct 146997
taccacgcct acctaattta tttgaatttt tagtagagac aagatctcgc tatgttgcat 147057
aggctgttct tgaactcctg agctcaagca aacctcctgc ctcagctgcc caaagtgcta 147117
ggattacagg tgtgagccac catgcccagc ctgagtaagt catttaactt aagttttctc 147177
tgaagtttat agaatgggat gaatatctct ctgtttacag cactggggta tggtgagggt 147237
cagatgtgac attgcaaatg aacatgtttt ataaaatatt aagcagtatg taaatactga 147297
tataaatatg gccggcacag tggctcacat ctgtaatccc agcattttgg gaggccgagg 147357
cgggccttga ggtcaggagt tcaagaacag cctatgcaac atagcgagat cttgtctcta 147417
ctaaaaatac aaataaatta gggcggtggg ggtaagtcca tgaaatggcg gctagtcagg 147477
agctgatgca agagaattct tgaacccaaa aggacacggt gcaatgaact gaaaagaacc 147537
cactgcattc catttgcgca ctagatgaca ctcagccccc aacaacaata aactcacaaa 147597
aatcctcccc cccattacaa acccaaaaca tccccactac tctctgcaca aaaactgcac 147657
ctcctcacca cacaaatnnn nnnnnnnnnn nnnnnnnnnn nnnnnnnnnn nnnnnnnnnn 147717
nnnnnnnnnn nnnnnnnnnn nnnnnnnnnn nnnnnnnnnn nnnnnnnnnn nnnnnnntgc 147777
tcagacaagg ttgatttca gggtttttta gcaaaagtga tctaattttt tgatgggctg 147837
ccttgccaac cccaacataa ttcattgata ataaagtccc atattcctgt gataattgaa 147897
atagttaagg ttatatttgt tttacattgg ggcataattt ttttttaata aaagtaaagt 147957
ttttttttag aaagctattt tttttgaaaa gggaggttct tttgtaggta atacctatgt 148017
tgagaatgtg atatgatgat atttatagac tcaacgttca gccaagattg acatttcctg 148077
cttctgatat tttttttttt ggatatatga tgaatatttt tttttttttt ttagaaaacc 148137
ccgagttttg gtgaaatatt gttttttttt tatatgctac cagacgccaa aatttacgga 148197
tttaaaagtt gatttacttt ttattaattt ttcccgaggg ggaccttaat tgtaagggga 148257
attttttttt tttttttttt tttttttttt tttttttttt tttttttttt ttttagttta 148317
```

gggtctcttt gtttttttcca acataatgtt tctgcattca tctattctta aaatgaaaac 148377
cacataattt acttcttata aagtcttaaa tgggaaacca agaaatttaa tcgagcagta 148437
aaaacattct caaaatgtag accatgatct cagtttcttc catttttctc ccgagtagaa 148497
aatagacttc tgcataagaa agctaaaatg tgttaatatt tttaagttaa aggtttaata 148557
ttatcagaat acaatccaaa gagtaaatca aattacataa ttacattttt atttattaaa 148617
tatggaatca tctactgaat tgcaatacat taaatatact gtttcctctt aaataaaact 148677
gcttgacagt taaaaaatta tgggcttgcc atacttgcag gtctcttatg tttttagatc 148737
ttatttactt atttatattt ttacagtgaa atagtaattt aaaaagagga tgggaaaatt 148797
ctgtagtcac ttgagtttcc tctagccaca ttttattgca aaccagttcc tcctttgaac 148857
atctttataa tttaagtctt taaaaatgct ttcatttcaa acactaaata tttctatatt 148917
agaaaagttt ttacagtata ttaaattatt ttttccacat gccccacccc tttacagtat 148977
atttaaaata ctatctttgg atttcatttc tttctgtttt gtaagatgga tactataatt 149037
caccctggta aactcagttt ttctttcagt attatgtgta caatatacat tgtactgtac 149097
aatgtacatt aatgaaaaac acataataca cattcagtgt acattttctt tcagtactat 149157
gtgtttttca ttaatgtaca cttcataatg tatattgaaa ctgaacatgt tgaagctcaa 149217
caagagtttt cgattaattc tgtttatatt ctgaacgatt agaatgtcta agtgtaaggc 149277
agagtacgag ctttggagtt gggcatctgg cttggtcact tacttggcaa actctttttg 149337
tcttgatgaa cttccatatc tctgtgcaca aaatgggaaa aacaaaaatc tcataaattt 149397
tggattaatt taattctcac aaaatgtcta tgaagcaaat tctaatgtta tcttcagaga 149457
aaaaaatggc caagctgaat agcaccatgt gtaagcacgt tctgcagaac tggcagagct 149517
tccagcataa aagaaaggga gagaggaaat gttctagagt caaagagact taagagacct 149577
cacttggatc ctcacttgaa aaaacaactg taaaaaggta ttttggagac aattggggaa 149637
atgtgaataa aattcattaa atgtcaagga gctattattt ttgtttggta tgataatggt 149697
tattatggtt agattttctt aatccccata atttacagat atatgtataa gtgaaatcac 149757
ataagggata agatttacct tgacatactt tagaagaaaa ccccacaact gattaaatga 149817
agcaagtgca gcttaattgt tgcagacttt tggatagttg tggaatctgg gtgatggtta 149877
tgtttgaaat gtttcagaat taaaaaaaga gaaaaattat gcagtggact cagatatgaa 149937
ataactggga tactagtgac acagatacag agactatgca aacatatgtt cccaggtgcc 149997
tggagaactc tcttgcatgc cagtgtatga caaaaatact ttcatccaag cactttcata 150057
ttcactttgt aattattgtg aatgtgtaga tatgctagtt tgccctaata tggtttatta 150117
agttggcctc cccatctaaa ctgtaatttt ctctgagact gagaagatcg gtttgatatc 150177
tttatccttt tcccattgcc cttgcatgat tactattcaa tcattgctga attaaacaac 150237
actttccttt gtttaggaag atgctggatg ctaaacacct gtcttactca ggcttcttat 150297
tgacatagca aattctaaac gtgttacata tacatgtgtt ccttttctgc tttaaataaa 150357
actgatgggt atttatttct cccattgtgt aatgtagtct gtggaaatag tagccagtgt 150417
aggatgcctc agatatatcc agctctgcag gccaaagctc agcttttaaa gtggcgattc 150477
ccagttattt tgttaaatgg atgttaaagt catccctggg ttggagttta gacttttatt 150537
gaaaagcttt tctactaatc accagttaat ggatgaataa aattcacact tttggtctct 150597
tcattgtttt attgtcaaca cattctttct caagggagag aattaatttg gaagttggag 150657
gtcttcaaat taggaaagtc tgacaaatag gccaactcta atattcatat ttacagtgga 150717 gattttcaaa gaagtttgac ataatacacc tcacaaaggg atgccaataa gtcagtttta 150777 ggcattattt ttgaatacaa ggagactgtt catttcttct tttctagtat aaacacacca 150837 tatgtttaag tgtttgtaag gcatgttgtc atcttaaata atatttaaaa aaatcaaagt 150897 ggtacagaca caagctcctg gaaatgtgct ggtatctttt ttttttttt tgattgttga 150957 gtaatcctga aatgaatttc ttccaaataa agggatgtag ctttgtatta aattttgtaa 151017 taaaagttct caaatgatag attcaaaatt ctaaacattt ttaaggatta taaaaagata 151077 tgcctgaaat cttgcatgtt ttaaaacgta gtacaaagta agctttttat atgtaggcat 151137 ttgtaattta aaaaaaagtt ttatttgtgt tttcagaata aacgagctaa cataaattgt 151197 acatatttac agcaataaac tacatttcag aagctgcaca acaactttta taagtacagc 151257 tgatgatttt tgacaccagc tttcaaatgt gttttcattc tttcatttgc tgcaacattt 151317 aaaatcttgt agtaccaaag caaaggaaac accaagttat tttatagcaa agccacatta 151377 ttaacaaaaa atactgagtg aactacagtc ccgtgactgt tatggtatct gtgagtcctg 151437 aaatcgagag cacaagcatt tcttgtgtcc atacctgatt gcatgtaaat tgattttgca 151497 ttttacaaga acacacaatt actcaaggaa taattaagaa tagaaaaaag gccatgaagg 151557 gtaaaagggt caggaatcag aggccactga acagtttctt attcactgat tcactgctta 151617 ggaggaaatt ggtttttttc tttcacgtgt ataaatcaca gtcaacaggc ttcatggatt 151677 ttgtccacag atagcttttg agataacaaa gccataaatg tcacatacat taagcacata 151737 aaaaggaatt aatgaaacgg ttagagtatt ttaatcaaat ccctaacaga aggggtacag 151797 ttaagcacac acagtatgaa agtttgcttt caaatgtaaa aagcaactac agaaaatcac 151857 aagtttcatt agacagaaca gcaatttcaa tcagaaaatg cagcatatat tgatacaaaa 151917 tagaaaactt gaaatataaa agtaaggagt ccacctttc ctttcttggc attttttaa 151977 acctgtccca tttcattaaa atttctacag gttttactga aatactcact cttgacattt 152037 agcttcttta gtgtctggta ggtatacaaa agtattacct gcttaggtaa gaaagcaaat 152097 gcttatgtca aagagcctta aaatattgta atttatgttt atttgcaatg aaagaagtct 152157 acttggtaaa aataaagagg gagaaaagga ttcttttatt tacaagaatt gtaataccaa 152217 tcaggatatg agttggttaa ataatgtttg gtaggaggat agatagcaaa ttggtaactg 152277 gagatctaaa aacacaagga atgaaacatt taacatgtaa cgtatttggt gagtttagca 152337 taacggattt tgagaggcaa cagaaggtat gtatttcttt ctgtatatac gtagcacctg 152397 cttttgaaag ccccagctat ttagtacagg atgctatgaa ttaaaattgc aggagactgg 152457 tgtggaaagt tcagctaatt ttctgattca atgaagtttt aggtgaggtg gtagccaaag 152517 aggtgtccca ttgctggcag gatagtagtt tcctaatttt tagtctcatg agtcctgctt 152577 tctcaaacct cctgaatcac tgtaggatta ggccccttga gtaaagtcaa gaggagcaaa 152637 ataatgttca gagatgatag acaggagaag ttttcaagca agccacgctc aacacagatg 152697 cctttctttc aaaaacaatt ttatttgtat taaacaatat taaacttccc aattttcatg 152757 tctgttaacc ttttaaatga catgccaaca ttatttcaca ttagccatca ggcttccatc 152817 atgatggcac agcatgctgc atggtggtta aaaaggataa agcttatttt aaaatatcaa 152877 aaagtttttg gtccttgtaa acatgtaagt catttggaat tttcaaaaat gttgtgaaat 152937 cttggctttg tataatgcca cgtggtagtt ttttttttt ttttttttt cctttattta 152997 ggcagtgtct cactctgtca cccaggctgg agtacagtgg cacgatctca gctcactgca 153057 gcctcagcca cccgggctca agtgatcctc ccacctcagc cctccgagta gctgagacta 153117

-continued caggcacgcg ccaccatgcc tggctaattt ttgtatttta agtagaaacg gggcttcacc 153177 acgttgtcct ggctggtctt gagctcatgg gctcaagaaa tcagcccacc tcagcctccc 153237 aaagtgctgg gattacaggt gtgaaccacc gtgcttggct gacatggtag tttttatcaa 153297 gaaaaagagt tactgactct ccttgagata agaagctgag caacacagtc aataaatata 153357 tgtgtatata atcatgaaca ttcccttctt ggaagagtac tggatgttct gaatatgaaa 153417 gaacacttgg atatataatt ctgttttcca tgacactgaa gttaagttag aataatcaaa 153477 ggacttccct aaaattgtct caggggcatt gttgtaaaat ttcaagcttt atccagtgag 153537 tattttaaaa agatctaaca aacagatcaa caatgaatta attagcttaa aaaaagaaaa 153597 agcagataca ctgcaattca atttatttga ggagtatcag gtagaaaaat acgttatcta 153657 gtaaactggg atggctggtt gccactctga ggtaaggctt gcaaattata tatttctttt 153717 atgcaaatta gtaaattatt taacaggaca actggaaagt taataattga aaaaaggggg 153777 tggaggcaga aaatgcattt ccttgtacat ctattatatt ttatgcactc ttgagaagca 153837 gtggtgaatg tcaagaactg tccatccctc ttatatagtt ctaaatcttc tatttatatc 153897 ttggcagaaa taggatttgt tgtgcagtac cttctgggag tattagaatt cacatgggaa 153957 tgttccatca ataatacagt gtagccccag cttcaagaat aaataccctg tagaacctag 154017 atttaaaagg ccattaataa ggcaaacaat gataaacagg ggaaaaaact ataaaagaaa 154077 actttccttt ttccataaag gaaaagcagc ggtaattagc aaggaatatt caattcttct 154137 agaactggta gaatctagat tggtggtatt atcaggattc agtctgcttg gaaaatccca 154197 gtagaaaaaa atcttaatga ccactttgca agacacaaac ctggattcaa ctgtaccttt 154257 gactgcattt tttattcttt gagaggttgt agatagaggc tctatgggac taaaataatt 154317 tgagagagga ggtcatctgt cccacaaggt attatctata atcctgaaat attgcctgtt 154377 atgaaaaagt gtttgtcttt tgctgccttt cccactgtag gtgatctaat cagcatttat 154437 agaccctgcc atgggcagaa caatagttgc tttggacaat acaaaagaat tagaaaatgg 154497 ggtgtttgct tttaaggacc tcacaaaggg aggcagaata tctctttgca aaactagaaa 154557 tgtgcaaata aactgtctat tattattgaa taaagtgacc acaagaattg agggagtgtt 154617 aacaggagag tgaacagaat gaggcagggt gctcatggac agcatttttg aggatgttgg 154677 cctgattcat aaaccacgat tgagatgggg ctaggaagaa aaatatctaa tcagtggaaa 154737 taaaatgtaa aacttcaagc acagcagtga ggacattttg ggatgatgtg tggatgttgg 154797 agtggaagga taaggaagac ctgaggatga gcttgcttgc agctaattaa ggaactcatg 154857 gagaaataag gtgagtatga acgagtggtg gagaagactg ggccagactt aaatgatttg 154917 tagggagcca agacatgttt tctgtagtgt gttaatgtta catttattaa tatttcccca 154977 cccttcaggt ggctgagatc ccataattat ggtggtcgta tcatttatta ttcacatgga 155037 caattttgag agtgaaaagg agttttatta ataattacac actgagactg tctgaggcaa 155097 attgggtcat atggtctaaa caataatgtt aaccaaaaag aactggagca catttcaggc 155157 tattttgctg ctgtgcaaac tttccttcta tatattttct caagagacta aggaaaggct 155217 tttatgtatg ggtaagcaag tgggtggaac agatggaaaa agcagaaaac aaaactggac 155277 acagagtgtc tactgagcat gatatttatc tgttgggagt gggaatagtt ctcttccccc 155337 ttactctcta ctcatttttg aactgcccaa aatctggatc atcaaggtaa aatggataaa 155397 atctagacag cttagtagag tggaaaaagc ttgaatggcc aggaaatact caggaaaatc 155457 atgaaagttt agagttggaa ggtatctttc aacaaagaag aaaaagttaa gaacatctgt 155517

-continued

```
ttacagaagt tgtattgagg acaatgttca gagaccggaa ttcttcatgc atgcttgaag 155577
aacatgaata gctagaatgc taatcacaaa ttaataaact gtcagttttg tcatggctgt 155637
gcctaacacc agtggattta actaggtaag tagttaacta ggtaagtagt taactaggta 155697
agccggggtg gaaggacttg agcaaggaga gtggataaca gatgttctaa agaccttgga 155757
tctttccaac tattatagat ggaaagctgc ttcttgcctg agagctcaaa aatatctgct 155817
actctacttt caggaaacaa gacagtgtgg ggtccaagac tgaggagggc actgcaacaa 155877
catttgggct tagatgctgc ctagagattg gcttttctac ccatgatggg gtgttgcatg 155937
gctgttcctt aattgaatta cagagaatgg tttaagaaca tctttatctt ccagggatct 155997
aaaaataaag gatttgtatt atctgagact ctctcttaaa gggaaatatt gtagttatag 156057
aaaattacaa aaatagtaac atttttccac ttggcttgca aatgtaactg tatgtcctat 156117
atatttttaa aggaacatga ataggtattg aattcaattc acttgatacc agatggctta 156177
ctctcaaaga catgatatca agaattatta ccaaattagt tgggttatgt tagcagaggc 156237
catggtcctc ctgtatcttt ctgctaacct cccatacaaa tgaacttctc taaaattacc 156297
tttgaaattt agttttggaa gagaacttgg aggtcatctg gtggcatgtt caaagtcatg 156357
ctcctaggca gtggcagaga cagcaccaag accaggtccc caatcatatt aataattcca 156417
aggtgtcttc catccactgt gaattccctc tctccatcat gatgctcact tattgttaac 156477
ttttcgaggt taggctgcat actctttggt atatgtttag agaactctct tccaaatcta 156537
tataaatgct gtctagagga aacagatgtt ctacatattt ttatgggaga aatttagaca 156597
gtttgcaggc tgtctgcaag gctgagggga agtgggtagg gtgttatata gaagtagaaa 156657
tttgtaatgg gggtaatata caaaaaagat gaaatggatc aaggatagtc tgtaactagt 156717
ggtgtgctat ttgaatgata agcccttcta ggaggaataa taataaattg taaaatgggc 156777
ctactggaga ctgaaaaagc taatgaataa acaagtttga taaaggattg atacacttta 156837
agttcactat attacaatta tagtgtaagg agatggcctt atcttcaaac tctggggtag 156897
ataatataaa tttctgtaag attgagctaa agatttttat ttccacttta ttttgaaata 156957
ggccgggaca gagaaggttt atgtaaatac atgtactctt tacataagtg acagaaaagc 157017
agaaaagaaa aacaactcaa ggcagttcag aggaggctat tatgattata caacctgcct 157077
ctaaaggact tttaaaggca atgggaataa gaatttggaa aaaaattatt aaaattcatt 157137
gttttagtga attcnnnnnn nnnnnnnnnn nnnnnnnnnn nnnnnnnnnn nnnnnnnnnn 157197
nnnnnnnnnn nnnnnnnnnn nnnnnnnnnn nnnnnnnnnn nnnnnnnnnn nnnnctaatc 157257
acttcccagg aggtcccagc tcttctcagg ccatcctcct accttggcct cccaaagcac 157317
tgggattaca gatatgaacc accacgcctg gccactggta gttaatttct tttttaaaa 157377
aaattattat gttaaaactt ttgtgggtac atagtaactg tatatattta tggggtacat 157437
gacataggca tgcgataagc aataatcaca tcatggaaaa tgaggtatcc atcccctcaa 157497
gcatttatcc tttgtattac agacaatcca attacactct tagatatttt taaatgtaca 157557
gttaaatatc attgactata atcactcttt tgtgctatca aatactaggt cttactcatt 157617
ctttctaact gtatacactt tttgttccca ctaaccatcc gcaggctggg cggagtggct 157677
cactcctgta atcccagcac tttgggaggc ccaggcaggc agatcacttg aggccaagaa 157737
ttcaagacca gcctggccaa catggcgaaa tcttatctct gctaaaaata caaaaattag 157797
caggtgtagt ggtgggtgcc tgtaacccca gctacttggg acactgaggc atgagaactg 157857
ctcgaagctg ggaggtggag gctgcagtga gccaagatca tgccactgca ctccagcctg 157917
```

tgacagtgtg tgactctgtc tcaaaacaaa aacaaaaacc atctccgctt acccccaacc 157977
cctcactacc cttcccagcc tctggtaact atccttctac tctctatctc cacaagttca 158037
attgtactga tttttaccac ccacaaataa gtaagaacat gtgaagtttg tctttctgtg 158097
tctgacttat ttcacttaag ataatgaccc ccagttccac acatgttgtt acaaatgaca 158157
gaatctcatt cttttcatgg ctgcatagta ctccattgta catatgtatc atattttctt 158217
tatccagtga tatgttgatg aacatttagg ttccttccaa atcttggcta ttgtgaacaa 158277
tgctgcaaca aacatggagg tgatagctga catactgatt tcctttcttt tgggtatata 158337
cccagcagtg ggattgctgg atcgcatgat agctctattt ttaggttttt tttgaggaac 158397
ctccaaactg ttgtctataa tggctatact aatttatatt ctcaccaaca gtgtatgagg 158457
gttccctttc ctccacatcc tcaccagcat ttgttattgc ctgtcttttg gagataagcc 158517
attttaactg gagtgaaatg atatctcact gtagttttga tttgcatttc tctgatgatc 158577
aatgatgttg agcacatttt tatatgcctg tttgccattt gcatggcttc tttggagaaa 158637
tgactattca aatcttttgc ccatttttaa atcagattat taaatttttc ctacagagag 158697
gtttgagctc cttatatatt ctcgttatta atctcttgtc agatgagtag tttgcaaata 158757
tttttttccc attctgtggg ttgtctcttg attttgttga ttgtttcctt ggctgtgcag 158817
aagcttttta acttgatgtg atcccatttg tccatttttg tttggttgcc tatgcttgtg 158877
gggtattact caagaatttt ttgcccagac caatgtcctg gagagtttcc tcagtgtttt 158937
cctgtagtaa tttcatagtt tgaggtctta agatcaagtc tttaatccat tttaatttga 158997
tttttgtata tgatgagtcg taggggtcta gttttatttt tctgtatatg gatatccagt 159057
tttcccagca ccatttattt aagagactgt ccttgctcca atgtatattc ttggcacctt 159117
tgtcaaaaat gagttaactg taggtgtata gatttgtttc tggcttcttt attctgttca 159177
attggtctat gtgtctgttt ttatgccagt accatgctgt tttgattact atagctttgt 159237
aatataattt gaagtcaggt aatgtgattt ttccagtttc attctttttg ctcaggatag 159297
ctttggtgag tctgggtctt tgtggttcca tataaatttt agcgttgttt tttctattcc 159357
tgtgaagaat gtcattggta ttttgatagg gattgtattt aatctgtaga ccgccttggg 159417
tagaatggac attttaacaa taatgattct tccaatacat gaatatggaa tatatttcta 159477
tttttaagtg tcctcttcca ttcctttcat cagtgtttta tagtttttat tgtagagatc 159537
tttcacatct ttggttaact cctgggcatt taattttatt tgtggctatt gtaaatggga 159597
ttccattttt gattcttttt cagattgttc actgttggca tatagaaatg ctacaaattt 159657
ttctatgttg attttgtaac ctgtaacttt actgaatttg tttattagtt ctaatagttt 159717
tttggtggag tctttaggtt tttttttaaa tataagatca tatcatctac atacaaggat 159777
aatttgactt ctttctttcc aatttggagg ccctttatct ttctcttgtt taatttttcc 159837
atttaggact tccagtactt tccattgttg aaagtggaca tacttgtgct ccagatctta 159897
gagaaaggct tccagttttt ccccatgcag tatgatacta gctgtgagtc tgtcatatat 159957
ggcttttatt atgttgaggt atgttccttc tatttccagt ttttggaggg tttttatcat 160017
gaagagatgt tgaattctat ctaatgcttt ctcagcatcg attgaaatga tcacatggtt 160077
tttgtctttc attctgttga tatgatgtgt tatatcacat tgattggttt gcgtatgttt 160137
gaccattctt gcatccctgg gataaatctt acttcatcat gatgaatgaa taatcttttt 160197
agtgtattgc tgaattagct tgctcatatt ttgttgagga tttttgcaaa aatattcttt 160257
agaggtattg gcctgtagtt ttcttttttt gatgtgtctt tgtctggttt tggtatcagg 160317 atgatactgg ccttgtagaa tgagtttgga agtatttccc tctcctctat tttttcagtt 160377 cattttgagc aggattggta ttatttcttc tttaaatgtt tgctagaatt cagcagagaa 160437 gctattaggt tctgggcttc tctttgctgg gagacctttt aattacggct ttgatctcat 160497 tatttgttat tggtctgttc aggttttgga tttcctcatg gttcaatctt ggtaggtagg 160557 ttgtatgtgt ctaggaattt atccatttcc tctagacttt ccaatgtgtt ggcatacagt 160617 tgctcatagt agccactaat gatccgttga atttctgtga tatcagttgt aatgcctcct 160677 ttttcatctc tgattttatt tattttgtct tctttctttt tatcttttag tctggataat 160737 gatttgccga ttttatattt tcaaaaaacc aactttttgt tctgtcaatt ttttgtattt 160797 ttcgttcatt ttaaattcat tcatttctgc tctgattttt tttttttttt tttttttttt 160857 tttttttttt taaaaaaaaa tctggctggg tcactcagga ggcacaaagg ggtgattttg 160917 gctcaaggca acccccacct ccggggttaa accttttctc ctgcctaacc cttttgggta 160977 gctgggatta caagggcccg tcaccatacc cagttaattt ttgttttttt agaaaaaacg 161037 gggtttcacc atgttggcca ggctggtctt gaactcctac ctgggattac agggggggagc 161097 caccaagccc ggcccataca ttacatttta aaaaaacggc atctgaattt ctgctctata 161157 ctctacattt tattgaaagg ccctctgatc aaaaagttcc caaatttatt aaaaatccct 161217 taaaaattat atttttttac actatcttcc tcaaaattgg gcaaattaaa acaaaccttc 161277 acaaattttt gaaagtaaac tgtttctcaa caattgaaat gggtagccct tgtagctaca 161337 cattttgact atgcccttca tatgataaaa attccctttg cacaatttct taaaggttgg 161397 aaaatttctc attaaaataa aaaaaaacca caagtcctct acccattgaa aaaatttttt 161457 gaaaaatgct atcaggtnnn nnnnnnnnnn nnnnnnnnnn nnnnnnnnnn nnnnnnnnnn 161517 nnnnnnnnnn nnnnnnnnnn nnnnnnnnnn nnnnnnnnnn nnnnnnnnnn nnnnnnnctt 161577 ggaacttttc tcttttttct tgattagtct agcttttgtt aaggtttgtc agttttgcta 161637 atctttaaaa aaaacaactc ttagtttcat tgttctttta tattgtttta tgagtccctg 161697 tttcatttat ttctgctctg atttttatta tttatttctt tttgctaaca ttaggcttac 161757 tttgtacttc cttttctatt tccttgaggc atagcactaa gttgtttatc tgcaatcttt 161817 cttctctttt gacgtaggca tttattgctt taaatttttt tcttagaact gcttttgcta 161877 aacccataag ttttggtatg ttgtgtttct attttcattt gtctcaagat aattttaaat 161937 ttccatttta atttctttat tgacctattg gttattcagg agcatgttgt ttaatttcca 161997 tgtatttgtg aattttctaa aatttcttct gctattgatt tctagtttca taccattgtg 162057 gtcaaaaaag tacttgatat gacttcagtc ttcttaagtt tactaagact tgtcttgtgg 162117 cctaacatat gatctattct ggagaatgtt ttatgtactt gagaagaatg tgtattctgt 162177 tgatgttaga tggaatgctc tatatatgtc tgttagatcc atttgttctt gaatgctgtt 162237 taagtccgat gtttacttgt ttattttctc tctgcatgat ttgtccatta ccaaaagtgg 162297 tatattgaag tcccctacac tattattcta ttgcagtcta tatctccttc agatttttaa 162357 atatttgctt tatatattta ggtgtgccat tattgcatgc atatatatat atatatatat 162417 atatatattt tttttttttt ttttgagatg ggggctcact ctgtcaccga gaatggagtg 162477 cagtggcttg atcttggctc actgcaacct ctgcctcttg ggctcaagtg aatctctgag 162537 tatctgggac cacacatgcg ccaccataca cgtgtttgta tttttggtag aggtggggtt 162597 ttgccatgtt gccaggctgg tctcaaactc ctgacctcag cttaagcgat ttgcctacct 162657 cggcctccca aagtgctggg attacaggca tgagccactg cacccagcca tcatgcatat 162717 atatttgcaa tcattttatc ctgttgatga attgacccct ttaccattat aaaatgtcct 162777 tcttggtctc gtttttacag tttttgactt aaaatctatt ttgtttaatt taactattgc 162837 tatccctgct ctttttttggt ttcatttata taaaacattt ttctattcct ttactttcag 162897 acaatgtgtg tccttaaaat tgaagtgagt ctcctatagg cagcatagag ttgggttttg 162957 tttttaaatc ccattcattc actctatgtc tttttttaaa aaaaaattaa gacaacattc 163017 atggcacatt taatcaggaa ttccaaatta gtgctacaaa cactaaaagt ataatgtttt 163077 attaatataa atatcacccc tcactgacat aagcaaaaaa aagctcaatt atgtggaaag 163137 aaatgtttac ccaaagaggt gccttccgct tataaacaca gactatatca catagcatat 163197 cagttctcaa aaggaagtaa ttctagatct aaagcttctt ctgtaagtaa catcaggttt 163257 atggacctgt atggaagaaa agtggctaca aaaaaaggac atgactattt ttctaatatc 163317 gttgtcgcgt gcaaacatta gcataagttt tacacattct tcaaaataca catacatgca 163377 tagaaaagtc acatttgcct taggctttct aagattgtgc tacactaagt tatggataaa 163437 agactatgtg ttgcttcacc tttaaaataa aaagattttc agtacaaaga agaaaatgac 163497 acactgactc tgcatctgga ttcagtgtaa taagtagtaa ttgtatctca ttacaggcag 163557 atttcctcca accatttaaa aagttacttc ctatcataat tcaatttttt aattccaaac 163617 tttagaacta catataacct caggatttag ctgaaattgt actatctgat tattttgtaa 163677 attagcaaag ctaaaaattc tagcttgaat aatttcttca tagtataagg gatagtattt 163737 tatagtaata aaattattct taaagtcaat agttatcatt tattgaacac tttttatgtg 163797 tgctctacaa actcatttac acccacctca atcctcagaa atagatacta ttgtcatttt 163857 aggaaaaaca gattcgaaat ttaaataact tgcttaaggt cagagacagc agacgtagga 163917 ttcaaacctt agcctttccc actccaaagt caaggctcct aattctcctt gaggacacta 163977 agatttgtaa aagaaatctt cagggtcaaa gtggtaaaag ggtgtcctgt tggtaaatgc 164037 agtgctgaga tctgttttag agaagtgacc agtaccaaaa ataaaaaaat ggttagtaac 164097 atcaaagaaa tcctgccaga gagtttatgt gcagcacata tgttgggttc tgtaaacttg 164157 aatgaaattt gaagtataat gttactagag gccttccaaa cttcatttct ttttattgaa 164217 taacttaacc catttacaat caaggtaatt attgacaggt aaggacttgc tactgccatt 164277 ttgttaatta ttttctgatt gttttgtaga gactgtttct ttcttcatct tttgctgtct 164337 ttttttgtgg tttgatagtt ttctttagtg atgtcttatg aatctttttc attttgtatt 164397 gtgtttctta taaatgttga ttttggttac catgaggctt acatagaata tcttatactt 164457 aacattgtat ttcaagctga taacaactta actttgattg tataaaataa cgctacattt 164517 tactatcccc tccaacattt tatgtttttg atgtctgaat ttacattatg ttataatatg 164577 tatcccttga ccatttatct taggtaacat tgttattaat aattttgtcc ttatactaga 164637 gataaaatta cactagagat aaacacttat actagagata aaattacttt acacactact 164697 atgataatcc tagagtattc tgactatttc tctatactac ttataccatt aagttttgta 164757 ctttcataag ttttatgtta ttaattagca gattttcgtt tccattaata aaaattttag 164817 caatacctat aaagaaggcc tagtggtgat gaactctctt agcttctgtt tgtgtgggaa 164877 agtttttatt tctcatttct gaaagacagt tttgctgggg aaagtactct tggttggcag 164937 ttttttttctt tcaacatttt gaatgtacca tcccactctc tcctggcctg tagggtttct 164997 gctgaaaagt atactgataa ttatattggg actcctttgt atgtggtaca tttattgtct 165057 ctaacttctc tcagaatttt ttctttgttt ttgatgcttg ataggttgat tattatgtgt 165117

```
cttggtgaac tcttctttgg gatgaatttg atgggagact tctgcactct ctgtacttgg 165177

attttggctt ctttcctcag attaagaaaa tttgcatcaa ttattccttt aaatatgctt 165237

tcnnnnnnnn nnnnnnnnnn nnnnnnnnnn nnnnnnnnnn nnnnnnnnnn nnnnnnnnnn 165297

nnnnnnnnnn nnnnnnnnnn nnnnnnnnnn nnnnnnnnnn nnaaggacaa tcaaatgggc 165357

acatactata tttatgcaca tacatacaca cacacacaca cacacacaca cacacaacca 165417

gatgtcattt ataatccatg taaaatattt ttggggaagt ttctctttaa taaagtttga 165477

agagacatat attttttttt tttgaagagg catatttttt ctaacttttt tttttttttt 165537

tgagatggag tcttgctctg tcacccaggc tggagtgcag cggtacgatc acggctcact 165597

gcaacctccg cctcctgggt tcaagcgatt cttcagcttc agcctcctga gtagctggga 165657

ttacaggcat gtgccaccat gcctggctaa tttttttttt tttgtatttt tagtagagat 165717

gggggtttca ccatgtttgt gaggctggtc tcgaactcct gacctcaagt gattcaccta 165777

ccttggcctc ccaaagtgct gggattacag gtgtgagtca tcacacccag cctataactt 165837

tttttaata ggtgatagaa tcccgtgctt gaaaaataat caaacaaaaa gagaatgcat 165897

tgtaagaagc ctcactgtac tcctgtcccc agctgcccag ttctcccctc ctccccacag 165957

ggaaacatct tcattagttt cattaggttc ttatgaaacc ttccagagtt tctttaagca 166017

aaatacaagc aagtaggact gtcatatcct gcagaccgct acatacaaat acatagaaag 166077

tgtcctcatt ctatcctcca gtgatattcc attttttggc tgaaccacct aaatgatgga 166137

tatttagggg aagcaagtat tttttaaaaa aggtaaaaat caaaggtttt tatttttat 166197

tttttaaag aaaagttggt aggctgtgtt tattcattca gaagtcaggc cgtggctgaa 166257

ctgatagctc ttggagatgg ccattgctca tctctgaatg tctggttttc tcttgtaaga 166317

attgtgtgta tgatccagac cttcagtgtg tgcactatat attgagaatt ccagaagaga 166377

tgatatggac aagaaaaaaa gatgacttta ctttttacag taaaaataaa acttaaattg 166437

aagagtacaa ttgtttaaac aattggaact tacttagcta ctgcttgttg aaacaaaatc 166497

cttttttaa aag g tat cga agc aaa tta aag ctg atc cgt gct aag gaa  166547
                Tyr Arg Ser Lys Leu Lys Leu Ile Arg Ala Lys Glu
                375                 380                 385

gaa gac agt ggc cat tat act att gta gct caa aat gaa gat gct gtg   166595
Glu Asp Ser Gly His Tyr Thr Ile Val Ala Gln Asn Glu Asp Ala Val
            390                 395                 400

aag agc tat act ttt gaa ctg tta act caa g gtatgtaaag ggagtataaa   166646
Lys Ser Tyr Thr Phe Glu Leu Leu Thr Gln
        405                 410

gataatgcta gctctgtaga tgagtgtctt ccaaggaaag cctggcactt ttctccccgg 166706

tcatggaaga aaagcagcac ttaggggaga agcagtgtct gcatatgtca catatcggga 166766

atacctctgc tggactcatg aattcaggta tttctgggag gttctgggtt actctagagt 166826

aggcgaggaa tccctaggct ccaccagcta gctttatttt tgtagagatg gagtcttgcc 166886

atgttgctca ggctggtctc ctgggttcaa gctatcttcc caccttggcc tctcaaagta 166946

ctgggattac aggtgtgagc cactgcacct ggcctccacc agcttactta gcacctgctt 167006

ctcaatctga gaagagagaa gcagatgacc ttagattgtt ctggagagtt ttgctacaag 167066

ttttccttat agacattgta cagtggtcct taccagaagg gagtgcccaa gtctgtttac 167126

attcaggctc agcacctatc cagagtccca gccatgagcc aggtgctgtc tgaggtgcgc 167186

tcatgtgatc ctcacagtaa aacctgtgat acaagcaaca ccgtatatct aatttatttg 167246

accacagatt tagaaaagaa tctttaaaac ctaataacat accacagatg cattttggta 167306
```

```
aatgctgctt tagattatac tttagctgaa tccattagtt gaatcctaag ctataatata 167366

attttaagaa cctccttgcc tttcaagcca aataaccaag ggactttctc tctctctttc 167426

cctccctccc ttccttcctt ccttccttct tctctccctc ccttgttatc tcttttcctt 167486

tcctttctct ccttccttcc ctcttccctt tttcctttct ctccttcctt ccttccttgc 167546

ttccttcttc cctccctcct ttgttctctc ttttcctttc ctttctcttt ttctttcctt 167606

ccttccttcc tcactcactc ttttcttttc ctttctctcc ttccttcctt ccttcctccc 167666

tccctcactc tctcttttct ttgcctttct ctccttcctt ccttcctttt cctccctccc 167726

tccctccctt gttctccctt ttccttcctt ccttctttcc tttcttcctt ccttccctct 167786

tccctcactc tctcttttcc tttctctcct tccttccttc cttcattctc ccctcccctc 167846

ccccctcccc tccccctccc ctccccccctc cccccctccc ctccccttcc cttcccttcc 167906

catttttctt ctcaccatgt tgcccaggct tgcctcaaac tcctgggctc aagtgtttct 167966

cttccacctc agcctcccaa gtagctgggg ctacatgtgt gaggcatcac aaccatggac 168026

ttttcacttt cttcactcca ggttaaaaac atcacaggga taaatctcaa aacaccaaaa 168086

ctgtgaaaat gctgctaacc atgtgggtct gtctaaactg gagtgttact tgtacaactg 168146

gtttcagccc ctccggagtg ttttgaatgc catgtagatg agttgtgaac tcatattcca 168206

ctttgtagtc tcatatgttc tgggacacga gctattccat tctgacttct ttctgcctct 168266

tgcag tt  cct tca tcc att ctg gac ttg gtc gat gat cac cat ggc tca 168315
      Val Pro Ser Ser Ile Leu Asp Leu Val Asp Asp His His Gly Ser
              415                 420                 425

act ggg gga cag acg gtg agg tgc aca gct gaa ggc acg ccg ctt cct   168363
Thr Gly Gly Gln Thr Val Arg Cys Thr Ala Glu Gly Thr Pro Leu Pro
        430                 435                 440

gat att gag tgg atg ata tgc aaa gat att aag aa  gtatggaaaa        168408
Asp Ile Glu Trp Met Ile Cys Lys Asp Ile Lys Lys
    445                 450

cagatgtgtc ttcttctttc gtggtcagaa tatttctccc ttgacacaaa tgatgtcaaa 168468

tacattttac ttattgacta taagataggg ttttgggtgt gatagcttca gggtgtgtat 168528

cttttgtcat gaatagctgt gagaagaagg tccagggctc tcattagacc ttcaaaatgt 168588

ctccaatcta aaaacaagag tgaattttaa gaaccactgt tctaagaaga tttttactac 168648

cctggctcac atatcttatt tggtgaactt tgtttggtag tcggactgca tgtaaacata 168708

aatgtgactg cttagtccct tatctgccca cctgctgttt ggtgggttaa ttcgccattc 168768

cctcctccct cccccgagtc ctcagccttc ttaaatgggc acatgagcaa tgtgtttaca 168828

cttcatccat ggtaactggt tgtgttcaga agcctcagtt gtttcttcct ctagacagag 168888

actcctcatc ttaacttcta gggctaagaa cagacttgga tgttgactgg ggtttctagt 168948

agattccagt gtggagcagg attctaggtc ttataactca atctgaggat catcgcaacc 169008

ctagtgacac cctaggggct cttcccagtg tgagtgttga gaagggaggg ctccaggcct 169068

ttttgaaggg gtgggagatt gagatcatta aatatggttg aagttgaact gttcagtttg 169128

ctcataggtt caagattggg gaatggtagt catattttat taaacttgat tatctctgcc 169188

tgctatgtaa acacttagct ttcagttgtt catgtgtgag ttattccctc ttcagcacat 169248

gcagacaagt tttaatgttc atctgcatgt aaaataaatc agtgtgtatt gccccgaaat 169308

gcagacaagg tcccaactcc ttgccatctt agagtgttcc cgtggctcca ctcattgcca 169368

tgactctcag gaattggccc tatacttagg ccctttttct ctctag a tgt aat aat  169424
                                                    Cys Asn Asn
```

-continued

```
gaa act tcc tgg act att ttg gcc aac aat gtc tca aac atc atc acg   169472
Glu Thr Ser Trp Thr Ile Leu Ala Asn Asn Val Ser Asn Ile Ile Thr
    460                 465                 470

gag atc cac tcc cga gac agg agt acc gtg gag ggc cgt gtg act ttc   169520
Glu Ile His Ser Arg Asp Arg Ser Thr Val Glu Gly Arg Val Thr Phe
475                 480                 485                 490

gcc aaa gtg gag gag acc atc gcc gtg cga tgc ctg gct aag aat ctc   169568
Ala Lys Val Glu Glu Thr Ile Ala Val Arg Cys Leu Ala Lys Asn Leu
                495                 500                 505

ctt gga gct gag aac cga gag ctg aag ctg gtg gct ccc a gtgagttcct  169618
Leu Gly Ala Glu Asn Arg Glu Leu Lys Leu Val Ala Pro
            510                 515

caacagtcag gacaactcat cagctgagcc gcatctgccc caggcggaac tttgaatccc 169678

agataggggt tatatagaaa tgaaggtccc aaggcagaaa ttcagttatg aatgctctta 169738

aagtcatgtg ggactttgtt ttattttgtt ttgtttttg agacagagtt ttgctctgtg 169798

gcccaggctg gagtgcaatg gcacaatatt ggctcactgc aacctctacc taggacgttg 169858

ttttagattc agatccaaaa ctgcattttt gcagaggccc ctcaacattt tgcttgtcta 169918

ataatatagc tacagtctct actttgaatg tctgtgtatg tggatggagt gtggggaagg 169978

atcttctgtc tcattgctcc ttaaaagata gatgaagcca aaagcaatat aagcaaaatg 170038

caacttacaa aataagcttt ataataaagc atatgaagta gaggtgtctg cccatatagt 170098

agctgtcaat tgcatttatc ctattcaaat tctgtccaca aggttactgt tggagcaact 170158

ttggagaaaa tactgagttc tcctgattga attttgtccc cttcttgtat aaggaaagag 170218

ttgatgtagt ttcctgggtg tagatggttt gagagatggt actgcctatc cctaaaatga 170278

accaggcagc cctcacactt ccccaccagc agtgagagat tcctggctca gacacagcca 170338

cactaccttg ctgcccctgt gcatgtctgc caggaaactt ttcattgtgc ctctctctct 170398

tgtcacgtag cc  ctg cgt tct gaa ctc acg gtg gct gct gca gtc ctg    170446
           Thr Leu Arg Ser Glu Leu Thr Val Ala Ala Ala Val Leu
                                525                 530

gtg ctg ttg gtg att gtg atc atc tca ctt att gtc ctg gtt gtc att   170494
Val Leu Leu Val Ile Val Ile Ile Ser Leu Ile Val Leu Val Val Ile
        535                 540                 545

tgg aaa cag gtagatattt tctcataaaa ctaaagatct ttgaagccaa           170543
Trp Lys Gln
    550

tgagaacaag catagcaacc tagttcagtg cttggcacag agaaggagct cagcaattac 170603

atgtggagtg aacgttgttg gactctactg tgtccagtca ctgtgctgct tcagtgaagc 170663

tctggtgcac tgggactttg gtaattcacc agttacctgt cctggtcatt tatag aaa  170721
                                                             Lys

ccg agg tat gaa att cgc tgg agg gtc att gaa tca atc agc cca gat   170769
Pro Arg Tyr Glu Ile Arg Trp Arg Val Ile Glu Ser Ile Ser Pro Asp
        555                 560                 565

gga cat gaa tat att tat gtg gac ccg atg cag ctg cct tat gac tca   170817
Gly His Glu Tyr Ile Tyr Val Asp Pro Met Gln Leu Pro Tyr Asp Ser
    570                 575                 580

aga tgg gag ttt cca aga gat gga cta gtg ctt g gtaagttcca          170861
Arg Trp Glu Phe Pro Arg Asp Gly Leu Val Leu
585                 590                 595

tggggtaacc tcccaagact ccctttttccc ttgcacacaa ctttacaatt tataggcctt 170921

ggcagaatag agatctgagc ttgtgcttag taagaactag gcaatggaaa tttgctttca 170981

gaaatacatt tctgtcttga cagtaagtta attggatcat tgcaatgatt tttttaaatc 171041

tctttccata acaaattata gttaaggaaa attttacaaa gggagaagag aatatgaaga 171101
```

```
gggctggcaa agatacccac caaaattgct tttctttaga aatgacacaa attgaaaatg 171161
aatttctgtg actaaaaatg agcagatgag aaatgaatga ggacaaccac aaaatgtatt 171221
ttgattcagt acattctgaa gatgcattag atactccttt ttacatattt ggaatatgga 171281
atataaaaat ataggtacat tttgaggcaa aatatgtaaa aataagcaag ccaacttatc 171341
acaagcattt caagtatttc aatcctgggc tgagaccaag tatatgaagc tttagtccaa 171401
gggagtattt ctttttaaa tcacattcct aatgaatgaa agcaagacaa aggcaaatga 171461
aagtagaggt agaggttgtg ttatgatgaa tgatctaaca gtatatatgt taaagaatgc 171521
caaatgcagg ttttaattat ccaccggtct cattgcaaaa tacagaagag tttaagtctt 171581
cttagagagt taggtaaact gaaatcaagc aaggcaccag agtgaaatca cctttgcaaa 171641
aattgtaact gaggaaatta tgacagtgaa tgagatatga cctaaccaac tccattttgc 171701
tttagcctcc aagttgtcct tgttccttcc tgggcatagg ccgaactaac tttgagagga 171761
acttagttta tagtttgact ttgaaaaaaa gacaataata gccctttgcc aaaacaaacc 171821
ctctttttcc ctgggaacta gactgccttt gcgggactaa cgaattagct acaagattag 171881
aaagtatggt ttaggggtca ctgttgtaaa acctgaggtc agtgcttgag atattttgga 171941
gaccctgtat ttcgatgcac cagctgacac cacccaggtc aataaactgg ctcatctgat 172001
cttggggccc ctacctagga actgactcag tgcaagagga cagcatcagc tccctataat 172061
ttcatctttg acccaaccaa tcagcactcc ccttttcacc ccctacccac caaatcatcc 172121
ttaaaaaccc cattcccccca gtttcagaga cactgatttg agtaatagca gaatagtaga 172181
aattccccca gtttcagaga cactgattcg agtaatagta gtaatagtag aataggtctc 172241
ccgtacagct ggctctgtgt gaattaaacc ctttttctat tgcaattccc ctgtcttggt 172301
aaatcggctc tgtctaggca gcggacaagg agaatccatg ggcggttat aagagctgcc 172361
ccccaatttc aaatatttat atctaagctt tctttatttt cctgcctatt tcccaacaag 172421
ggatgaggag cttagggagt taaaaagtag taaaatatgg ggaaaagggc ataattccca 172481
ttataccaag aggcattgct ggtgaagcaa tacctttcca ggtacgattt tcagtaacac 172541
agacgtgcag taagaggcag tgttggctgt tagtgtcttt tatgagccaa gtcttttcct 172601
ggcttggcta tccgtggtga gactgacacc ccgggaaatg tttctctcag ggtgagctct 172661
ttcagggtgg gacaacagct tcagtgtctt tacgtatgtc tcctcccaac atgaagctaa 172721
ttgctgtgct ctcgggcatg tttagctctt ggtagagtgg ctttcctaac aaatagggag 172781
cagtgagccc agcctgaagt ttttatttag tcactcctta gaatcagtga tattttgaat 172841
actgaagtat ttccagtggc tagtaattta ctaagacaaa agatgcccct gtttgcatat 172901
ggaaaacaga aggggagaga gccaggaggt gtgggtgaga gccccgaagg caagaggatc 172961
ccaggggctg gcccagcacg gagctggtag acagcgcgct cacaccaggg agggctgcac 173021
cctcctttct cccgtctgtg ttttctttcc cttgcaagtg ttattcgaca aaagcaatta 173081
tgctaatttc cttccctgtg ggctcaattc cttttttgac acgatgactt ggaggagtca 173141
ttatgattac tccaaacagg aaagacactc gcccagctgt ccgcccgcag agagctggct 173201
acggtgcaga aagctgagga ggcgtctgga gtttttgggt gttaatgatt ctgcctgccc 173261

acag gt  cgg gtc ttg ggg tct gga gcg ttt ggg aag gtg gtt gaa gga  173309
     Gly Arg Val Leu Gly Ser Gly Ala Phe Gly Lys Val Val Glu Gly
                    600                 605                 610

aca gcc tat gga tta agc cgg tcc caa cct gtc atg aaa gtt gca gtg   173357
Thr Ala Tyr Gly Leu Ser Arg Ser Gln Pro Val Met Lys Val Ala Val
                615                 620                 625
```

```
aag atg cta aaa c gtaagtgctc cttcctgggg attttttgag cacggggatt     173410
Lys Met Leu Lys
            630

ttttgagcat ggggatatta agggaatttc tcaaaatcat gcagctagta aataagacat 173470

ttaggactag gtcctgatta ttttgactcc aggttttatg tgtatttaga ttaggtttat 173530

ttagattgct cttgctgcct gtatgttgga aaattaagag cttgttattt ccagtgactt 173590

ctttttacta gaaagaccag gaattagtta ttagcactga ggccaagtag ctatctgctt 173650

cttttagact tctggtaaat agaatgatat ccaatcacag gattagtcat attcttggtt 173710

tttttctgag aacaggaagt tggtagctca gctggactga tatgtgattt attctttcaa 173770

cag cc  acg gcc aga tcc agt gaa aaa caa gct ctc atg tct gaa ctg   173817
    Pro Thr Ala Arg Ser Ser Glu Lys Gln Ala Leu Met Ser Glu Leu
                    635                 640                 645

aag ata atg act cac ctg ggg cca cat ttg aac att gta aac ttg ctg   173865
Lys Ile Met Thr His Leu Gly Pro His Leu Asn Ile Val Asn Leu Leu
                650                 655                 660

gga gcc tgc acc aag tca g gtgggctcac tgacctggag tgaggatttt        173914
Gly Ala Cys Thr Lys Ser
            665

cactggacac atgtggttgt gaaaactgtt caatcaggct taaatcctcc actctccatc 173974

cccacacatg gcagggaata gaagtccctt gaatggagct gactggtccc ttgaattgat 174034

ggaagctcat tggtttttga gcaaaatctg ttgccagtcc agtcatagcc attcatggct 174094

ctttattaaa aaaaaaaaaa aaaaaaaaaa aaaaaaactt ttttggtatc ttattttttt 174154

ctgtgccata tggtctgcag gacaattcat ggcttttctg ttcttcattt tcatacccat 174214

ctcctaacgg cttttgtccc catag gc  ccc att tac atc atc aca gag tat   174265
                            Gly Pro Ile Tyr Ile Ile Thr Glu Tyr
                                    670                 675

tgc ttc tat gga gat ttg gtc aac tat ttg cat aag aat agg gat agc   174313
Cys Phe Tyr Gly Asp Leu Val Asn Tyr Leu His Lys Asn Arg Asp Ser
            680                 685                 690

ttc ctg agc cac cac cca gag aag cca aag aaa gag ctg gat atc ttt   174361
Phe Leu Ser His His Pro Glu Lys Pro Lys Lys Glu Leu Asp Ile Phe
        695                 700                 705

gga ttg aac cct gct gat gaa agc aca cgg ag  gtgggtgcaa agagagatgt 174413
Gly Leu Asn Pro Ala Asp Glu Ser Thr Arg Ser
    710                 715

tgctgtctat cattatctta caggcatcac aaatggaaag acccatgtcc tgatagatat 174473

catgtctgca gattcagtgc ccaaggtagc aagacttaga gtcaaaccac cctgtccagt 174533

ctttccatgg tcatgcagag agatgcatga tgtctaaagg tgttttggac tggggtgtca 174593

catgggaagg ccttgctgat aggtttgaat gagagtgagt tagaatgact ctgggagctc 174653

ttctgctatt tacatgtgat ccacttagac ctataaaatg cagctctggc cagggatgct 174713

tgagttctgg aaccttgcaa gaactgtctg tggatctcca agctcgaggt ccttgctgaa 174773

cctggaccta taaatgacgt caatgatagt gatccctact gcagaaatct acaagtggct 174833

ataaagaact ctgtaggtaa gaaattctgt aagatcagaa agtacaatga attcacttca 174893

taataaatta cttggtggac accaaatggg tgctaaattg attgggtaga aggaattgta 174953

tgcccaagcc acatggccac acggctcaag ttccaaccaa ggcttgtgag ttgaaaaact 175013

gagaaagaat aatgacagac ttaacgtagt gaattcttca aactttaagt gtaatggact 175073

tacaggtcca tgggagcaca gccccactgt cttagatgtg gctcttcagg atgtgcgggc 175133

tcctgctaag gatgtgcagg gaactggctc tgaaaacaag tgaacagtag tcatcatggc 175193
```

```
agctgacatt tgtggagtcc tttgtatgtg ccaggtgcca tgacaaatat tccgctagtc 175253

tttcccatct ttgtcagtgg gatccattct acgtcttctg aaaagtgctt ccttgacccc 175313

cagatcaagt cattttcctt acaagctatt gaaacctttc ttccttcaca acacagctga 175373

gtttgagttg atctgtgtat ttattttgtt ttttacattt cttttttttcc ctatttaaaa 175433

aatttttttta tttccatagg tttttgggga acaagtggta tttggttaca tgagtaaatt 175493

cttcagtggt gatttgtgag attttggtgc acccatcact ggagcagtat acactgaacc 175553

cagtttgtag tcttttatcc ctcacctgcc tctcaatttt tccccgagtc cccaagtcca 175613

ttgtgtcatt cttatgcctt tgcatcctca tagcttagct ctcacttatg agtgagaacg 175673

tacgatgttt ggtttccatt tctgagttac ttcacttaga ataatagtct ctaatcccat 175733

ccaggttgct gcaaaagcca ttaattcatt cctttttata gctgagttac atatatatat 175793

atatatatgc acacctacac atacatatgt atagatacac tgcagtttct ttatccactc 175853

cttgattgat gggcatttgg ggttggttcc acatttttttc aatatgtgaa ttgtgctgct 175913

ataaacatgt gtgtgcaagt atctttttag tatgacttcc tttcctctgg tagataccca 175973

gtagtggaat tgctgtgatg catgtatttg tgcgactatt tgattaatgc tcatttcctt 176033

gactagatca cctcatgtga aaggtatgga ttggttttgc ttttacccag ttagctccca 176093

tgcctacctc agtacctggc acataatcat catctactga aagtggaatg accacttcag 176153

aagggcaccc tgggtaagat ttctctttct gtttttacag c tat gtt att tta tct 176209
                                              Tyr Val Ile Leu Ser
                                              720

ttt gaa aac aat ggt gac tac atg gac atg aag cag gct gat act aca   176257
Phe Glu Asn Asn Gly Asp Tyr Met Asp Met Lys Gln Ala Asp Thr Thr
725                 730                 735                 740

cag tat gtc ccc atg cta gaa agg aaa gag gtt tct aaa tat tcc gac   176305
Gln Tyr Val Pro Met Leu Glu Arg Lys Glu Val Ser Lys Tyr Ser Asp
                745                 750                 755

atc cag aga tca ctc tat gat cgt cca gcc tca tat aag aag aaa tct   176353
Ile Gln Arg Ser Leu Tyr Asp Arg Pro Ala Ser Tyr Lys Lys Lys Ser
            760                 765                 770

atg tta g gtaaaagtgt ctatactcac tctgggtgtt gggactttcc agtggtttaa  176410
Met Leu

tatgatactt aaagtattta gagggaagtg tatagggatg gtaagtgaac ctggcagccc 176470

acgtggtctc taaatgcagg tctgcacaac cagttctgtg acatgtttcc aggtttgtgg 176530

cctgtaaatt gaaaagaata aaagctgaca atgtaacaaa ttttttaaac tttaaattta 176590

atagttttaa agaattttct tggtgtgttc ctgcagtaaa catttttttaa aaaaaataat 176650

tatttattct gatataatga acttcctttt ttattgctgt ctttttcttt tttaatgaaa 176710

atatggtgat tgattttttt taatgccctt acttggcaga attacaagtt ggctgtctta 176770

tgttggttcc tcaccttgct ttttttccct taagttttag aagtctctga tgtctatgag 176830

ttcagtaacc cttgctttta cttttcctaa cattcaattt gtgataggaa ctctagagta 176890

gataatttgc agttatattt tctggaccag tgtttctgtt gaatgtattt tgaaggtggg 176950

tctatctgtt tttcaagtac atgaatatgt ggcagggtta aattgattta taaactccag 177010

ggagtccagc tgatgcccag accagatgga tcacttcaca tctgctcagg gtggttcctc 177070

cagagccctg aactggtcac agacatgaag ctggaagtct gacattggct tgtcctgtga 177130

gcttgccttt ttgggtctga gccttcccat tagtcaatgc aaaaaagtgt tgagctgccc 177190

tggacattgt tttggaaatt attgatgtgc tctgaatgtt ttcaggttct taagtgaaag 177250
```

gtacaatcca tttaaaaaag aatgtgtttg ttttgcaaag ctcagtacac aatattttcc 177310
atttctgcgg ttccaagttc cattcacttc tcattgccaa atgggtgaac ttccaagcgc 177370
ttttaaaaga ttagccagtg agagttatcg gaaccagtac ttcctctccc ctcccatatt 177430
gttaaaaata gtttacattg cttcccaggc tgggctggtg gagttggcac gagatgtcag 177490
aggaacctga gtcatgctca ggcccaagcc ctgttggcag gcagaccact gctttctggc 177550
cttccgtgac tatctgaaaa aaatcgtgaa tggctagagc tactcttcac ttgctgaaca 177610
ttttcaaaaa gaattgagaa cttctggatt aaattgcctt cttcctcgaa aaccctggga 177670
cccttccaga tgggactaac tggggaaagt ggacaagtta caaacaaaga aactcaaagg 177730
aaagtcattg gcactgatct ctaagatgct atcacatgtg attggtggtt gattttatta 177790
acaaattata agcaaagtac tacaaaggtg gctttaaaaa gaaaataaag caattcacag 177850
aaactacttt ttcatgtagc ttgtatgtgt gctccatgta tttcatcatg gaagatttta 177910
gtgtgtgttt atgtgtatgt gtgttttaaa ggtagctgag atgatttgct aattatggtt 177970
gaaaaaaaga aatttaggag gtaaacaaaa taattatgtg taagattggt ccttgtggct 178030
gtgtgtgtgt tttgtgtgtg cgtgtatgtc tctgtgtgtt ttaggctgtt cttttattgc 178090
tataaataaa tacttgagac tgggtaattt ataagggaaa gaggtttaat tagttcatga 178150
ttctgcaggc tttacaggaa tcaagatact ggtagatctg ctcagttttt ggagaggcct 178210
catgaagcca tgaagtcatg gcagaaggca aagcagtgca ggcacatcac atggccagag 178270
caagagcaag cgagagagag aaagagagag gtgccacaca cttctaaaca gtcagatctt 178330
acaagaagtc acttactatt gcgaggacag caccagaagg atggtgctaa attgttcgta 178390
agaaatctgt ccccatgatc cattcatctg ccaccagtcc ccacctccaa tactggagat 178450
tacaattcaa catgagattt gggtggggac acatattcaa actatatcat actgaccctg 178510
gaccctccca aatctcatgt ccttctcaca tttcaaaata caatcatccc tccacaatag 178570
tcccctcaag ccttaactca ttccagcatc aactcaaagt ccaaagtctt atctgacaca 178630
aggcaggtcc cttccaccta tgagcctgta aaataaagaa caagttattt actttcaaga 178690
tacaatgggg ttataggcat tgggtcaaca ttcccattcc caaagggaga aatcggccaa 178750
aagaaagggg ctacaagccc cacagaagtt cagaacccag cagggctgaa aactccaaat 178810
aaactccatt gactccatat cccatgtcca gagcacactg atgcaagggg tggagctctt 178870
gggagggatg gaacaccctg tggctttgca gggtttagcc cctgcagctg ctctcagggg 178930
ctgttgtcga gtgcctgtgg tttttcctgg tgcagagtgc aggctgttgg tggatatatt 178990
attcatggag gatggtggcc ctcccctcgt agcttcacga ggcagtgccc cagtggagac 179050
tctgtgtggg gacttcaacc ccacatttcc cctctgcagt gccctagtag aggttctctg 179110
tgagggctcc aatcctgcag catgcttctg tctggacacc ctggtttttt aatatatcct 179170
ccgaaatcta ggcagaggct cccaagcctc aactcttaac actctgtgca cccacaggct 179230
aacaccacat ggaagcggcc aaggtttatg gctgtcacaa gctgaagcag cagcccaagc 179290
tgcacctgaa ctcctttgag ccacagctgg agctggagtc atagggatgc agggagcagt 179350
gtctcgaggc tgcacagggc agtggaccct ggggctggcc catgagacca ttcttccctc 179410
ctaggcctct gggcctgtga tgggaggggc tgccatgaag gtgtctgaaa tgccttaaag 179470
gcctttttcc cattgttttg gcaatcagcc tttgcctcct ttttagttat gcaaatttct 179530
ctagcaagtg gttgcccagc agccctcttt aattctctcc caaaaaagct tttactttct 179590
ctgtcacatg gccaagctac aaattttcca accttttatg ctctgcttcc cttttacttt 179650

-continued

```
tttttattt taaagagatg gggtctcact atgttgtcca ggctagtttg aactcttgga 179710

ctcaagcaat cctctcactc atcctcccaa agtgttggga ttataggtgt gagccactgc 179770

gcccagcctc tgcttctctt ttaaatataa gtttcaactt caagtcattt ctttgcttct 179830

gcatctgact gtaggctatt ggaagcagcc aggccatatc gtgaacactt tgctgcttag 179890

aaatttcttc caccagatat cctaggtcat cactctcaag ttcaaacttc cacatattcc 179950

tagggcatgg acataatgtg gccaagttct ttgctgaagc ttaacaaggg tgacctttac 180010

tccagttccc aataagttct tcattttcat ccgagacctt ggcagcctgg atttcattgt 180070

ccatatcatt atcagcattt tggtcacaag catttaacca gtctctaaga agttccaaac 180130

tttccttcat cttcctgtct tcttctgagc cctccaaact cttcttatct ctgcctgtta 180190

cccagttatc tttacagcaa ttccccattc cttgatacca attttctcta ttaggctgtt 180250

tttgcattgc tataaagaaa tacctgagac tgagtaattt ataaagaaaa gaggtttcat 180310

tggcacatgg attctgcagg ctatacaggc atttgcttct ggagaggcct caggaagctt 180370

ccaatcatgg tggaaggtaa agggggagca ggcatatcac atggccagag caggagcaag 180430

tgagagagag acagagagag agagagagag agagagagag agagaggtgc catacagttt 180490

taaacaggca gatcttgtaa gaagtcactc actttgcaa ggatagcacc aaggggatgg 180550

tgctaaacca tttgtgagaa attcaccccc atgatccagt cacctcccac caggccccac 180610

ctccaatact ggggattaca cttcaacatg agatttgggt ggggacacat atccaaacta 180670

tatcattgcg tgtgtgtgtg tgtgtataat ttttaaacca gatatatgtt tctgcatatc 180730

tctttccttt ctttcattct ttctatcttt tttttttttt tttttttttg agacagagtc 180790

tcactctgtc acccaggctg cagtgcagtg gtgtgatctt ggctcactgc aactcattgc 180850

aacctcctcc tccctgattc aagcaattcc cctgcctcag cctcctgagt agctgggatt 180910

acaggcacat gccaccatgc ctggctaatt tttttgtatt attagtagag atagggtttt 180970

accatgttgg ccagactggt ctcaaacttc tgacctcagg caatccaccc acctcggcct 181030

cccaaagtgc tgggattata ggcataagcc accatgcctg gcctatatat ctattttcta 181090

agatagaatc tttgcatagt gatattcatc tgtgagatct aaacattcta caaaaaaatt 181150

aagaaaatat ttttggatgt gttctttggg catgcctctg caacctgatg atttcctgct 181210

gcctgccagc accaatacat ttaatttctt ttctgcag ac  tca gaa gtc aaa aac 181265
                                         Asp Ser Glu Val Lys Asn
                                                             780

ctc ctt tca gat gat aac tca gaa ggc ctt act tta ttg gat ttg ttg   181313
Leu Leu Ser Asp Asp Asn Ser Glu Gly Leu Thr Leu Leu Asp Leu Leu
                785                 790                 795

agc ttc acc tat caa gtt gcc cga gga atg gag ttt ttg gct tca aaa   181361
Ser Phe Thr Tyr Gln Val Ala Arg Gly Met Glu Phe Leu Ala Ser Lys
            800                 805                 810

aat gtaagttcaa ggaacacaga ccttttttaga cccagatttc agtgagtgga       181414
Asn

gtgtggacgg agatgctagg agatagatgt tggaaaggcc attaataaca ggggcctctt 181474

acttacctgt ctctctcctt catcccctac gcaggtcagg gagtctgaaa tcatcaggca 181534

tctactcttc tctagagctt tctctctgtt gggagtgggt ggagtgagaa cctgggagaa 181594

ggccagccct ttatatccag gcagacagct ccaagtgcca ccatggatca gccagtcttg 181654

caggggtgat gctattcagc tacagatggc ttgatcctga gtcatttctt ccttttccat 181714

gcag tgt gtc cac cgt gat ctg gct gct cgc aac gtc ctc ctg gca caa   181763
     Cys Val His Arg Asp Leu Ala Ala Arg Asn Val Leu Leu Ala Gln
         815                 820                 825
```

```
gga aaa att gtg aag atc tgt gac ttt ggc ctg gcc aga gac atc atg   181811
Gly Lys Ile Val Lys Ile Cys Asp Phe Gly Leu Ala Arg Asp Ile Met
    830                 835                 840

cat gat tcg aac tat gtg tcg aaa ggc agt gtacgtcctc acttccctca     181861
His Asp Ser Asn Tyr Val Ser Lys Gly Ser
845                 850

ctggtcaggc tcatcctcct tcactttaat ctctaaagtc aggtgttgct tctagagatt 181921

cggtgcctgt tttttaaaac atcaatagat ttcaaggggt cagtacactg ccttggcagc 181981

agattgccca ggtttgagtg ccagctccac cacttactta atttggattt ggggctagat 182041

acttgactgt tctgcccctc tgtctccctg attgtagtgg gaggtgataa tagtacctat 182101

ttgctgagtt gctatgggga ttaaatcaat gaattcatgt aaagtgctta ggacagtgcc 182161

tggcatatag aaacagcact caataatgtt agctatttta tttatttatt tatttattta 182221

tttatttatt tatttatttt cttttttttt gagacagagt ctcactctgt cacccaggct 182281

ggagtgcagt ggcgcaatct tggctcactg caaacttctg cctcccaggt tgaagcaatt 182341

ctcctgcctt agcctcccga gtaggtggga ttacaggcat gcaccaccat gttcagctaa 182401

tttttgtatt tttagtagag acagggtttc accatgttgc ccagactggt ctcgaactcc 182461

tggcctcaag tgatctacct gcctcagcct cccaaagtgc tgggatgaca ggtgtgagcc 182521

actgcatctg gcaagtgtta gctattaata tgtcaattgc gtgtatgcat ggacaagcat 182581

gcattcccaa ggatggtgtc tttacatttt aagcttttat cagattttca aaagccatct 182641

gtgaccccta aaatagattg gaaccatttg ggtttatgta tcttggaggc acagtttcct 182701

taaagatact cattttgttg tctacttgaa ccattcttcc catcccttcc acttctcagc 182761

agatgacata gctccctgtg ggatatatc tgctccctgt aggtacaatt ccaaatcacc 182821

tcactgcact ggatgtgaga cagcttatgg cagctgctgc ttccacctag agaaagacat 182881

gggcctgcat ccatgctgtg tgtgattcat gtactcatgt ggccgtgata gctgtaatcg 182941

gctcatagat cattggatct gttcttagtt ttgttcccag gaatatctaa aaataggaaa 183001

ctggtccatt cagggcttac accttttggg tgaaaattca ggattaatgt ttttggatat 183061

tattcctttg gaggacataa aaggcaatat tgaccattca tcattcatct agtatttatt 183121

gagcacctac tatgtgccag ggactgagag ttcagtaatg aacaaaacac atgtaaaaga 183181

cactcaaatg ggacaagata attagcacaa gttattaaga gcccaagggg aaccctttc 183241

tatttccact gctgtggatc atcagtgagt agacatgggt ttaactgtct ccctccttcc 183301

ttgcag acc ttt ctg ccc gtg aag tgg atg gct cct gag agc atc ttt    183349
       Thr Phe Leu Pro Val Lys Trp Met Ala Pro Glu Ser Ile Phe
       855                 860                 865

gac aac ctc tac acc aca ctg agt gat gtc tgg tct tat ggc att ctg   183397
Asp Asn Leu Tyr Thr Thr Leu Ser Asp Val Trp Ser Tyr Gly Ile Leu
    870                 875                 880

ctc tgg gag atc ttt tcc ctt g gtatgggcct gacattgctg cttatttggg    183449
Leu Trp Glu Ile Phe Ser Leu
885                 890

ctgttctgaa acaccactgg aaggaaaatg tgttctttca agccccagga tgtagacagt 183509

gttaagataa cctggtgtga ggccagtatg ctgcagccac ctcaaaccac atgttgtgcc 183569

ttattgtgtc tgagataggc ccatgcaggt ggagatgggg gtttttgttg ggggttgcgt 183629

cttactcctg gcctctgccc ctcctctcct ttgggctatg ccagagtgac ttcctcccac 183689

tggaagtggt cccaatgaca ttcgcatccc agctgctttt tcattttggg ctttgggtca 183749

catgggttca cccatggaga gtgggccctc cctcacctgg tggcgattga tgctcaggtg 183809
```

```
aaaaggggta cgtggcggga agggcagggc tctcattcct ggttgtcatt ggccagtctt 183869

gacaacccag gtgctgaaca acccaggtgc cctgggctat ccggtgaggt ccctaagaga 183929

aggatgagcc ataaccctga catctggatg gttcatctgg ggagatgaga cttacacact 183989

tagggataaa cagtgtgctg ctgatttaaa attgtaattt gagtcttgag taaagagaaa 184049

ggagtcctgg aatagtgtgg gaaggcttca gagagggaac ttaacttgac ctggccttgg 184109

ctttgaaagt gtgaaatgtt tcatgaattt atctgtgatc aggatgtaat agtaaagtgt 184169

gtcttcctgc cccgtctcct ttttcatcct agttctccct ccatggatga tcacaatgga 184229

tcatccccca gtggcttaat ggagtcctgt actcccttaa aagcagagag gccacaactt 184289

tgatttttgc tttagctatt tgaacatacc tggtgaaaaa gactctctgg gttttaatga 184349

ttcagaattt ctccttgctt ttctagttca ttttgtctgt gttgatccag tagtcataca 184409

cattgaaaaa cacttgaacg cttatttcta aagatgtaga atttttgtga tggtacttgg 184469

acttgaccaa cctggagtcc taattaaact taaggtttga gctggtctct gaagtcaagg 184529

agatgatgac actgaatttt cttgaaaaaa ccagtgcttc aaggctatag gatctgaaag 184589

gttttctaac agtgttctat catgccaagt gtttcagcaa tgcactgagc gtttgttagt 184649

cctggtgttt tattgtttgg cttttag gt  ggc acc cct tac ccc ggc atg atg 184702
                              Gly Gly Thr Pro Tyr Pro Gly Met Met
                                          895                 900

gtg gat tct act ttc tac aat aag atc aag agt ggg tac cgg atg gcc   184750
Val Asp Ser Thr Phe Tyr Asn Lys Ile Lys Ser Gly Tyr Arg Met Ala
                905                 910                 915

aag cct gac cac gct acc agt gaa gt  gtgagctcct tccccatccc         184796
Lys Pro Asp His Ala Thr Ser Glu Val
            920

gggggcctgt gttcacagtc tgtgggtcta gggggaggga ggggccctga gacttccccc 184856

tgtgcccact cttgagttct gtccccacag c tac gag atc atg gtg aaa tgc    184908
                                   Tyr Glu Ile Met Val Lys Cys
                                                   930

tgg aac agt gag ccg gag aag aga ccc tcc ttt tac cac ctg agt gag   184956
Trp Asn Ser Glu Pro Glu Lys Arg Pro Ser Phe Tyr His Leu Ser Glu
        935                 940                 945

att gtg gag aat ctg ctg cct gga caa tat aaa aag gtgtgtttgg        185002
Ile Val Glu Asn Leu Leu Pro Gly Gln Tyr Lys Lys
    950                 955                 960

atctgtgggt ggaaaggtct ggataaagct ggaagttata ccagtgagct gtgctgttcc 185062

gcagttctag aggagcattt tcaaaagagg caaaagactg tgtgatccag tggctgggct 185122

tcatggcggt gctccacgag accctagtag caatgatgaa tgaaaaccct ccccttcccg 185182

tggggctttc ctttcatctt atatgtacag tacctgtaag cactattctc cagatgtttg 185242

agtatcagaa gttagtgtgc agttagaaga ctcagggcat ccatggccat tacatcacta 185302

atttgagtgc acttaaatcc atgcgaaatt ggcttttacc agcggactgg aaggaacaac 185362

ctcagctgtt atctgtggca ccagctggtt ttttgtggaa tgggaagcat tgttcaaagg 185422

aacaaatgta atttcttgga accaggcagg atatgtaaat gaatgaaaca actttctgct 185482

gaggtgttga gaggaaaact cagacataac ctcagtttct tagattgaga ttagtccctg 185542

tgtagacttt ttatacttat catttttctt ccttcttctc aaggaggaat agtgttagga 185602

gattgtgtgc cgaactggaa gttaaatgct tctgtctgtt aattatctca ctgcccacta 185662

caactttcac aggtgaggca gtgaggaggc agaaggaaat taaccctcag ttggtcaaag 185722

atgctctgac tggtggaaat gtgttggtgg gaagagattg aagttattgt tgaaaatagg 185782
```

```
gtcttttcac atccaatgtt agacctctcc aatgtttaag gatcatgaag gctttgggta 185842

ttatccaccc aatagaaggc ctcactgcct ctctatggga cccatccaag ccctggaaag 185902

gcaacgtgat ggggaccaga aggattctca gttgtagcta ctgacttgga gaaggggcta 185962

ctggtatctt agcacctaat ggcagaagct ctttaccatt ggtggcccct tcttcatgtt 186022

ctatgtctct ggggatagtt gacatgactc tccttcaact aagtcccaca tcttccaggt 186082

agtttggaga tatgtacagt taaataatag taagttctga gtgtctctat tcatttttga 186142

ggtttggttg ttaacacttg attaaatatg ttcaatgaat gtttatag agt tat gaa  186199
                                                    Ser Tyr Glu

aaa att cac ctg gac ttc ctg aag agt gac cat cct gct gtg gca cgc   186247
Lys Ile His Leu Asp Phe Leu Lys Ser Asp His Pro Ala Val Ala Arg
    965                 970                 975

atg cgt gtg gac tca gac aat gca tac att ggt gtc acc tac aaa aac   186295
Met Arg Val Asp Ser Asp Asn Ala Tyr Ile Gly Val Thr Tyr Lys Asn
980                 985                 990                 995

gag gaa gac aag ctg  aag gac tgg gag ggt  ggt ctg gat gag cag     186340
Glu Glu Asp Lys Leu  Lys Asp Trp Glu Gly  Gly Leu Asp Glu Gln
                1000                 1005                 1010

aga ctg agc gct gac  agt ggc tac atc att  cct ctg cct gac att     186385
Arg Leu Ser Ala Asp  Ser Gly Tyr Ile Ile  Pro Leu Pro Asp Ile
                1015                 1020                 1025

gac cct gtc cct gag  gag gag gac ctg ggc  aag agg aac aga cac     186430
Asp Pro Val Pro Glu  Glu Glu Asp Leu Gly  Lys Arg Asn Arg His
                1030                 1035                 1040

ag  gtagctgtgg gggcagcctc ggtgtctcac ctttcccctc ccctataggc        186482
Ser

cctgaaggag aggacccatt ttcccgataa tggtgcactc ccggttggta aatatgtact 186542

cagggacaag ttgcagaatc ctcaggaggt ccacgtggtt ttgaaaatgc ttcccagatg 186602

attctaatat gttccccctg gggctgggag agggatgtgc atgttgtggg gagagggaca 186662

tgcttccctg gtggagaatc tttgagctaa attctcaggt aatttgatca aattgataca 186722

gaactgtgat tactgagatc atataagcct ctcctgccat tgtcttaaat agtcattgaa 186782

ctggggaaaa agtgaagaga ggcgggactg ggtcctttga cgctataccc tacctgtgaa 186842

ttggaatcac ctgcagagat ttaaaaactg ctgatctaca agcctcaccc aaaacaacaa 186902

attagaatcc ctgggggtgg tggccaactg ctccctggct gatttgtttc ttctttcttt 186962

taaattttgt attatggaag atttctaacg tgtgcacaat tcacatagta tagtgagctg 187022

ttcagtattc gtcacccagc ttcaatgact atgccctctg ccagcctgga tgcacacatg 187082

gccatgtctg tctctcctca gcctcctctg gattgtttgg aagcaaatcc tagacacctt 187142

atcatttcac ccataaatat tccagtgtgt gtctcttaaa gataagggct ctattttaaa 187202

gaagaacaac agttattaaa aataactaca atgccgttat ctcacccaaa acagggacaa 187262

taaatcgtta aggcatcagg cagccagtta aagttcaaat tatctcacaa atattatcat 187322

actccattaa aaagtgggca gaggacataa gcagacactt ttcaaaagaa gacatacctg 187382

cagccaacaa gcatatgaaa aaatgctcaa catcactgat cactagagaa atgcaaatca 187442

gaaccgtgat gagataccat ctcacaccag acagaatggt tattattaaa aagtcaaaaa 187502

ataacagatg ctggtgaggt tgtggagaaa aggggaagcg tatacactgc ttgttgaagt 187562

gcaaattagt tcagctattg tggaaagcag tgtggtgatt tctcaaagaa cttttaacag 187622

aattaccatt ggatccagca atcccattac tgggtatata accaaaggaa tataaatcat 187682

tctaccataa agacatgcat acgtatgttc actgcagcac tattcacgat agcaaagaca 187742
```

tggaatcatc ctaaatgccc attgacagta gactggataa agaacatctg gcacatatac 187802
accatggaat actatgtgtt gataaaaaag aacaagatct gagataccat ctcccaccag 187862
tcagaatggc tattatttaa aagtcaaaaa gcaacagatt gtggcgaggt tgtggagaaa 187922
aagaaacact tttacaatgt tggttggagt gtaaattagt tcaaccattg tggaagacag 187982
tgtggcgatt ccccaaagac ctagaggcag aaatactgtt tgacccatca atcccattac 188042
tgagtatata cccagagtga tgtaaatcat tctattataa aggcacatga atgtgtatgt 188102
tcactgctgc actgttcaca atagcaaaat catggaatca acctaaatgc ccatcaatga 188162
tagactggat aaagaaaatg tgatacatat acaccatgga atacgatgca gccgtaaaaa 188222
ggaatgagat catgtccttt gcagggacat ggatggagct ggaagccgtt accgtcagca 188282
aactaacaca ggaacagaaa accaaacacc acatgttctc acttataagt gggagctgaa 188342
cgatgaggac acatggacac atggagggaa acaacacaca ctggagcctt tcaggggttg 188402
gggattgggt ggaacatcag gaagaatagc taatggatac tggcataat acctgggtga 188462
tgggatgatc tgtgcggcaa accaccatga cgcatgttta cccatgtaac aaacctgcac 188522
atcctgcata tgtacccctg aacttaaaaa gtggaaaata caaaaatgaa attaaaaaaa 188582
gaacaagatc atgtcctttg cagcaacgtg gatggagccg gaggtcacta tccttagcaa 188642
actaatacgg gaacagaaga ccagataccg catgttctca cttataagtg ggagctaaaa 188702
ctacgagaac acatggacac aaagagggga acaacagaca ccagggcata gttgagggtg 188762
cagggtggga gaaggaagag gatcagaaaa aatacctatc ggatactgtg cttattattt 188822
gggtgatgaa ataatctgta catcaaaccg ccatgacatg tgatttatcc atgtaacctg 188882
cacacgtgcc cttgaacata aaataaaagt taaaaaaaaa ttatcataca cttgttttgt 188942
tctgtctgag atccagataa gagtcacaca ttgcacttgg ttgctatgtc tctgtaagtt 189002
cactatgtct ctattttttg ccctcttaca tattatttgt gaagaaacca tagtgtttgc 189062
ctgtggagtt cccacaatcg gcattttgct gattacatcc ttgaagtgtc cttctcaggt 189122
gcttctgtct tctctatgtg ttgtaaactg gtagttagtc taggaactta acctgactca 189182
ggttagatct ttggcaaaca tgcttcatag atggttctgt gtgcttctgt caagaggtat 189242
gcactgtcca gttgtctgcc ttttgtaaca ttatcagtca ttgggtgatc attacctaga 189302
atttcttttt tttttttttt ttttgagatg gagtctcgct ctgtcaccca ggctggagtg 189362
cagtggtgtg atctcagctt actgtaacct ccacctcctg agttcaagcc attctcatac 189422
ctccgcctcc tgagtagctg ggattacagg cacatgccac catgcccagc taatttttgt 189482
atttttagta gaaatggggt ttcagcatgt tggccaggct ggttttgaac tcctgacctc 189542
aagtgatctg ccggtctcgg cctcccaaga tgctgggatt ataggcatga accacctcac 189602
ccggcctaga ttctttaact cagcaccaag gtggagctaa tgcccaggca ggactgagaa 189662
tcactggctg acgtggtcag atggaggaga ccatgcccca gttctccgct gtctttgcat 189722
ggcccttgga cagaggtagg agaaggtgat gatagtggcc cctagttcaa ggtccaagtt 189782
gcttgtgtgt gtgtgtgtgt gtgtgtgtgt gtgtgtgttt tcctcttctt tcccatcaga 189842
acattatttt ggaggcttat gactgtgacc tttgttaacc aatttaggta taatatgtag 189902
acagcccttg tttatttgta tggactgggt aattttgaaa gtatggcttt tctattttgt 189962
tttagaatat gttatgtgat ttgaagatgg gacacagtgg cccatcagtc ttcggttttt 190022
tattatgctt tgctcaggcc agtttttata acgtgtttat atctcttgag catacggtgt 190082
tcctccaagt tttgggggtc tgcgatggaa cttcacgggg gtcggggaag gctgggcagt 190142

```
gaatctaggg ctctctgtct cagatccttt ctcaatttgg ttactttgtg tttgtgggct 190202

ctgaataata tttgagttgt aagagggttc tgcttttata taaagttaga aagtcacatt 190262

ggaataaata acatgagaaa ggtgcccaga agttttctag ggctacaaca ggctgagctg 190322

cagaatttga cacgccagga attgaacttt ctcagttgaa gttcacgttc aagttaagta 190382

acttgtgtgg catcacacag ctagtaagtg gggggaccat tccagaccta aggctttctg 190442

actccagaac tccccttca gccacttctc tagtacgtaa ggagccgtca cctgggccct 190502

caagttgggg gttggtgggg gggcatttga tgtcaagaga gaggggaaga gggcattcca 190562

ggcaagtggc aggagatcct gagaacacag tttggatgct caggaggctt ccgggagagc 190622

acctgatggg cctggctgca gcttgcaccc tgatgggcct gacttcaccc cctgctctgc 190682

cttcccaggc ctttggatca ggcattgctt atgttctctt ccactaggat tgagtaggga 190742

aagtagaaat tcttgcagct tgtcagtaac tttgatgaaa gacccagcag aaaagcagga 190802

aagctgaaga gtaaaaatga tgggtggacc ttggttttcc acgtggccta ccacagcatg 190862

tcaggcctgg gggcagaatc ttgccatact gtgcagccca aatttgaatg ccaaaggctt 190922

tcgtttgtct ctggggggcc acagtctagg tctagttctg tgcaggagtt gtaatatttg 190982

ctcttctctc cctcctccag c tcg cag acc tct  gaa gag agt gcc att  gag 191033
                        Ser Gln Thr Ser  Glu Glu Ser Ala Ile  Glu
                                    1045                 1050

acg ggt tcc agc  agt tcc acc ttc atc  aag aga gag gac gag  acc    191078
Thr Gly Ser Ser  Ser Ser Thr Phe Ile  Lys Arg Glu Asp Glu  Thr
            1055                 1060                 1065

att gaa gac atc  gac atg atg gat gac  atc ggc ata gac tct  tca    191123
Ile Glu Asp Ile  Asp Met Met Asp Asp  Ile Gly Ile Asp Ser  Ser
            1070                 1075                 1080

gac ctg gtg gaa  gac agc ttc ctg taa                              191150
Asp Leu Val Glu  Asp Ser Phe Leu
            1085
```

<210> SEQ ID NO 20
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 20

```
ttctccccgc cccccagttg ttgtcgaagt ctgggggttg ggactggacc ccctgattgc     60

gtaagagcaa aaagcgaagg cgcaatctgg acactgggag attcggagcg cagggagttt    120

gagagaaact tttattttga agagaccaag gttgaggggg ggcttatttc ctgacagcta    180

tttacttaga gcaaatgatt agttttagaa ggatggacta taacattgaa tcaattacaa    240

aacgcggttt ttgagcccat tactgttgga gctacaggga gagaaacagg aggagactgc    300

aagagatcat ttgggaaggc cgtgggcacg ctctttactc catgtgtggg acattcattg    360

cggaataaca tcggaggaga agtttcccag agct atg ggg act tcc cat ccg gcg    415
                                      Met Gly Thr Ser His Pro Ala
                                      1               5

ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35
```

```
cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355
```

```
ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg agg gac att gaa tca atc agc ccg      2095
Lys Pro Arg Tyr Glu Ile Arg Trp Arg Asp Ile Glu Ser Ile Ser Pro
            555                 560                 565

gat gga cat gaa tat att tat gtg gac ccg atg cag ctg cct tat gac      2143
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg      2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta      2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc      2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata      2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc      2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat      2431
Cys Thr Lys Ser Gly Pro Ile Tyr Ile Ile Thr Glu Tyr Cys Phe Tyr
    665                 670                 675
```

-continued

```
gga gat ttg gtc aac tat ttg cat aag aat agg gat agc ttc ctg agc      2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac      2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac      2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc      2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga      2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac      2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act      2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag      2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac      2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg      2911
Val Leu Leu Ala Gln Gly Lys Ile Val Lys Ile Cys Asp Phe Gly Leu
    825                 830                 835

gcc aga gac atc atg cat gat tcg aac tat gtg tcg aaa ggc agt acc      2959
Ala Arg Asp Ile Met His Asp Ser Asn Tyr Val Ser Lys Gly Ser Thr
840                 845                 850                 855

ttt ctg ccc gtg aag tgg atg gct cct gag agc atc ttt gac aac ctc      3007
Phe Leu Pro Val Lys Trp Met Ala Pro Glu Ser Ile Phe Asp Asn Leu
                860                 865                 870

tac acc aca ctg agt gat gtc tgg tct tat ggc att ctg ctc tgg gag      3055
Tyr Thr Thr Leu Ser Asp Val Trp Ser Tyr Gly Ile Leu Leu Trp Glu
            875                 880                 885

atc ttt tcc ctt ggt ggc acc cct tac ccc ggc atg atg gtg gat tct      3103
Ile Phe Ser Leu Gly Gly Thr Pro Tyr Pro Gly Met Met Val Asp Ser
        890                 895                 900

act ttc tac aat aag atc aag agt ggg tac cgg atg gcc aag cct gac      3151
Thr Phe Tyr Asn Lys Ile Lys Ser Gly Tyr Arg Met Ala Lys Pro Asp
    905                 910                 915

cac gct acc agt gaa gtc tac gag atc atg gtg aaa tgc tgg aac agt      3199
His Ala Thr Ser Glu Val Tyr Glu Ile Met Val Lys Cys Trp Asn Ser
920                 925                 930                 935

gag ccg gag aag aga ccc tcc ttt tac cac ctg agt gag att gtg gag      3247
Glu Pro Glu Lys Arg Pro Ser Phe Tyr His Leu Ser Glu Ile Val Glu
                940                 945                 950

aat ctg ctg cct gga caa tat aaa aag agt tat gaa aaa att cac ctg      3295
Asn Leu Leu Pro Gly Gln Tyr Lys Lys Ser Tyr Glu Lys Ile His Leu
            955                 960                 965

gac ttc ctg aag agt gac cat cct gct gtg gca cgc atg cgt gtg gac      3343
Asp Phe Leu Lys Ser Asp His Pro Ala Val Ala Arg Met Arg Val Asp
        970                 975                 980

tca gac aat gca tac att ggt gtc acc tac aaa aac gag gaa gac aag      3391
Ser Asp Asn Ala Tyr Ile Gly Val Thr Tyr Lys Asn Glu Glu Asp Lys
    985                 990                 995
```

```
ctg  aag gac tgg gag ggt  ggt ctg gat gag cag  aga ctg agc gct      3436
Leu  Lys Asp Trp Glu Gly  Gly Leu Asp Glu Gln  Arg Leu Ser Ala
1000                 1005                 1010

gac  agt ggc tac atc att  cct ctg cct gac att  gac cct gtc cct      3481
Asp  Ser Gly Tyr Ile Ile  Pro Leu Pro Asp Ile  Asp Pro Val Pro
1015                 1020                 1025

gag  gag gag gac ctg ggc  aag agg aac aga cac  agc tcg cag acc      3526
Glu  Glu Glu Asp Leu Gly  Lys Arg Asn Arg His  Ser Ser Gln Thr
1030                 1035                 1040

tct  gaa gag agt gcc att  gag acg ggt tcc agc  agt tcc acc ttc      3571
Ser  Glu Glu Ser Ala Ile  Glu Thr Gly Ser Ser  Ser Ser Thr Phe
1045                 1050                 1055

atc  aag aga gag gac gag  acc att gaa gac atc  gac atg atg gac      3616
Ile  Lys Arg Glu Asp Glu  Thr Ile Glu Asp Ile  Asp Met Met Asp
1060                 1065                 1070

gac  atc ggc ata gac tct  tca gac ctg gtg gaa  gac agc ttc ctg      3661
Asp  Ile Gly Ile Asp Ser  Ser Asp Leu Val Glu  Asp Ser Phe Leu
1075                 1080                 1085

taa ctggcggatt cgaggggttc cttccacttc tggggccacc tctggatccc          3714

gttcagaaaa ccactttatt gcaatgcgga ggttgagagg aggacttggt tgatgtttaa   3774

agagaagttc ccagccaagg gcctcgggga gcgttctaaa tatgaatgaa tgggatattt   3834

tgaaatgaac tttgtcagtg ttgcctctcg caatgcctca gtagcatctc agtggtgtgt   3894

gaagtttgga gatagatgga taagggaata ataggccaca gaaggtgaac tttgtgcttc   3954

aaggacattg gtgagagtcc aacagacaca atttatactg cgacagaact tcagcattgt   4014

aattatgtaa ataactctaa ccaaggctgt gtttagattg tattaactat cttctttgga   4074

cttctgaaga gaccactcaa tccatccatg tacttccctc ttgaaacctg atgtcagctg   4134

ctgttgaact ttttaaagaa gtgcatgaaa aaccattttt gaaccttaaa aggtactggt   4194

actatagcat tttgctatct tttttagtgt taagagataa agaataataa ttaaccaacc   4254

ttgtttaata gatttgggtc atttagaagc ctgacaactc attttcatat tgtaatctat   4314

gtttataata ctactactgt tatcagtaat gctaaatgtg taataatgta acatgatttc   4374

cctccagaga aagcacaatt taaaacaatc cttactaagt aggtgatgag tttgacagtt   4434

tttgacattt atattaaata acatgtttct ctataaagta tggtaatagc tttagtgaat   4494

taaatttagt tgagcataga gaacaaagta aaagtagtgt tgtccaggaa gtcagaattt   4554

ttaactgtac tgaataggtt ccccaatcca tcgtattaaa aaacaattaa ctgccctctg   4614

aaataatggg attagaaaca aacaaaactc ttaagtccta aaagttctca atgtagaggc   4674

ataaacctgt gctgaacata acttctcatg tatattaccc aatggaaaat ataatgatca   4734

gcaaaaagac tggatttgca gaagtttttt ttttttttct tcatgcctga tgaaagcttt   4794

ggcaacccca atatatgtat tttttgaatc tatgaacctg aaaagggtca gaaggatgcc   4854

cagacatcag cctccttctt tcacccctta ccccaaagag aaagagtttg aaactcgaga   4914

ccataaagat attctttagt ggaggctgga tgtgcattag cctggatcct cagttctcaa   4974

atgtgtgtgg cagccaggat gactagatcc tgggtttcca tccttgagat tctgaagtat   5034

gaagtctgag ggaaaccaga gtctgtattt ttctaaactc cctggctgtt ctgatcggcc   5094

agttttcgga aacactgact taggtttcag gaagttgcca tgggaaacaa ataatttgaa   5154

ctttggaaca gggttggaat tcaaccacgc aggaagccta ctatttaaat ccttggcttc   5214

aggttagtga catttaatgc catctagcta gcaattgcga ccttaattta actttccagt   5274

cttagctgag gctgagaaag ctaaagtttg gttttgacag gttttccaaa agtaaagatg   5334
```

ctacttccca ctgtatgggg gagattgaac tttccccgtc tcccgtcttc tgcctcccac 5394 tccatacccc gccaaggaaa ggcatgtaca aaaattatgc aattcagtgt tccaagtctc 5454 tgtgtaacca gctcagtgtt ttggtggaaa aaacatttta agttttactg ataatttgag 5514 gttagatggg aggatgaatt gtcacatcta tccacactgt caaacaggtt ggtgtgggtt 5574 cattggcatt ctttgcaata ctgcttaatt gctgatacca tatgaatgaa acatgggctg 5634 tgattactgc aatcactgtg ctatcggcag atgatgcttt ggaagatgca gaagcaataa 5694 taaagtactt gactacctac tggtgtaatc tcaatgcaag ccccaacttt cttatccaac 5754 tttttcatag taagtgcgaa gactgagcca gattggccaa ttaaaaacga aaacctgact 5814 aggttctgta gagccaatta gacttgaaat acgtttgtgt ttctagaatc acagctcaag 5874 cattctgttt atcgctcact ctcccttgta cagccttatt ttgttggtgc tttgcatttt 5934 gatattgctg tgagccttgc atgacatcat gaggccggat gaaacttctc agtccagcag 5994 tttccagtcc taacaaatgc tcccacctga atttgtatat gactgcattt gtgggtgtgt 6054 gtgtgttttc agcaaattcc agatttgttt ccttttggcc tcctgcaaag tctccagaag 6114 aaaatttgcc aatctttcct actttctatt tttatgatga caatcaaagc cggcctgaga 6174 aacactattt gtgacttttt aaacgattag tgatgtcctt aaaatgtggt ctgccaatct 6234 gtacaaaatg gtcctatttt tgtgaagagg gacataagat aaaatgatgt tatacatcaa 6294 tatgtatata tgtatttcta tatagacttg gagaatactg ccaaaacatt tatgacaagc 6354 tgtatcactg ccttcgttta tattttttta actgtgataa tccccacagg cacattaact 6414 gttgcacttt tgaatgtcca aaatttatat tttagaaata ataaaaagaa agatacttac 6474 atgttcccaa aacaatggtg tggtgaatgt gtgagaaaaa ctaacttgat agggtctacc 6534 aatacaaaat gtattacgaa tgcccctgtt catgtttttg ttttaaaacg tgtaaatgaa 6594 gatctttata tttcaataaa tgatatataa tttaaagtt 6633

<210> SEQ ID NO 21
<211> LENGTH: 1089
<212> TYPE: PRT
<213> ORGANISM: Homo sapiens

<400> SEQUENCE: 21

Met Gly Thr Ser His Pro Ala Phe Leu Val Leu Gly Cys Leu Leu Thr
1 5 10 15

Gly Leu Ser Leu Ile Leu Cys Gln Leu Ser Leu Pro Ser Ile Leu Pro
20 25 30

Asn Glu Asn Glu Lys Val Val Gln Leu Asn Ser Ser Phe Ser Leu Arg
35 40 45

Cys Phe Gly Glu Ser Glu Val Ser Trp Gln Tyr Pro Met Ser Glu Glu
50 55 60

Glu Ser Ser Asp Val Glu Ile Arg Asn Glu Glu Asn Asn Ser Gly Leu
65 70 75 80

Phe Val Thr Val Leu Glu Val Ser Ser Ala Ser Ala Ala His Thr Gly
85 90 95

Leu Tyr Thr Cys Tyr Tyr Asn His Thr Gln Thr Glu Glu Asn Glu Leu
100 105 110

Glu Gly Arg His Ile Tyr Ile Tyr Val Pro Asp Pro Asp Val Ala Phe
115 120 125

Val Pro Leu Gly Met Thr Asp Tyr Leu Val Ile Val Glu Asp Asp Asp
130 135 140

Ser Ala Ile Ile Pro Cys Arg Thr Thr Asp Pro Glu Thr Pro Val Thr

```
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Asp Ile Glu Ser Ile Ser Pro Asp Gly His Glu Tyr Ile Tyr Val Asp
                565                 570                 575
```

-continued

```
Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005
```

```
Glu Gln  Arg Leu Ser Ala Asp  Ser Gly Tyr Ile Ile  Pro Leu Pro
    1010                 1015                 1020

Asp Ile  Asp Pro Val Pro Glu  Glu Glu Asp Leu Gly  Lys Arg Asn
    1025                 1030                 1035

Arg His  Ser Ser Gln Thr Ser  Glu Glu Ser Ala Ile  Glu Thr Gly
    1040                 1045                 1050

Ser Ser  Ser Ser Thr Phe Ile  Lys Arg Glu Asp Glu  Thr Ile Glu
    1055                 1060                 1065

Asp Ile  Asp Met Met Asp Asp  Ile Gly Ile Asp Ser  Ser Asp Leu
    1070                 1075                 1080

Val Glu  Asp Ser Phe Leu
    1085


<210> SEQ ID NO 22
<211> LENGTH: 6618
<212> TYPE: DNA
<213> ORGANISM: Homo sapiens
<220> FEATURE:
<221> NAME/KEY: CDS
<222> LOCATION: (395)..(3649)

<400> SEQUENCE: 22

ttctccccgc cccccagttg ttgtcgaagt ctgggggttg ggactggacc ccctgattgc      60

gtaagagcaa aaagcgaagg cgcaatctgg acactgggag attcggagcg cagggagttt     120

gagagaaact tttattttga agagaccaag gttgaggggg ggcttatttc ctgacagcta     180

tttacttaga gcaaatgatt agttttagaa ggatggacta taacattgaa tcaattacaa     240

aacgcggttt ttgagcccat tactgttgga gctacaggga gagaaacagg aggagactgc     300

aagagatcat ttgggaaggc cgtgggcacg ctctttactc catgtgtggg acattcattg     360

cggaataaca tcggaggaga agtttcccag agct atg ggg act tcc cat ccg gcg     415
                                      Met Gly Thr Ser His Pro Ala
                                      1               5

ttc ctg gtc tta ggc tgt ctt ctc aca ggg ctg agc cta atc ctc tgc       463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg       511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg       559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc       607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg       655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac       703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc       751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat       799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc       847
Tyr Leu Val Ile Val Glu Asp Asp Asp Ser Ala Ile Ile Pro Cys Arg
```

```
              140                 145                 150

aca act gat ccc gag act cct gta acc tta cac aac agt gag ggg gtg      895
Thr Thr Asp Pro Glu Thr Pro Val Thr Leu His Asn Ser Glu Gly Val
        155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
    170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct     1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag     1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc     1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca     1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat     1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat     1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat     1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt     1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat     1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc     1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa     1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac     1807
Cys Asn Asn Glu Thr Ser Trp Thr Ile Leu Ala Asn Asn Val Ser Asn
```

```
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg atc agc ccg gat gga cat gaa tat      2095
Lys Pro Arg Tyr Glu Ile Arg Trp Ile Ser Pro Asp Gly His Glu Tyr
            555                 560                 565

att tat gtg gac ccg atg cag ctg cct tat gac tca aga tgg gag ttt      2143
Ile Tyr Val Asp Pro Met Gln Leu Pro Tyr Asp Ser Arg Trp Glu Phe
        570                 575                 580

cca aga gat gga cta gtg ctt ggt cgg gtc ttg ggg tct gga gcg ttt      2191
Pro Arg Asp Gly Leu Val Leu Gly Arg Val Leu Gly Ser Gly Ala Phe
    585                 590                 595

ggg aag gtg gtt gaa gga aca gcc tat gga tta agc cgg tcc caa cct      2239
Gly Lys Val Val Glu Gly Thr Ala Tyr Gly Leu Ser Arg Ser Gln Pro
600                 605                 610                 615

gtc atg aaa gtt gca gtg aag atg cta aaa ccc acg gcc aga tcc agt      2287
Val Met Lys Val Ala Val Lys Met Leu Lys Pro Thr Ala Arg Ser Ser
                620                 625                 630

gaa aaa caa gct ctc atg tct gaa ctg aag ata atg act cac ctg ggg      2335
Glu Lys Gln Ala Leu Met Ser Glu Leu Lys Ile Met Thr His Leu Gly
            635                 640                 645

cca cat ttg aac att gta aac ttg ctg gga gcc tgc acc aag tca ggc      2383
Pro His Leu Asn Ile Val Asn Leu Leu Gly Ala Cys Thr Lys Ser Gly
        650                 655                 660

ccc att tac atc atc aca gag tat tgc ttc tat gga gat ttg gtc aac      2431
Pro Ile Tyr Ile Ile Thr Glu Tyr Cys Phe Tyr Gly Asp Leu Val Asn
    665                 670                 675

tat ttg cat aag aat agg gat agc ttc ctg agc cac cac cca gag aag      2479
Tyr Leu His Lys Asn Arg Asp Ser Phe Leu Ser His His Pro Glu Lys
680                 685                 690                 695

cca aag aaa gag ctg gat atc ttt gga ttg aac cct gct gat gaa agc      2527
Pro Lys Lys Glu Leu Asp Ile Phe Gly Leu Asn Pro Ala Asp Glu Ser
                700                 705                 710

aca cgg agc tat gtt att tta tct ttt gaa aac aat ggt gac tac atg      2575
Thr Arg Ser Tyr Val Ile Leu Ser Phe Glu Asn Asn Gly Asp Tyr Met
            715                 720                 725

gac atg aag cag gct gat act aca cag tat gtc ccc atg cta gaa agg      2623
Asp Met Lys Gln Ala Asp Thr Thr Gln Tyr Val Pro Met Leu Glu Arg
        730                 735                 740

aaa gag gtt tct aaa tat tcc gac atc cag aga tca ctc tat gat cgt      2671
Lys Glu Val Ser Lys Tyr Ser Asp Ile Gln Arg Ser Leu Tyr Asp Arg
    745                 750                 755

cca gcc tca tat aag aag aaa tct atg tta gac tca gaa gtc aaa aac      2719
Pro Ala Ser Tyr Lys Lys Lys Ser Met Leu Asp Ser Glu Val Lys Asn
760                 765                 770                 775

ctc ctt tca gat gat aac tca gaa ggc ctt act tta ttg gat ttg ttg      2767
Leu Leu Ser Asp Asp Asn Ser Glu Gly Leu Thr Leu Leu Asp Leu Leu
```

-continued

```
                780                 785                 790

agc ttc acc tat caa gtt gcc cga gga atg gag ttt ttg gct tca aaa     2815
Ser Phe Thr Tyr Gln Val Ala Arg Gly Met Glu Phe Leu Ala Ser Lys
            795                 800                 805

aat tgt gtc cac cgt gat ctg gct gct cgc aac gtc ctc ctg gca caa     2863
Asn Cys Val His Arg Asp Leu Ala Ala Arg Asn Val Leu Leu Ala Gln
        810                 815                 820

gga aaa att gtg aag atc tgt gac ttt ggc ctg gcc aga gac atc atg     2911
Gly Lys Ile Val Lys Ile Cys Asp Phe Gly Leu Ala Arg Asp Ile Met
    825                 830                 835

cat gat tcg aac tat gtg tcg aaa ggc agt acc ttt ctg ccc gtg aag     2959
His Asp Ser Asn Tyr Val Ser Lys Gly Ser Thr Phe Leu Pro Val Lys
840                 845                 850                 855

tgg atg gct cct gag agc atc ttt gac aac ctc tac acc aca ctg agt     3007
Trp Met Ala Pro Glu Ser Ile Phe Asp Asn Leu Tyr Thr Thr Leu Ser
                860                 865                 870

gat gtc tgg tct tat ggc att ctg ctc tgg gag atc ttt tcc ctt ggt     3055
Asp Val Trp Ser Tyr Gly Ile Leu Leu Trp Glu Ile Phe Ser Leu Gly
            875                 880                 885

ggc acc cct tac ccc ggc atg atg gtg gat tct act ttc tac aat aag     3103
Gly Thr Pro Tyr Pro Gly Met Met Val Asp Ser Thr Phe Tyr Asn Lys
        890                 895                 900

atc aag agt ggg tac cgg atg gcc aag cct gac cac gct acc agt gaa     3151
Ile Lys Ser Gly Tyr Arg Met Ala Lys Pro Asp His Ala Thr Ser Glu
    905                 910                 915

gtc tac gag atc atg gtg aaa tgc tgg aac agt gag ccg gag aag aga     3199
Val Tyr Glu Ile Met Val Lys Cys Trp Asn Ser Glu Pro Glu Lys Arg
920                 925                 930                 935

ccc tcc ttt tac cac ctg agt gag att gtg gag aat ctg ctg cct gga     3247
Pro Ser Phe Tyr His Leu Ser Glu Ile Val Glu Asn Leu Leu Pro Gly
                940                 945                 950

caa tat aaa aag agt tat gaa aaa att cac ctg gac ttc ctg aag agt     3295
Gln Tyr Lys Lys Ser Tyr Glu Lys Ile His Leu Asp Phe Leu Lys Ser
            955                 960                 965

gac cat cct gct gtg gca cgc atg cgt gtg gac tca gac aat gca tac     3343
Asp His Pro Ala Val Ala Arg Met Arg Val Asp Ser Asp Asn Ala Tyr
        970                 975                 980

att ggt gtc acc tac aaa aac gag gaa gac aag ctg aag gac tgg gag     3391
Ile Gly Val Thr Tyr Lys Asn Glu Glu Asp Lys Leu Lys Asp Trp Glu
    985                 990                 995

ggt  ggt ctg gat gag cag  aga ctg agc gct gac  agt ggc tac atc      3436
Gly  Gly Leu Asp Glu Gln  Arg Leu Ser Ala Asp  Ser Gly Tyr Ile
1000                 1005                1010

att  cct ctg cct gac att  gac cct gtc cct gag  gag gag gac ctg      3481
Ile  Pro Leu Pro Asp Ile  Asp Pro Val Pro Glu  Glu Glu Asp Leu
1015                 1020                1025

ggc  aag agg aac aga cac  agc tcg cag acc tct  gaa gag agt gcc      3526
Gly  Lys Arg Asn Arg His  Ser Ser Gln Thr Ser  Glu Glu Ser Ala
1030                 1035                1040

att  gag acg ggt tcc agc  agt tcc acc ttc atc  aag aga gag gac      3571
Ile  Glu Thr Gly Ser Ser  Ser Ser Thr Phe Ile  Lys Arg Glu Asp
1045                 1050                1055

gag  acc att gaa gac atc  gac atg atg gac gac  atc ggc ata gac      3616
Glu  Thr Ile Glu Asp Ile  Asp Met Met Asp Asp  Ile Gly Ile Asp
1060                 1065                1070

tct  tca gac ctg gtg gaa  gac agc ttc ctg taa ctggcggatt            3659
Ser  Ser Asp Leu Val Glu  Asp Ser Phe Leu
1075                 1080

cgaggggttc cttccacttc tggggccacc tctggatccc gttcagaaaa ccactttatt   3719
```

-continued gcaatgcgga ggttgagagg aggacttggt tgatgtttaa agagaagttc ccagccaagg 3779 gcctcgggga gcgttctaaa tatgaatgaa tgggatattt tgaaatgaac tttgtcagtg 3839 ttgcctctcg caatgcctca gtagcatctc agtggtgtgt gaagtttgga gatagatgga 3899 taagggaata ataggccaca gaaggtgaac tttgtgcttc aaggacattg gtgagagtcc 3959 aacagacaca atttatactg cgacagaact tcagcattgt aattatgtaa ataactctaa 4019 ccaaggctgt gtttagattg tattaactat cttctttgga cttctgaaga gaccactcaa 4079 tccatccatg tacttccctc ttgaaacctg atgtcagctg ctgttgaact ttttaaagaa 4139 gtgcatgaaa aaccattttt gaaccttaaa aggtactggt actatagcat tttgctatct 4199 tttttagtgt taagagataa agaataataa ttaaccaacc ttgtttaata gatttgggtc 4259 atttagaagc ctgacaactc attttcatat tgtaatctat gtttataata ctactactgt 4319 tatcagtaat gctaaatgtg taataatgta acatgatttc cctccagaga aagcacaatt 4379 taaaacaatc cttactaagt aggtgatgag tttgacagtt tttgacattt atattaaata 4439 acatgtttct ctataaagta tggtaatagc tttagtgaat taaatttagt tgagcataga 4499 gaacaaagta aaagtagtgt tgtccaggaa gtcagaattt ttaactgtac tgaataggtt 4559 ccccaatcca tcgtattaaa aaacaattaa ctgccctctg aaataatggg attagaaaca 4619 aacaaaactc ttaagtccta aaagttctca atgtagaggc ataaacctgt gctgaacata 4679 acttctcatg tatattaccc aatggaaaat ataatgatca gcaaaaagac tggatttgca 4739 gaagtttttt ttttttttct tcatgcctga tgaaagcttt ggcaacccca atatatgtat 4799 tttttgaatc tatgaacctg aaaagggtca gaaggatgcc cagacatcag cctccttctt 4859 tcacccctta ccccaaagag aaagagtttg aaactcgaga ccataaagat attctttagt 4919 ggaggctgga tgtgcattag cctggatcct cagttctcaa atgtgtgtgg cagccaggat 4979 gactagatcc tgggtttcca tccttgagat tctgaagtat gaagtctgag ggaaaccaga 5039 gtctgtattt ttctaaactc cctggctgtt ctgatcggcc agttttcgga aacactgact 5099 taggtttcag gaagttgcca tgggaaacaa ataatttgaa ctttggaaca gggttggaat 5159 tcaaccacgc aggaagccta ctatttaaat ccttggcttc aggttagtga catttaatgc 5219 catctagcta gcaattgcga ccttaattta actttccagt cttagctgag gctgagaaag 5279 ctaaagtttg gttttgacag gttttccaaa agtaaagatg ctacttccca ctgtatgggg 5339 gagattgaac tttccccgtc tcccgtcttc tgcctcccac tccatacccc gccaaggaaa 5399 ggcatgtaca aaaattatgc aattcagtgt tccaagtctc tgtgtaacca gctcagtgtt 5459 ttggtggaaa aaacatttta agttttactg ataatttgag gttagatggg aggatgaatt 5519 gtcacatcta tccacactgt caaacaggtt ggtgtgggtt cattggcatt ctttgcaata 5579 ctgcttaatt gctgatacca tatgaatgaa acatgggctg tgattactgc aatcactgtg 5639 ctatcggcag atgatgcttt ggaagatgca gaagcaataa taaagtactt gactacctac 5699 tggtgtaatc tcaatgcaag ccccaacttt cttatccaac tttttcatag taagtgcgaa 5759 gactgagcca gattggccaa ttaaaaacga aaacctgact aggttctgta gagccaatta 5819 gacttgaaat acgtttgtgt ttctagaatc acagctcaag cattctgttt atcgctcact 5879 ctcccttgta cagccttatt ttgttggtgc tttgcatttt gatattgctg tgagccttgc 5939 atgacatcat gaggccggat gaaacttctc agtccagcag tttccagtcc taacaaatgc 5999 tcccacctga atttgtatat gactgcattt gtgggtgtgt gtgtgttttc agcaaattcc 6059 agatttgttt ccttttggcc tcctgcaaag tctccagaag aaaatttgcc aatctttcct 6119

-continued

```
actttctatt tttatgatga caatcaaagc cggcctgaga aacactattt gtgacttttt   6179

aaacgattag tgatgtcctt aaaatgtggt ctgccaatct gtacaaaatg gtcctatttt   6239

tgtgaagagg gacataagat aaaatgatgt tatacatcaa tatgtatata tgtatttcta   6299

tatagacttg gagaatactg ccaaaacatt tatgacaagc tgtatcactg ccttcgttta   6359

tattttttta actgtgataa tccccacagg cacattaact gttgcacttt tgaatgtcca   6419

aaatttatat tttagaaata ataaaaagaa agatacttac atgttcccaa aacaatggtg   6479

tggtgaatgt gtgagaaaaa ctaacttgat agggtctacc aatacaaaat gtattacgaa   6539

tgcccctgtt catgtttttg ttttaaaacg tgtaaatgaa gatctttata tttcaataaa   6599

tgatatataa tttaaagtt                                                6618
```

<210> SEQ ID NO 23
<211> LENGTH: 1084
<212> TYPE: PRT
<213> ORGANISM: Homo sapiens

<400> SEQUENCE: 23

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285
```

```
Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Ile
545                 550                 555                 560

Ser Pro Asp Gly His Glu Tyr Ile Tyr Val Asp Pro Met Gln Leu Pro
                565                 570                 575

Tyr Asp Ser Arg Trp Glu Phe Pro Arg Asp Gly Leu Val Leu Gly Arg
            580                 585                 590

Val Leu Gly Ser Gly Ala Phe Gly Lys Val Val Glu Gly Thr Ala Tyr
        595                 600                 605

Gly Leu Ser Arg Ser Gln Pro Val Met Lys Val Ala Val Lys Met Leu
    610                 615                 620

Lys Pro Thr Ala Arg Ser Ser Glu Lys Gln Ala Leu Met Ser Glu Leu
625                 630                 635                 640

Lys Ile Met Thr His Leu Gly Pro His Leu Asn Ile Val Asn Leu Leu
                645                 650                 655

Gly Ala Cys Thr Lys Ser Gly Pro Ile Tyr Ile Ile Thr Glu Tyr Cys
            660                 665                 670

Phe Tyr Gly Asp Leu Val Asn Tyr Leu His Lys Asn Arg Asp Ser Phe
        675                 680                 685

Leu Ser His His Pro Glu Lys Pro Lys Lys Glu Leu Asp Ile Phe Gly
    690                 695                 700

Leu Asn Pro Ala Asp Glu Ser Thr Arg Ser Tyr Val Ile Leu Ser Phe
705                 710                 715                 720
```

```
Glu Asn Asn Gly Asp Tyr Met Asp Met Lys Gln Ala Asp Thr Thr Gln
                725                 730                 735

Tyr Val Pro Met Leu Glu Arg Lys Glu Val Ser Lys Tyr Ser Asp Ile
            740                 745                 750

Gln Arg Ser Leu Tyr Asp Arg Pro Ala Ser Tyr Lys Lys Lys Ser Met
        755                 760                 765

Leu Asp Ser Glu Val Lys Asn Leu Leu Ser Asp Asp Asn Ser Glu Gly
    770                 775                 780

Leu Thr Leu Leu Asp Leu Leu Ser Phe Thr Tyr Gln Val Ala Arg Gly
785                 790                 795                 800

Met Glu Phe Leu Ala Ser Lys Asn Cys Val His Arg Asp Leu Ala Ala
                805                 810                 815

Arg Asn Val Leu Leu Ala Gln Gly Lys Ile Val Lys Ile Cys Asp Phe
            820                 825                 830

Gly Leu Ala Arg Asp Ile Met His Asp Ser Asn Tyr Val Ser Lys Gly
        835                 840                 845

Ser Thr Phe Leu Pro Val Lys Trp Met Ala Pro Glu Ser Ile Phe Asp
    850                 855                 860

Asn Leu Tyr Thr Thr Leu Ser Asp Val Trp Ser Tyr Gly Ile Leu Leu
865                 870                 875                 880

Trp Glu Ile Phe Ser Leu Gly Gly Thr Pro Tyr Pro Gly Met Met Val
                885                 890                 895

Asp Ser Thr Phe Tyr Asn Lys Ile Lys Ser Gly Tyr Arg Met Ala Lys
            900                 905                 910

Pro Asp His Ala Thr Ser Glu Val Tyr Glu Ile Met Val Lys Cys Trp
        915                 920                 925

Asn Ser Glu Pro Glu Lys Arg Pro Ser Phe Tyr His Leu Ser Glu Ile
    930                 935                 940

Val Glu Asn Leu Leu Pro Gly Gln Tyr Lys Lys Ser Tyr Glu Lys Ile
945                 950                 955                 960

His Leu Asp Phe Leu Lys Ser Asp His Pro Ala Val Ala Arg Met Arg
                965                 970                 975

Val Asp Ser Asp Asn Ala Tyr Ile Gly Val Thr Tyr Lys Asn Glu Glu
            980                 985                 990

Asp Lys Leu Lys Asp Trp Glu Gly  Gly Leu Asp Glu Gln  Arg Leu Ser
        995                 1000                1005

Ala Asp  Ser Gly Tyr Ile Ile  Pro Leu Pro Asp Ile  Asp Pro Val
    1010                1015                1020

Pro Glu  Glu Glu Asp Leu Gly  Lys Arg Asn Arg His  Ser Ser Gln
    1025                1030                1035

Thr Ser  Glu Glu Ser Ala Ile  Glu Thr Gly Ser Ser  Ser Ser Thr
    1040                1045                1050

Phe Ile  Lys Arg Glu Asp Glu  Thr Ile Glu Asp Ile  Asp Met Met
    1055                1060                1065

Asp Asp  Ile Gly Ile Asp Ser  Ser Asp Leu Val Glu  Asp Ser Phe
    1070                1075                1080

Leu
```

<210> SEQ ID NO 24
<211> LENGTH: 6633
<212> TYPE: DNA
<213> ORGANISM: Homo sapiens
<220> FEATURE:
<221> NAME/KEY: CDS
<222> LOCATION: (395)..(3664)

<400> SEQUENCE: 24

```
ttctccccgc cccccagttg ttgtcgaagt ctgggggttg ggactggacc ccctgattgc     60

gtaagagcaa aaagcgaagg cgcaatctgg acactgggag attcggagcg cagggagttt    120

gagagaaact tttattttga agagaccaag gttgaggggg ggcttatttc ctgacagcta    180

tttacttaga gcaaatgatt agttttagaa ggatggacta taacattgaa tcaattacaa    240

aacgcggttt ttgagcccat tactgttgga gctacaggga gagaaacagg aggagactgc    300

aagagatcat ttgggaaggc cgtgggcacg ctctttactc catgtgtggg acattcattg    360

cggaataaca tcggaggaga agtttcccag agct atg ggg act tcc cat ccg gcg    415
                                      Met Gly Thr Ser His Pro Ala
                                      1               5

ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
```

-continued

```
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag      1231
Ile Lys Val Pro Ser Ile Lys Leu Val Tyr Thr Leu Thr Val Pro Glu
    265                 270                 275

gcc acg gtg aaa gac agt gga gat tac gaa tgt gct gcc cgc cag gct      1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag      1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc      1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca      1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg agg gtc att gaa tca atc agc ccg      2095
Lys Pro Arg Tyr Glu Ile Arg Trp Arg Val Ile Glu Ser Ile Ser Pro
            555                 560                 565

gat gga cat gaa tat att tat gtg gac ccg atg cag ctg cct tat gac      2143
```

```
Asp Gly His Glu Tyr Ile Tyr Val Asp Pro Met Gln Leu Pro Tyr Asp
        570                 575                 580

tca aga tgg gag ttt cca aga gat gga cta gtg ctt ggt cgg gtc ttg      2191
Ser Arg Trp Glu Phe Pro Arg Asp Gly Leu Val Leu Gly Arg Val Leu
    585                 590                 595

ggg tct gga gcg ttt ggg aag gtg gtt gaa gga aca gcc tat gga tta      2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc      2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata      2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc      2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat      2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc      2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac      2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac      2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc      2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga      2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac      2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act      2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag      2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac      2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg      2911
Val Leu Leu Ala Gln Gly Lys Ile Val Lys Ile Cys Asp Phe Gly Leu
    825                 830                 835

gcc aaa atc atc atg cat gat tcg aac tat gtg tcg aaa ggc agt acc      2959
Ala Lys Ile Ile Met His Asp Ser Asn Tyr Val Ser Lys Gly Ser Thr
840                 845                 850                 855

ttt ctg ccc gtg aag tgg atg gct cct gag agc atc ttt gac aac ctc      3007
Phe Leu Pro Val Lys Trp Met Ala Pro Glu Ser Ile Phe Asp Asn Leu
                860                 865                 870

tac acc aca ctg agt gat gtc tgg tct tat ggc att ctg ctc tgg gag      3055
Tyr Thr Thr Leu Ser Asp Val Trp Ser Tyr Gly Ile Leu Leu Trp Glu
            875                 880                 885

atc ttt tcc ctt ggt ggc acc cct tac ccc ggc atg atg gtg gat tct      3103
```

```
Ile Phe Ser Leu Gly Gly Thr Pro Tyr Pro Gly Met Met Val Asp Ser
        890                 895                 900

act ttc tac aat aag atc aag agt ggg tac cgg atg gcc aag cct gac     3151
Thr Phe Tyr Asn Lys Ile Lys Ser Gly Tyr Arg Met Ala Lys Pro Asp
    905                 910                 915

cac gct acc agt gaa gtc tac gag atc atg gtg aaa tgc tgg aac agt     3199
His Ala Thr Ser Glu Val Tyr Glu Ile Met Val Lys Cys Trp Asn Ser
920                 925                 930                 935

gag ccg gag aag aga ccc tcc ttt tac cac ctg agt gag att gtg gag     3247
Glu Pro Glu Lys Arg Pro Ser Phe Tyr His Leu Ser Glu Ile Val Glu
                940                 945                 950

aat ctg ctg cct gga caa tat aaa aag agt tat gaa aaa att cac ctg     3295
Asn Leu Leu Pro Gly Gln Tyr Lys Lys Ser Tyr Glu Lys Ile His Leu
            955                 960                 965

gac ttc ctg aag agt gac cat cct gct gtg gca cgc atg cgt gtg gac     3343
Asp Phe Leu Lys Ser Asp His Pro Ala Val Ala Arg Met Arg Val Asp
        970                 975                 980

tca gac aat gca tac att ggt gtc acc tac aaa aac gag gaa gac aag     3391
Ser Asp Asn Ala Tyr Ile Gly Val Thr Tyr Lys Asn Glu Glu Asp Lys
    985                 990                 995

ctg  aag gac tgg gag ggt  ggt ctg gat gag cag  aga ctg agc gct      3436
Leu  Lys Asp Trp Glu Gly  Gly Leu Asp Glu Gln  Arg Leu Ser Ala
1000                1005                1010

gac  agt ggc tac atc att  cct ctg cct gac att  gac cct gtc cct      3481
Asp  Ser Gly Tyr Ile Ile  Pro Leu Pro Asp Ile  Asp Pro Val Pro
1015                1020                1025

gag  gag gag gac ctg ggc  aag agg aac aga cac  agc tcg cag acc      3526
Glu  Glu Glu Asp Leu Gly  Lys Arg Asn Arg His  Ser Ser Gln Thr
1030                1035                1040

tct  gaa gag agt gcc att  gag acg ggt tcc agc  agt tcc acc ttc      3571
Ser  Glu Glu Ser Ala Ile  Glu Thr Gly Ser Ser  Ser Ser Thr Phe
1045                1050                1055

atc  aag aga gag gac gag  acc att gaa gac atc  gac atg atg gac      3616
Ile  Lys Arg Glu Asp Glu  Thr Ile Glu Asp Ile  Asp Met Met Asp
1060                1065                1070

gac  atc ggc ata gac tct  tca gac ctg gtg gaa  gac agc ttc ctg      3661
Asp  Ile Gly Ile Asp Ser  Ser Asp Leu Val Glu  Asp Ser Phe Leu
1075                1080                1085

taa ctggcggatt cgaggggttc cttccacttc tggggccacc tctggatccc          3714

gttcagaaaa ccactttatt gcaatgcgga ggttgagagg aggacttggt tgatgtttaa   3774

agagaagttc ccagccaagg gcctcgggga gcgttctaaa tatgaatgaa tgggatattt   3834

tgaaatgaac tttgtcagtg ttgcctctcg caatgcctca gtagcatctc agtggtgtgt   3894

gaagtttgga gatagatgga taagggaata ataggccaca gaaggtgaac tttgtgcttc   3954

aaggacattg gtgagagtcc aacagacaca atttatactg cgacagaact tcagcattgt   4014

aattatgtaa ataactctaa ccaaggctgt gtttagattg tattaactat cttctttgga   4074

cttctgaaga gaccactcaa tccatccatg tacttccctc ttgaaacctg atgtcagctg   4134

ctgttgaact ttttaaagaa gtgcatgaaa aaccattttt gaaccttaaa aggtactggt   4194

actatagcat tttgctatct tttttagtgt taagagataa agaataataa ttaaccaacc   4254

ttgtttaata gatttgggtc atttagaagc ctgacaactc attttcatat tgtaatctat   4314

gtttataata ctactactgt tatcagtaat gctaaatgtg taataatgta acatgatttc   4374

cctccagaga aagcacaatt taaaacaatc cttactaagt aggtgatgag tttgacagtt   4434

tttgacattt atattaaata acatgtttct ctataaagta tggtaatagc tttagtgaat   4494

taaatttagt tgagcataga gaacaaagta aaagtagtgt tgtccaggaa gtcagaattt   4554
```

-continued ttaactgtac tgaataggtt ccccaatcca tcgtattaaa aaacaattaa ctgccctctg 4614 aaataatggg attagaaaca aacaaaactc ttaagtccta aaagttctca atgtagaggc 4674 ataaacctgt gctgaacata acttctcatg tatattaccc aatggaaaat ataatgatca 4734 gcaaaaagac tggatttgca gaagtttttt tttttttct tcatgcctga tgaaagcttt 4794 ggcaacccca atatatgtat tttttgaatc tatgaacctg aaaagggtca gaaggatgcc 4854 cagacatcag cctccttctt tcacccctta ccccaaagag aaagagtttg aaactcgaga 4914 ccataaagat attctttagt ggaggctgga tgtgcattag cctggatcct cagttctcaa 4974 atgtgtgtgg cagccaggat gactagatcc tgggtttcca tccttgagat tctgaagtat 5034 gaagtctgag ggaaaccaga gtctgtattt ttctaaactc cctggctgtt ctgatcggcc 5094 agttttcgga aacactgact taggtttcag gaagttgcca tgggaaacaa ataatttgaa 5154 ctttggaaca gggttggaat tcaaccacgc aggaagccta ctatttaaat ccttggcttc 5214 aggttagtga catttaatgc catctagcta gcaattgcga ccttaattta actttccagt 5274 cttagctgag gctgagaaag ctaaagtttg gttttgacag gttttccaaa agtaaagatg 5334 ctacttccca ctgtatgggg gagattgaac tttccccgtc tcccgtcttc tgcctcccac 5394 tccatacccc gccaaggaaa ggcatgtaca aaaattatgc aattcagtgt tccaagtctc 5454 tgtgtaacca gctcagtgtt ttggtggaaa aaacatttta agttttactg ataatttgag 5514 gttagatggg aggatgaatt gtcacatcta tccacactgt caaacaggtt ggtgtgggtt 5574 cattggcatt ctttgcaata ctgcttaatt gctgatacca tatgaatgaa acatgggctg 5634 tgattactgc aatcactgtg ctatcggcag atgatgcttt ggaagatgca gaagcaataa 5694 taaagtactt gactacctac tggtgtaatc tcaatgcaag ccccaacttt cttatccaac 5754 tttttcatag taagtgcgaa gactgagcca gattggccaa ttaaaaacga aaacctgact 5814 aggttctgta gagccaatta gacttgaaat acgtttgtgt ttctagaatc acagctcaag 5874 cattctgttt atcgctcact ctcccttgta cagccttatt ttgttggtgc tttgcatttt 5934 gatattgctg tgagccttgc atgacatcat gaggccggat gaaacttctc agtccagcag 5994 tttccagtcc taacaaatgc tcccacctga atttgtatat gactgcattt gtgggtgtgt 6054 gtgtgttttc agcaaattcc agatttgttt ccttttggcc tcctgcaaag tctccagaag 6114 aaaatttgcc aatctttcct actttctatt tttatgatga caatcaaagc cggcctgaga 6174 aacactattt gtgacttttt aaacgattag tgatgtcctt aaaatgtggt ctgccaatct 6234 gtacaaaatg gtcctatttt tgtgaagagg gacataagat aaaatgatgt tatacatcaa 6294 tatgtatata tgtatttcta tatagacttg gagaatactg ccaaaacatt tatgacaagc 6354 tgtatcactg ccttcgttta tatttttta actgtgataa tccccacagg cacattaact 6414 gttgcacttt tgaatgtcca aaatttatat tttagaaata ataaaaagaa agatacttac 6474 atgttcccaa aacaatggtg tggtgaatgt gtgagaaaaa ctaacttgat agggtctacc 6534 aatacaaaat gtattacgaa tgcccctgtt catgtttttg ttttaaaacg tgtaaatgaa 6594 gatctttata tttcaataaa tgatatataa tttaaagtt 6633

<210> SEQ ID NO 25
<211> LENGTH: 1089
<212> TYPE: PRT
<213> ORGANISM: Homo sapiens

<400> SEQUENCE: 25

Met Gly Thr Ser His Pro Ala Phe Leu Val Leu Gly Cys Leu Leu Thr

-continued

```
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430
```

-continued

```
Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Lys Ile Ile Met His Asp Ser Asn
        835                 840                 845

Tyr Val Ser Lys Gly Ser Thr Phe Leu Pro Val Lys Trp Met Ala Pro
    850                 855                 860
```

```
Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                 1015                 1020

Asp Ile  Asp Pro Val Pro Glu  Glu Glu Asp Leu Gly  Lys Arg Asn
    1025                 1030                 1035

Arg His  Ser Ser Gln Thr Ser  Glu Glu Ser Ala Ile  Glu Thr Gly
    1040                 1045                 1050

Ser Ser  Ser Ser Thr Phe Ile  Lys Arg Glu Asp Glu  Thr Ile Glu
    1055                 1060                 1065

Asp Ile  Asp Met Met Asp Asp  Ile Gly Ile Asp Ser  Ser Asp Leu
    1070                 1075                 1080

Val Glu  Asp Ser Phe Leu
    1085


<210> SEQ ID NO 26
<211> LENGTH: 6633
<212> TYPE: DNA
<213> ORGANISM: Homo sapiens
<220> FEATURE:
<221> NAME/KEY: CDS
<222> LOCATION: (395)..(3664)
<220> FEATURE:
<221> NAME/KEY: misc_feature
<222> LOCATION: (2072)..(2086)
<223> OTHER INFORMATION: Any N may equal either no nucleotide (i.e., a
      deletion) or any nucleotide (i.e., a, t, g, or c)
<220> FEATURE:
<221> NAME/KEY: misc_feature
<222> LOCATION: (2074)..(2075)
<223> OTHER INFORMATION: Insertion of the sequence “GAGAGG” in PDGFRA
      insertion ER561-562
<220> FEATURE:
<221> NAME/KEY: misc_feature
<222> LOCATION: (2090)..(2107)
<223> OTHER INFORMATION: Any N may equal either no nucleotide (i.e., a
      deletion) or any nucleotide (i.e., a, t, g, or c)
<220> FEATURE:
<221> NAME/KEY: misc_feature
<222> LOCATION: (2916)..(2937)
<223> OTHER INFORMATION: Any N may equal either no nucleotide (i.e., a
      deletion) or any nucleotide (i.e., a, t, g, or c)

<400> SEQUENCE: 26

ttctccccgc cccccagttg ttgtcgaagt ctgggggttg ggactggacc ccctgattgc      60

gtaagagcaa aaagcgaagg cgcaatctgg acactgggag attcggagcg cagggagttt     120
```

```
gagagaaact tttattttga agagaccaag gttgaggggg ggcttatttc ctgacagcta    180

tttacttaga gcaaatgatt agttttagaa ggatggacta taacattgaa tcaattacaa    240

aacgcggttt ttgagcccat tactgttgga gctacaggga gagaaacagg aggagactgc    300

aagagatcat ttgggaaggc cgtgggcacg ctctttactc catgtgtggg acattcattg    360

cggaataaca tcggaggaga agtttcccag agct atg ggg act tcc cat ccg gcg    415
                                      Met Gly Thr Ser His Pro Ala
                                      1               5

ttc ctg gtc tta ggc tgt ctt ctc aca ggg ctg agc cta atc ctc tgc      463
Phe Leu Val Leu Gly Cys Leu Leu Thr Gly Leu Ser Leu Ile Leu Cys
        10                  15                  20

cag ctt tca tta ccc tct atc ctt cca aat gaa aat gaa aag gtt gtg      511
Gln Leu Ser Leu Pro Ser Ile Leu Pro Asn Glu Asn Glu Lys Val Val
    25                  30                  35

cag ctg aat tca tcc ttt tct ctg aga tgc ttt ggg gag agt gaa gtg      559
Gln Leu Asn Ser Ser Phe Ser Leu Arg Cys Phe Gly Glu Ser Glu Val
40                  45                  50                  55

agc tgg cag tac ccc atg tct gaa gaa gag agc tcc gat gtg gaa atc      607
Ser Trp Gln Tyr Pro Met Ser Glu Glu Glu Ser Ser Asp Val Glu Ile
                60                  65                  70

aga aat gaa gaa aac aac agc ggc ctt ttt gtg acg gtc ttg gaa gtg      655
Arg Asn Glu Glu Asn Asn Ser Gly Leu Phe Val Thr Val Leu Glu Val
            75                  80                  85

agc agt gcc tcg gcg gcc cac aca ggg ttg tac act tgc tat tac aac      703
Ser Ser Ala Ser Ala Ala His Thr Gly Leu Tyr Thr Cys Tyr Tyr Asn
        90                  95                  100

cac act cag aca gaa gag aat gag ctt gaa ggc agg cac att tac atc      751
His Thr Gln Thr Glu Glu Asn Glu Leu Glu Gly Arg His Ile Tyr Ile
    105                 110                 115

tat gtg cca gac cca gat gta gcc ttt gta cct cta gga atg acg gat      799
Tyr Val Pro Asp Pro Asp Val Ala Phe Val Pro Leu Gly Met Thr Asp
120                 125                 130                 135

tat tta gtc atc gtg gag gat gat gat tct gcc att ata cct tgt cgc      847
Tyr Leu Val Ile Val Glu Asp Asp Asp Ser Ala Ile Ile Pro Cys Arg
                140                 145                 150

aca act gat ccc gag act cct gta acc tta cac aac agt gag ggg gtg      895
Thr Thr Asp Pro Glu Thr Pro Val Thr Leu His Asn Ser Glu Gly Val
            155                 160                 165

gta cct gcc tcc tac gac agc aga cag ggc ttt aat ggg acc ttc act      943
Val Pro Ala Ser Tyr Asp Ser Arg Gln Gly Phe Asn Gly Thr Phe Thr
        170                 175                 180

gta ggg ccc tat atc tgt gag gcc acc gtc aaa gga aag aag ttc cag      991
Val Gly Pro Tyr Ile Cys Glu Ala Thr Val Lys Gly Lys Lys Phe Gln
    185                 190                 195

acc atc cca ttt aat gtt tat gct tta aaa gca aca tca gag ctg gat     1039
Thr Ile Pro Phe Asn Val Tyr Ala Leu Lys Ala Thr Ser Glu Leu Asp
200                 205                 210                 215

cta gaa atg gaa gct ctt aaa acc gtg tat aag tca ggg gaa acg att     1087
Leu Glu Met Glu Ala Leu Lys Thr Val Tyr Lys Ser Gly Glu Thr Ile
                220                 225                 230

gtg gtc acc tgt gct gtt ttt aac aat gag gtg gtt gac ctt caa tgg     1135
Val Val Thr Cys Ala Val Phe Asn Asn Glu Val Val Asp Leu Gln Trp
            235                 240                 245

act tac cct gga gaa gtg aaa ggc aaa ggc atc aca atg ctg gaa gaa     1183
Thr Tyr Pro Gly Glu Val Lys Gly Lys Gly Ile Thr Met Leu Glu Glu
        250                 255                 260

atc aaa gtc cca tcc atc aaa ttg gtg tac act ttg acg gtc ccc gag     1231
Ile Lys Val Pro Ser Ile Lys Leu Val Tyr Thr Leu Thr Val Pro Glu
    265                 270                 275
```

```
gcc acg gtg aaa gac agt gga gat tac gaa tgt gct gcc cgc cag gct      1279
Ala Thr Val Lys Asp Ser Gly Asp Tyr Glu Cys Ala Ala Arg Gln Ala
280                 285                 290                 295

acc agg gag gtc aaa gaa atg aag aaa gtc act att tct gtc cat gag      1327
Thr Arg Glu Val Lys Glu Met Lys Lys Val Thr Ile Ser Val His Glu
                300                 305                 310

aaa ggt ttc att gaa atc aaa ccc acc ttc agc cag ttg gaa gct gtc      1375
Lys Gly Phe Ile Glu Ile Lys Pro Thr Phe Ser Gln Leu Glu Ala Val
            315                 320                 325

aac ctg cat gaa gtc aaa cat ttt gtt gta gag gtg cgg gcc tac cca      1423
Asn Leu His Glu Val Lys His Phe Val Val Glu Val Arg Ala Tyr Pro
        330                 335                 340

cct ccc agg ata tcc tgg ctg aaa aac aat ctg act ctg att gaa aat      1471
Pro Pro Arg Ile Ser Trp Leu Lys Asn Asn Leu Thr Leu Ile Glu Asn
    345                 350                 355

ctc act gag atc acc act gat gtg gaa aag att cag gaa ata agg tat      1519
Leu Thr Glu Ile Thr Thr Asp Val Glu Lys Ile Gln Glu Ile Arg Tyr
360                 365                 370                 375

cga agc aaa tta aag ctg atc cgt gct aag gaa gaa gac agt ggc cat      1567
Arg Ser Lys Leu Lys Leu Ile Arg Ala Lys Glu Glu Asp Ser Gly His
                380                 385                 390

tat act att gta gct caa aat gaa gat gct gtg aag agc tat act ttt      1615
Tyr Thr Ile Val Ala Gln Asn Glu Asp Ala Val Lys Ser Tyr Thr Phe
            395                 400                 405

gaa ctg tta act caa gtt cct tca tcc att ctg gac ttg gtc gat gat      1663
Glu Leu Leu Thr Gln Val Pro Ser Ser Ile Leu Asp Leu Val Asp Asp
        410                 415                 420

cac cat ggc tca act ggg gga cag acg gtg agg tgc aca gct gaa ggc      1711
His His Gly Ser Thr Gly Gly Gln Thr Val Arg Cys Thr Ala Glu Gly
    425                 430                 435

acg ccg ctt cct gat att gag tgg atg ata tgc aaa gat att aag aaa      1759
Thr Pro Leu Pro Asp Ile Glu Trp Met Ile Cys Lys Asp Ile Lys Lys
440                 445                 450                 455

tgt aat aat gaa act tcc tgg act att ttg gcc aac aat gtc tca aac      1807
Cys Asn Asn Glu Thr Ser Trp Thr Ile Leu Ala Asn Asn Val Ser Asn
                460                 465                 470

atc atc acg gag atc cac tcc cga gac agg agt acc gtg gag ggc cgt      1855
Ile Ile Thr Glu Ile His Ser Arg Asp Arg Ser Thr Val Glu Gly Arg
            475                 480                 485

gtg act ttc gcc aaa gtg gag gag acc atc gcc gtg cga tgc ctg gct      1903
Val Thr Phe Ala Lys Val Glu Glu Thr Ile Ala Val Arg Cys Leu Ala
        490                 495                 500

aag aat ctc ctt gga gct gag aac cga gag ctg aag ctg gtg gct ccc      1951
Lys Asn Leu Leu Gly Ala Glu Asn Arg Glu Leu Lys Leu Val Ala Pro
    505                 510                 515

acc ctg cgt tct gaa ctc acg gtg gct gct gca gtc ctg gtg ctg ttg      1999
Thr Leu Arg Ser Glu Leu Thr Val Ala Ala Ala Val Leu Val Leu Leu
520                 525                 530                 535

gtg att gtg atc atc tca ctt att gtc ctg gtt gtc att tgg aaa cag      2047
Val Ile Val Ile Ile Ser Leu Ile Val Leu Val Val Ile Trp Lys Gln
                540                 545                 550

aaa ccg agg tat gaa att cgc tgg nnn nnn nnn nnn nnn atc nnn nnn      2095
Lys Pro Arg Tyr Glu Ile Arg Trp Xaa Xaa Xaa Xaa Xaa Ile Xaa Xaa
            555                 560                 565

nnn nnn nnn nnn tat att tat gtg gac ccg atg cag ctg cct tat gac      2143
Xaa Xaa Xaa Xaa Tyr Ile Tyr Val Asp Pro Met Gln Leu Pro Tyr Asp
        570                 575                 580

tca aga tgg gag ttt cca aga gat gga cta gtg ctt ggt cgg gtc ttg      2191
Ser Arg Trp Glu Phe Pro Arg Asp Gly Leu Val Leu Gly Arg Val Leu
    585                 590                 595
```

```
ggg tct gga gcg ttt ggg aag gtg gtt gaa gga aca gcc tat gga tta      2239
Gly Ser Gly Ala Phe Gly Lys Val Val Glu Gly Thr Ala Tyr Gly Leu
600                 605                 610                 615

agc cgg tcc caa cct gtc atg aaa gtt gca gtg aag atg cta aaa ccc      2287
Ser Arg Ser Gln Pro Val Met Lys Val Ala Val Lys Met Leu Lys Pro
                620                 625                 630

acg gcc aga tcc agt gaa aaa caa gct ctc atg tct gaa ctg aag ata      2335
Thr Ala Arg Ser Ser Glu Lys Gln Ala Leu Met Ser Glu Leu Lys Ile
            635                 640                 645

atg act cac ctg ggg cca cat ttg aac att gta aac ttg ctg gga gcc      2383
Met Thr His Leu Gly Pro His Leu Asn Ile Val Asn Leu Leu Gly Ala
        650                 655                 660

tgc acc aag tca ggc ccc att tac atc atc aca gag tat tgc ttc tat      2431
Cys Thr Lys Ser Gly Pro Ile Tyr Ile Ile Thr Glu Tyr Cys Phe Tyr
    665                 670                 675

gga gat ttg gtc aac tat ttg cat aag aat agg gat agc ttc ctg agc      2479
Gly Asp Leu Val Asn Tyr Leu His Lys Asn Arg Asp Ser Phe Leu Ser
680                 685                 690                 695

cac cac cca gag aag cca aag aaa gag ctg gat atc ttt gga ttg aac      2527
His His Pro Glu Lys Pro Lys Lys Glu Leu Asp Ile Phe Gly Leu Asn
                700                 705                 710

cct gct gat gaa agc aca cgg agc tat gtt att tta tct ttt gaa aac      2575
Pro Ala Asp Glu Ser Thr Arg Ser Tyr Val Ile Leu Ser Phe Glu Asn
            715                 720                 725

aat ggt gac tac atg gac atg aag cag gct gat act aca cag tat gtc      2623
Asn Gly Asp Tyr Met Asp Met Lys Gln Ala Asp Thr Thr Gln Tyr Val
        730                 735                 740

ccc atg cta gaa agg aaa gag gtt tct aaa tat tcc gac atc cag aga      2671
Pro Met Leu Glu Arg Lys Glu Val Ser Lys Tyr Ser Asp Ile Gln Arg
    745                 750                 755

tca ctc tat gat cgt cca gcc tca tat aag aag aaa tct atg tta gac      2719
Ser Leu Tyr Asp Arg Pro Ala Ser Tyr Lys Lys Lys Ser Met Leu Asp
760                 765                 770                 775

tca gaa gtc aaa aac ctc ctt tca gat gat aac tca gaa ggc ctt act      2767
Ser Glu Val Lys Asn Leu Leu Ser Asp Asp Asn Ser Glu Gly Leu Thr
                780                 785                 790

tta ttg gat ttg ttg agc ttc acc tat caa gtt gcc cga gga atg gag      2815
Leu Leu Asp Leu Leu Ser Phe Thr Tyr Gln Val Ala Arg Gly Met Glu
            795                 800                 805

ttt ttg gct tca aaa aat tgt gtc cac cgt gat ctg gct gct cgc aac      2863
Phe Leu Ala Ser Lys Asn Cys Val His Arg Asp Leu Ala Ala Arg Asn
        810                 815                 820

gtc ctc ctg gca caa gga aaa att gtg aag atc tgt gac ttt ggc ctg      2911
Val Leu Leu Ala Gln Gly Lys Ile Val Lys Ile Cys Asp Phe Gly Leu
    825                 830                 835

gcc ana nnn nnn nnn nnn nnn nnn nnc tat gtg tcg aaa ggc agt acc      2959
Ala Xaa Xaa Xaa Xaa Xaa Xaa Xaa Xaa Tyr Val Ser Lys Gly Ser Thr
840                 845                 850                 855

ttt ctg ccc gtg aag tgg atg gct cct gag agc atc ttt gac aac ctc      3007
Phe Leu Pro Val Lys Trp Met Ala Pro Glu Ser Ile Phe Asp Asn Leu
                860                 865                 870

tac acc aca ctg agt gat gtc tgg tct tat ggc att ctg ctc tgg gag      3055
Tyr Thr Thr Leu Ser Asp Val Trp Ser Tyr Gly Ile Leu Leu Trp Glu
            875                 880                 885

atc ttt tcc ctt ggt ggc acc cct tac ccc ggc atg atg gtg gat tct      3103
Ile Phe Ser Leu Gly Gly Thr Pro Tyr Pro Gly Met Met Val Asp Ser
        890                 895                 900

act ttc tac aat aag atc aag agt ggg tac cgg atg gcc aag cct gac      3151
Thr Phe Tyr Asn Lys Ile Lys Ser Gly Tyr Arg Met Ala Lys Pro Asp
    905                 910                 915
```

```
cac gct acc agt gaa gtc tac gag atc atg gtg aaa tgc tgg aac agt      3199
His Ala Thr Ser Glu Val Tyr Glu Ile Met Val Lys Cys Trp Asn Ser
920                 925                 930                 935

gag ccg gag aag aga ccc tcc ttt tac cac ctg agt gag att gtg gag      3247
Glu Pro Glu Lys Arg Pro Ser Phe Tyr His Leu Ser Glu Ile Val Glu
                940                 945                 950

aat ctg ctg cct gga caa tat aaa aag agt tat gaa aaa att cac ctg      3295
Asn Leu Leu Pro Gly Gln Tyr Lys Lys Ser Tyr Glu Lys Ile His Leu
            955                 960                 965

gac ttc ctg aag agt gac cat cct gct gtg gca cgc atg cgt gtg gac      3343
Asp Phe Leu Lys Ser Asp His Pro Ala Val Ala Arg Met Arg Val Asp
        970                 975                 980

tca gac aat gca tac att ggt gtc acc tac aaa aac gag gaa gac aag      3391
Ser Asp Asn Ala Tyr Ile Gly Val Thr Tyr Lys Asn Glu Glu Asp Lys
    985                 990                 995

ctg  aag gac tgg gag ggt  ggt ctg gat gag cag  aga ctg agc gct       3436
Leu  Lys Asp Trp Glu Gly  Gly Leu Asp Glu Gln  Arg Leu Ser Ala
1000                 1005                 1010

gac  agt ggc tac atc att  cct ctg cct gac att  gac cct gtc cct       3481
Asp  Ser Gly Tyr Ile Ile  Pro Leu Pro Asp Ile  Asp Pro Val Pro
1015                 1020                 1025

gag  gag gag gac ctg ggc  aag agg aac aga cac  agc tcg cag acc       3526
Glu  Glu Glu Asp Leu Gly  Lys Arg Asn Arg His  Ser Ser Gln Thr
1030                 1035                 1040

tct  gaa gag agt gcc att  gag acg ggt tcc agc  agt tcc acc ttc       3571
Ser  Glu Glu Ser Ala Ile  Glu Thr Gly Ser Ser  Ser Ser Thr Phe
1045                 1050                 1055

atc  aag aga gag gac gag  acc att gaa gac atc  gac atg atg gac       3616
Ile  Lys Arg Glu Asp Glu  Thr Ile Glu Asp Ile  Asp Met Met Asp
1060                 1065                 1070

gac  atc ggc ata gac tct  tca gac ctg gtg gaa  gac agc ttc ctg       3661
Asp  Ile Gly Ile Asp Ser  Ser Asp Leu Val Glu  Asp Ser Phe Leu
1075                 1080                 1085

taa ctggcggatt cgaggggttc cttccacttc tggggccacc tctggatccc           3714

gttcagaaaa ccactttatt gcaatgcgga ggttgagagg aggacttggt tgatgtttaa    3774

agagaagttc ccagccaagg gcctcgggga gcgttctaaa tatgaatgaa tgggatattt    3834

tgaaatgaac tttgtcagtg ttgcctctcg caatgcctca gtagcatctc agtggtgtgt    3894

gaagtttgga gatagatgga taagggaata ataggccaca gaaggtgaac tttgtgcttc    3954

aaggacattg gtgagagtcc aacagacaca atttatactg cgacagaact tcagcattgt    4014

aattatgtaa ataactctaa ccaaggctgt gtttagattg tattaactat cttctttgga    4074

cttctgaaga gaccactcaa tccatccatg tacttccctc ttgaaacctg atgtcagctg    4134

ctgttgaact ttttaaagaa gtgcatgaaa aaccattttt gaaccttaaa aggtactggt    4194

actatagcat tttgctatct tttttagtgt taagagataa agaataataa ttaaccaacc    4254

ttgtttaata gatttgggtc atttagaagc ctgacaactc attttcatat tgtaatctat    4314

gtttataata ctactactgt tatcagtaat gctaaatgtg taataatgta acatgatttc    4374

cctccagaga aagcacaatt taaaacaatc cttactaagt aggtgatgag tttgacagtt    4434

tttgacattt atattaaata acatgtttct ctataaagta tggtaatagc tttagtgaat    4494

taaatttagt tgagcataga gaacaaagta aaagtagtgt tgtccaggaa gtcagaattt    4554

ttaactgtac tgaataggtt ccccaatcca tcgtattaaa aaacaattaa ctgccctctg    4614

aaataatggg attagaaaca aacaaaactc ttaagtccta aaagttctca atgtagaggc    4674

ataaacctgt gctgaacata acttctcatg tatattaccc aatggaaaat ataatgatca    4734
```

```
gcaaaaagac tggatttgca gaagtttttt ttttttttct tcatgcctga tgaaagcttt   4794
ggcaacccca atatatgtat tttttgaatc tatgaacctg aaaagggtca gaaggatgcc   4854
cagacatcag cctccttctt tcacccctta ccccaaagag aaagagtttg aaactcgaga   4914
ccataaagat attctttagt ggaggctgga tgtgcattag cctggatcct cagttctcaa   4974
atgtgtgtgg cagccaggat gactagatcc tgggtttcca tccttgagat tctgaagtat   5034
gaagtctgag ggaaaccaga gtctgtattt ttctaaactc cctggctgtt ctgatcggcc   5094
agttttcgga aacactgact taggtttcag gaagttgcca tgggaaacaa ataatttgaa   5154
ctttggaaca gggttggaat tcaaccacgc aggaagccta ctatttaaat ccttggcttc   5214
aggttagtga catttaatgc catctagcta gcaattgcga ccttaattta actttccagt   5274
cttagctgag gctgagaaag ctaaagtttg gttttgacag gttttccaaa agtaaagatg   5334
ctacttccca ctgtatgggg gagattgaac tttccccgtc tcccgtcttc tgcctcccac   5394
tccatacccc gccaaggaaa ggcatgtaca aaaattatgc aattcagtgt tccaagtctc   5454
tgtgtaacca gctcagtgtt ttggtggaaa aaacatttta agttttactg ataatttgag   5514
gttagatggg aggatgaatt gtcacatcta tccacactgt caaacaggtt ggtgtgggtt   5574
cattggcatt ctttgcaata ctgcttaatt gctgatacca tatgaatgaa acatgggctg   5634
tgattactgc aatcactgtg ctatcggcag atgatgcttt ggaagatgca gaagcaataa   5694
taaagtactt gactacctac tggtgtaatc tcaatgcaag ccccaacttt cttatccaac   5754
tttttcatag taagtgcgaa gactgagcca gattggccaa ttaaaaacga aaacctgact   5814
aggttctgta gagccaatta gacttgaaat acgtttgtgt ttctagaatc acagctcaag   5874
cattctgttt atcgctcact ctcccttgta cagccttatt ttgttggtgc tttgcatttt   5934
gatattgctg tgagccttgc atgacatcat gaggccggat gaaacttctc agtccagcag   5994
tttccagtcc taacaaatgc tcccacctga atttgtatat gactgcattt gtgggtgtgt   6054
gtgtgttttc agcaaattcc agatttgttt ccttttggcc tcctgcaaag tctccagaag   6114
aaaatttgcc aatctttcct actttctatt tttatgatga caatcaaagc cggcctgaga   6174
aacactattt gtgacttttt aaacgattag tgatgtcctt aaaatgtggt ctgccaatct   6234
gtacaaaatg gtcctatttt tgtgaagagg gacataagat aaaatgatgt tatacatcaa   6294
tatgtatata tgtatttcta tatagacttg gagaatactg ccaaaacatt tatgacaagc   6354
tgtatcactg ccttcgttta tattttttta actgtgataa tccccacagg cacattaact   6414
gttgcacttt tgaatgtcca aaatttatat tttagaaata ataaaaagaa agatacttac   6474
atgttcccaa aacaatggtg tggtgaatgt gtgagaaaaa ctaacttgat agggtctacc   6534
aatacaaaat gtattacgaa tgcccctgtt catgtttttg ttttaaaacg tgtaaatgaa   6594
gatctttata tttcaataaa tgatatataa tttaaagtt                         6633
```

<210> SEQ ID NO 27
<211> LENGTH: 1089
<212> TYPE: PRT
<213> ORGANISM: Homo sapiens
<220> FEATURE:
<221> NAME/KEY: misc_feature
<222> LOCATION: (560)..(560)
<223> OTHER INFORMATION: The 'Xaa' at location 560 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (561)..(561)
<223> OTHER INFORMATION: The 'Xaa' at location 561 stands for Lys, Asn, Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (562)..(562)
<223> OTHER INFORMATION: The 'Xaa' at location 562 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (563)..(563)
<223> OTHER INFORMATION: The 'Xaa' at location 563 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (564)..(564)
<223> OTHER INFORMATION: The 'Xaa' at location 564 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (566)..(566)
<223> OTHER INFORMATION: The 'Xaa' at location 566 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (567)..(567)
<223> OTHER INFORMATION: The 'Xaa' at location 567 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (568)..(568)
<223> OTHER INFORMATION: The 'Xaa' at location 568 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (569)..(569)
<223> OTHER INFORMATION: The 'Xaa' at location 569 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (570)..(570)
<223> OTHER INFORMATION: The 'Xaa' at location 570 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (571)..(571)
<223> OTHER INFORMATION: The 'Xaa' at location 571 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (841)..(841)
<223> OTHER INFORMATION: The 'Xaa' at location 841 stands for Lys, Arg,
Thr, or Ile.
<220> FEATURE:
<221> NAME/KEY: misc_feature
<222> LOCATION: (842)..(842)
<223> OTHER INFORMATION: The 'Xaa' at location 842 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (843)..(843)
<223> OTHER INFORMATION: The 'Xaa' at location 843 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:
<221> NAME/KEY: misc_feature
<222> LOCATION: (844)..(844)
<223> OTHER INFORMATION: The 'Xaa' at location 844 stands for Lys, Asn,
Arg, Ser, Thr, Ile, Met, Glu, Asp, Gly, Ala, Val, Gln, His, Pro,
Leu, Tyr, Trp, Cys, or Phe.
<220> FEATURE:

<221> NAME/KEY: misc_feature
<222> LOCATION: (845)..(845)
<223> OTHER INFORMATION: The 'Xaa' at location 845 stands for Lys, Asn, Arg, Ser, Thr, Ile, Met, Glu, Asp, Gly, Ala, Val, Gln, His, Pro, Leu, Tyr, Trp, Cys, or Phe.
<220> FEATURE:
<221> NAME/KEY: misc_feature
<222> LOCATION: (846)..(846)
<223> OTHER INFORMATION: The 'Xaa' at location 846 stands for Lys, Asn, Arg, Ser, Thr, Ile, Met, Glu, Asp, Gly, Ala, Val, Gln, His, Pro, Leu, Tyr, Trp, Cys, or Phe.
<220> FEATURE:
<221> NAME/KEY: misc_feature
<222> LOCATION: (847)..(847)
<223> OTHER INFORMATION: The 'Xaa' at location 847 stands for Lys, Asn, Arg, Ser, Thr, Ile, Met, Glu, Asp, Gly, Ala, Val, Gln, His, Pro, Leu, Tyr, Trp, Cys, or Phe.
<220> FEATURE:
<221> NAME/KEY: misc_feature
<222> LOCATION: (848)..(848)
<223> OTHER INFORMATION: The 'Xaa' at location 848 stands for Asn, Ser, Thr, Ile, Asp, Gly, Ala, Val, His, Arg, Pro, Leu, Tyr, Cys, or Phe.

<400> SEQUENCE: 27

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285
```

-continued

```
Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
    530                 535                 540

Leu Val Val Ile Trp Lys Gln Lys Pro Arg Tyr Glu Ile Arg Trp Xaa
545                 550                 555                 560

Xaa Xaa Xaa Xaa Ile Xaa Xaa Xaa Xaa Xaa Xaa Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
    610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
    690                 695                 700

Leu Asp Ile Phe Gly Leu Asn Pro Ala Asp Glu Ser Thr Arg Ser Tyr
705                 710                 715                 720
```

```
Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
    770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Xaa Xaa Xaa Xaa Xaa Xaa Xaa Xaa
        835                 840                 845

Tyr Val Ser Lys Gly Ser Thr Phe Leu Pro Val Lys Trp Met Ala Pro
    850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
    930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                1015                1020

Asp Ile  Asp Pro Val Pro Glu  Glu Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser  Ser Ser Thr Phe Ile  Lys Arg Glu Asp Glu  Thr Ile Glu
    1055                1060                1065

Asp Ile  Asp Met Met Asp Asp  Ile Gly Ile Asp Ser  Ser Asp Leu
    1070                1075                1080

Val Glu  Asp Ser Phe Leu
    1085
```

<210> SEQ ID NO 28
<211> LENGTH: 400
<212> TYPE: DNA
<213> ORGANISM: Homo sapiens
<220> FEATURE:
<221> NAME/KEY: Intron

```
<222> LOCATION: (1)..(168)
<223> OTHER INFORMATION: Intron sequence
<220> FEATURE:
<221> NAME/KEY: exon
<222> LOCATION: (169)..(291)
<223> OTHER INFORMATION: Exon
<220> FEATURE:
<221> NAME/KEY: CDS
<222> LOCATION: (169)..(291)
<223> OTHER INFORMATION: intron
<220> FEATURE:
<221> NAME/KEY: Intron
<222> LOCATION: (292)..(400)
<223> OTHER INFORMATION: intron

<400> SEQUENCE: 28

gctttctctc tgttgggagt gggtggagtg agaacctggg agaaggccag ccctttatat     60

ccaggcagac agctccaagt gccaccatgg atcagccagt cttgcagggg tgatgctatt    120

cagctacaga tggcttgatc ctgagtcatt tcttcctttt ccatgcag tgt gtc cac     177
                                                     Cys Val His
                                                     1

cgt gat ctg gct gct cgc aac gtc ctc ctg gca caa gga aaa att gtg      225
Arg Asp Leu Ala Ala Arg Asn Val Leu Leu Ala Gln Gly Lys Ile Val
    5                   10                  15

aag atc tgt gac ttt ggc ctg gcc aga gac atc atg cat gat tcg aac      273
Lys Ile Cys Asp Phe Gly Leu Ala Arg Asp Ile Met His Asp Ser Asn
20                  25                  30                  35

tat gtg tcg aaa ggc agt gtacgtcctc acttccctca ctggtcaggc             321
Tyr Val Ser Lys Gly Ser
                40

tcatcctcct tcactttaat ctctaaagtc aggtgttgct tctagagatt cggtgcctgt    381

tttttaaaac atcaataga                                                 400


<210> SEQ ID NO 29
<211> LENGTH: 41
<212> TYPE: PRT
<213> ORGANISM: Homo sapiens

<400> SEQUENCE: 29

Cys Val His Arg Asp Leu Ala Ala Arg Asn Val Leu Leu Ala Gln Gly
1               5                   10                  15

Lys Ile Val Lys Ile Cys Asp Phe Gly Leu Ala Arg Asp Ile Met His
            20                  25                  30

Asp Ser Asn Tyr Val Ser Lys Gly Ser
        35                  40


<210> SEQ ID NO 30
<211> LENGTH: 400
<212> TYPE: DNA
<213> ORGANISM: Homo sapiens
<220> FEATURE:
<221> NAME/KEY: Intron
<222> LOCATION: (1)..(168)
<220> FEATURE:
<221> NAME/KEY: exon
<222> LOCATION: (169)..(300)
<220> FEATURE:
<221> NAME/KEY: CDS
<222> LOCATION: (169)..(300)
<220> FEATURE:
<221> NAME/KEY: Intron
<222> LOCATION: (301)..(400)

<400> SEQUENCE: 30

aagcatagca acctagttca gtgcttggca cagagaagga gctcagcaat tacatgtgga     60
```

-continued

```
gtgaacgttg ttggactcta ctgtgtccag tcactgtgct gcttcagtga agctctggtg    120

cactgggact ttggtaattc accagttacc tgtcctggtc atttatag aaa ccg agg     177
                                                     Lys Pro Arg
                                                     1

tat gaa att cgc tgg agg gtc att gaa tcc atc agc cca gat gga cat      225
Tyr Glu Ile Arg Trp Arg Val Ile Glu Ser Ile Ser Pro Asp Gly His
    5                   10                  15

gaa tat att tat gtg gac ccg atg cag ctg cct tat gac tca aga tgg      273
Glu Tyr Ile Tyr Val Asp Pro Met Gln Leu Pro Tyr Asp Ser Arg Trp
20                  25                  30                  35

gag ttt cca aga gat gga cta gtg ctt ggttagttcc atggggtaac            320
Glu Phe Pro Arg Asp Gly Leu Val Leu
                40

ctcccaagac tccctttcc cttgcacaca actttacaat ttataggcct tggcagaata     380

gagatctgag cttgtgctta                                                400


<210> SEQ ID NO 31
<211> LENGTH: 44
<212> TYPE: PRT
<213> ORGANISM: Homo sapiens

<400> SEQUENCE: 31

Lys Pro Arg Tyr Glu Ile Arg Trp Arg Val Ile Glu Ser Ile Ser Pro
1               5                   10                  15

Asp Gly His Glu Tyr Ile Tyr Val Asp Pro Met Gln Leu Pro Tyr Asp
            20                  25                  30

Ser Arg Trp Glu Phe Pro Arg Asp Gly Leu Val Leu
        35                  40
```